(12) United States Patent
Ma et al.

(10) Patent No.: US 11,444,252 B2
(45) Date of Patent: Sep. 13, 2022

(54) NITROGEN-CONTAINING COMPOUND, ORGANIC ELECTROLUMINESCENT DEVICE AND ELECTRONIC APPARATUS

(71) Applicant: Shaanxi Lighte Optoelectronics Material Co., Ltd., Xi'an (CN)

(72) Inventors: Linnan Ma, Xi'an (CN); Tiantian Ma, Xi'an (CN); Peng Nan, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 0 days.

(21) Appl. No.: 17/596,885

(22) PCT Filed: Jul. 24, 2020

(86) PCT No.: PCT/CN2020/104580
§ 371 (c)(1),
(2) Date: Dec. 20, 2021

(87) PCT Pub. No.: WO2021/135182
PCT Pub. Date: Jul. 8, 2021

(65) Prior Publication Data
US 2022/0216426 A1    Jul. 7, 2022

(30) Foreign Application Priority Data

Dec. 30, 2019 (CN) .......................... 201911404332.5
Jun. 4, 2020 (CN) .......................... 202010501534.8

(51) Int. Cl.
*C07D 209/86* (2006.01)
*C07D 401/14* (2006.01)
(Continued)

(52) U.S. Cl.
CPC ........ *H01L 51/0072* (2013.01); *C07D 209/86* (2013.01); *C07D 401/14* (2013.01);
(Continued)

(58) Field of Classification Search
CPC .................................................. C07D 209/86
See application file for complete search history.

(56) References Cited

FOREIGN PATENT DOCUMENTS

| CN | 102918134 A | 2/2013 |
|----|-------------|--------|
| CN | 105308026 A | 2/2016 |

(Continued)

OTHER PUBLICATIONS

International Search Report from corresponding International Application No. PCT/CN2020/104580, dated Oct. 10, 2020, 5 pages.

*Primary Examiner* — Vu A Nguyen
(74) *Attorney, Agent, or Firm* — Tucker Ellis LLP

(57) ABSTRACT

The present disclosure relates to the technical field of organic materials, and provided therein is a nitrogen-containing compound, comprising at least three directly or indirectly linked fused ring systems. A first fused ring system is a fluorenyl group spiro-linked by adamantane, and adamantyl can greatly increase the electron cloud density of a conjugated structure of the first fused ring system by means of a hyperconjugation effect, which can increase hole mobility. The three fused ring systems enable the nitrogen-containing compound of the present disclosure to have a high first triplet energy level so that the nitrogen-containing compound of the present disclosure is suitable as the host material of an organic light-emitting layer in an organic electroluminescent device. Further provided in the present disclosure are an organic electroluminescent device comprising the described nitrogen-containing compound and an electronic apparatus, and the described nitrogen-containing compound can improve the performance of the organic electroluminescent device.

13 Claims, 1 Drawing Sheet

(51) Int. Cl.
  *C07D 403/14* (2006.01)
  *C07D 405/04* (2006.01)
  *C07D 405/14* (2006.01)
  *C07D 409/04* (2006.01)
  *C07D 409/14* (2006.01)
  *C09K 11/06* (2006.01)
  *H01L 51/00* (2006.01)
  *H01L 51/50* (2006.01)

(52) U.S. Cl.
  CPC ......... *C07D 403/14* (2013.01); *C07D 405/04* (2013.01); *C07D 405/14* (2013.01); *C07D 409/04* (2013.01); *C07D 409/14* (2013.01); *C09K 11/06* (2013.01); *H01L 51/0056* (2013.01); *H01L 51/0058* (2013.01); *H01L 51/0067* (2013.01); *H01L 51/0073* (2013.01); *H01L 51/0074* (2013.01); *C09K 2211/1018* (2013.01); *H01L 51/5012* (2013.01)

(56) References Cited

FOREIGN PATENT DOCUMENTS

| | | | | |
|---|---|---|---|---|
| CN | 106316925 A | 1/2017 | | |
| CN | 106565592 A | 4/2017 | | |
| CN | 107148408 A | 9/2017 | | |
| CN | 109593042 A | 4/2019 | | |
| CN | 110028459 A | 7/2019 | | |
| CN | 110128279 A | 8/2019 | | |
| CN | 110156756 A | 8/2019 | | |
| CN | 110183332 A | 8/2019 | | |
| CN | 110183333 A | 8/2019 | | |
| CN | 110467536 A | 11/2019 | | |
| CN | 110615759 A | 12/2019 | | |
| CN | 111018797 A | * | 4/2020 | ........... C07D 251/24 |
| EP | 1505053 A1 | 2/2005 | | |
| JP | 2013108015 A | 6/2013 | | |
| WO | 2019132545 A1 | 7/2019 | | |
| WO | 2019164341 A1 | 8/2019 | | |
| WO | WO-2020045924 A1 | * | 3/2020 | ........... C07C 211/61 |

* cited by examiner

NITROGEN-CONTAINING COMPOUND, ORGANIC ELECTROLUMINESCENT DEVICE AND ELECTRONIC APPARATUS

CROSS REFERENCE TO RELATED APPLICATION

The present application claims priority to Chinese patent application No. CN201911404332.5 filed on Dec. 30, 2019, and Chinese patent application No. CN202010501534.8 filed on Jun. 4, 2019, which are incorporated herein by reference in their entirety.

TECHNICAL FIELD

The application relates to the technical field of organic materials, particularly to a nitrogen-containing compound, an organic electroluminescent device and an electronic apparatus.

BACKGROUND

Organic electroluminescent devices, for example, organic light emitting diode (OLED), usually include a cathode and an anode oppositely arranged, and a functional layer arranged between the cathode and the anode. The functional layer consists of a plurality of organic or inorganic membrane layers, and generally includes an organic light emitting layer, a hole transport layer between the organic light emitting layer and the anode, and an electron transport layer between the organic light emitting layer and the cathode. When voltage is applied to the cathode and the anode, the two electrodes generate an electric field. The electrons on the cathode side move to the electroluminescent layer under the action of the electric field, and the holes on the anode side also move to the light emitting layer. The electrons and the holes are combined at the electroluminescent layer to generate excitons. The excitons release energy outwards in an excited state, so that the electroluminescent layer emits light to the outside.

In the prior art, KR1020190028591, KR1020190007789A and the like disclose materials available for preparing luminescent layers in organic electroluminescent devices. However, it is still necessary to continue to develop new materials in order to further improve the performance of organic electroluminescent devices.

The above information disclosed in the background section is only used to strengthen the understanding of the background of the application, so it may include information that does not constitute the prior art known to those skilled in the art.

SUMMARY

The present application is intended to provide a nitrogen-containing compound, an organic electroluminescent device and an electronic apparatus to improve the performance of the organic electroluminescent device.

The following technical solution is used for the present application in order to achieve the above purpose of the application.

According to the first aspect of the present application, provided is a nitrogen-containing compound, and the structural formula of the nitrogen-containing compound is as shown in formula 1:

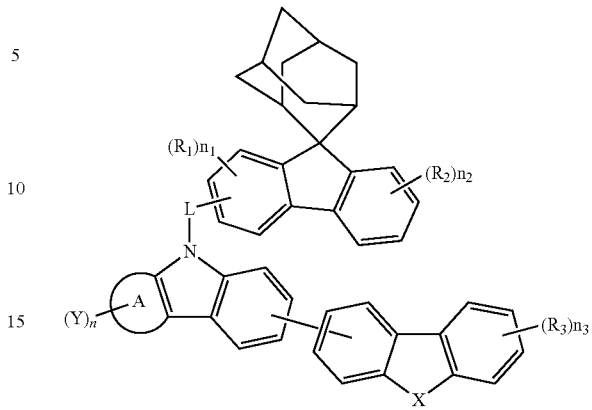

Formula 1 wherein n is an integer selected from 0 to 4; ring A is selected from benzene ring, naphthalene ring or fused heteroaromatic ring with 10 to 14 ring-forming carbon atoms;

X is selected from $C(Z^1Z^2)$, $Si(Z^1Z^2)$, $N(Z^3)$, O, Se or S;

$Z^1$, $Z^2$ and $Z^3$ are each independently selected from hydrogen, deuterium, substituted or unsubstituted alkyl with 1 to 20 carbon atoms, substituted or unsubstituted aryl with 6 to 30 carbon atoms, substituted or unsubstituted heteroaryl with 3 to 30 carbon atoms, substituted or unsubstituted cycloalkyl with 3 to 20 carbon atoms, alternatively, $Z^1$ and $Z^2$ are connected with each other to form saturated or unsaturated 5-to-13-membered ring together with the atoms to which they are jointly connected;

Y, $R_1$, $R_2$ and $R_3$ are the same or different, and are each independently selected from deuterium, fluorine, chlorine, bromine, cyano, aryl with 6 to 20 carbon atoms, heteroaryl with 6 to 18 carbon atoms, alkylsilyl with 3 to 18 carbon atoms, triarylsilyl with 6 to 18 carbon atoms, alkyl with 1 to 12 carbon atoms, haloalkyl with 1 to 12 carbon atoms, alkenyl with 2 to 12 carbon protons, cycloalkyl with 3 to 10 carbon atoms, heterocycloalkyl with 2 to 12 carbon atoms, alkylamine with 1 to 10 carbon atoms, alkylthiol with 1 to 10 carbon atoms, aryloxy with 6 to 18 carbon atoms and arylthio with 6 to 18 carbon atoms; n and $n_3$ are the same or different, and are each independently selected from 0, 1, 2, 3 or 4; $n_1$ and $n_2$ are the same or different, and are each independently selected from 0, 1, 2 or 3;

when n is 2, 3 or 4, any two Y are the same or different; when $n_1$ is 2 or 3, any two $R_1$ are the same or different; when $n_2$ is 2 or 3, any two $R_2$ are the same or different; when $n_2$ is 2 or 3, any two $R_2$ are the same or different; when $n_3$ is 2, 3 or 4, any two $R_3$ are the same or different;

L is selected from single bond, substituted or unsubstituted arylene with 6 to 30 carbon atoms, and substituted or unsubstituted heteroarylene with 3 to 30 carbon atoms.

Optionally, the substituents of L are the same or different from each other, and are each independently selected from deuterium, fluorine, chlorine, bromine, cyano, alkyl with 1 to 12 carbon atoms, alkoxy with 1 to 12 carbon atoms, alkthio with 1 to 12 carbon atoms, haloalkyl with 1 to 12 carbon atoms, cycloalkyl with 3 to 10 carbon atoms, heterocycloalkyl with 2 to 12 carbon atoms, alkylamine with 1 to 12 carbon atoms, aryl with 6 to 20 carbon atoms, heteroaryl with 6 to 18 carbon atoms, alkylsilyl with 3 to 18 carbon atoms, arylsilyl with 6 to 18 carbon atoms, aryloxy with 6 to 18 carbon atoms, and arylthio with 6 to 18 carbon atoms.

The nitrogen-containing compound provided in the present disclosure comprises at least three directly or indirectly connected fused ring systems. Wherein the first fused ring system is adamantanyl spiro fluorenyl, and adamantyl can greatly increase the electron cloud density of a conjugated structure of the first fused ring system through the hyperconjugation effect, so that the adamantanyl spiro fluorenyl has high hole mobility, and then the hole mobility of the nitrogen-containing compound in the present disclosure can be improved. The second fused ring system is a fused ring system containing a carbazole group, and the hole mobility of the nitrogen-containing compound in the present disclosure can be improved because the carbazole group has high hole mobility. The third fused ring system is fluorenyl, carbazolyl, dibenzothiophenyl or dibenzofuranyl, and the like, which directly connected to the second fused ring system; since fluorenyl, carbazolyl, dibenzothiophenyl and dibenzofuranyl are groups with high hole mobility, the third fused ring system also has high hole mobility, so that the hole mobility of the nitrogen-containing compound in the present disclosure can further be improved. Therefore, the nitrogen-containing compound in the disclosure has at least three fused ring groups with high hole mobility, so that it has high hole mobility as a whole. Moreover, the three fused ring groups are combined to make different fused ring groups cooperate to further improve the hole mobility of the nitrogen-containing compound in the disclosure.

According to the second aspect of the present application, provided is an organic electroluminescent device, comprising an anode, a cathode arranged opposite the anode, and a functional layer arranged between the anode and the cathode; wherein the functional layer contains the above nitrogen-containing compound.

According to the third aspect of the present application, provided is an electronic apparatus, comprising the above organic electroluminescent device.

BRIEF DESCRIPTION OF THE DRAWINGS

The above-mentioned and other characteristics and advantages in the present disclosure will become more apparent by describing the example embodiments in detail in combination with the drawings.

Figure 1:
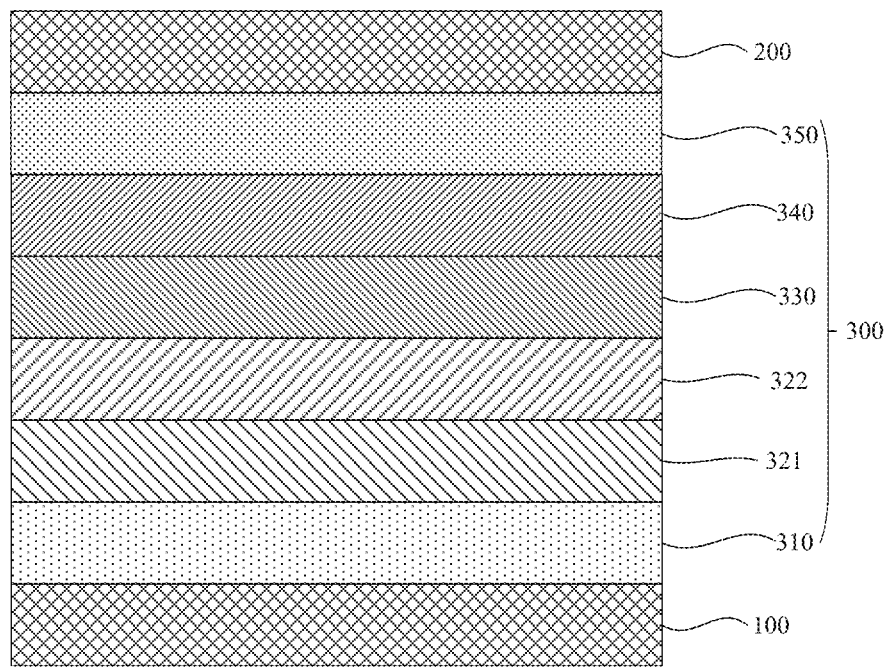
FIG. 1 illustrates a structural view of the organic electroluminescent device in accordance with the embodiment in the disclosure.

The reference numerals of main elements in the drawings are described as follows:

100. anode; 200. cathode; 300. functional layer; 310. hole injection layer; 321. first hole transport layer; 322. second hole transport layer; 330. organic light emitting layer; 340. electron transport layer; 350. electron injection layer; 400. electronic apparatus.

DETAILED DESCRIPTION OF THE EMBODIMENTS

The example embodiments are now described more thoroughly in combination with the drawings. However, the example embodiments can be implemented in multiple forms and shall not be construed as limitations to the examples set forth herein; on the contrary, these embodiments are provided to make the disclosure more comprehensive and complete, and fully convey the concept of the example embodiments to those skilled in the art. The described characteristics, structures or features may be integrated into one or more embodiments in any suitable manner. In the following description, many specific details are provided to give a full understanding of the embodiments in the disclosure.

For clarity, the thicknesses of areas and layers may be exaggerated in figures. The same reference numerals in figures represent the same or similar structures, thus detailed description of the reference numerals will be omitted.

An embodiment in the present disclosure provides a nitrogen-containing compound, and the structural formula of the nitrogen-containing compound is as shown in formula 1:

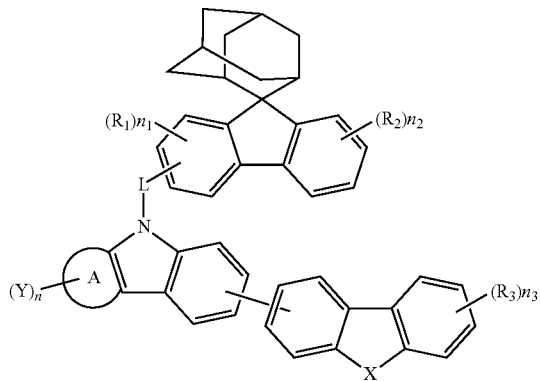

Formula I wherein n is the number of substituent Y, $n_1$ is the number of substituent $R_1$, $n_2$ is the number of substituent $R_2$, and $n_3$ is the number of substituent $R_3$;

the ring A is selected from benzene ring, naphthalene ring or fused heteroaromatic ring with 10 to 14 ring-forming carbon atoms;

X is selected from $C(Z^1Z^2)$, $Si(Z^1Z^2)$, $N(Z^3)$, O, Se or S;

$Z^1$, $Z^2$ and $Z^3$ are each independently selected from hydrogen, deuterium, substituted or unsubstituted alkyl with 1 to 20 carbon atoms, substituted or unsubstituted aryl with 6 to 30 carbon atoms, substituted or unsubstituted heteroaryl with 3 to 30 carbon atoms, substituted or unsubstituted cycloalkyl with 3 to 20 carbon atoms, alternatively, $Z^1$ and $Z^2$ are connected with each other to form saturated or unsaturated 5-to-13-membered ring together with the atoms to which they are jointly connected.

For example, "alternatively, $Z^1$ and $Z^2$ in

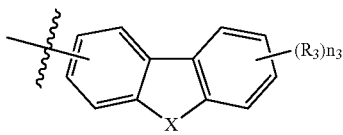

in formula 1 are connected with each other to form a ring", which means that $Z^1$ and $Z^2$ are either connected with each other to form a ring or exist independently of each other; when they form a ring, the number of carbon atoms of the ring may be either a 5-membered ring, for example

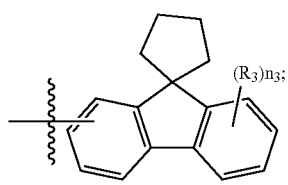

or a 6-membered ring, for example

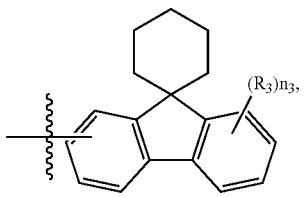

or a 10-membered ring, for example

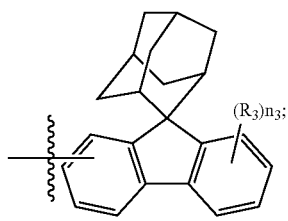

or a 13 membered-ring, for example

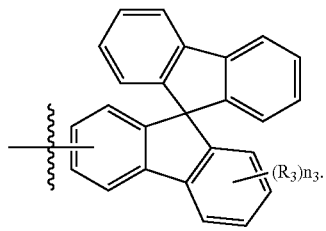

Of course, the number of carbon atoms of the ring formed by connecting $Z^1$ with $Z^2$ may also be other values, which will not be listed one by one here.

Y, $R_1$, $R_2$ and $R_3$ are the same or different, and are each independently selected from deuterium, fluorine, chlorine, bromine, cyano, aryl with 6 to 20 carbon atoms, heteroaryl with 6 to 18 carbon atoms, alkylsilyl with 3 to 18 carbon atoms, triarylsilyl with 6 to 18 carbon atoms, alkyl with 1 to 12 carbon atoms, haloalkyl with 1 to 12 carbon atoms, alkenyl with 2 to 12 carbon protons, cycloalkyl with 3 to 10 carbon atoms, heterocycloalkyl with 2 to 12 carbon atoms, alkylamine with 1 to 10 carbon atoms, alkylthiol with 1 to 10 carbon atoms, aryloxy with 6 to 18 carbon atoms and arylthio with 6 to 18 carbon atoms; n and $n_3$ are the same or different, and are each independently selected from 0, 1, 2, 3 or 4; $n_1$ and $n_2$ are the same or different, and are each independently selected from 0, 1, 2 or 3;

when n is 2, 3 or 4, any two Y are the same or different; when $n_1$ is 2 or 3, any two $R_1$ are the same or different; when $n_2$ is 2 or 3, any two $R_2$ are the same or different; when $n_3$ is 2, 3 or 4, any two $R_3$ are the same or different;

L is selected from single bond, a substituted or unsubstituted rylene with 6 to 30 carbon atoms, and substituted or unsubstituted heteroarylene with 3 to 30 carbon atoms.

In the present disclosure, the ring A refers to

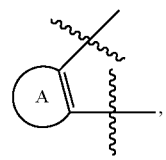

which may be selected from benzene ring, naphthalene ring or fused heteroaromatic ring. Optionally, in some embodiments, the ring A is benzene ring, naphthalene ring or fused heteroaromatic ring with 10 to 14 ring-forming carbon atoms, and the fused heteroaromatic ring with 10 to 14 ring-forming carbon atoms is selected from quinoline ring, isoquinoline ring, phenanthroline ring and the like. Wherein

represents a chemical bond. For example, in the compound

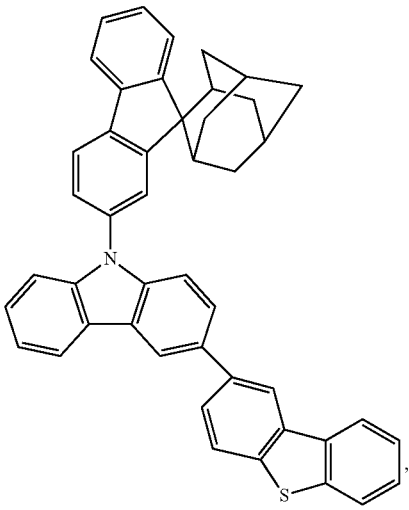 [SMILES: c1ccc2c(c1)-c1ccc(-n3c4ccccc4c4cc(-c5ccc6sc7ccccc7c6c5)ccc43)cc1C21C2CC3CC(C2)CC1C3]

the ring A is a benzene ring, and the number n of substituents Y of the ring A is 0. It is understood that the ring A comprises at least one benzene ring structure, so that the nitrogen-containing compound in the disclosure comprises at least one carbazole structure.

The nitrogen-containing compound provided in the present disclosure comprises at least three directly or indirectly connected fused ring systems. Wherein the first fused ring system is adamantanyl spiro fluorenyl, and adamantyl can greatly increase the electron cloud density of a conjugated structure of the first fused ring system through the hyper-conjugation effect, so that the adamantanyl spiro fluorenyl has high hole mobility, and then the hole mobility of the nitrogen-containing compound in the present disclosure can be improved. The second fused ring system is a fused ring system containing the ring A; since the ring A is a benzene ring or fused aromatic ring, the fused ring system containing the ring A contains at least the carbazole group, that is, the second fused ring system is a fused ring system containing a carbazole group. The hole mobility of the nitrogen-containing compound in the present disclosure can be improved because the carbazole group has high hole mobility. The third fused ring system is fluorenyl, carbazolyl, dibenzothiophenyl or dibenzofuranyl, which directly connected to the second fused ring system; since fluorenyl, carbazolyl, dibenzothiophenyl and dibenzofuranyl are groups with high hole mobility, the third fused ring system also has high hole mobility, so that the hole mobility of the nitrogen-containing compound in the present disclosure can be improved. Therefore, the nitrogen-containing compound in the present disclosure has at least three fused ring groups with high hole mobility, so that it has high hole mobility as a whole. Moreover, the three fused ring groups are combined to make different fused ring groups cooperate to further improve the hole mobility of the nitrogen-containing compound in the present disclosure.

The three fused ring systems are connected to form a large conjugate plane, especially the connection between the second fused ring system and the third fused ring system makes the conjugate plane very rigid, so that the nitrogen-containing compound in the present disclosure has a high first triplet energy level, so that the nitrogen-containing compound in the present disclosure is suitable for serving as a host material for the organic light-emitting layer in the organic electroluminescent device. When the nitrogen-containing compound in the present disclosure is used as the host material of the organic light emitting layer, it can enhance the hole mobility of the organic light emitting layer, help to promote the transport balance of holes and electrons in the organic light emitting layer, improve the luminous efficiency of the organic electroluminescent device, and reduce the driving voltage of the organic electroluminescent device. The improvement in the hole mobility of the nitrogen-containing compound in the present disclosure can also increase the recombination rate of electrons and holes in the organic light emitting layer, and reduce or avoid the transport of electrons through the organic light emitting layer to the hole transport layer, thus effectively protecting the hole transport layer material against the impact of electrons and improving the lifetime of the organic electroluminescent device.

Moreover, the adamantyl spiro to the fluorenyl has a large space volume and high rigidity, so the adamantyl can reduce the interactive force between large plane conjugated structures, reduce the π-π stacking between molecules and regulate the stacking degree between molecules. The third fused ring system is connected to the second fused ring system, so that the molecular symmetry of the nitrogen-containing compound in the present disclosure can be reduced. All these enable the nitrogen-containing compound in the present disclosure to be in a more stable amorphous form during film formation, improve the film-forming properties of the nitrogen-containing compound in the present disclosure, and further increase the lifetime of the organic electroluminescent device.

In the present disclosure, the number of carbon atoms of $Z^1$, $Z^2$, $Z^3$ and L refers to the number of all carbon atoms. For example, if $Z^3$ is selected from substituted aryl with 10 carbon atoms, the number of all carbon atoms of the aryl and the substitute thereon is 10. In another example, if $Z^3$ is a 9,9-dimethylfluorenyl, $Z^3$ is substituted fluorenyl with 15 carbon atoms, and the number of ring-forming carbon atoms of $Z^3$ is 13.

In the present disclosure, "hetero" means that one functional group comprises at least 1 heteroatom, such as B, N, O, S, Si, Se or P and the rest atoms are carbon and hydrogen when no specific definition is additionally provided. Unsubstituted alkyl may be a "saturated alkyl group" without any double or triple bond.

In the present disclosure, the term such as "substituted or unsubstituted" means that the functional group recorded following the term may or may not have a substituent. For example, "substituted or unsubstituted alkyl" refers to alkyl with a substituent, or unsubstituted alkyl. "Substituted" means that it can be substituted by a substituent selected from the following groups: deuterium, halogen group, heteroaryl, aryl, trialkylsilyl, alkyl, haloalkyl, alkenyl, cycloalkyl, heterocycloalkyl, cycloalkenyl, heterocycloalkenyl, alkoxyl, alkylthiol, aryloxy, arylthio, triarylsilyl, boron alkyl, alkylphosphinoxy and the like.

In the present disclosure, "alkyl" may include linear alkyl or branched alkyl. The alkyl can have 1 to 20 carbon atoms. And a numerical range such as "1 to 20" refers to integers in a given range herein. For example, "1 to 20 carbon atoms" refers to the alkyl that can contain 1 carbon atom, 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms or 20 carbon atoms. The alkyl may also be median size alkyl with 1 to 10 carbon atoms. The alkyl may also be lower alkyl with 1 to 6 carbon atoms. In some additional embodiments, the alkyl group contains 1 to 4 carbon atoms. Also in some embodiments, the alkyl group contains 1 to 3 carbon atoms. The alkyl group may be optionally substituted by one or more substituent(s) described in the present disclosure. Examples of the alkyl group include, but are not limited to, methyl (Me, —CH$_3$), ethyl (Et, —CH$_2$CH$_3$), n-propyl (n-Pr, —CH$_2$CH$_2$CH$_3$), isopropyl (i-Pr, —CH(CH$_3$)$_2$), n-butyl (n-Bu, —CH$_2$CH$_2$CH$_2$CH$_3$), isobutyl (i-Bu, —CH$_2$CH(CH$_3$)$_2$), sec-butyl (s-Bu, —CH(CH$_3$)CH$_2$CH$_3$), tertiary butyl (t-Bu, —C(CH$_3$)$_3$) and the like. In addition, the alkyl may be substituted or unsubstituted.

In the present disclosure, "alkenyl" refers to a hydrocarbyl containing one or more double bonds in a linear or branched hydrocarbon chain. The alkenyl may be substituted or unsubstituted. The alkenyl can have 1 to 20 carbon atoms. And a numerical range such as "1 to 20" refers to integers in a given range whenever it appears herein. For example, "1 to 20 carbon atoms" refers to the alkenyl that can contain 1 carbon atom, 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms or 20 carbon atoms. For example, the alkenyl may be vinyl, butadiene, or 1,3,5-hexatriene.

In the present disclosure, cycloalkyl refers to cyclic saturated hydrocarbon, including monocyclic and polycyclic structures. The cycloalkyl can have 3 to 20 carbon atoms, and a numerical range such as "3 to 20" refers to integers in a given range herein. For example, "3 to 20 carbon atoms" refers to the cycloalkyl that can contain 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms or 20 carbon atoms. The cycloalkyl may also be lower alkyl, common ring or large ring with 3 to 20 carbon atoms. The cycloalkyl can also be divided into monocyclic—only one ring, bicyclic—two rings, or polycyclic—three or more rings. The cycloalkyl can also be divided into two rings sharing one carbon atom—spiro, two rings sharing two carbon atoms—fused ring, and two rings sharing more than two carbon atoms—bridged ring. In addition, the cycloalkyl may be substituted or unsubstituted. In some embodiments, the cycloalkyl is 5-to-10-membered cycloalkyl, and in other embodiments, the cycloalkyl is 5-to-8-membered cycloalkyl, for example, examples of cycloalkyl may be, but are not limited to: 5-membered cycloalkyl, i.e., cyclopentyl, 6-membered cycloalkyl, i.e., cyclohexyl, 10-membered polycyclic alkyl, such as adamantyl and the like.

In the present disclosure, the "ring" includes saturated rings and unsaturated rings; saturated rings are cycloalkyl and heterocycloalkyl, and unsaturated rings are cycloalkenyl, heterocycloalkenyl, aryl and heteroaryl.

In the present disclosure, the "aryl" may be used interchangeably with the "aromatic ring". The aryl refers to a monocyclic structure formed by a plurality of carbon atoms, or a bicyclic or polycyclic system formed by a plurality of carbon atoms, wherein at least one aromatic ring system is contained, wherein each ring system can contain a ring consisting of 3 to 7 atoms, that is, the aryl is either monocyclic aryl or polycyclic aryl. In other words, the aryl may be monocyclic aryl, polycyclic aryl, two or more monocyclic aryls conjugated by carbon-carbon bonds, monocyclic aryl and polycyclic aryl conjugated by carbon-carbon bonds, and two or more polycyclic aryls conjugated by carbon-carbon bonds. That is, two or more aromatic groups conjugated by carbon-carbon bonds can also be regarded as the aryls in the present disclosure. For example, biphenyl, triphenyl and the like are aryls in the disclosure. The "aryl" in the disclosure may contain 6 to 30 carbon atoms, in some embodiments, the number of carbon atoms in the aryl may be 6 to 25, in other embodiments, the number of carbon atoms in the aryl may be 6 to 18, and in other embodiments, the number of carbon atoms in the aryl may be 6 to 13. For example, the number of carbon atoms in aryl may be 6, 12, 13, 18, 20, 25 or 30, and of course, the number of carbon atoms may also be other numbers, which will not be listed one by one here.

In the present disclosure, the aryl with 6 to 20 ring-forming carbon atoms means that the number of carbon atoms on a main aromatic ring in the aryl is 6 to 20, and the number of carbon atoms in a substituent on the aryl is not included. The number of ring-forming carbon atoms in the aryl may be, but is not limited to, 6 to 20, 6 to 18, 6 to 14 or 6 to 10. For example, the number of ring-forming carbon atoms in diphenylfluorene is 13.

Examples of aryls may include, but are not limited to, phenyl, naphthyl, fluorenyl, anthracyl, phenanthryl, biphenyl, triphenyl, tetradiphenyl, pentadiphenyl, benzo [9,10] phenanthryl, fluoranthenyl, pyrenyl, benzofluoranthenyl, chrysenyl, pyrylo and the like.

In the disclosure, the ring system formed by n atoms is an n-membered ring. For example, phenyl is a 6-membered aryl. 6- to 10-membered aromatic ring refer to benzene ring, naphthalene ring, indene ring and the like.

The "aryl" herein can have one or more connection points connected with the rest of the molecule. In the present disclosure, the interpretation of aryl can be applied to arylene.

In the present disclosure, substituted aryl means that one or more hydrogen atoms in the aryl are substituted by groups, for example, at least one hydrogen atom is substituted by a deuterium atom, F, Cl, Br, CN, azyl, alkyl, haloalkyl, cycloalkyl, aryloxy, arylthio, alkylsilyl, aryl silyl, alkylamino, arylamino, boryl, phosphino or other groups.

It is understood that "substituted C6-C30 aryl" is substituted aryl with the number of carbon atoms of 6 to 30, means that the total number of carbon atoms of the aryl and a substituent on the aryl is 6 to 30. The aryl with 6 to 18 ring-forming carbon atoms means that the number of carbon atoms of an aromatic ring in the aryl is 6 to 18, and the number of carbon atoms in a substituent of the aryl is not included. The number of ring-forming carbon atoms in the aryl may be, but is not limited to, 6 to 30, 6 to 25, 6 to 24, 6 to 18 or 6 to 13. Exemplarily, fluorenyl belongs to an aryl with 13 ring-forming carbon atoms, 9,9-dimethylfluorenyl belongs to a substituted aryl with 15 carbon atoms, and spirodifluorenyl belongs to an aryl with 25 ring-forming carbon atoms.

In the present disclosure, "heteroaryl" is monocyclic, bicyclic and polycyclic system, wherein at least one ring system is aromatic, at least one aromatic ring system contains one or more heteroatoms selected from B, O, N, P, Si, Se and S, wherein each ring system contains a ring consisting of 5 to 7 atoms, and one or more connection points are connected with the rest of the molecule. In the present disclosure, the number of carbon atoms of heteroaryl may be 3 to 30, 3 to 18, or 3 to 12. The heteroaryl may be monocyclic or polycyclic heteroaryl, in other words, the heteroaryl is either a single aromatic ring system or a plurality of aromatic ring systems conjugated by carbon-carbon bonds, and any aromatic ring system is an aromatic monocycle or an aromatic fused ring. Exemplarily, the heteroaryl may include, but is not limited to, thienyl, furyl, pyrrolyl, imidazolyl, thiazolyl, oxazolyl, pyridyl, bipyridyl, pyrimidinyl, triazinyl, acridinyl, pyridazinyl, pyrazinyl, quinolyl, quinazolinyl, quinoxalinyl, phenoxazinyl, phthalazinyl, pyridopyrimidyl, pyridopyrazinyl, pyrazinopyrazinyl, isoquinolinyl, indolyl, carbazolyl, benzoxazolyl, benzimidazolyl, benzothiazolyl, benzocarbazolyl, benzothiophenyl, dibenzothiophenyl, thiophenothiophenyl, benzofuranyl, phenanthrolinyl, isoxazolyl, thiadiazolyl, benzothiazolyl, phenothiazinyl, dibenzosilyl, dibenzofuranyl and the like. Wherein thienyl, furyl, phenanthrolinyl and the like are heteroaryls of a single aromatic ring system, and N-arylcarbazolyl, N-heteroarylcarbazolyl, phenyl substituted dibenzofuranyl, pyridine substituted pyridinyl and the like are heteroaryls of a plurality of aromatic ring systems conjugated by carbon-carbon bonds.

In the present disclosure, substituted heteroaryl means that one or more hydrogen atoms in the heteroaryl are substituted by groups, for example, at least one hydrogen atom is substituted by a deuterium atom, F, Cl, Br, CN, azyl, alkyl, haloalkyl, cycloalkyl, aryloxy, arylthio, alkylsilyl, arylsilyl, alkylamino, arylamino, boryl, phosphino or other groups.

It is understood that there may be one bond, two bonds or more bonds connected with other parts in the molecule of the "heteroaryl".

It is understood that "substituted heteroaryl with 3 to 30 carbon atoms" means that the total number of carbon atoms of the heteroary and substituent of the heteroary is 3 to 30.

The heteroary with 3 to 18 ring-forming carbon atoms means that the number of carbon atoms on an aromatic ring in the heteroary is 3 to 18, and the number of carbon atoms in substituent of the heteroary is not included. The number of carbon atoms of the heteroary may be, but is not limited to, 3 to 18, 4 to 18, 3 to 12, or 3 to 8.

In the present disclosure, the interpretation of heteroary can be applied to heteroarylene.

As description used herein, "each . . . is independently" is interchangeable with " . . . are separately and independently" and " . . . is each independently selected from", all of which shall be understood in a broad sense; it can mean that the specific options expressed between the same symbols in different groups do not affect each other, and can also indicate that the specific options expressed between the same symbols in the same group do not affect each other.

For example:

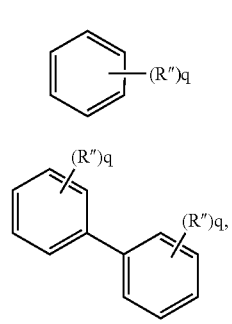

(Q-1)

(Q-2)

wherein in the description that each q is independently 0, 1, 2 or 3, and each R" is independently selected from hydrogen, fluorine and chlorine, the meaning is that: formula Q-1 indicates that there are q R" on a benzene ring, the R" may be the same or different, and the options of each R" do not affect each other; formula Q-2 indicates that there are q R" on each benzene ring of biphenyl, the number q of R" substituents on the two benzene rings may be the same or different, the R" may be the same or different, and the options of each R" do not affect each other.

A non-orientating connection bond herein refers to single bond

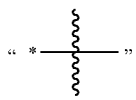

protruding from a ring system, which means that one end of the connection bond can be connected to any position in the ring system penetrated by the bond, and the other end is connected to the rest of a compound molecule.

For example, as shown in formula (f) below, the naphthyl represented by formula (f) is connected with other positions of the molecule through two non-orientating connection bonds penetrating double rings, and what it means includes any possible connection mode represented by formula (f-1) to formula (f-10).

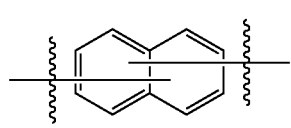

(f)

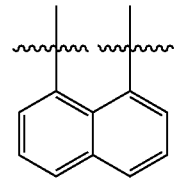

(f-1)

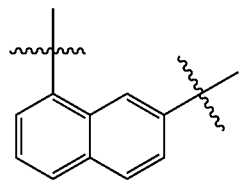

(f-2)

(f-3)

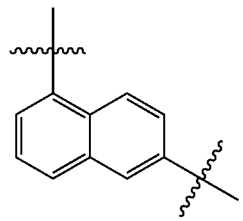

(f-4)

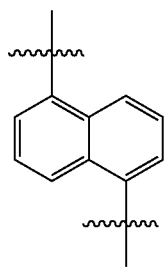

(f-5)

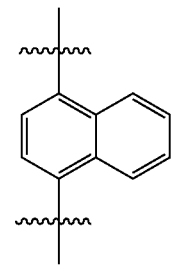

(f-6)

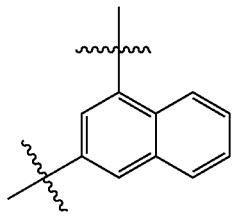

(f-7)

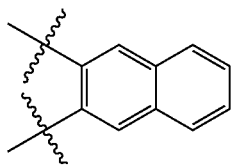

(f-8)
(f9)
(f-10)

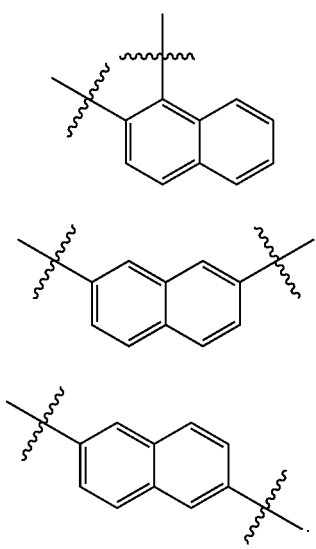

In other examples, as shown in formula (X') below, the phenanthryl represented by formula (X') is connected with other positions of the molecule through a non-orientating connection bond protruding from a benzene ring at one side, and what it means includes any possible connection mode represented by formula (X'-1) to formula (X'-4).

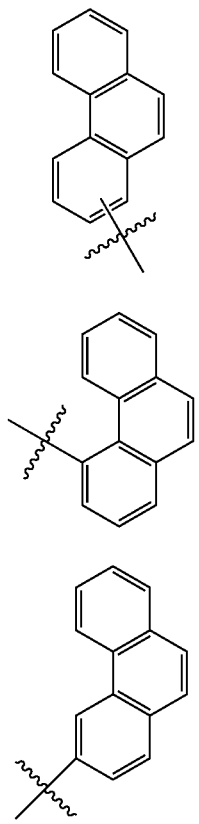

(X')

(X'-1)

(X'-2)

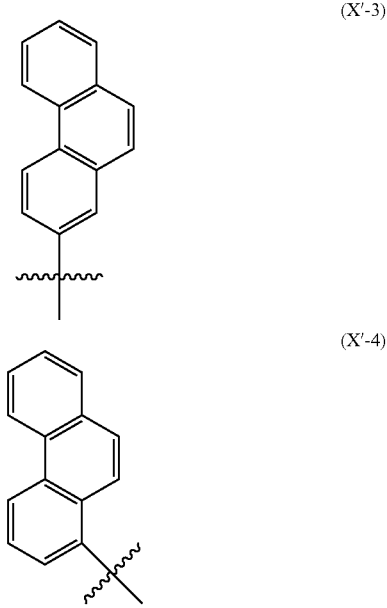

(X'-3)

(X'-4)

A non-orientating substituent herein refers to a substituent connected by a single bond protruding from the center of ring system, which means that the substituent can be connected in any possible position in the ring system. For example, as shown in formula (Y) below, the substituent R group represented by formula (Y) is connected with a quinoline ring through a non-orientating connection bond, and what it means includes any possible connection mode represented by formula (Y-1) to formula (Y-7).

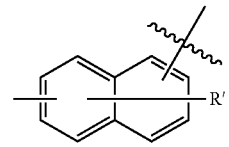
(Y)

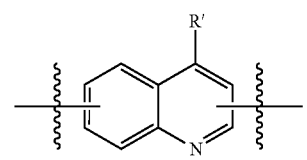
(Y-1)

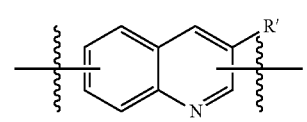
(Y-2)

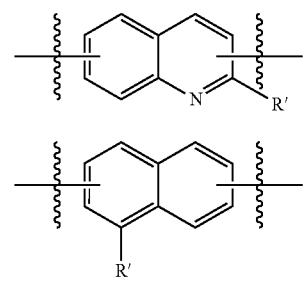
(Y-3)

(Y-4)

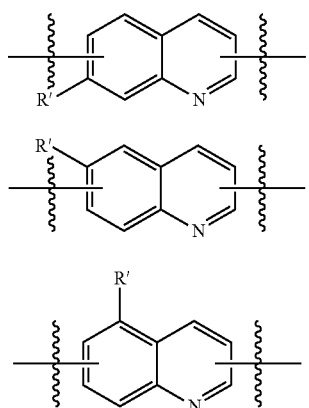

(Y-5)

(Y-6)

(Y-7)

Optionally, in the nitrogen-containing compound as shown in formula 1, the substituents on the $Z^1$, $Z^2$, $Z^3$ and L are the same or different from each other, and are separately and independently selected from: deuterium, fluorine, chlorine, bromine, cyano, alkyl with 1 to 12 carbon atoms, alkoxy with 1 to 12 carbon atoms, alkthio with 1 to 12 carbon atoms, haloalkyl with 1 to 12 carbon atoms, cycloalkyl with 3 to 10 carbon atoms, heterocycloalkyl with 2 to 12 carbon atoms, alkylamine with 1 to 12 carbon atoms, aryl with 6 to 20 carbon atoms, heteroaryl with 6 to 18 carbon atoms, alkylsilyl with 3 to 18 carbon atoms, arylsilyl with 6 to 18 carbon atoms, aryloxy with 6 to 18 carbon atoms, and arylthio with 6 to 18 carbon atoms.

Optionally, L is selected from single bond, substituted or unsubstituted arylene with 6 to 25 ring-forming carbon atoms, and substituted or unsubstituted heteroarylene with 4 to 18 carbon atoms.

Optionally, the substituents of L are the same or different from each other, and are separately and independently selected from deuterium, fluorine, chlorine, bromine, cyano, alkyl with 1 to 12 carbon atoms, alkoxy with 1 to 12 carbon atoms, alkthio with 1 to 12 carbon atoms, haloalkyl with 1 to 12 carbon atoms, cycloalkyl with 3 to 10 carbon atoms, heterocycloalkyl with 2 to 12 carbon atoms, alkylamine with 1 to 12 carbon atoms, aryl with 6 to 20 carbon atoms, heteroaryl with 6 to 18 carbon atoms, alkylsilyl with 3 to 18 carbon atoms, arylsilyl with 6 to 18 carbon atoms, aryloxy with 6 to 18 carbon atoms, and arylthio with 6 to 18 carbon atoms.

Optionally, L is selected from single bond or the group consisting of substituents as shown in formula j-1 to formula j-13:

j-1

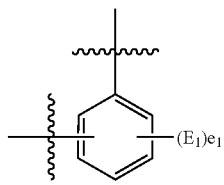

j-2

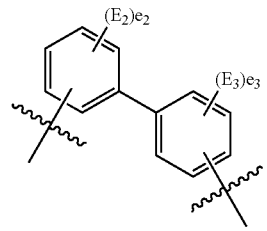

j-3

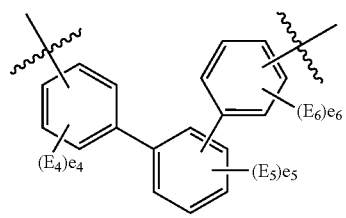

j-4

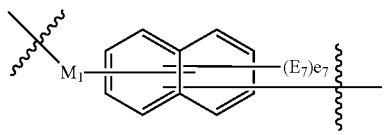

j-5

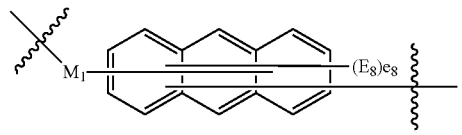

j-6

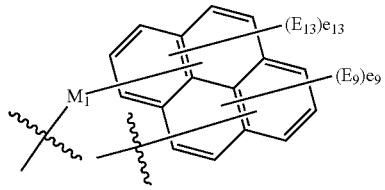

j-7

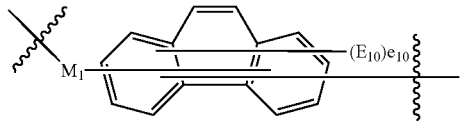

j-8

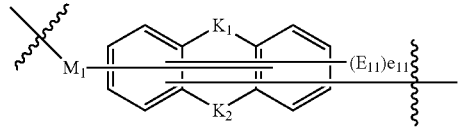

j-9

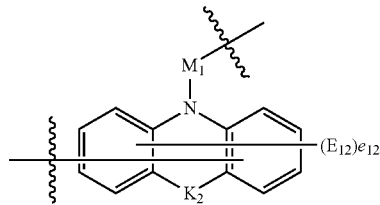

-continued

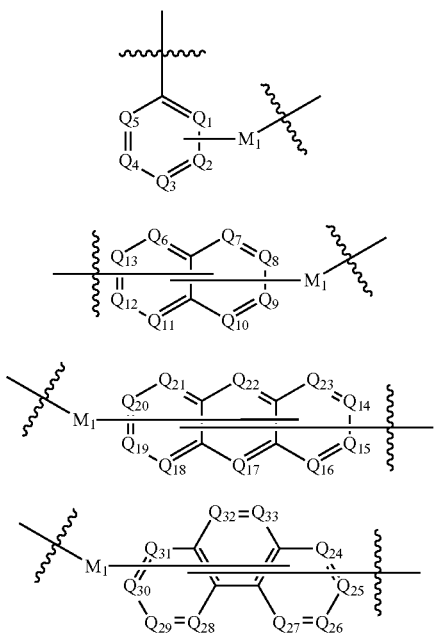

j-10 j-11 j-12 j-13 wherein $M_1$ is selected from single bond or

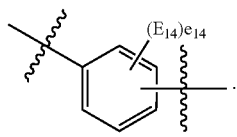

$Q_1$ to $Q_5$ are each independently selected from N or $C(F_1)$, and at least one of $Q_1$ to $Q_5$ is selected from N; when two or more of $Q_1$ to $Q_5$ are selected from $C(F_1)$, any two $F_1$s are the same or different.

$Q_6$ to $Q_{13}$ are each independently selected from N or $C(F_2)$, and at least one of $Q_6$ to $Q_{13}$ is selected from N; when two or more of $Q_6$ to $Q_{13}$ are selected from $C(F_2)$, any two $F_2$s are the same or different.

$Q_{14}$ to $Q_{23}$ are each independently selected from N or $C(F_3)$, and at least one of $Q_{14}$ to $Q_{23}$ is selected from N; when two or more of $Q_{14}$ to $Q_{23}$ are selected from $C(F_3)$, any two $F_3$s are the same or different.

$Q_{24}$ to $Q_{33}$ are each independently selected from N or $C(F_4)$, and at least one of $Q_{24}$ to $Q_{33}$ is selected from N; when two or more of $Q_{24}$ to $Q_{33}$ are selected from $C(F_4)$, any two $F_4$s are the same or different.

$E_1$ to $E_{14}$, $F_1$ to $F_4$ are each independently selected from: deuterium, fluorine, chlorine, bromine, cyano, heteroaryl with 3 to 18 carbon atoms, aryl with 6 to 18 carbon atoms, trialkylsilyl with 3 to 12 carbon atoms, arylsilyl with 8 to 12 carbon atoms, alkyl with 1 to 10 carbon atoms, haloalkyl with 1 to 10 carbon atoms, cycloalkyl with 3 to 10 carbon atoms, heterocycloalkyl with 2 to 10 carbon atoms, alkoxy with 1 to 10 carbon atoms, alkylamine with 1 to 10 carbon atoms, alkylthio with 1 to 10 carbon atoms, aryloxy with 6 to 18 carbon atoms and arylthio with 6 to 18 carbon atoms; any one of $F_1$, $F_2$, $F_3$ and $F_4$ can also be independently selected from hydrogen.

$e_r$ is the number of substituent $E_r$, and r is any integer from 1 to 14. When r is selected from 1, 2, 3, 4, 5, 6, 9, 13 or 14, $e_r$ is selected from 0, 1, 2, 3 or 4. When r is selected from 7 or 11, $e_r$ is selected from 0, 1, 2, 3, 4, 5 or 6. When r is 12, $e_r$ is selected from 0, 1, 2, 3, 4, 5, 6 or 7. When r is selected from 8 or 10, $e_r$ is selected from 0, 1, 2, 3, 4, 5, 6, 7 or 8. When $e_r$ is greater than 1, any two Ers are the same or different.

$K_1$ is selected from O, S, Se, $N(E_{15})$, $C(E_{16}E_{17})$ and $Si(E_{16}E_{17})$. Wherein $E_{15}$, $E_{16}$ and $E_{17}$ are each independently selected from: aryl with 6 to 18 carbon atoms, heteroaryl with 3 to 18 carbon atoms, alkyl with 1 to 10 carbon atoms, cycloalkyl with 3 to 10 carbon atoms and heterocycloalkyl with 2 to 10 carbon atoms, or, $E_{16}$ and $E_{17}$ are connected with each other to form saturated or unsaturated 5-to-13-membered rings together with atoms to which they are jointly connected. For example, in formula j-8, when $K_2$ is single bond, $M_1$ is single bond and $K_1$ is $C(E_{16}E_{17})$, $E_{16}$ and $E_{16}$ may be connected with each other to either exist in the form of forming saturated or unsaturated rings together with atoms to which they are jointly connected, or exist independently of each other. When $E_{16}$ and $E_{17}$ form a ring, the ring formed by $E_{16}$ and $E_{17}$ is spir-connected with other parts of the molecule. It should be noted that when $E_{16}$ and $E_{17}$ are connected with each other to form a saturated or unsaturated ring with the atoms to which they are jointly connected, the number of carbon atoms of the ring is either a 5-membered ring, that is,

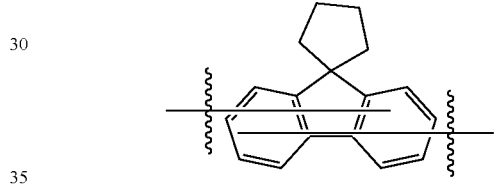

is formed; or a 6-membered ring, that is,

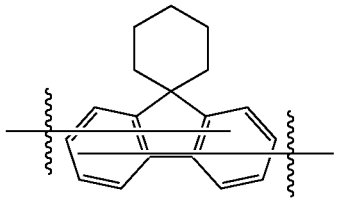

is formed, or a 13-membered ring, that is,

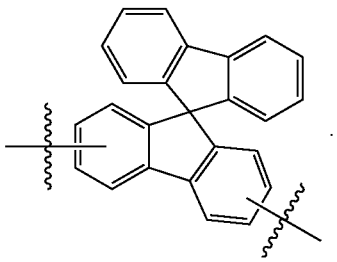

Of course, the number of carbon atoms on the ring formed by connecting $E_{16}$ with $E_{17}$ may also be other values, which will not be listed one by one here.

$K_2$ is selected from single bond, O, S, Se, $N(E_{18})$, $C(E_{19}E_{20})$ and $Si(E_{19}E_{20})$; wherein $E_{18}$, $E_{19}$ and $E_{20}$ are each independently selected from: aryl with 6 to 18 carbon atoms, heteroaryl with 3 to 18 carbon atoms, alkyl with 1 to 10 carbon atoms, cycloalkyl with 3 to 10 carbon atoms and heterocycloalkyl with 2 to 10 carbon atoms, or, $E_{19}$ and $E_{20}$ are connected with each other to form saturated or unsaturated 5-to-13-membered ring together with atoms to which they are jointly connected. The understanding that $E_{19}$ and $E_{20}$ optionally form a ring here is consistent with that in other technical solutions (when $E_{16}$ and $E_{17}$ are connected with each other to form a ring) in the disclosure.

Optionally, L is selected from single bond, unsubstituted $T_1$ or substituted $T_1$, wherein the unsubstituted $T_1$ is selected from the group consisting of the following substituents:

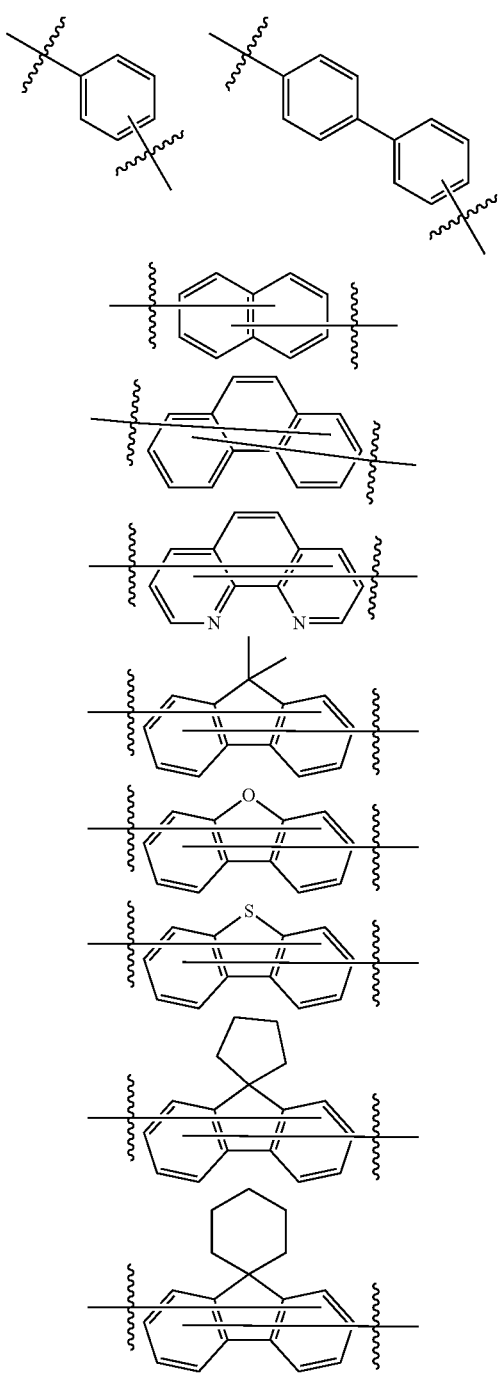

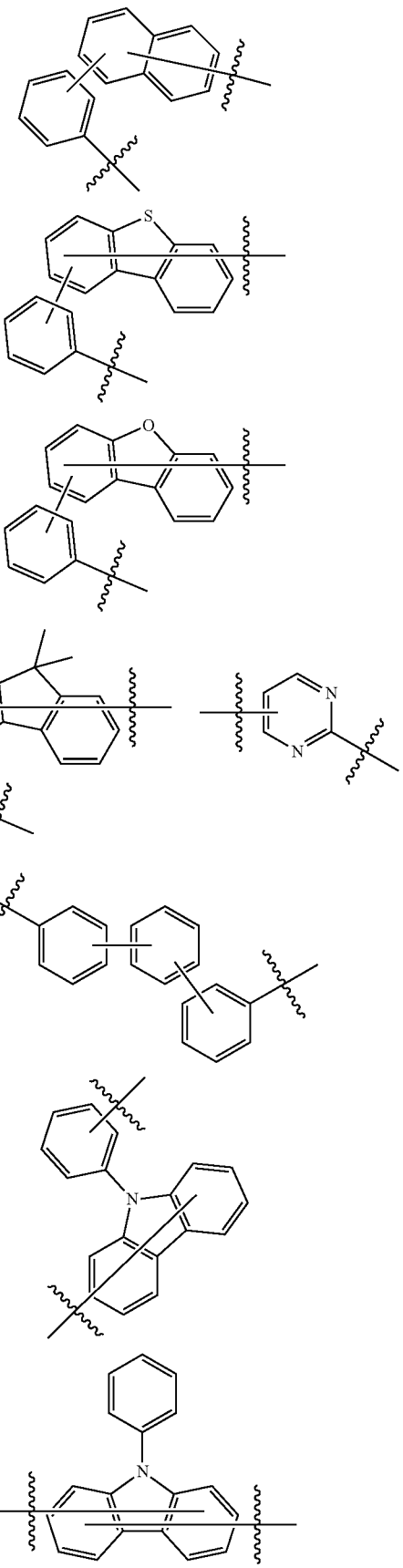

-continued

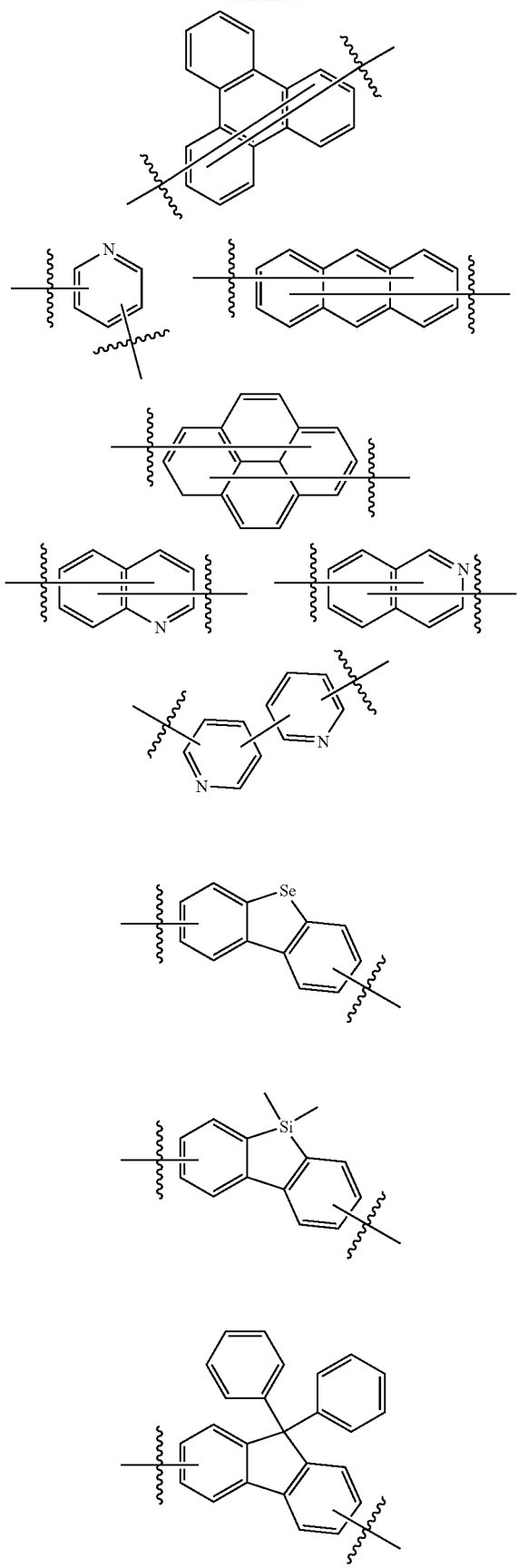

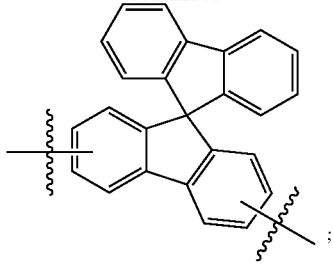

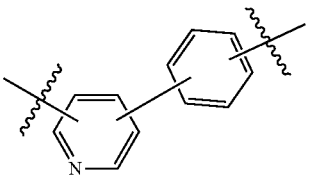

substituted $T_1$ is a group formed by substituting the unsubstituted $T_1$ by one or more substituent(s) selected from deuterium, fluorine, chlorine, cyano, alkyl with 1 to 6 carbon atoms, alkoxy with 1 to 4 carbon atoms, haloalkyl with 1 to 4 carbon atoms, alkylsilyl with 3 to 9 carbon atoms, cycloalkyl with 3 to 10 carbon atoms, aryl with 6 to 13 carbon atoms and heteroaryl with 3 to 12 carbon atoms, and when a plurality of substituents are included on the substituted $T_1$, any two substituents are the same or different.

In some other embodiments, the L in the compound in the disclosure is

In other embodiments, the L in the compound in the disclosure is selected from substituted or unsubstituted phenylene, substituted or unsubstituted biphenylene, substituted or unsubstituted terphenyl, substituted or unsubstituted naphthylene, substituted or unsubstituted dibenzofuranylene, substituted or unsubstituted dibenzothienylene, substituted or unsubstituted quinolylene, substituted or unsubstituted carbazolylene, substituted or unsubstituted naphthylene, substituted or unsubstituted fluorenylene, substituted or unsubstituted anthrylene, substituted or unsubstituted phenanthrylene, substituted or unsubstituted perylenylene, substituted or unsubstituted pyrenylene, substituted or unsubstituted 9,9-diphenylfluorenylene, substituted or unsubstituted spirodifluorenylene, substituted or unsubstituted dibenzothienylene, substituted or unsubstituted dibenzofuranylene, substituted or unsubstituted carbazolylene, substituted or unsubstituted pyrimidinylene, substituted or unsubstituted pyridylene, substituted or unsubstituted pyrazinylene, substituted or unsubstituted quinolylene, substituted or unsubstituted isoquinolylene, substituted or unsubstituted quinazolinylene, or a subunit group formed by single-bond connection of two or three of them; the "substituted" refers to being optionally substituted by 0, 1, 2, 3 or 4 substituent(s) selected from deuterium, fluorine, chlorine, cyano, methyl, ethyl, isopropyl, tertiary butyl, methoxyl, ethoxyl, isopropoxy, propoxy, trifluoromethyl, phenyl, naphthyl, trimethylsilyl and triphenylsilyl.

In other words, one or more substituent(s) are included on the substituted $T_1$, and any substituent is independently selected from deuterium, fluorine, chlorine, cyano, alkyl with 1 to 6 carbon atoms, alkoxy with 1 to 4 carbon atoms, haloalkyl with 1 to 4 carbon atoms, alkylsilyl with 3 to 9 carbon atoms, cycloalkyl with 3 to 10 carbon atoms, aryl with 6 to 13 carbon atoms and heteroaryl with 3 to 12 carbon atoms.
Optionally, L is selected from single bond, unsubstituted $T_2$ or substituted $T_2$, wherein unsubstituted $T_2$ is selected from the group consisting of the following substituents:
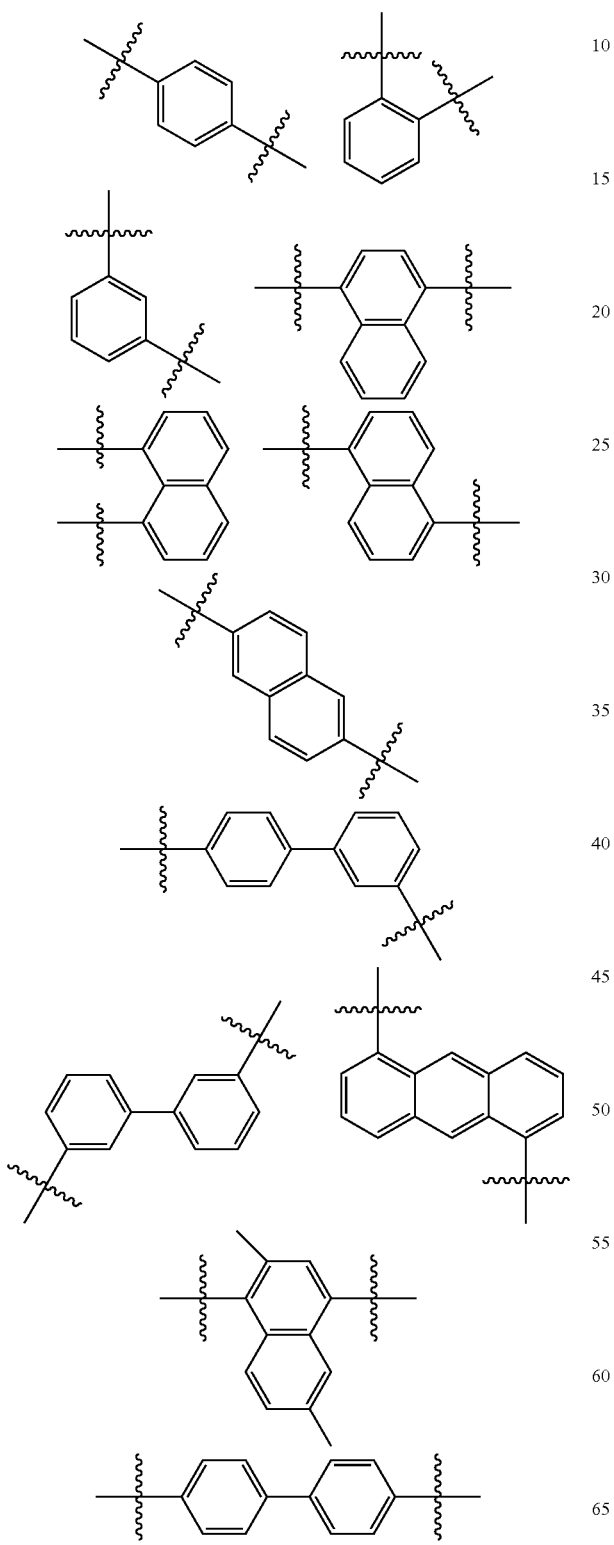
-continued
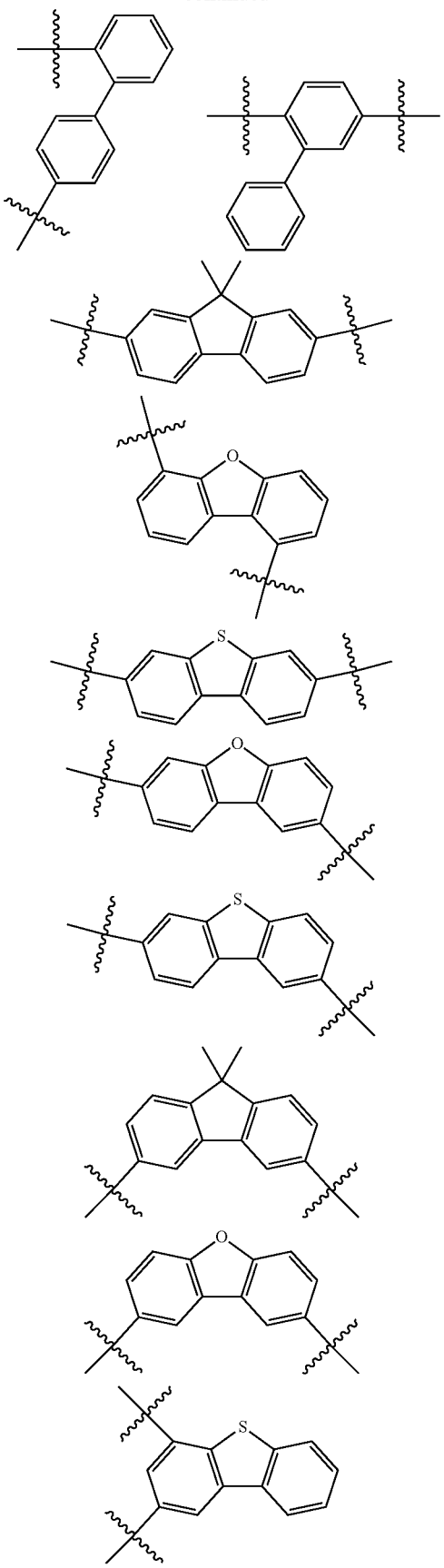

-continued
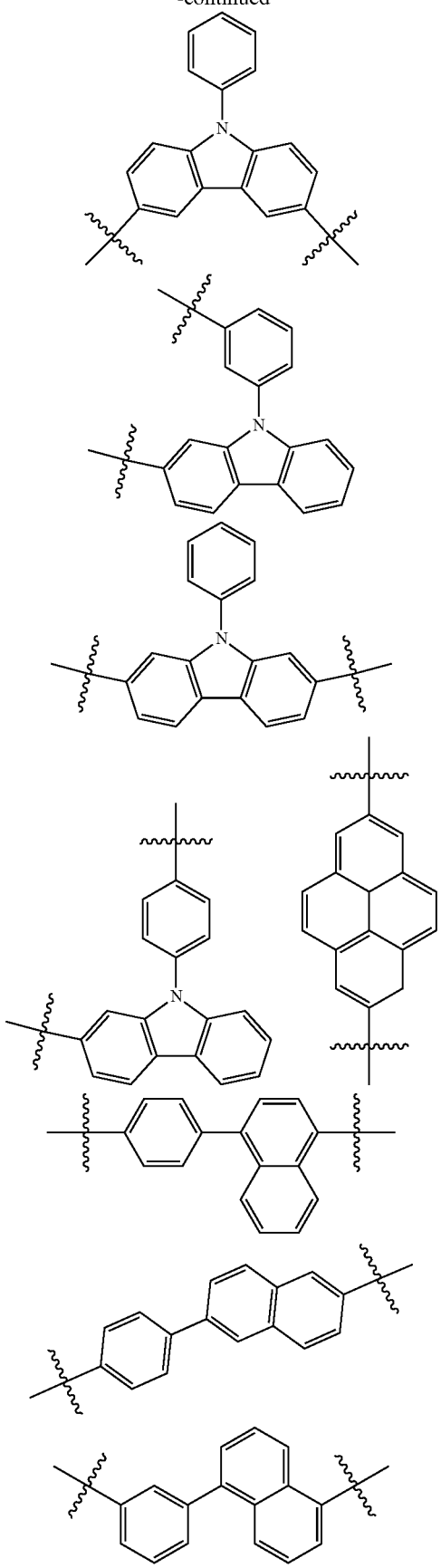
-continued
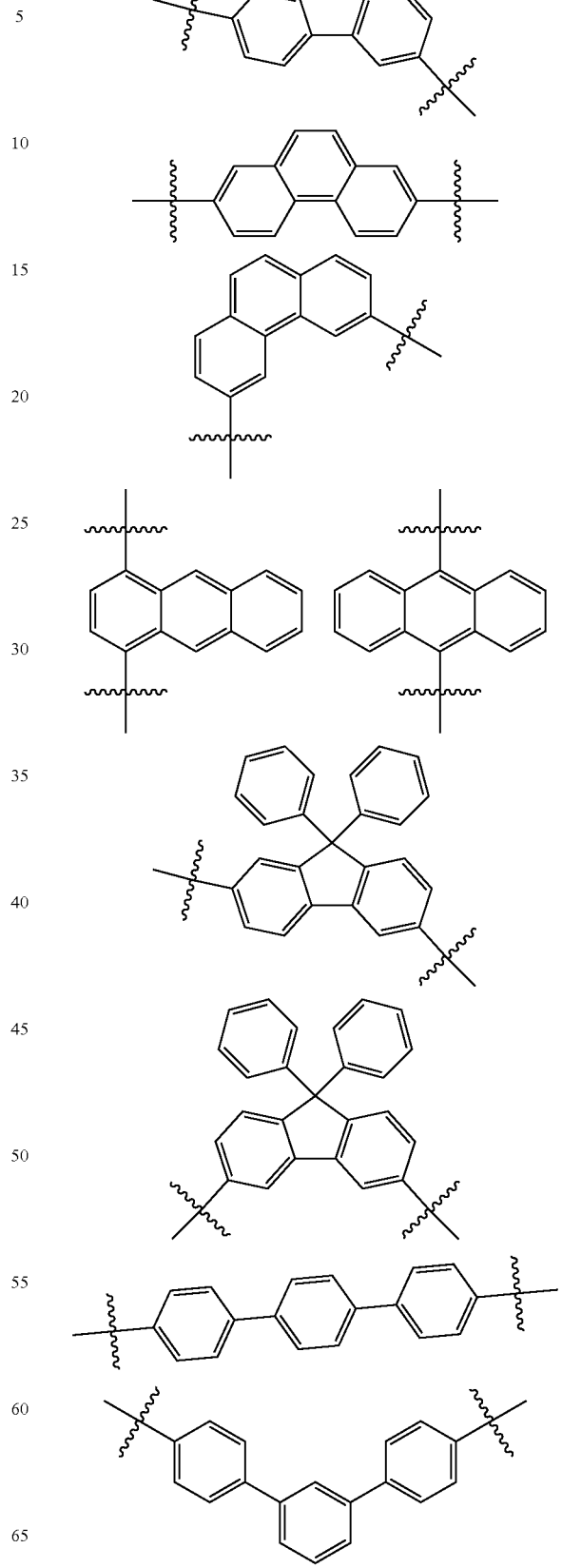

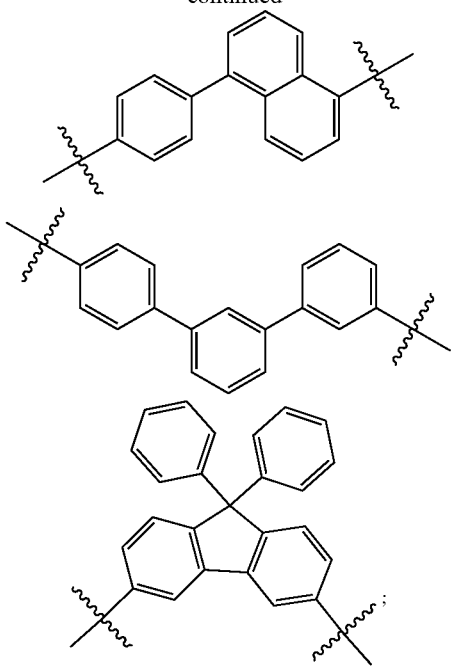

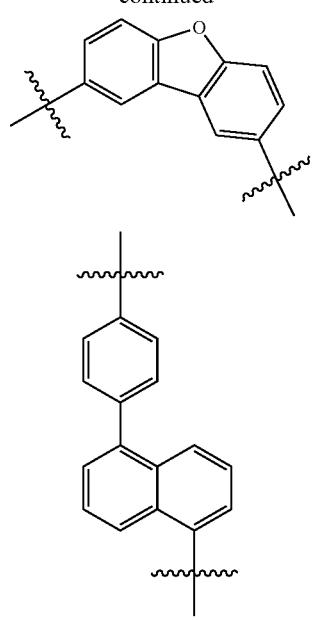

substituted T₂ is a group formed by substituting the unsubstituted T₂ by one or more substituent(s) selected from deuterium, fluorine, chlorine, cyano, methyl, ethyl, isopropyl, tertiary butyl, methoxyl, ethoxyl, isopropoxy, propoxy, cyclopentyl, cyclohexyl, trifluoromethyl, trimethylsilyl, phenyl and pyridinyl, and when a plurality of substituents are included on the substituted T₂, any two substituents are the same or different.

In other words, one or more substituent(s) are included on the substituted T₂, and any substituent is independently selected from deuterium, fluorine, chlorine, cyano, methyl, ethyl, isopropyl, tertiary butyl, methoxyl, ethoxyl, isopropoxy, n-propoxy, cyclopentyl, cyclohexyl, trifluoromethyl, trimethylsilyl, phenyl, naphthyl, pyridyl, dibenzothiophenyl, dibenzofuranyl, quinolyl and isoquinolyl.

Further, L is optionally selected from single bond or the group consisting of the following substituents:

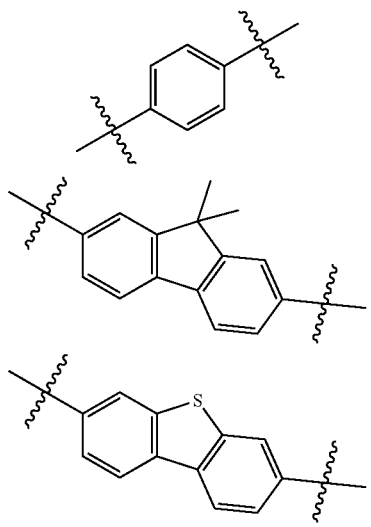

Optionally, $Z^1$, $Z^2$ and $Z^3$ are the same or different from each other, and are each independently selected from substituted or unsubstituted alkyl with 1 to 10 carbon atoms, substituted or unsubstituted aryl with 6 to 25 ring-forming carbon atoms, and substituted or unsubstituted heteroaryl with 4 to 18 ring-forming carbon atoms; alternatively, $Z^1$ and $Z^2$ are connected with each other to form saturated or unsaturated 5- to 13-membered rings together with the atoms to which they are jointly connected;

The substituents on the $Z^1$, $Z^2$ and $Z^3$ are the same or different from each other, and are each independently selected from: deuterium, fluorine, chlorine, bromine, cyano, alkyl with 1 to 12 carbon atoms, alkoxy with 1 to 12 carbon atoms, alkylthiol with 1 to 12 carbon atoms, haloalkyl with 1 to 12 carbon atoms, cycloalkyl with 3 to 10 carbon atoms, heterocycloalkyl with 2 to 12 carbon atoms, alkylamine with 1 to 12 carbon atoms, aryl with 6 to 20 carbon atoms, heteroaryl with 6 to 18 carbon atoms, alkylsilyl with 3 to 18 carbon atoms, aryloxy with 6 to 18 carbon atoms and arylthio with 6 to 18 carbon atoms.

Optionally, $Z^1$, $Z^2$ and $Z^3$ are the same or different from each other, and are each independently selected from substituted or unsubstituted alkyl with 1 to 10 carbon atoms, a set consisting of substituents represented by formula S-1 to formula S-10; alternatively, $Z^1$ and $Z^2$ are connected with each other to form 5- to 13-membered rings together with the atoms to which they are jointly connected. Wherein formula S-1 to formula S-10 are as shown below:

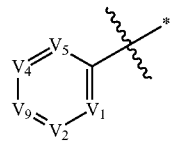

S-1

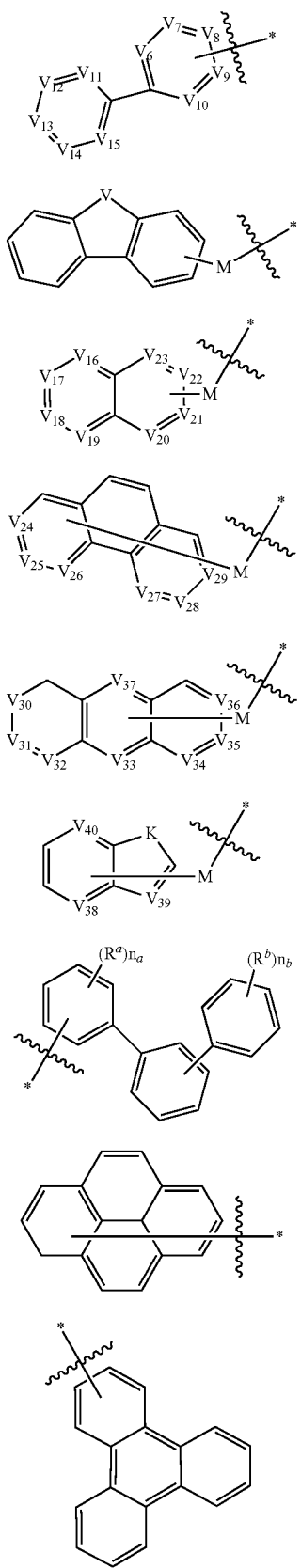

In the above groups, M is selected from single bond or

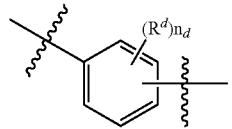

$n_a$ and $n_d$ are each independently 1, 2, 3 or 4, and when a plurality of $R^a$ are contained in one group, the $R^a$ are the same or different from each other; when a plurality of $R^d$ are contained in one group, the $R^d$ are the same or different from each other; $n_b$ is 1, 2, 3, 4 or 5, and when a plurality of $R^b$ are contained in one group, the $R^b$s are the same or different from each other.

$V_1$ to $V_{40}$ are each independently selected from $C(R^v)$ and N, and when a plurality of $R^v$ are contained in one group, any two $R^v$ are the same or different from each other.

V is selected from a set consisting of O, S, Se, $N(R^{v1})$, $C(R^{v2}R^{v3})$ and $Si(R^{v2}R^{v3})$.

K is selected from O, S or $N(R^k)$.

$R^a$, $R^b$, $R^d$, $R^k$, $R^{v1}$, $R^{v2}$ and $R^{v3}$ are each independently hydrogen, aryl with 6 to 18 carbon atoms, heteroaryl with 3 to 18 carbon atoms, alkyl with 1 to 10 carbon atoms, cycloalkyl with 3 to 10 carbon atoms and heterocycloalkyl with 2 to 10 carbon atoms; alternatively, $R^{v2}$ and $R^{v3}$ connected to the same atom are connected with each other to form saturated or unsaturated 5- to 13-membered rings together with atoms to which they are jointly connected.

For example, in formula S-3

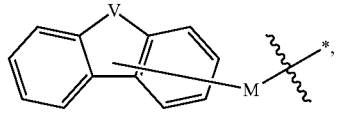

when M is single bond and V is $(R^{v2}R^{v3})$, $R^{v2}$ and $R^{v3}$ are connected with each other to form a ring, which means that $R^{v2}$ and $R^{v3}$ are either connected with each other to form a ring or exist independently of each other; when they form a ring, the number of carbon atoms of the ring may be either a 5-membered ring, for example

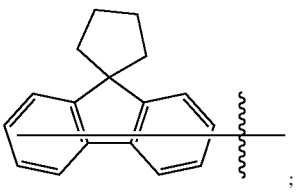

or a 6-membered ring, for example

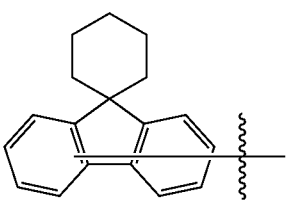

or a 13-membered ring, for example

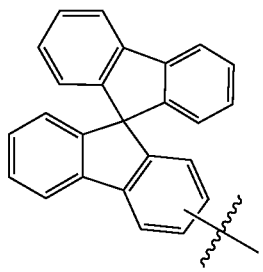

Of course, the number of carbon atoms on the ring formed by connecting $R^{v2}$ with $R^{v3}$ may also be other values, which will not be listed one by one here.

$R^v$ are independently selected from hydrogen, deuterium, fluorine, chlorine, bromine, cyano, heteroaryl with 3 to 18 carbon atoms, aryl with 6 to 18 carbon atoms, trialkylsilyl with 3 to 12 carbon atoms, arylsilyl with 8 to 12 carbon atoms, alkyl with 1 to 10 carbon atoms, haloalkyl with 1 to 10 carbon atoms, cycloalkyl with 3 to 10 carbon atoms, alkoxyl with 1 to 10 carbon atoms, alkylamine with 1 to 10 carbon atoms, alkylthiol with 1 to 10 carbon atoms, aryloxy with 6 to 18 carbon atoms and arylthio with 6 to 18 carbon atoms.

Wherein "a plurality of" means two or more.

In some embodiments in the disclosure, X is $N(Z^3)$, wherein $Z^3$ may be selected from aryl, electron-rich heteroaryl or electron-deficient heteroaryl. The heteroatoms of the electron-rich heteroaryl can increase the electron cloud density of the conjugated system of heteroaryl as a whole, rather than reducing the electron cloud density of the conjugated system of heteroaryl, e.g., lone pair electrons of heteroatoms can participate in the conjugated system, thus increasing the electron cloud density of the conjugated system of heteroaryl. For example, electron-rich heteroaryl may include, but is not limited to, carbazolyl, dibenzofuranyl, dibenzothiophenyl, furyl, pyrrolyl and the like. Since both aryl and electron-rich heteroaryl can effectively enhance the electron cloud density of the nitrogen-containing compound and adjust the HOMO energy level of the nitrogen-containing compound, the nitrogen-containing compound will have better hole transport capability. So the nitrogen-containing compound can be used as the host materials for a hole-type organic light emitting layer and form the host materials for the organic light emitting layer together with an electronic organic light emitting layer used for electron transport. $Z^3$ may also be electron-deficient heteroaryl (also known as electron-poor heteroaryl), heteroatoms of the electron-deficient heteroaryl can reduce the electron cloud density of the conjugated system of heteroaryl as a whole, rather than increasing the electron cloud density of the conjugated system of heteroaryl, e.g., the lone pair electrons on the heteroatoms do not participate in the conjugated system, and the electron cloud density of the conjugated system is reduced due to strong electronegativity of the heteroatoms. For example, the electron-deficient heteroaryl can include, but is not limited to, pyridinyl, substituted pyrimidinyl, substituted triazinyl, quinolyl, isoquinolyl, benzpyrazolyl, benzimidazolyl, quinoxalinyl, phenanthrolinyl and the like. So $Z^3$ can form electron transport core group of the nitrogen-containing compound, so that the nitrogen-containing compound can effectively realize electron transport, and can effectively balance the transport rate of electrons and holes in the organic light emitting layer. So the nitrogen-containing compound can be used as both the host material for a bipolar organic light emitting layer to transport both electrons and holes, and the host material for the electronic organic light emitting layer to cooperate with the host material for the hole-type organic light emitting layer.

Optionally, $Z^1$ and $Z^2$ are each independently selected from alkyl with 1 to 6 carbon atoms and substituted or unsubstituted $T_3$, and $Z^3$ is selected from substituted or unsubstituted $T_3$; alternatively, $Z^1$ and $Z^2$ are connected with each other to form 5- to 10-membered cycloalkyl together with the atoms to which they are jointly connected; wherein the unsubstituted $T_3$ is selected from the group consisting of the following substituents:

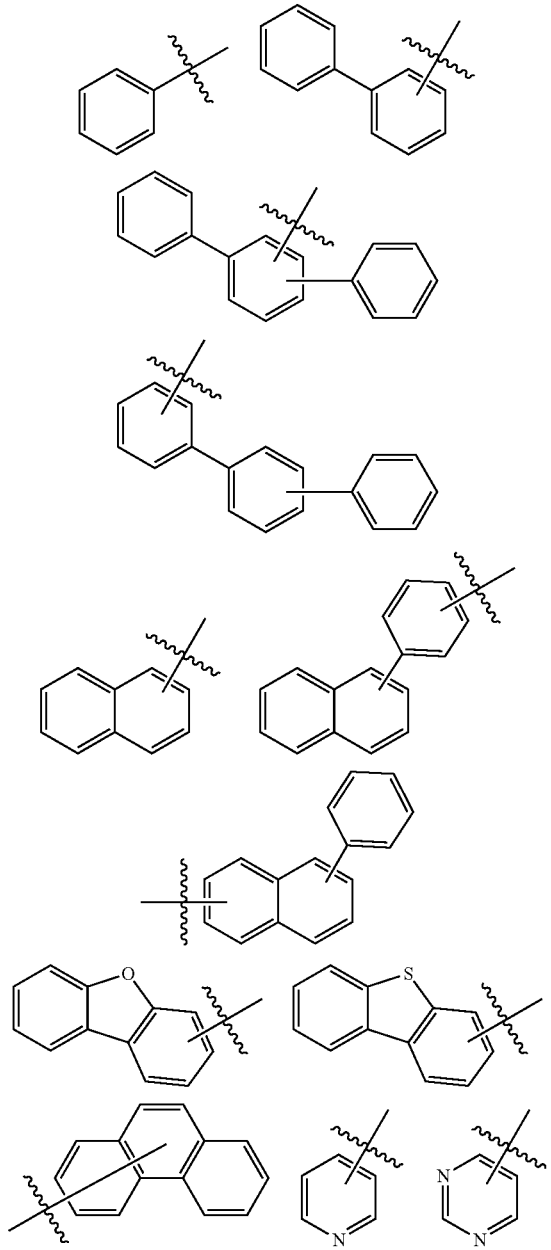

-continued

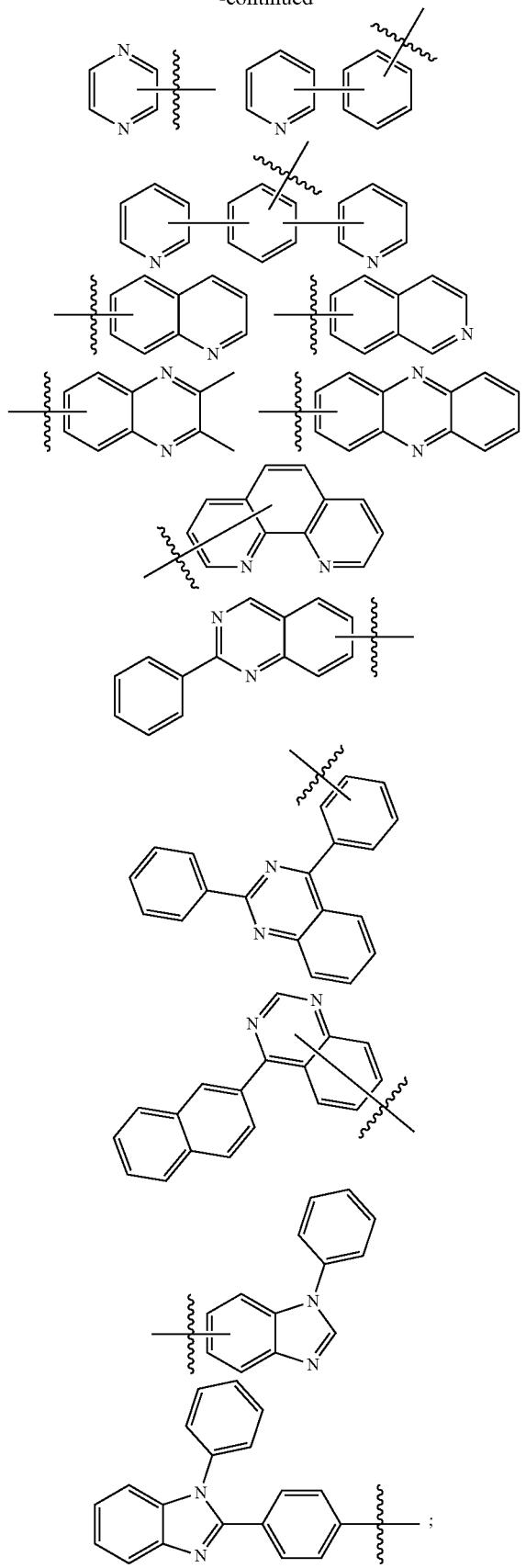

substituted $T_3$ is a group formed by substituting the unsubstituted $T_3$ by one or more substituent(s) selected from deuterium, fluorine, chlorine, cyano, alkyl with 1 to 6 carbon atoms, alkoxy with 1 to 4 carbon atoms, haloalkyl with 1 to 4 carbon atoms, alkylsilyl with 3 to 9 carbon atoms, cycloalkyl with 3 to 10 carbon atoms, aryl with 6 to 13 carbon atoms and heteroaryl with 3 to 12 carbon atoms, and when a plurality of substituents are included on the substituted $T_3$, any two substituents are the same or different.

In other words, one or more substituent(s) are included on the substituted $T_3$, and any substituent is independently selected from deuterium, fluorine, chlorine, cyano, alkyl with 1 to 6 carbon atoms, alkoxy with 1 to 4 carbon atoms, haloalkyl with 1 to 4 carbon atoms, alkylsilyl with 3 to 9 carbon atoms, cycloalkyl with 3 to 10 carbon atoms, aryl with 6 to 13 carbon atoms and heteroaryl with 3 to 12 carbon atoms.

Further, $Z^1$ and $Z^2$ are each independently selected from alkyl with 1 to 6 carbon atoms and substituted or unsubstituted $T_4$, and $Z^3$ is selected from substituted or unsubstituted $T_4$; alternatively, $Z^1$ and $Z^2$ are connected with each other to form cyclopentyl, cyclohexyl or adamantyl together with the atoms to which they are jointly connected; wherein the unsubstituted $T_4$ is selected from the group consisting of the following substituents:

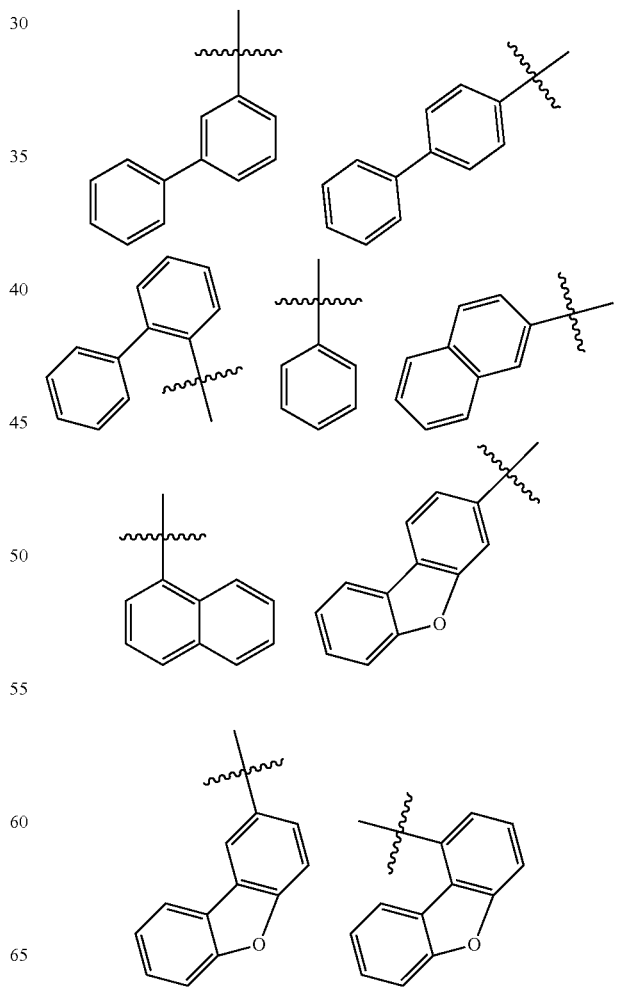

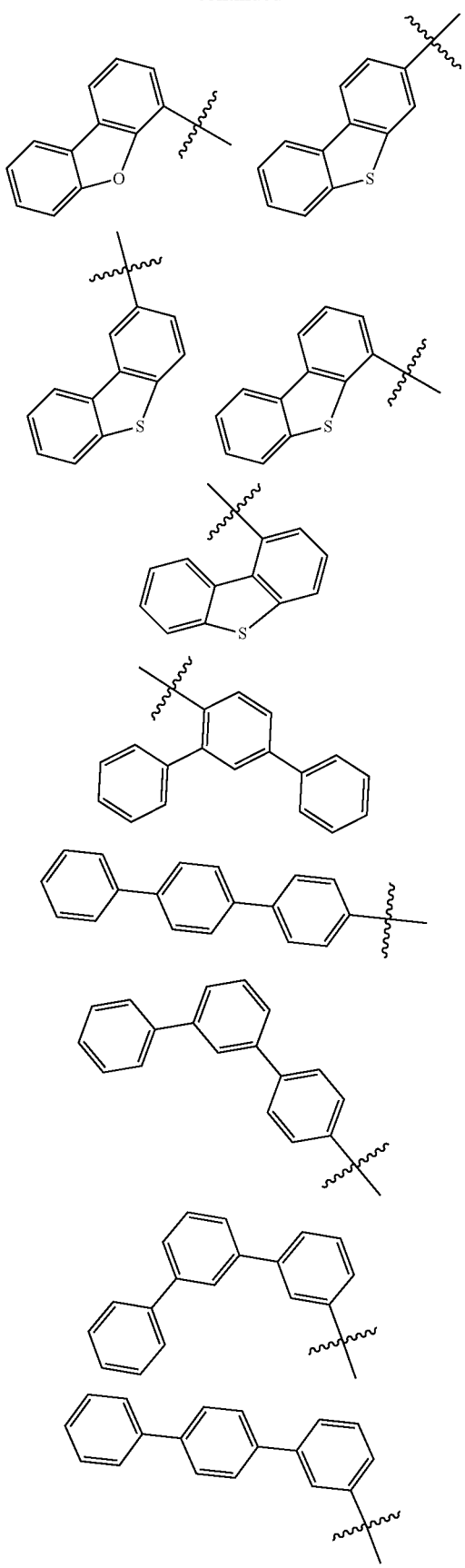
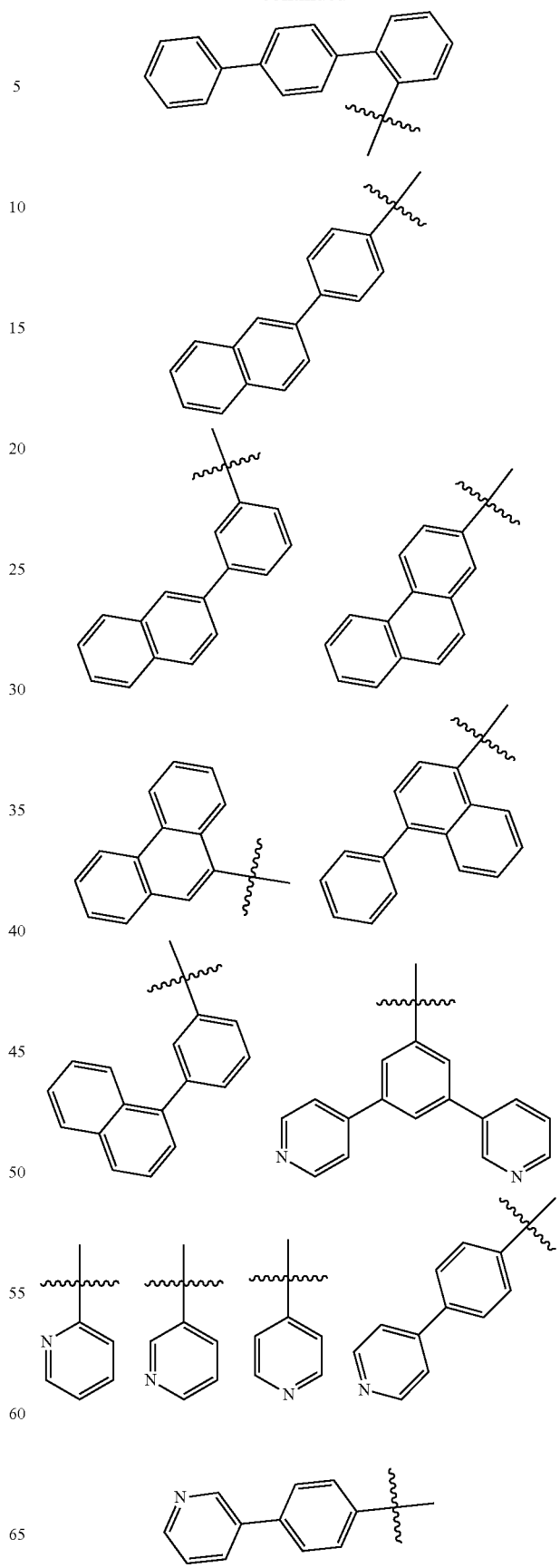

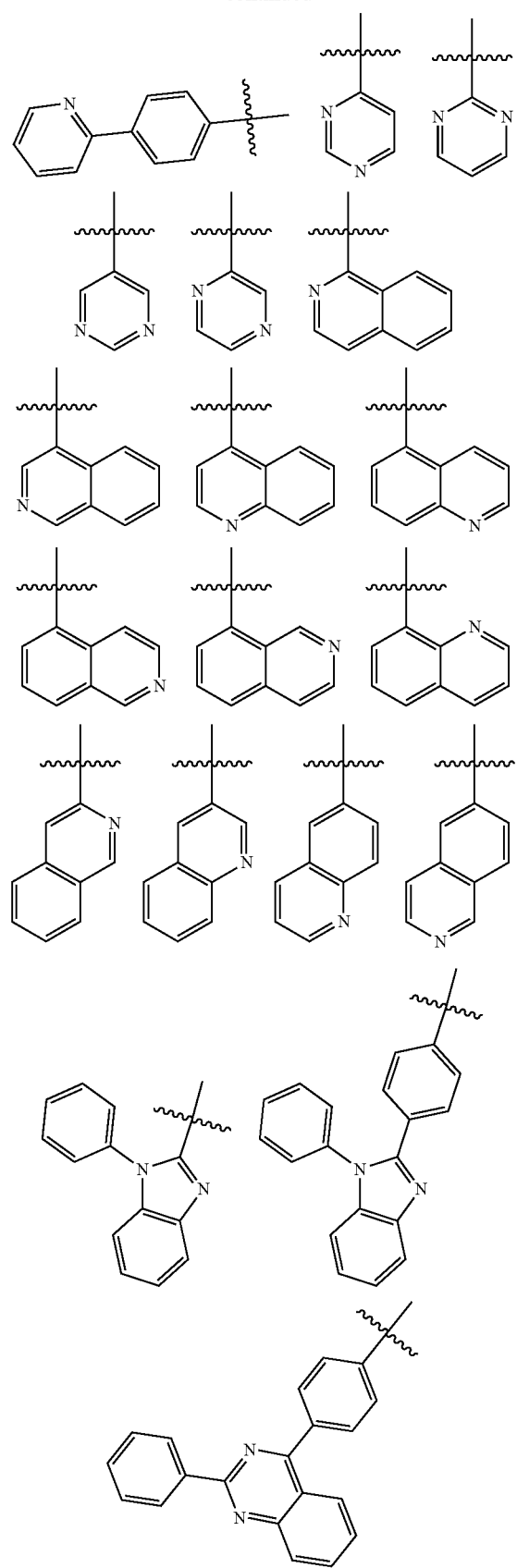
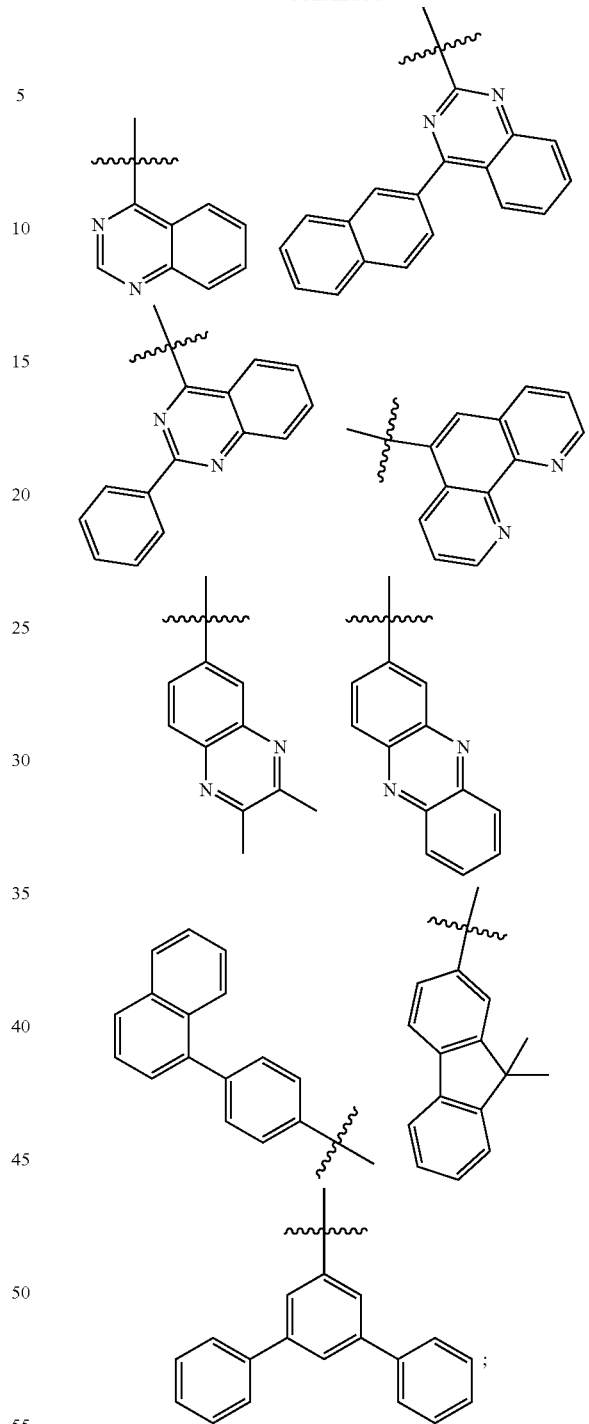

substituted $T_4$ is a group formed by substituting the unsubstituted $T_4$ by one or more substituent(s) selected from deuterium, fluorine, chlorine, cyano, methyl, ethyl, isopropyl, tertiary butyl, methoxyl, ethoxyl, isopropoxy, propoxy, cyclopentyl, cyclohexyl, trifluoromethyl, trimethylsilyl, phenyl, naphthyl, pyridyl, pyrimidinyl, 1,3,5-triazinyl, dibenzothiophenyl, dibenzofuranyl, quinolyl, isoquinolyl and phenanthrolinyl, and when a plurality of substituents are included on the substituted $T_4$, any two substituents are the same or different.

In other words, one or more substituent(s) are included on the substituted $T_4$, and any substituent is independently selected from deuterium, fluorine, chlorine, cyano, methyl, ethyl, isopropyl, tertiary butyl, methoxyl, ethoxyl, isopropoxy, propoxy, cyclopentyl, cyclohexyl, trifluoromethyl, trimethylsilyl, phenyl, naphthyl, pyridyl, pyrimidinyl, 1,3,5-triazinyl, dibenzothiophenyl, dibenzofuranyl, quinolyl, isoquinolyl and phenanthrolinyl.

Further optionally, $Z^1$ and $Z^2$ are each independently selected from alkyl with 1 to 5 carbon atoms and $T_5$, and $Z^3$ is $T_5$; wherein $T_5$ is selected from the group consisting of the following substituents:

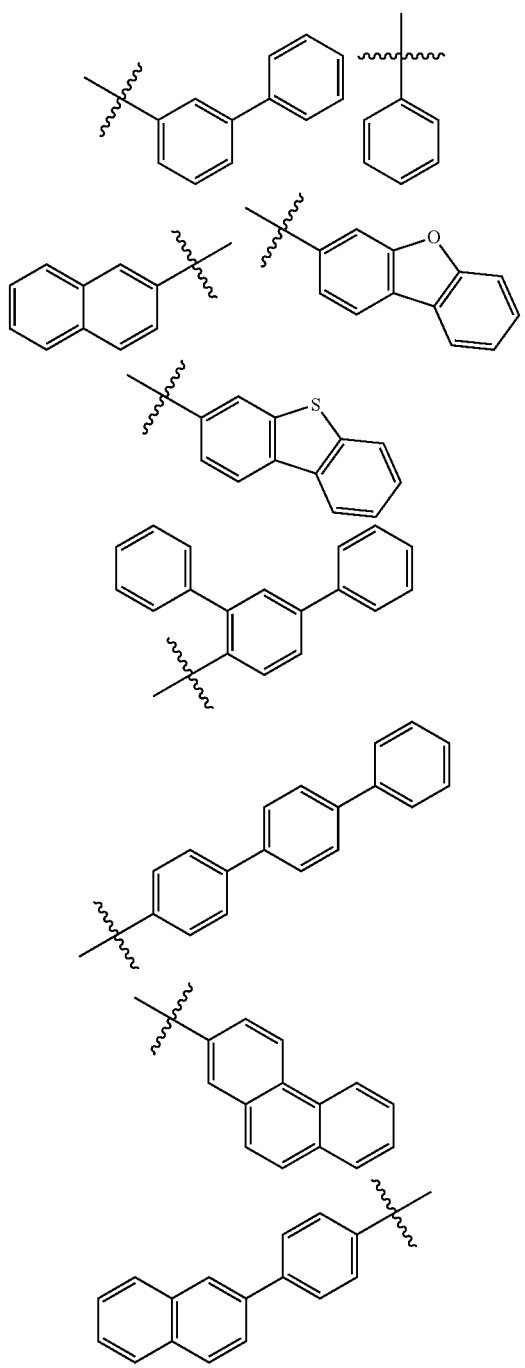

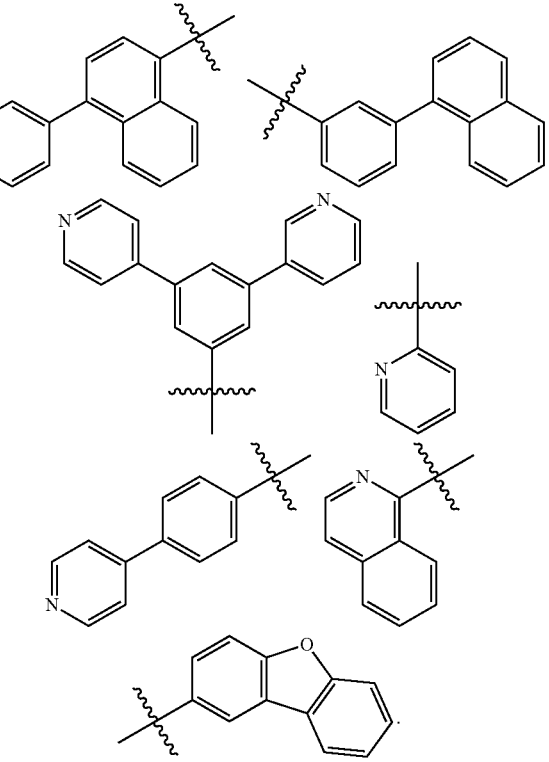

In other embodiments, $Z^3$ is also independently selected from substituted or unsubstituted alkyl with 1 to 4 carbon atoms, or electron-deficient heteroaryl (also known as electron-poor heteroaryl) groups as shown in formula S-11 to formula S-14 below:

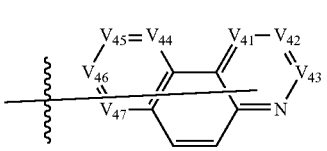

S-11

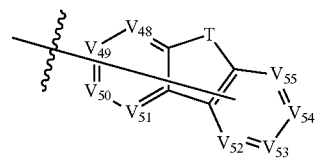

S-12

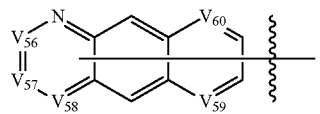

S-13

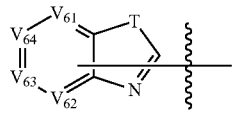

S-14

Wherein $V_{41}$ to $V_{64}$ are each independently selected from $C(R'^4)$ and N, at least one of $V_{48}$ to $V_{55}$ is N, at least one of $V_{61}$ to $V_{64}$ is N, and when a plurality of $R'^4$ are contained in the same group, any two $R'^4$ are the same or different from each other.

T is selected from a set consisting of O, S, Se, N($R^{t1}$), C($R^{t2}R^{t3}$) and Si($R^{t2}R^{t3}$).

$R^{t1}$, $R^{t2}$ and $R^{t3}$ are each independently hydrogen, aryl with 6 to 18 carbon atoms, heteroaryl with 3 to 18 carbon atoms, alkyl with 1 to 10 carbon atoms, cycloalkyl with 3 to 10 carbon atoms and heterocycloalkyl with 2 to 10 carbon atoms; alternatively, $R^{t2}$ and $R^{t3}$ connected to the same atom are connected with each other to form saturated or unsaturated 5-to-13-membered rings together with atoms to which they are jointly connected;

each $R^{v4}$ are independently selected from hydrogen, deuterium, fluorine, chlorine, bromine, cyano, heteroaryl with 3 to 18 carbon atoms, aryl with 6 to 18 carbon atoms, trialkylsilyl with 3 to 12 carbon atoms, arylsilyl with 8 to 12 carbon atoms, alkyl with 1 to 10 carbon atoms, haloalkyl with 1 to 10 carbon atoms, cycloalkyl with 3 to 10 carbon atoms, alkoxyl with 1 to 10 carbon atoms, alkylamine with 1 to 10 carbon atoms, alkylthiol with 1 to 10 carbon atoms, aryloxy with 6 to 18 carbon atoms and arylthio with 6 to 18 carbon atoms.

In some embodiments, the $Z^3$ is also independently selected from substituted or unsubstituted $T_6$, wherein the unsubstituted $T_6$ is independently selected from the groups as shown below:

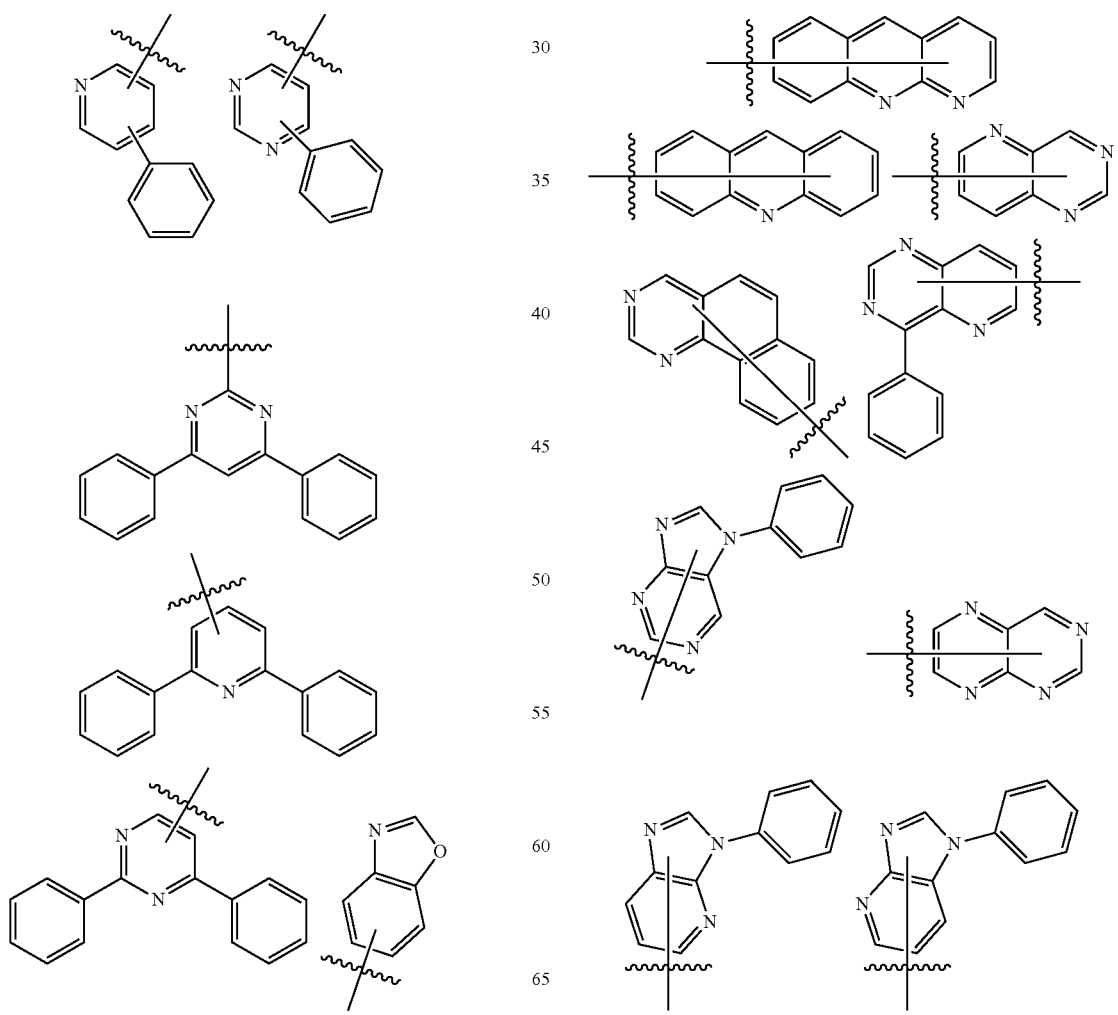

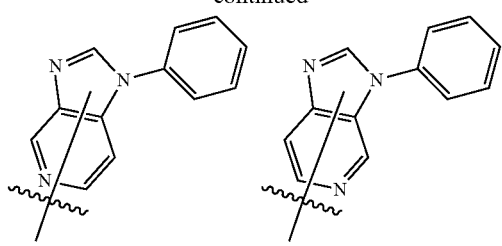

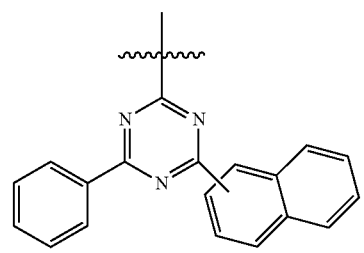

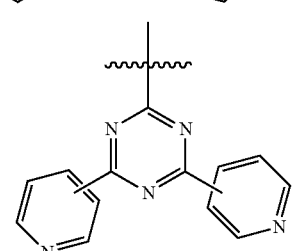

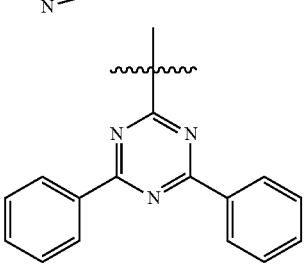

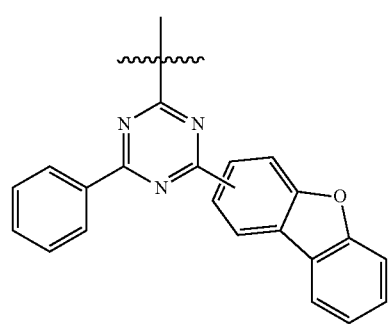

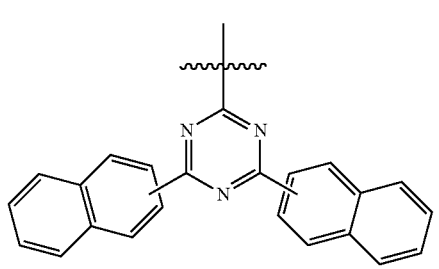

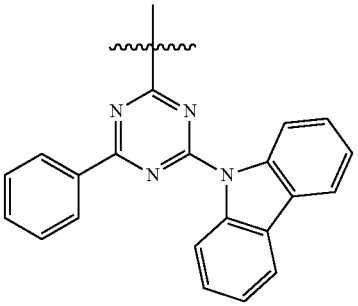

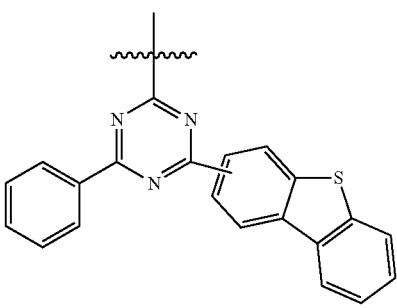

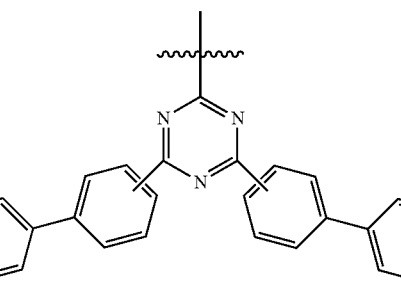

The substituted $T_6$ is a group formed by substituting the unsubstituted $T_6$ by one or more substituent(s) selected from deuterium, fluorine, chlorine, cyano, alkyl with 1 to 4 carbon atoms, alkoxy with 1 to 4 carbon atoms, haloalkyl with 1 to 4 carbon atoms, alkylsilyl with 3 to 9 carbon atoms, cycloalkyl with 5 to 7 carbon atoms, aryl with 6 to 13 carbon atoms and heteroaryl with 3 to 12 carbon atoms, and when a plurality of substituents are included on the substituted $T_6$, any two substituents are the same or different.

Further, $Z^3$ is independently selected from substituted or unsubstituted $T_7$, wherein the unsubstituted $T_7$ is independently selected from the groups as shown below:

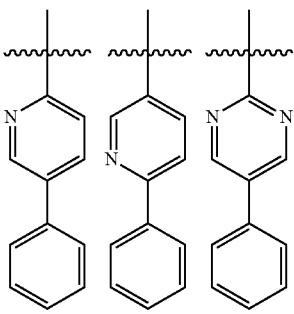

-continued
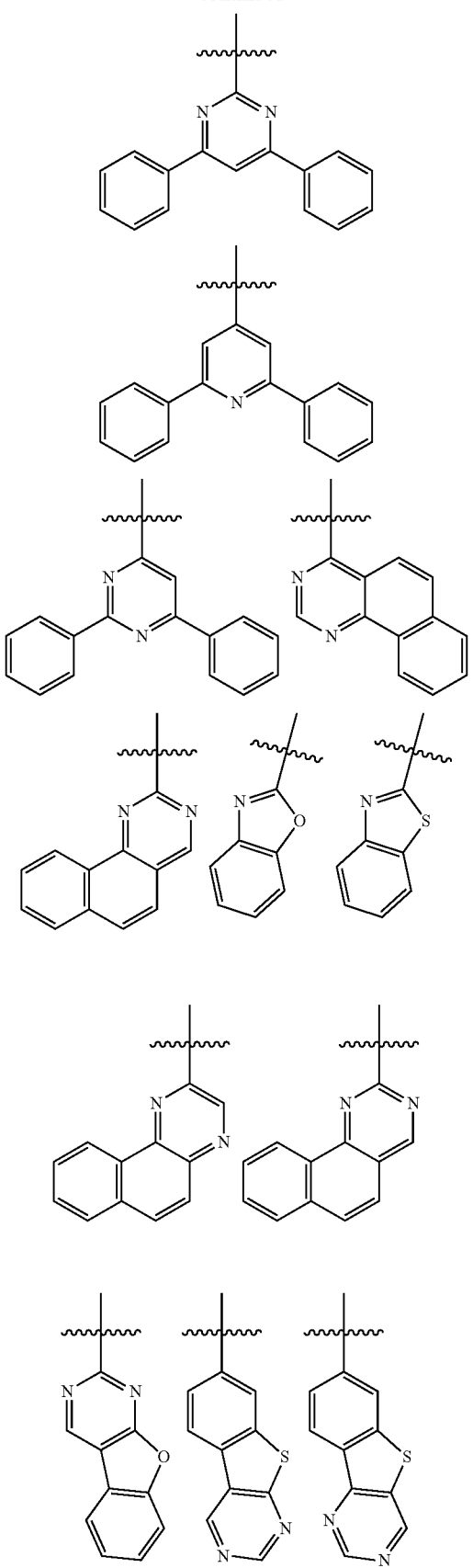
-continued
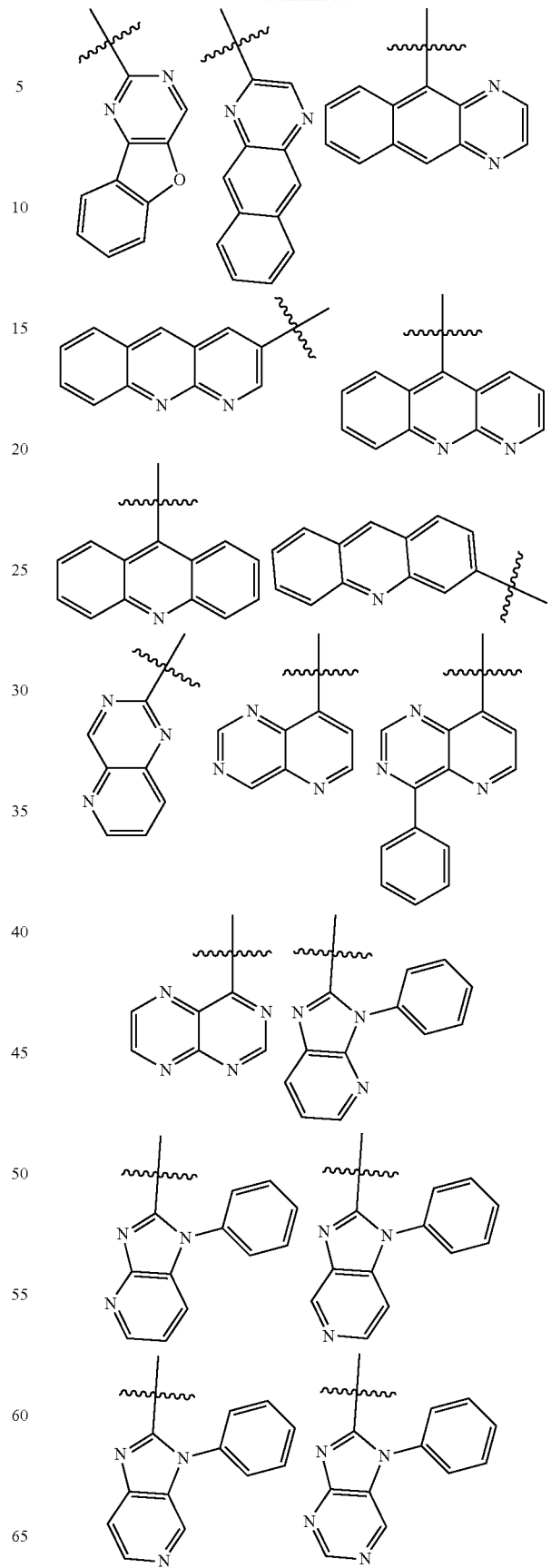

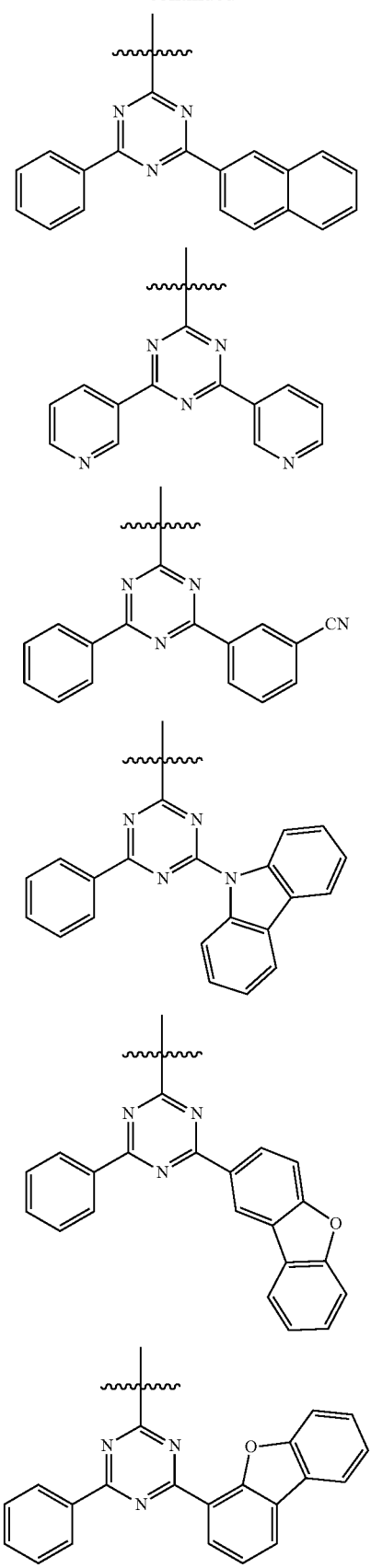

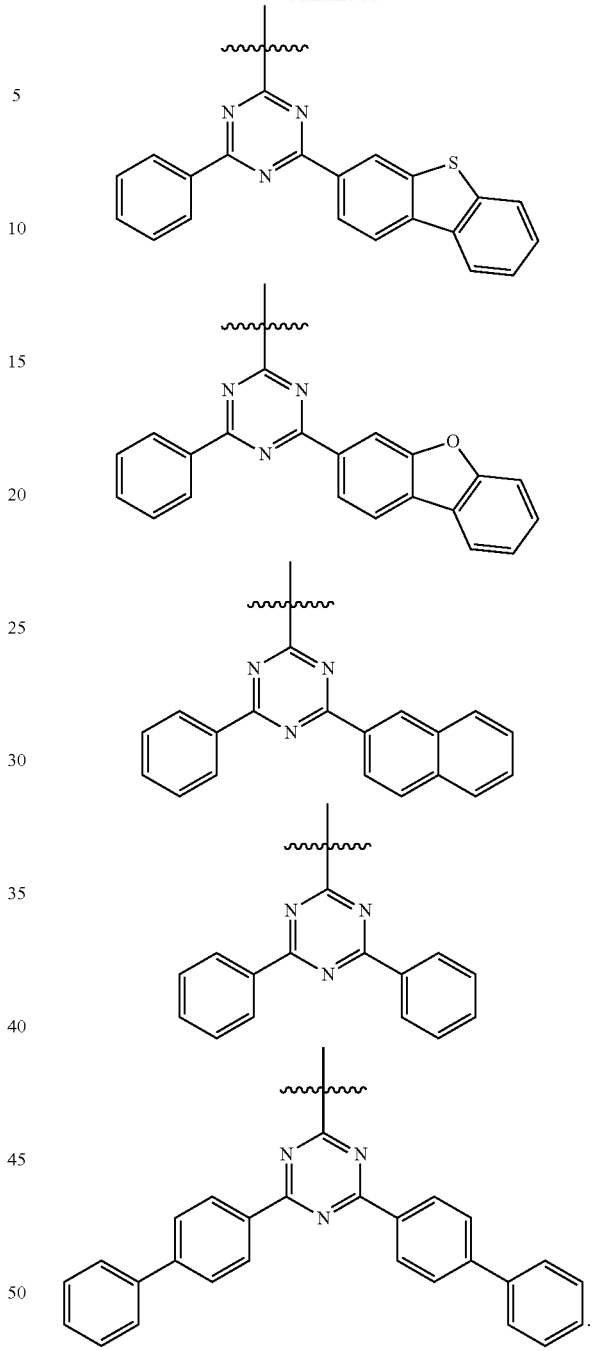

Substituted $T_7$ is a group formed by substituting the unsubstituted $T_7$ by one or more substituent(s) selected from deuterium, fluorine, chlorine, cyano, methyl, ethyl, isopropyl, tertiary butyl, methoxyl, ethoxyl, isopropoxy, propoxy, cyclopentyl, cyclohexyl, trifluoromethyl, trim ethyl silyl, phenyl, naphthyl, pyridyl, pyrimidinyl, 1,3,5-triazinyl, dibenzothiophenyl, dibenzofuranyl, quinolyl, isoquinolyl and phenanthrolinyl, and when a plurality of substituents are included on the substituted $T_7$, any two substituents are the same or different.

Further optionally, $Z^1$ and $Z^2$ are each independently selected from alkyl with 1 to 5 carbon atoms, or, $Z^1$ and $Z^2$ are connected with atoms to which they are jointly connected to form a saturated aliphatic ring with 5 to 10 ring-forming atoms. For example, $Z^1$ and $Z^2$ are connected with each other to form spiro adamantane ring, pentane ring, hexane ring and the like.

Further optionally, $Z^1$ and $Z^2$ are each independently selected from methyl, ethyl, propyl, isopropyl, butyl, isobutyl or tertiary butyl, or $Z^1$ and $Z^2$ are connected with atoms to which they are jointly connected to form cyclopentane, cyclohexane or adamantane.

Optionally,

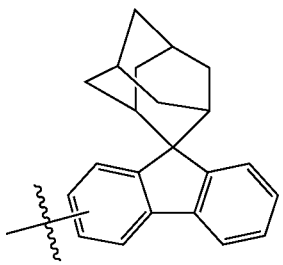

is selected from

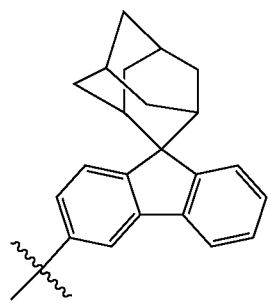

,

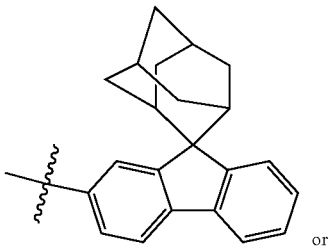

or

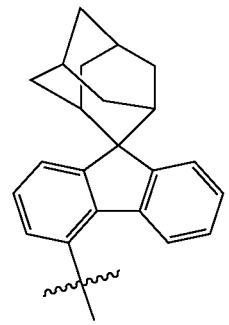

That is, the nitrogen-containing compound in the disclosure has the following structure:

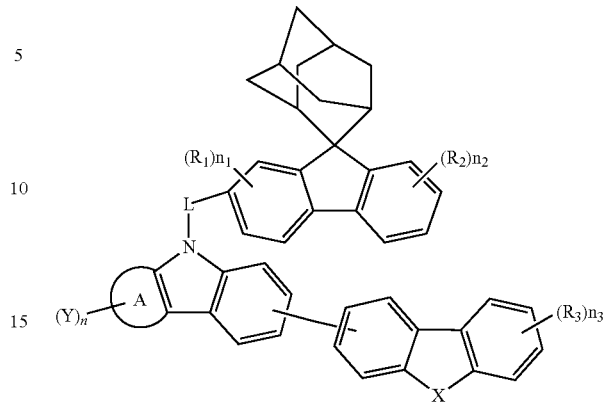

Formula 2-1

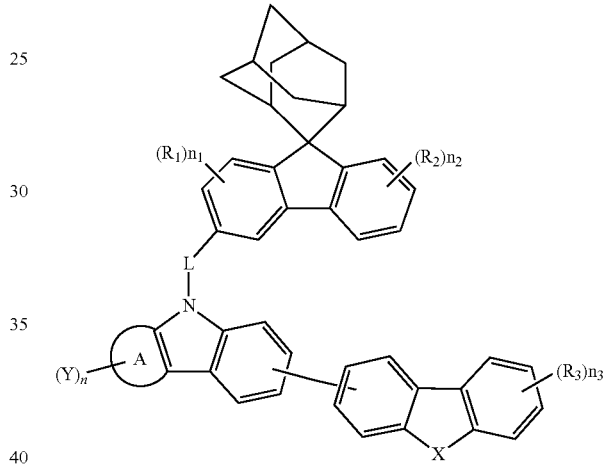

Formula 2-2

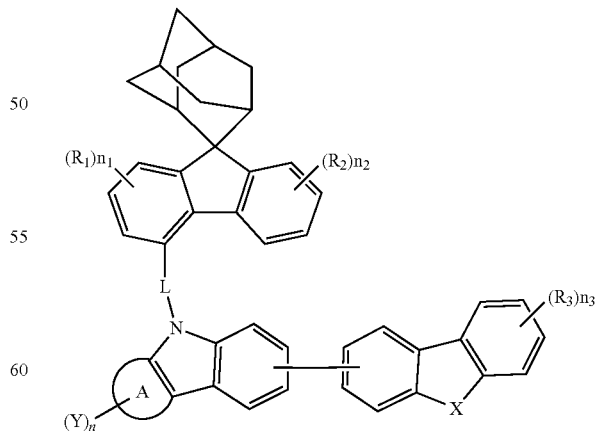

Formula 2-3

Optionally, the nitrogen-containing compound in the disclosure has the structure as shown in formula 2-4 to formula 2-19 below:

Formula 2-4
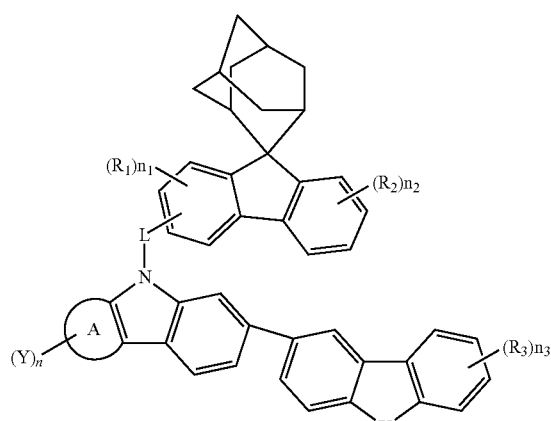
Formula 2-5
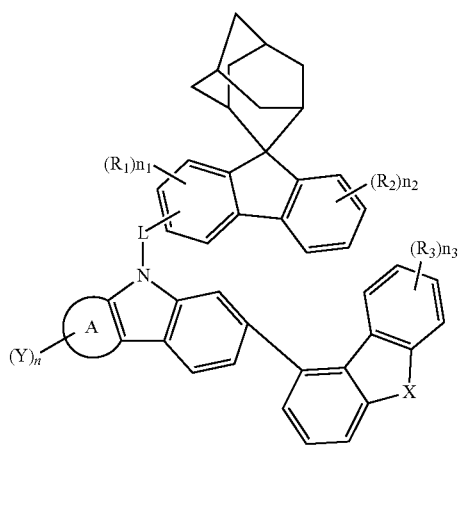
Formula 2-6
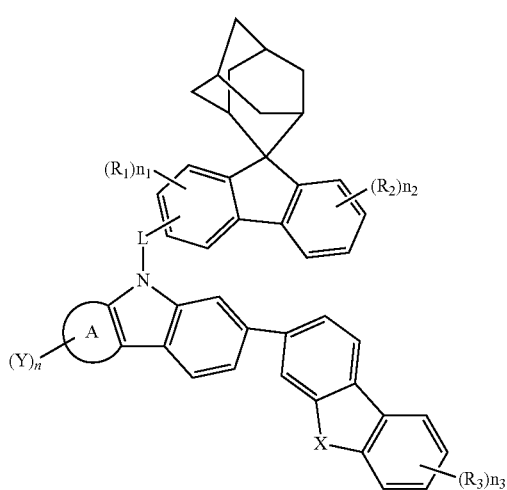
Formula 2-7
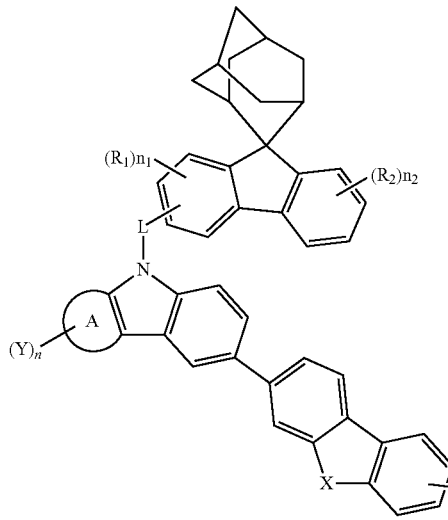
Formula 2-8
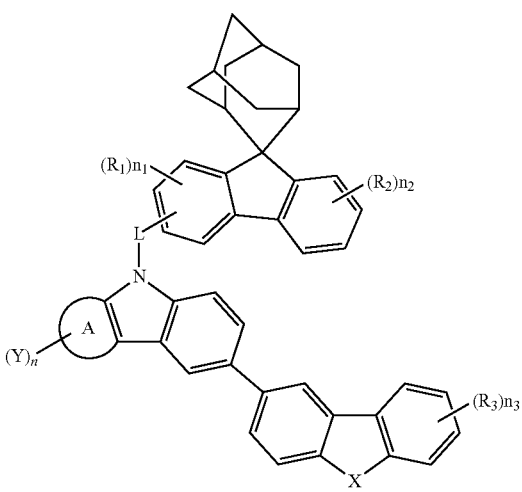
Formula 2-9
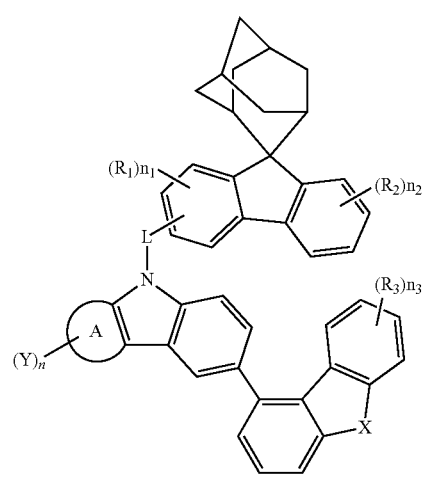

Formula 2-10
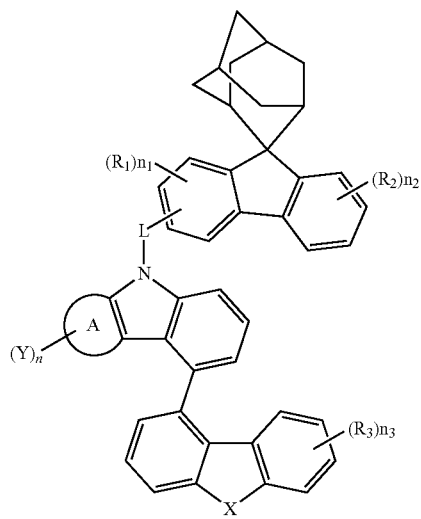
Formula 2-12
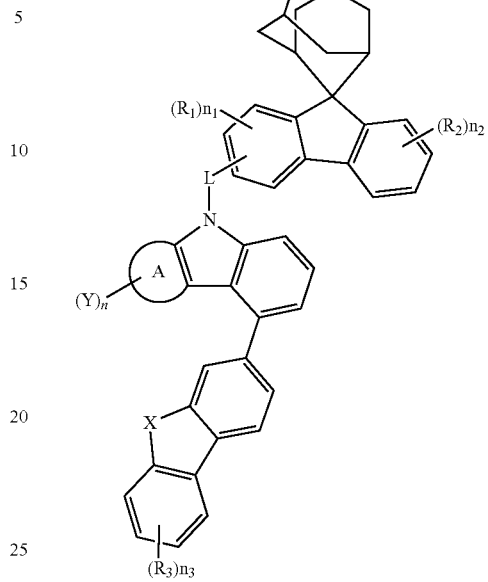
Formula 2-11
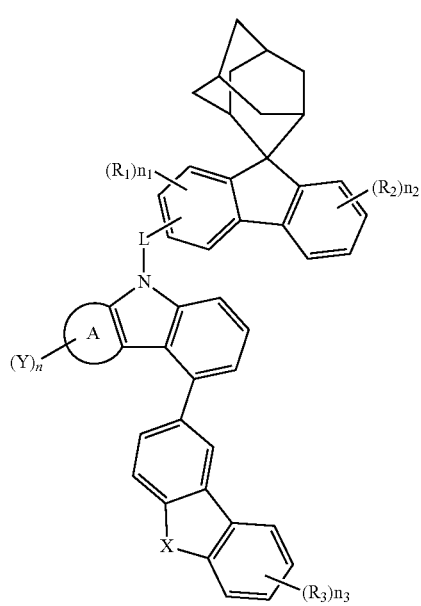
Formula 2-13
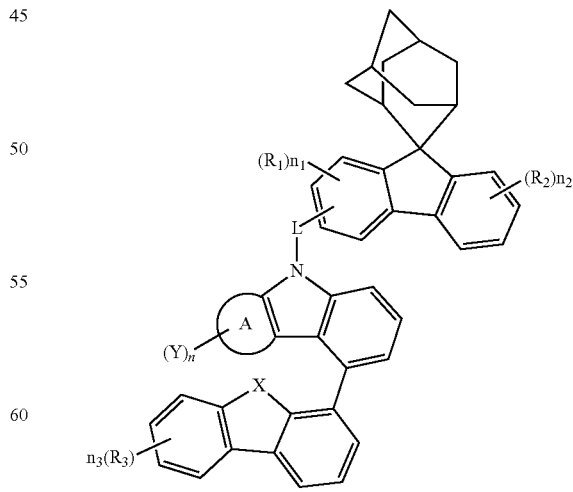

Formula 2-14

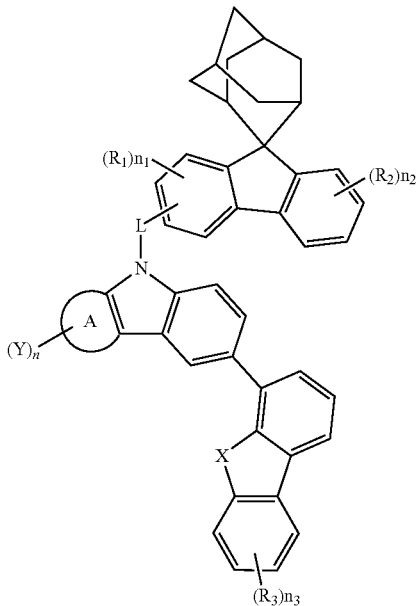

Formula 2-15

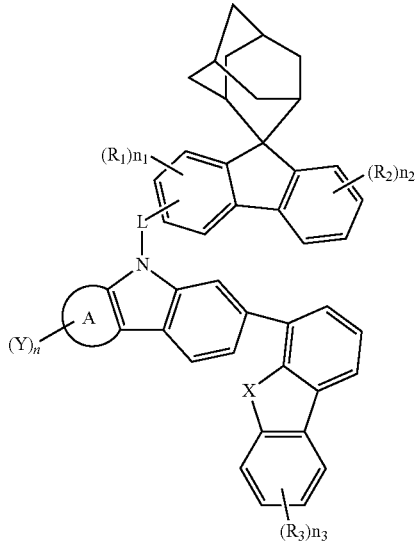

Formula 2-16

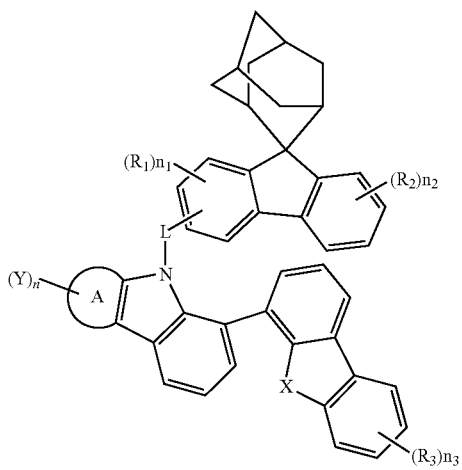

Formula 2-17

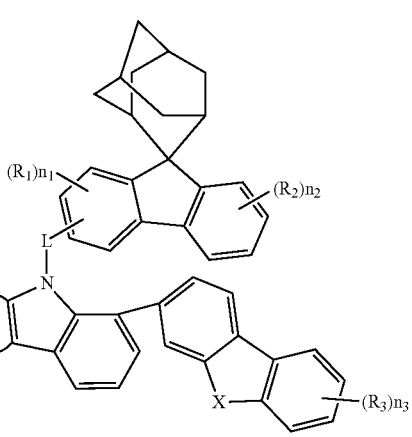

Formula 2-18

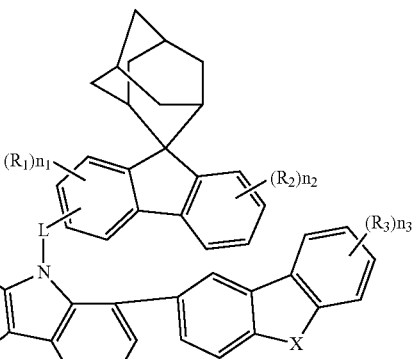

Formula 2-19

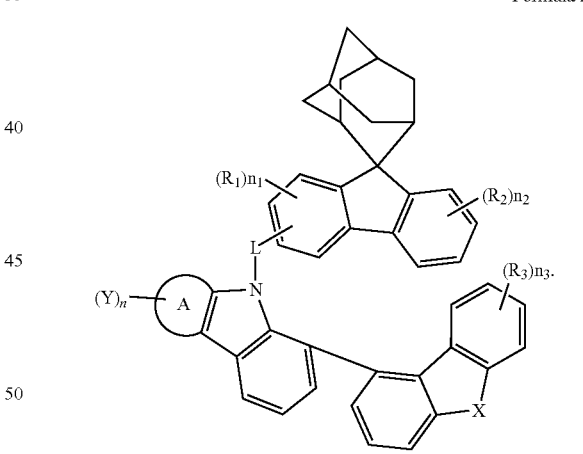

Optionally, Y, $R_1$, $R_2$ and $R_3$ in the compound in the disclosure are the same or different, and are each independently selected from: deuterium, fluorine, chlorine, bromine, cyano, aryl with 6 to 20 carbon atoms, heteroaryl with 3 to 18 carbon atoms, alkylsilyl with 3 to 18 carbon atoms, triarylsilyl with 6 to 18 carbon atoms, alkyl with 1 to 12 carbon atoms, haloalkyl with 1 to 12 carbon atoms, alkenyl with 2 to 12 carbon protons, cycloalkyl with 3 to 10 carbon atoms, heterocycloalkyl with 2 to 12 carbon atoms, alkylamine with 1 to 10 carbon atoms, alkylthiol with 1 to 10 carbon atoms, aryloxy with 6 to 18 carbon atoms and arylthio with 6 to 18 carbon atoms.

Optionally, Y, $R_1$, $R_2$ and $R_3$ are the same or different, and are each independently selected from: hydrogen, deuterium, fluorine, chlorine, bromine, cyano, aryl with 6 to 18 carbon atoms, heteroaryl with 3 to 14 carbon atoms, trialkylsilyl with 3 to 12 carbon atoms, alkyl with 1 to 6 carbon atoms, haloalkyl with 1 to 4 carbon atoms, cycloalkyl with 3 to 8 carbon atoms, heterocycloalkyl with 2 to 10 carbon atoms, alkoxyl with 1 to 6 carbon atoms, alkylthiol with 1 to 4 carbon atoms, alkylamine with 1 to 10 carbon atoms, alkylthiol with 1 to 10 carbon atoms and aryloxy with 6 to 18 carbon atoms.

Further optionally, Y, $R_1$, $R_2$ and $R_3$ are the same or different, and are each independently selected from deuterium, fluorine, chlorine, bromine, cyano, methyl, ethyl, isopropyl, tertiary butyl, methoxyl, ethoxyl, isopropoxy, cyclopentyl, cyclohexyl, trifluoromethyl, trimethylsilyl, triphenylsilyl, phenyl, dibiphenyl, naphthyl, methylthio, phenoxyl, 9,9-dimethylfluorenyl, dibenzothiophenyl, dibenzofuranyl, quinolyl, isoquinolyl and phenanthrolinyl.

Further optionally, n is 0 or 1, that is, at most one substituent exists on ring A.

Optionally, the nitrogen-containing compound in the disclosure is selected from the group consisting of the following compounds:

1

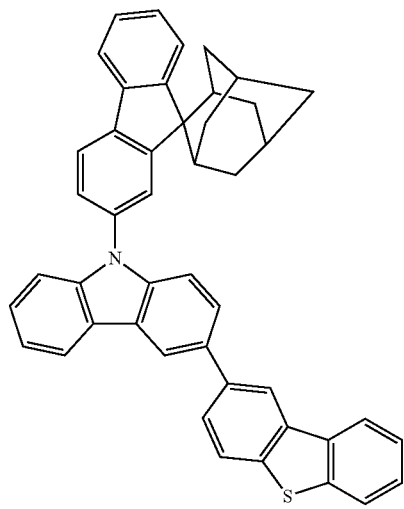

2

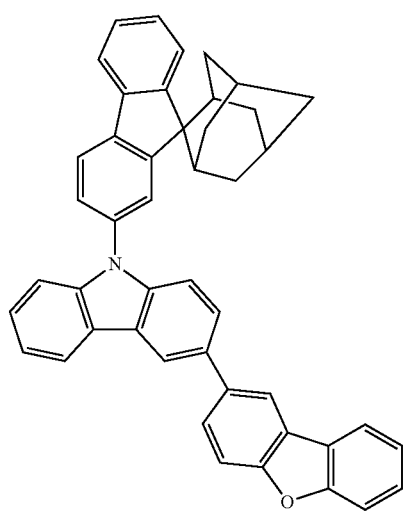

3

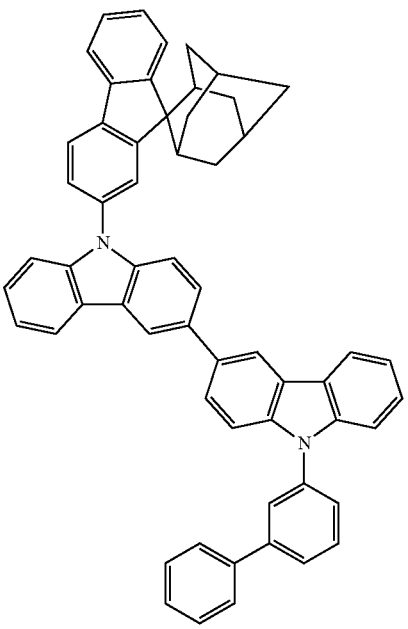

4

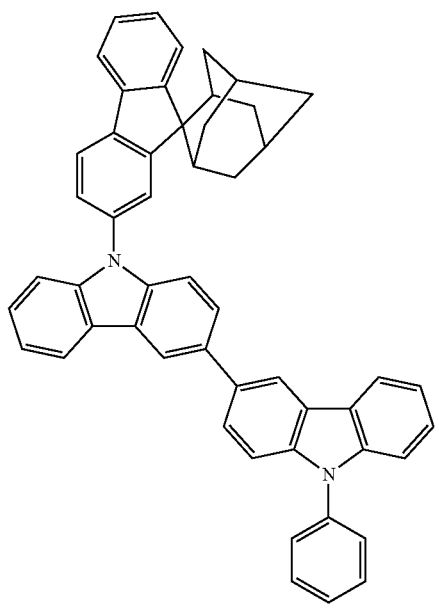

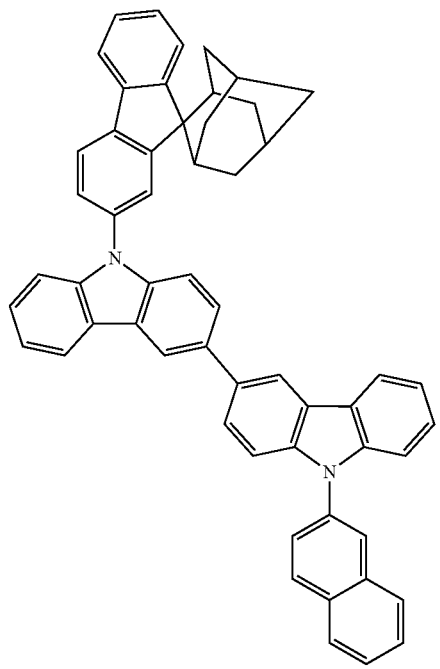
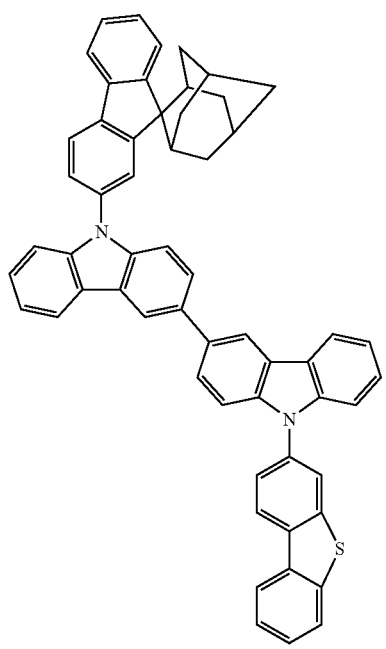
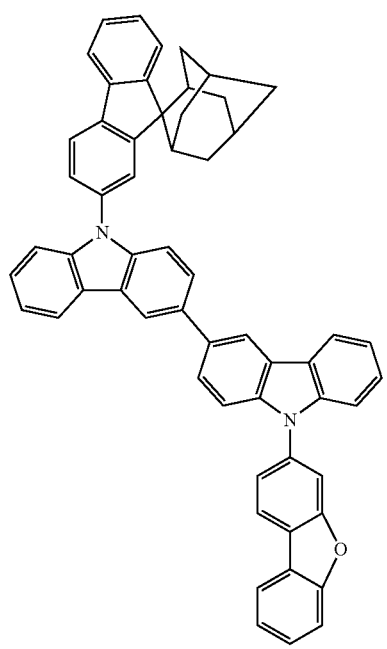
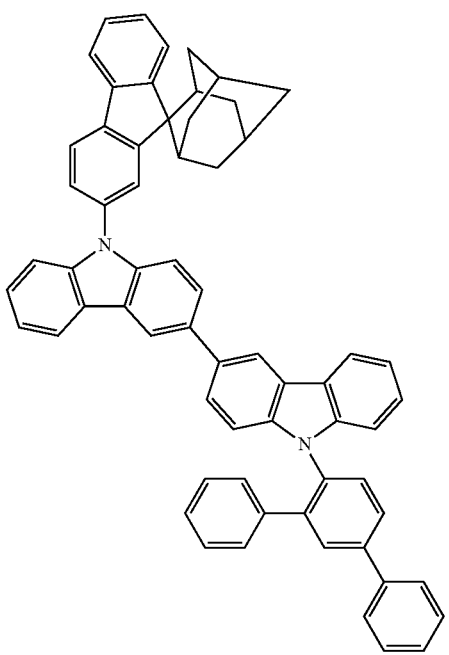

9
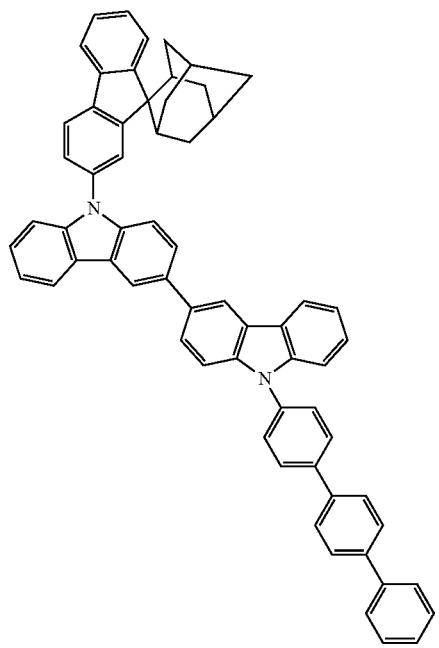
10
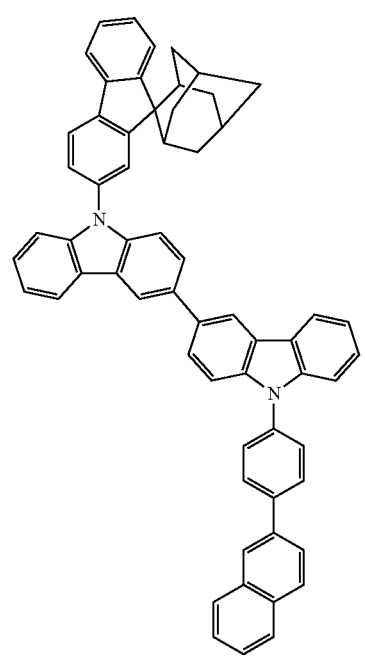
11
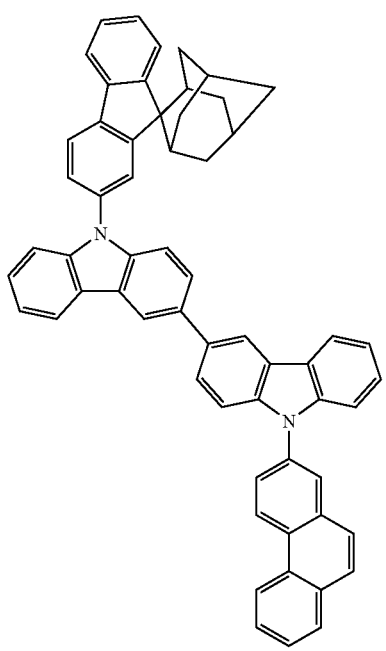
12
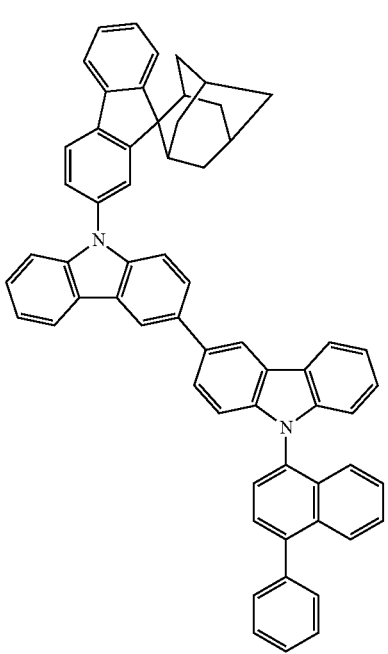

13
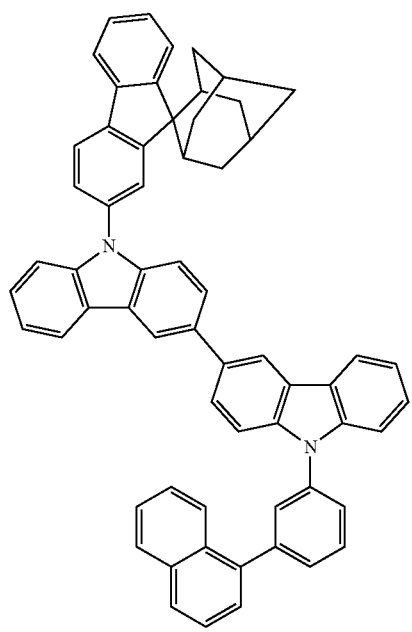
14
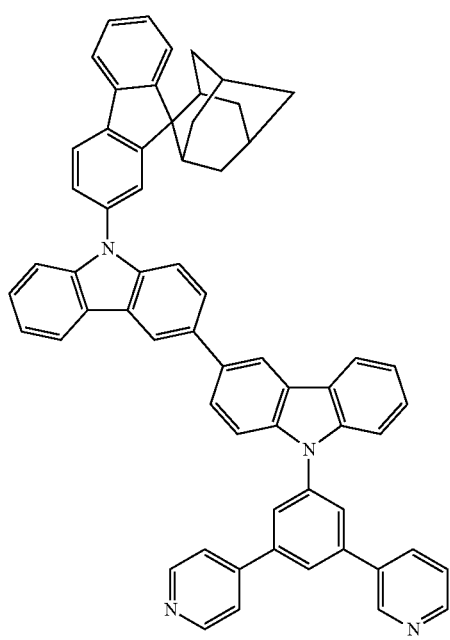
15
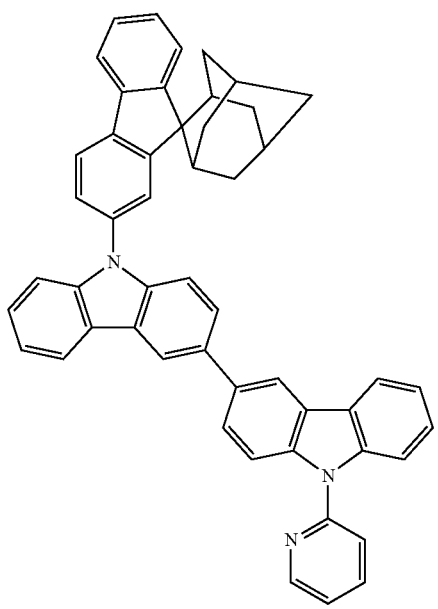
16

17
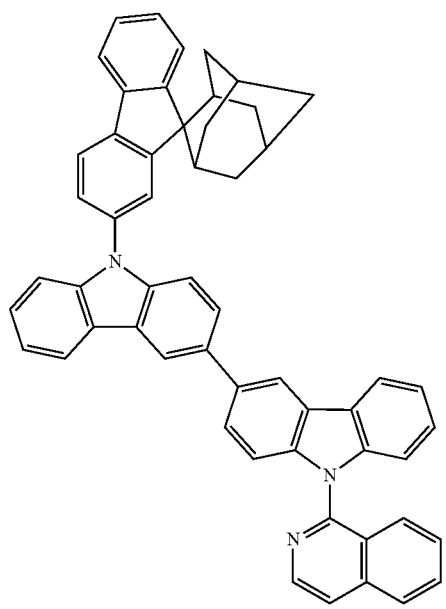
18
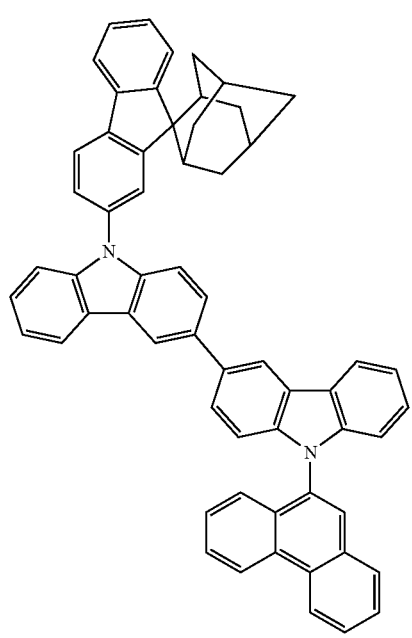
19
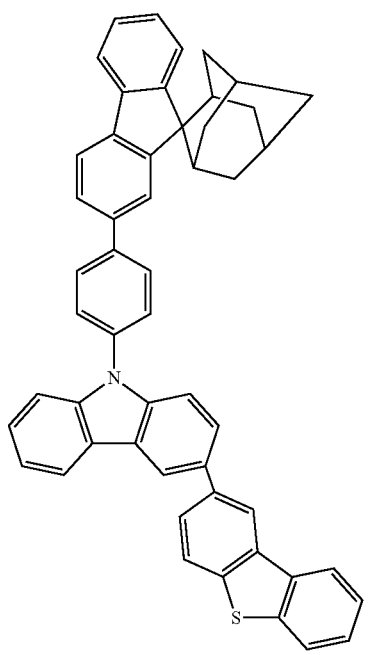
20
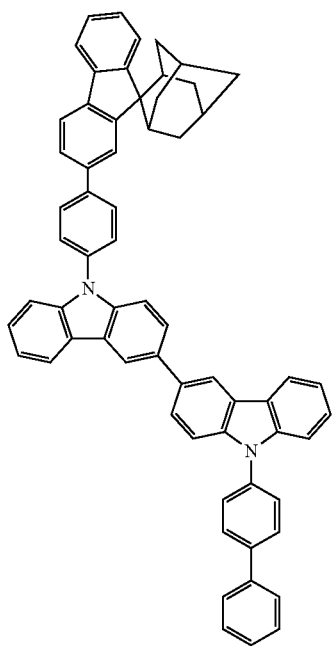

21
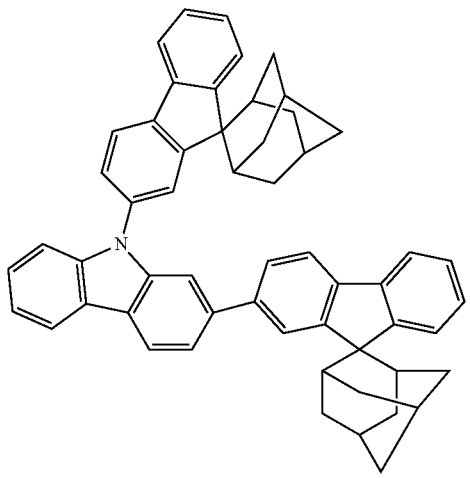
22
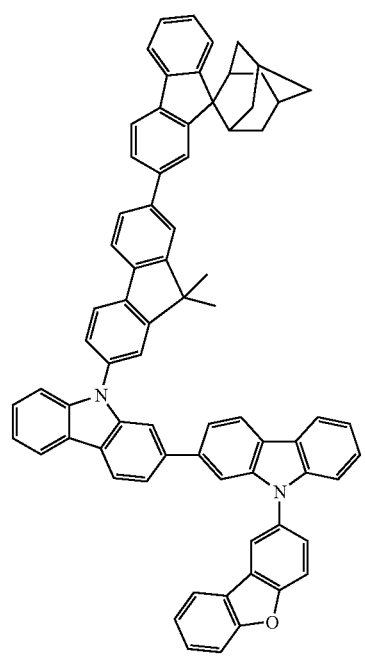
23
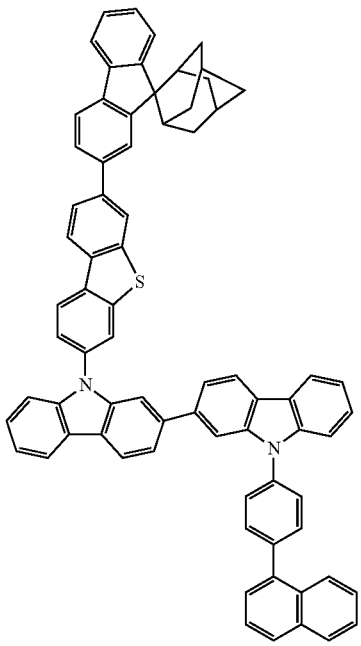
24
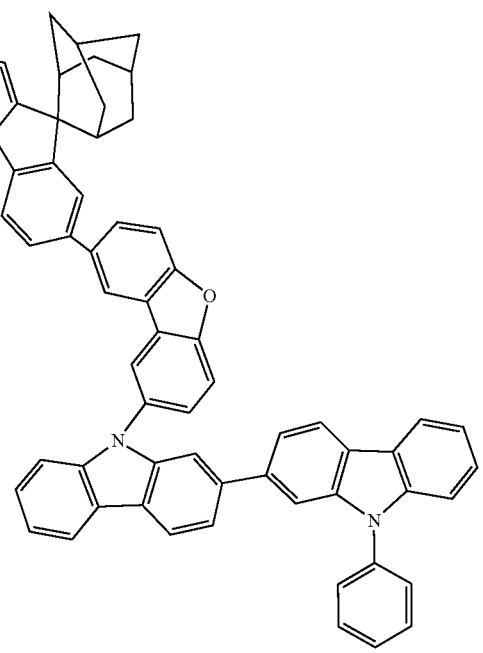

69
-continued
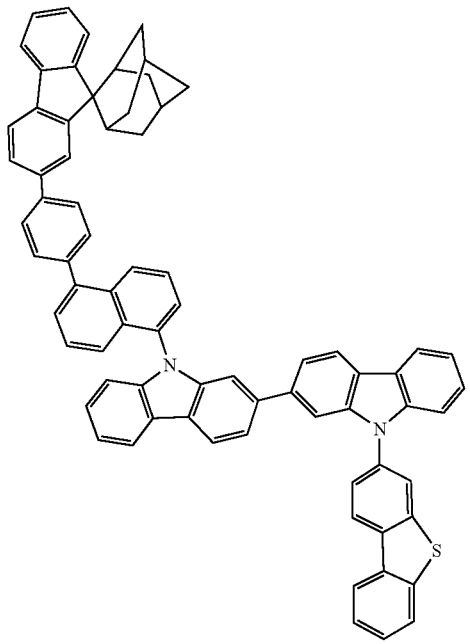
70
-continued
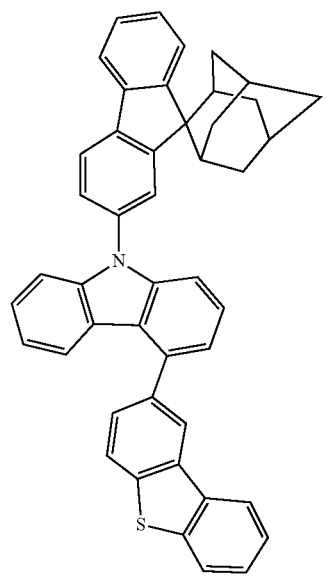
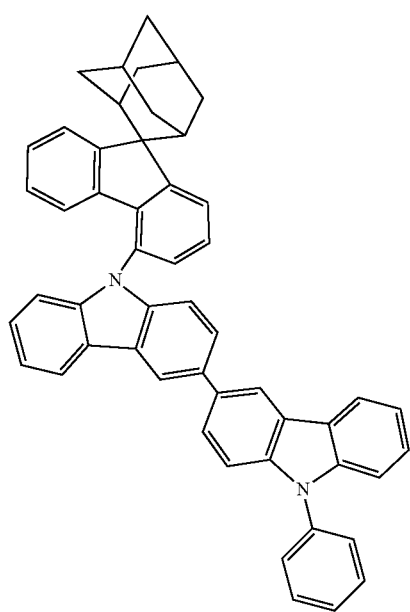
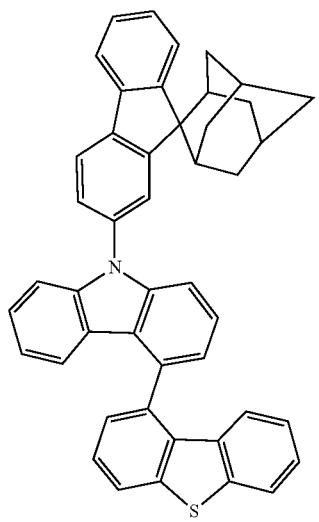
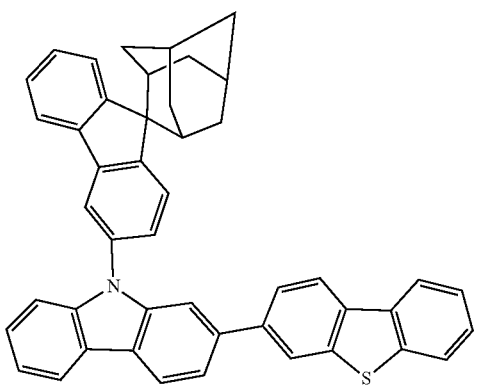

30
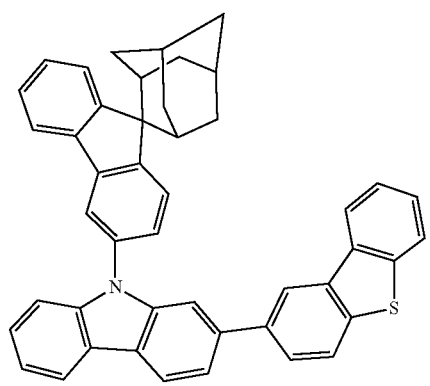
31
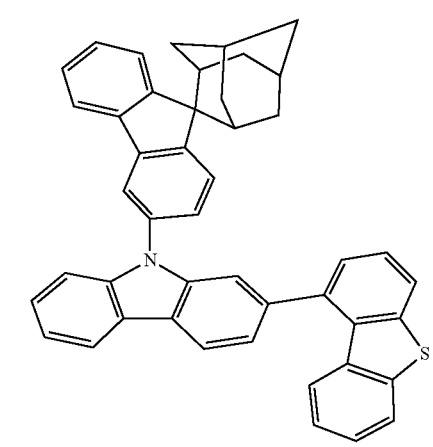
32
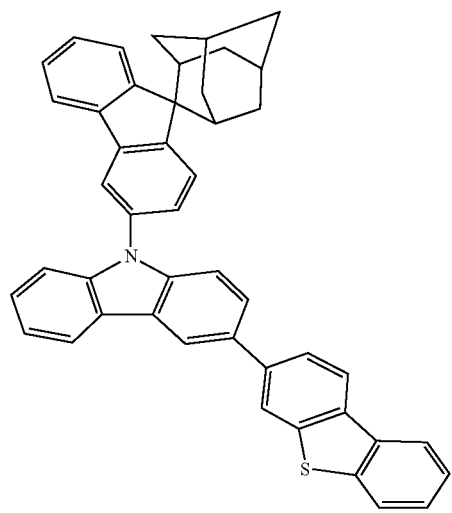
33
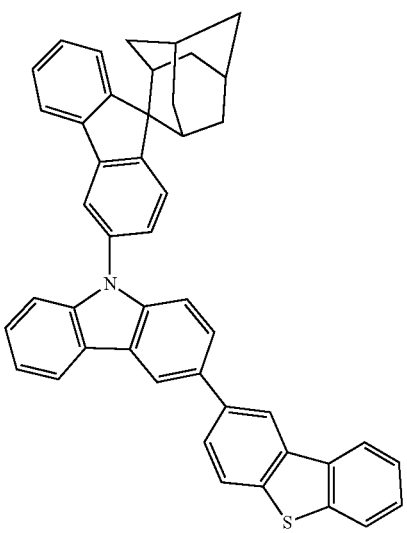
34
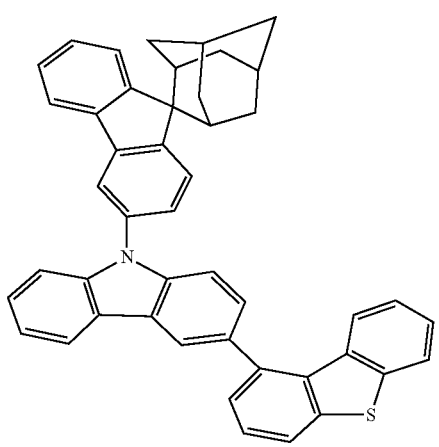
35
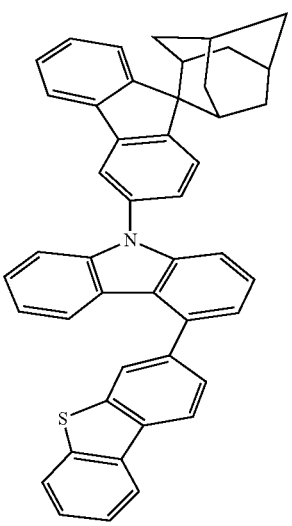

36
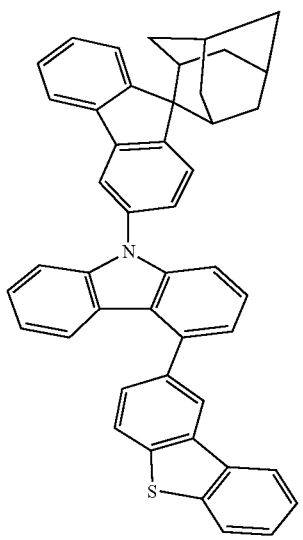
37
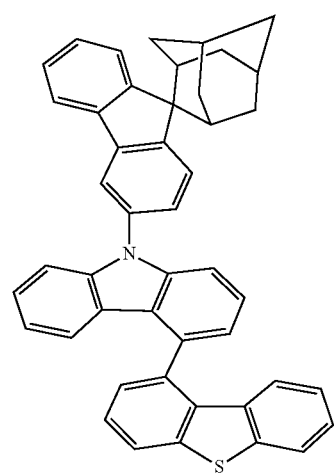
38
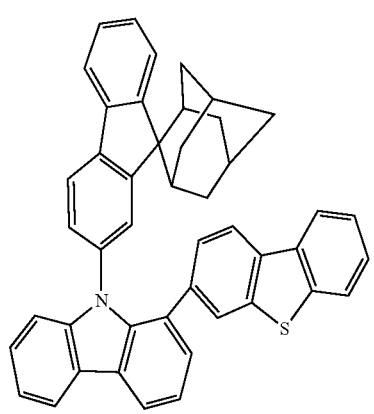
39
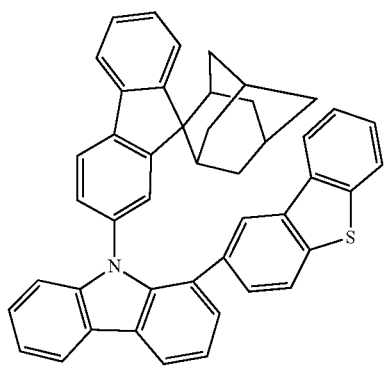
40
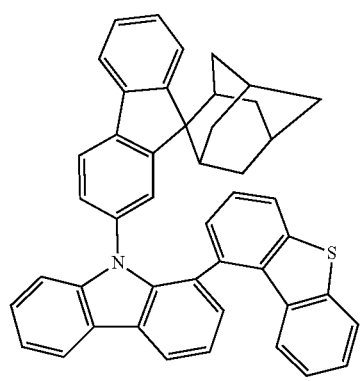
41
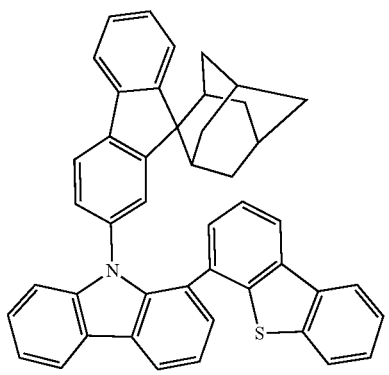
42
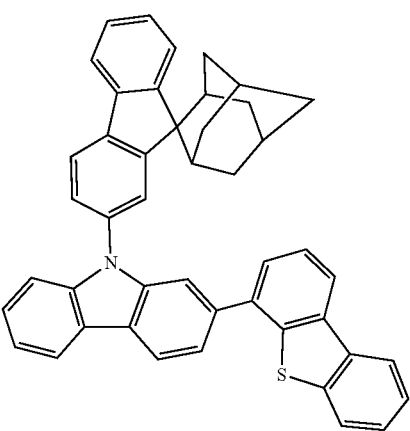

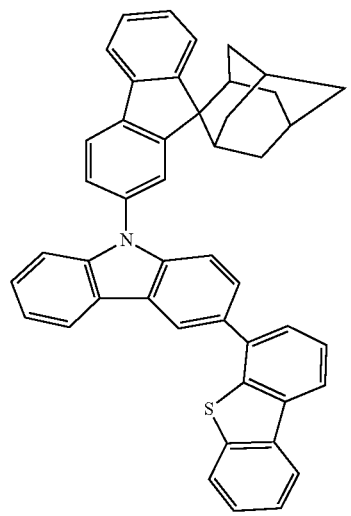
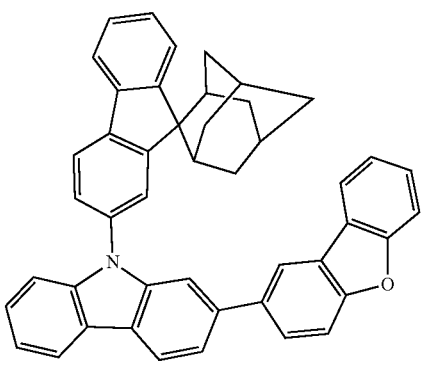
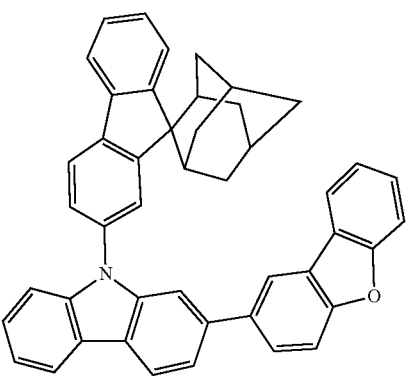
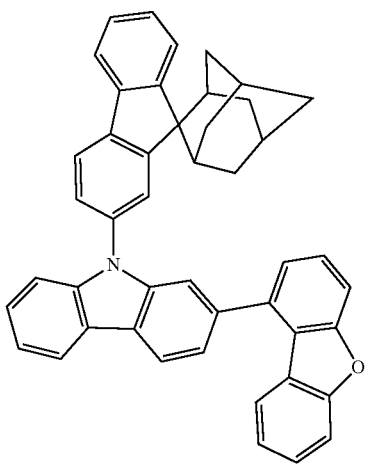

49
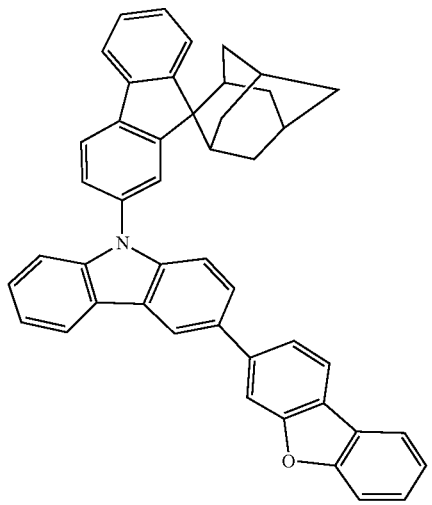
50
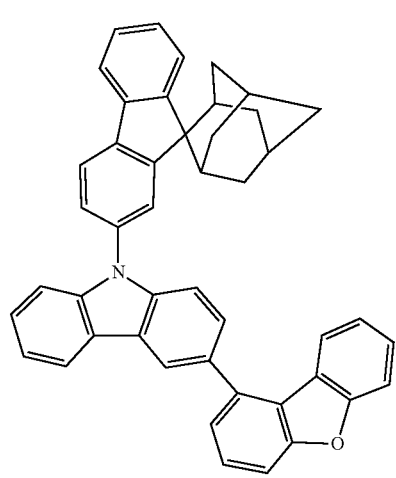
51
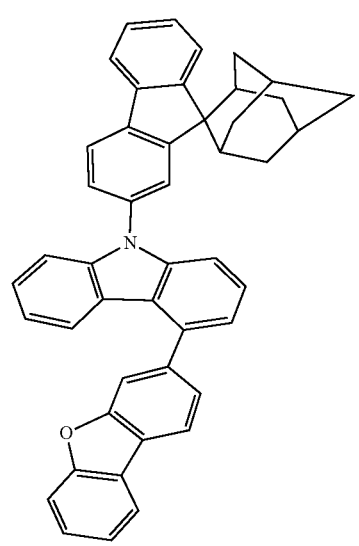
52
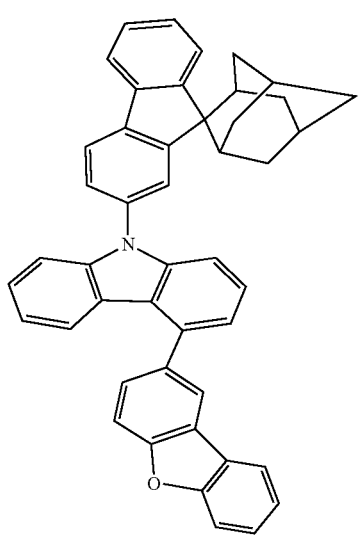
53
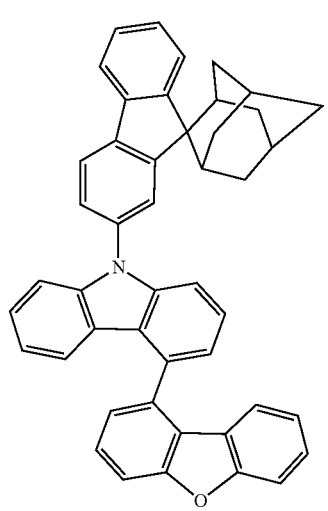
54
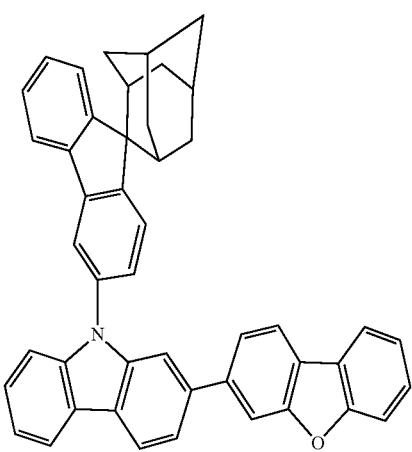

79
-continued
55
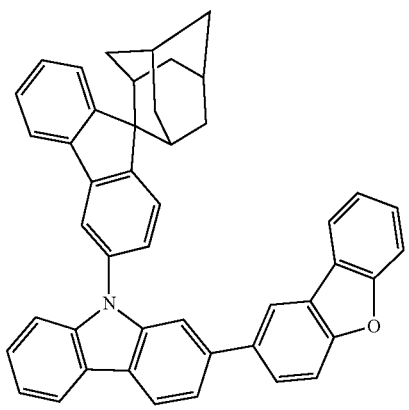
56
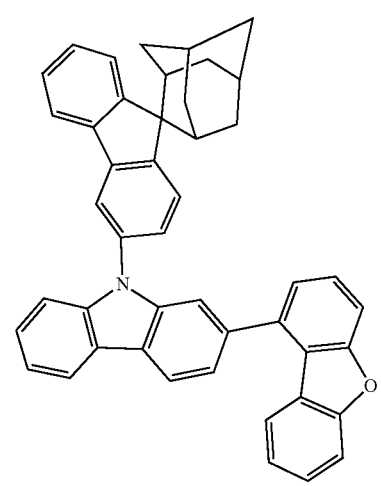
57
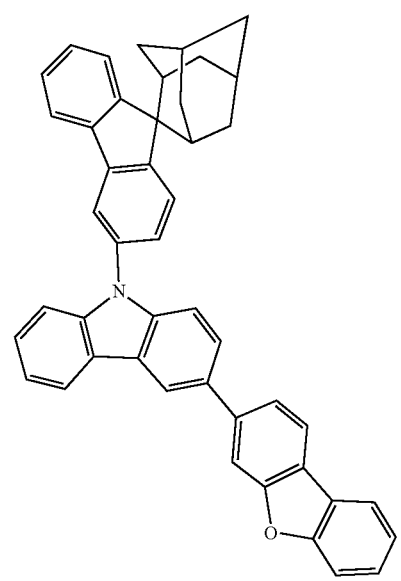
80
-continued
58
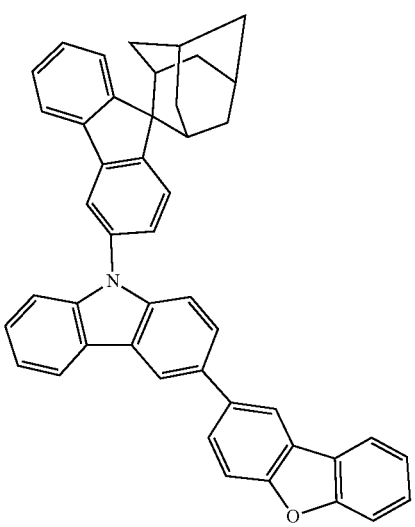
59
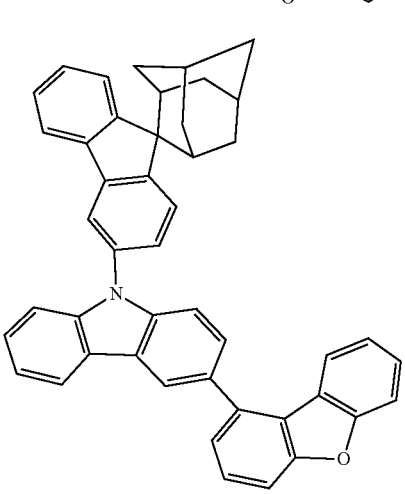
60
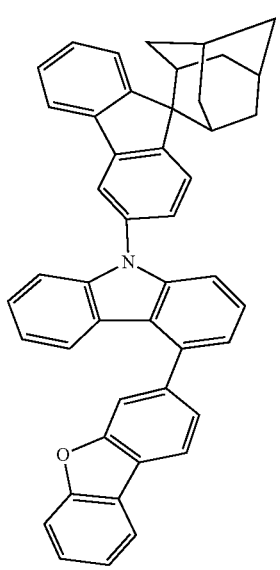

-continued
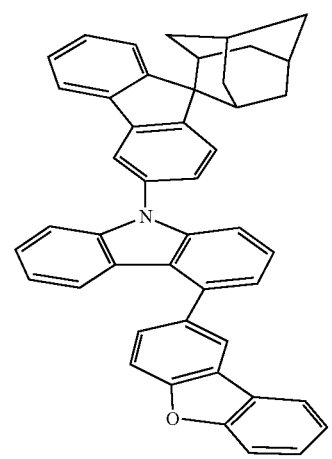
61
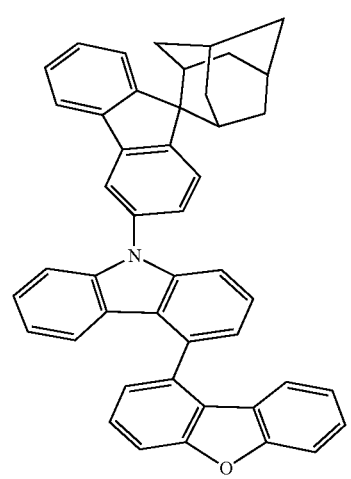
62
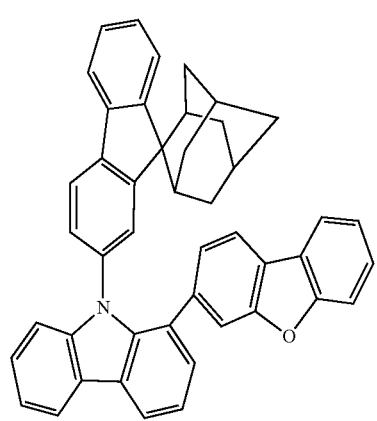
63
-continued
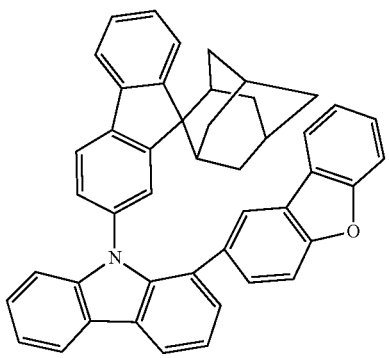
64
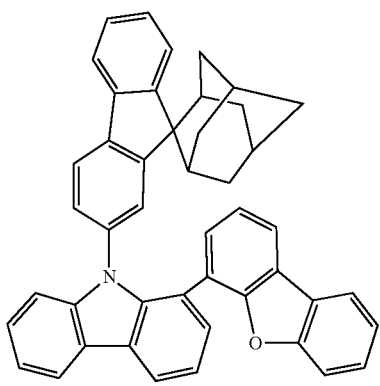
65
66
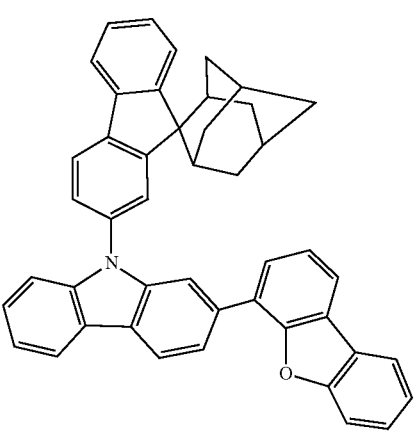
67

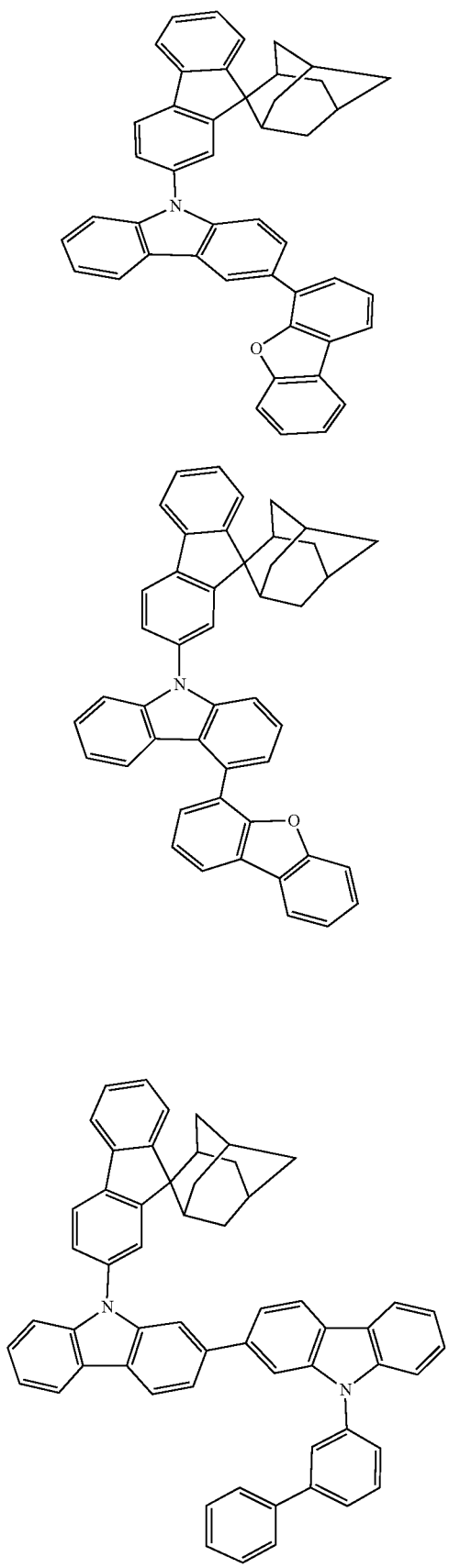
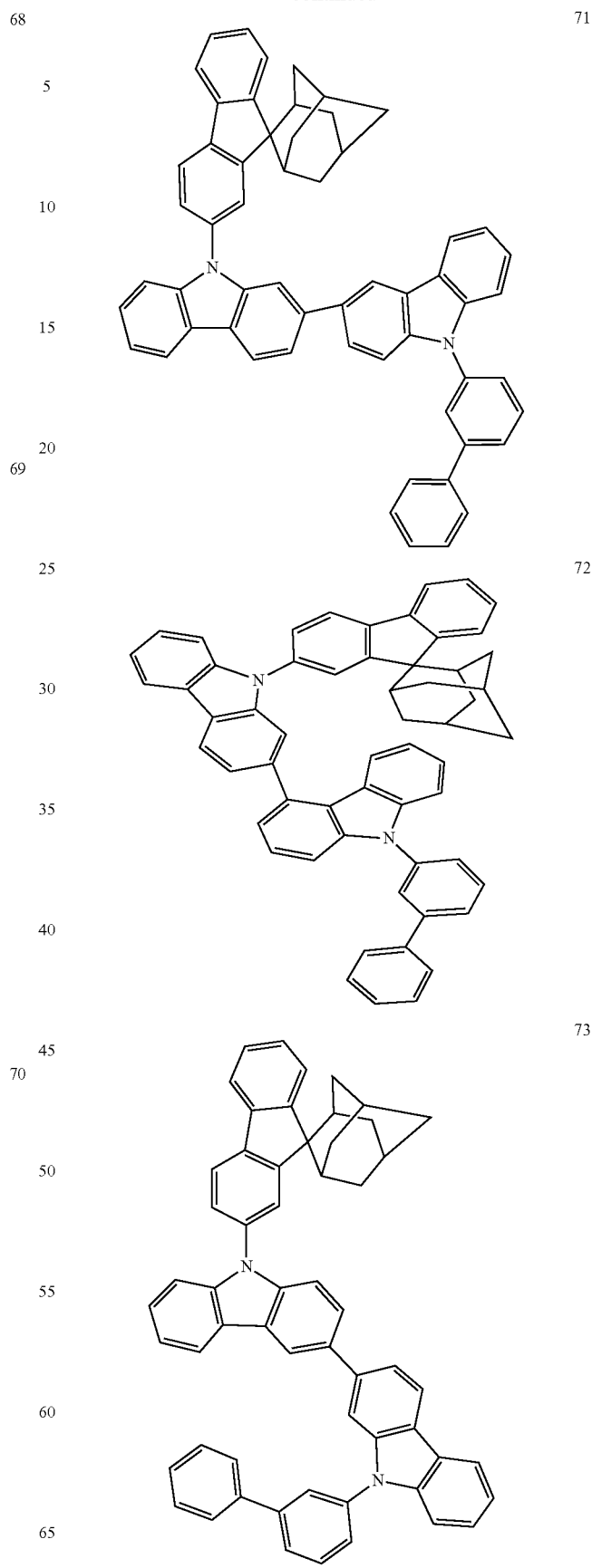

-continued
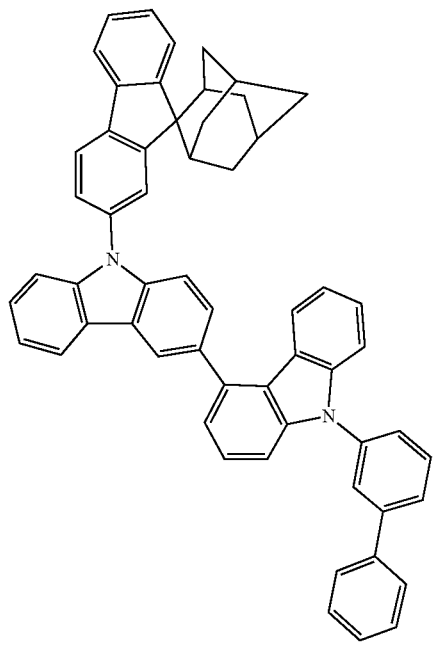
74
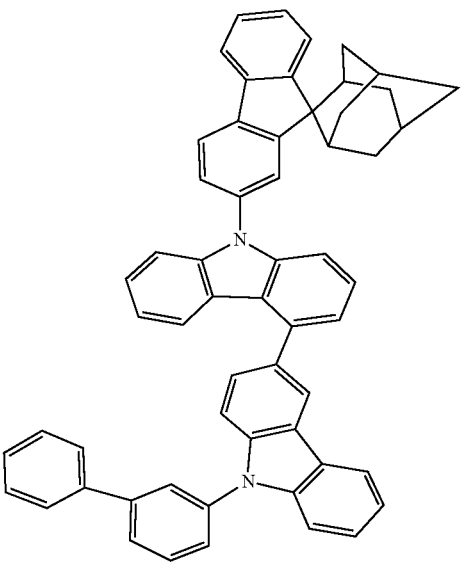
76
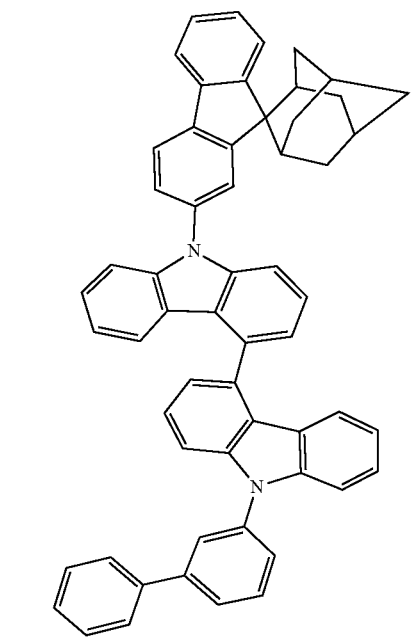
77

78
-continued
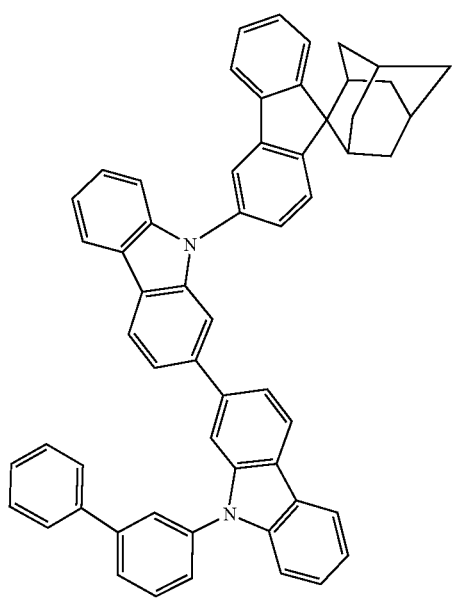
79
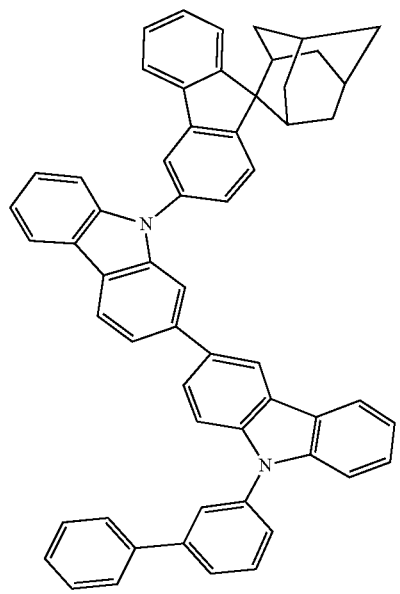
80
-continued
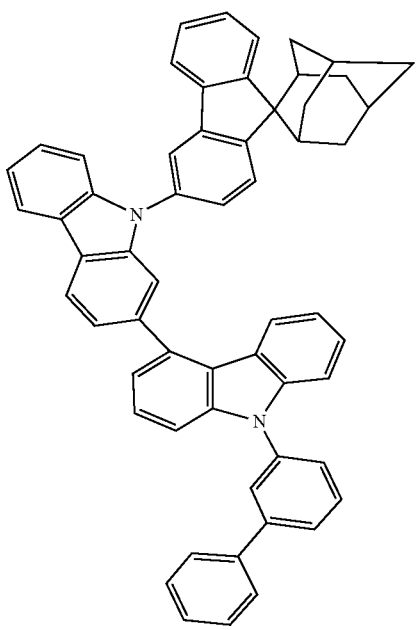
81
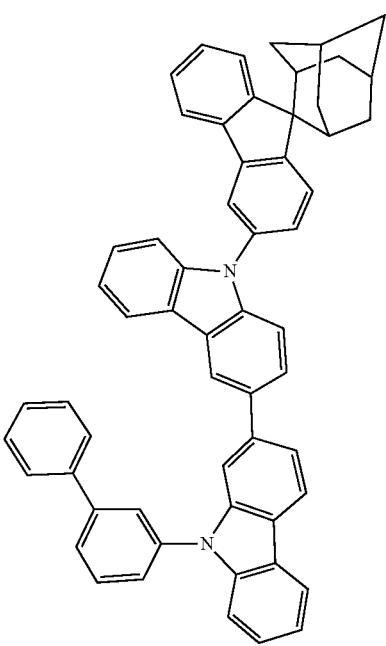

82
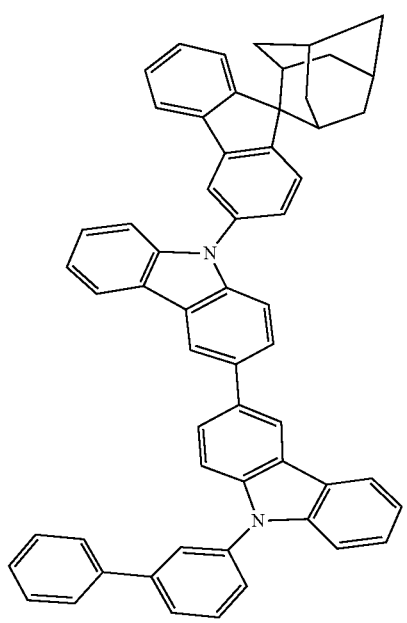
83
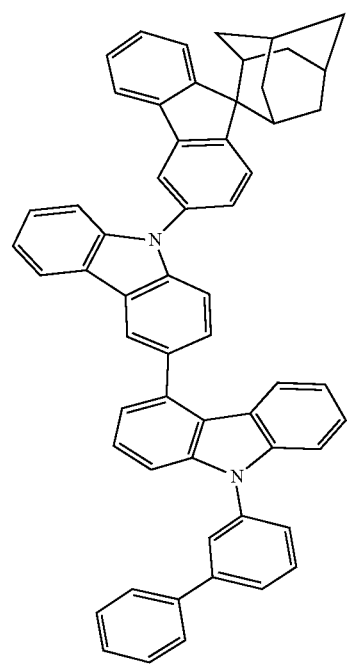
84
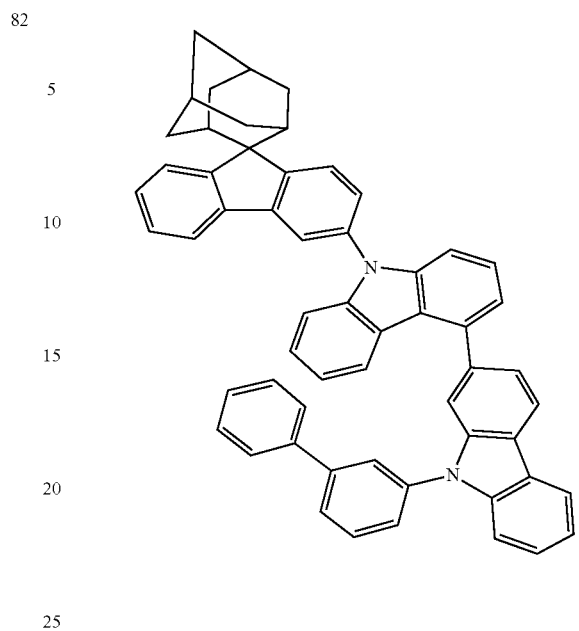
85
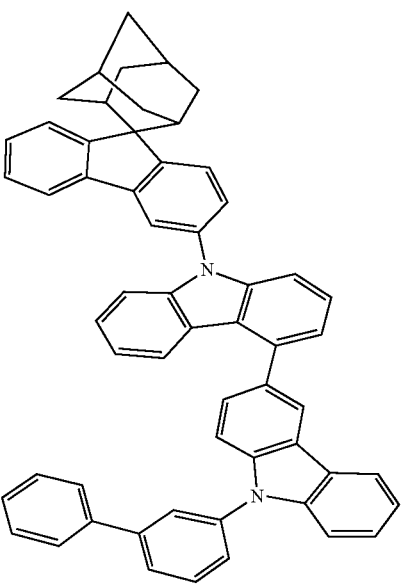

86
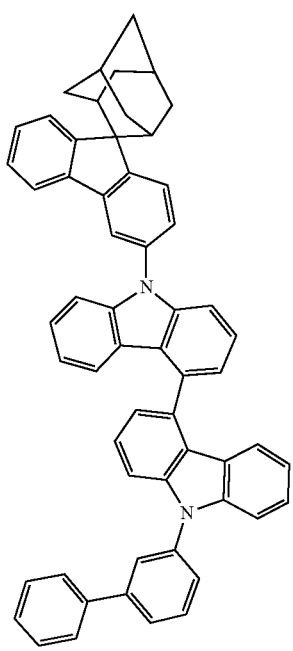
87
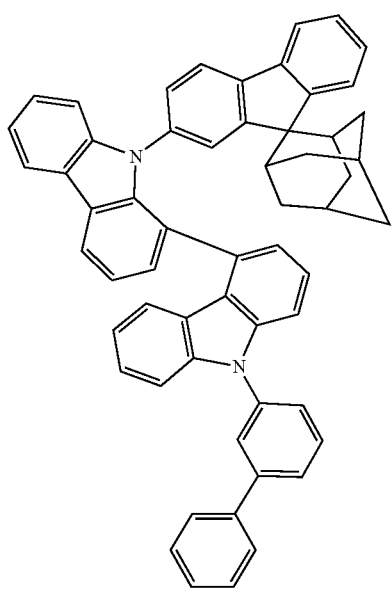
88
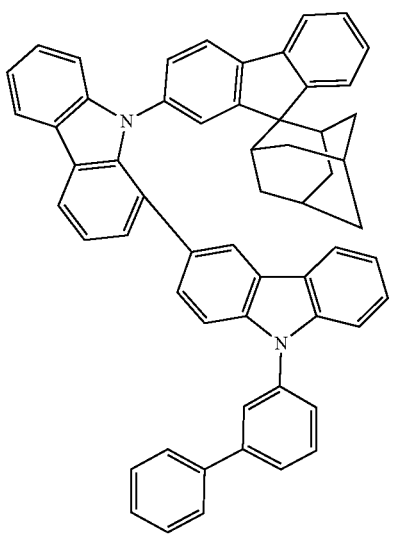
89
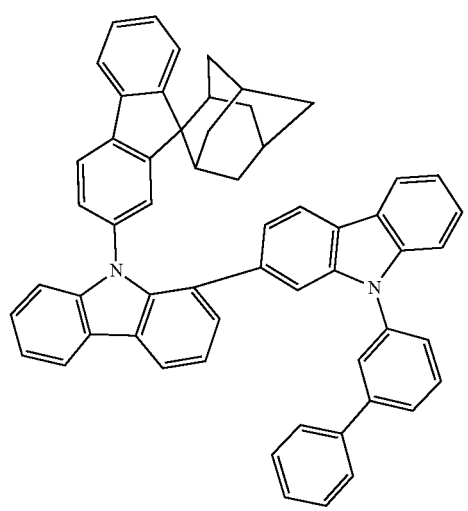
90

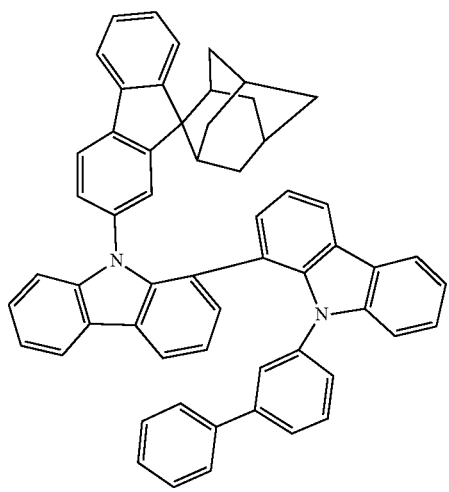
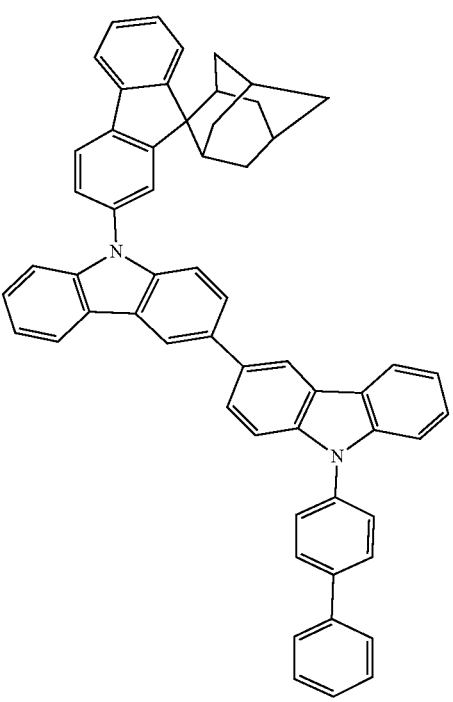
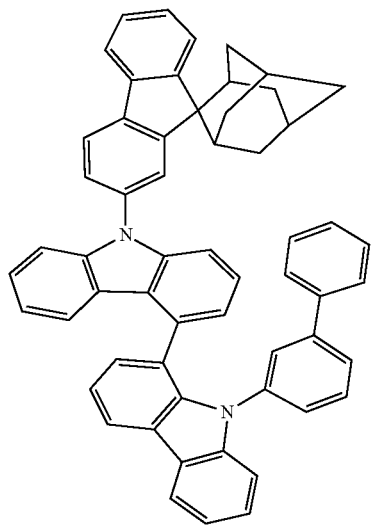
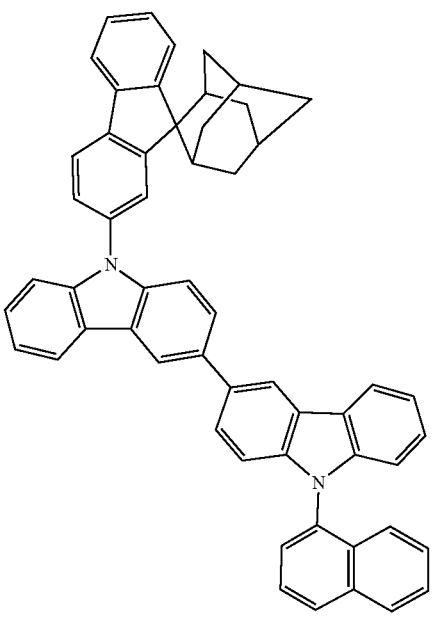

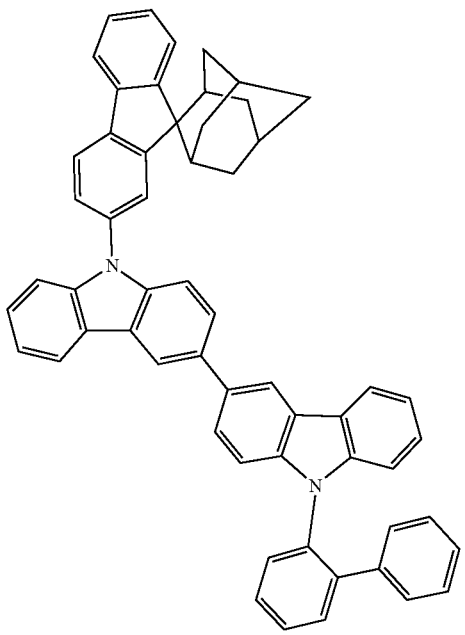
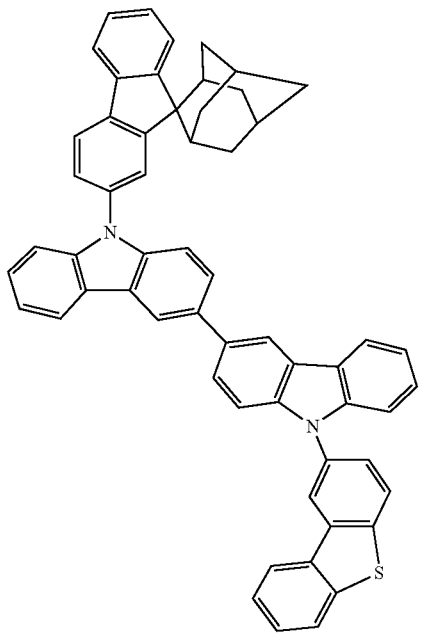
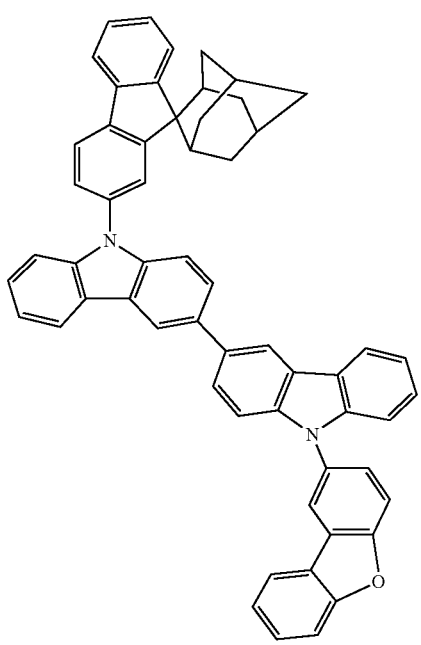
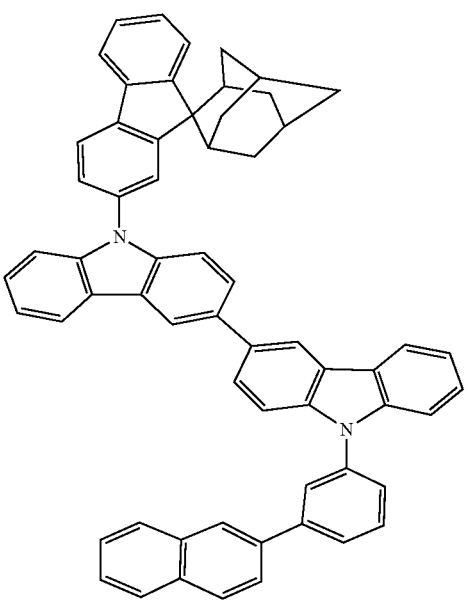

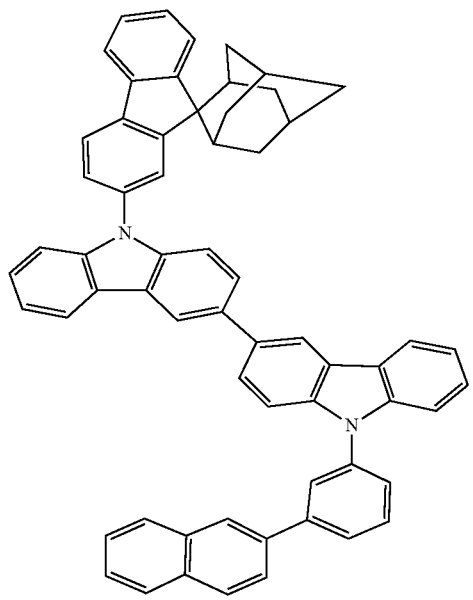
100
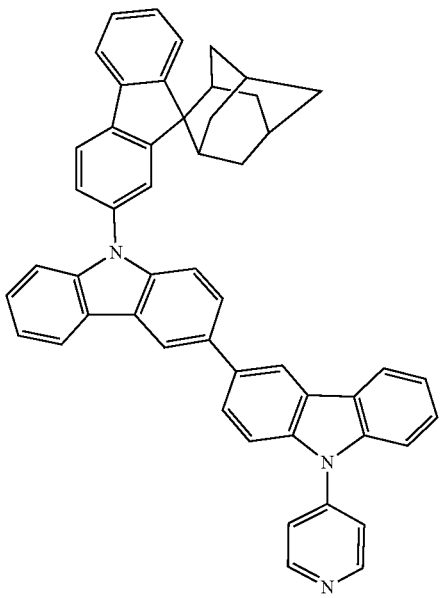
102
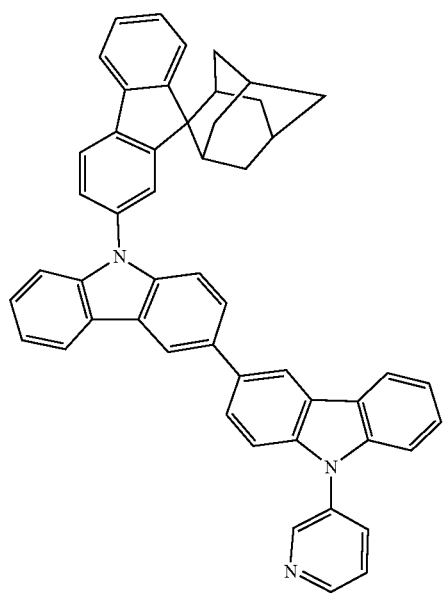
101
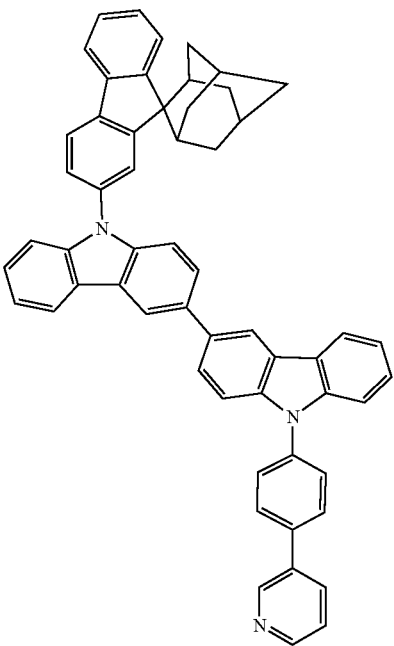
103

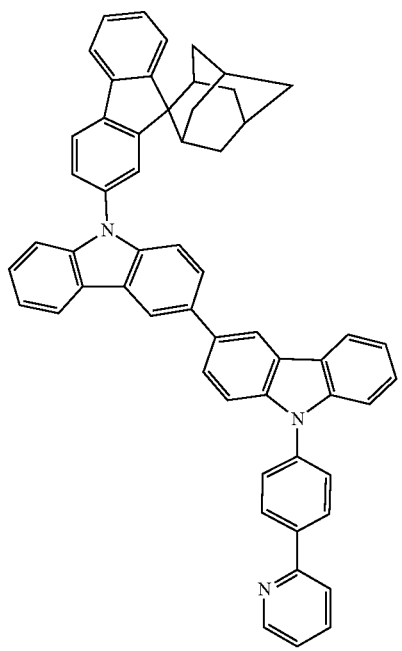
104
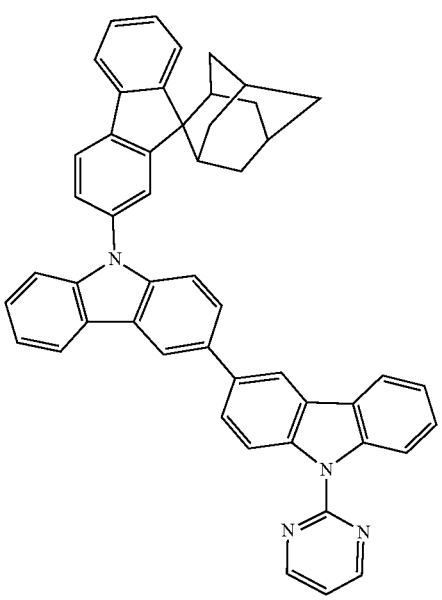
106
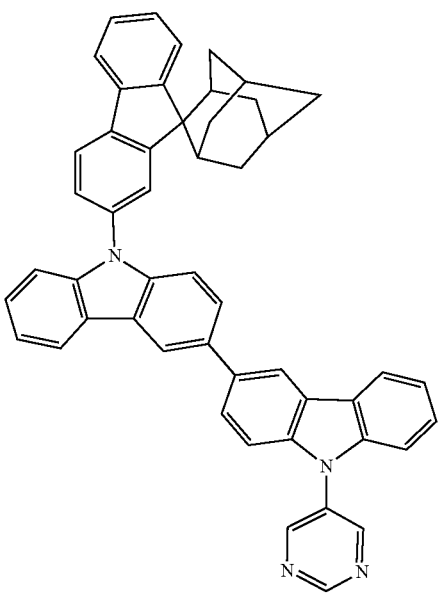
107

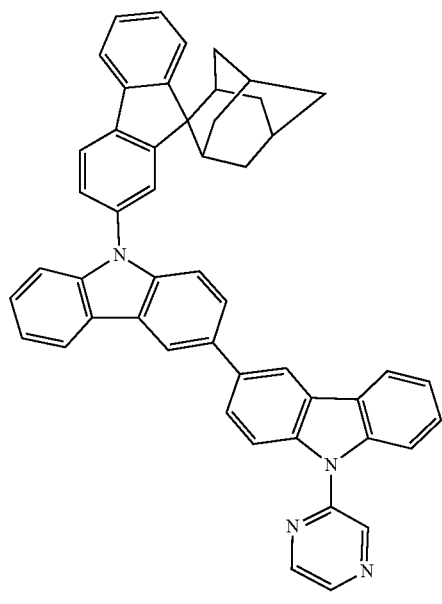
108
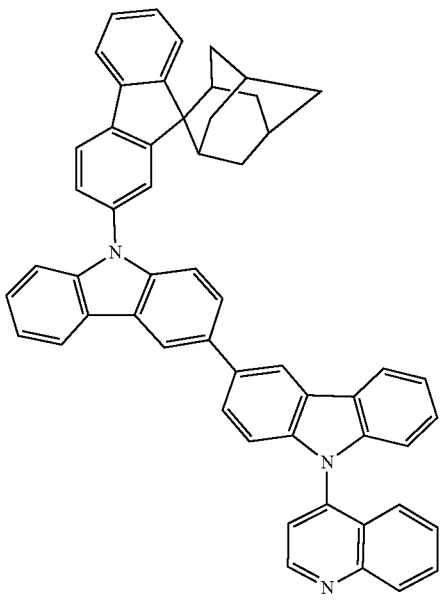
110
109
111

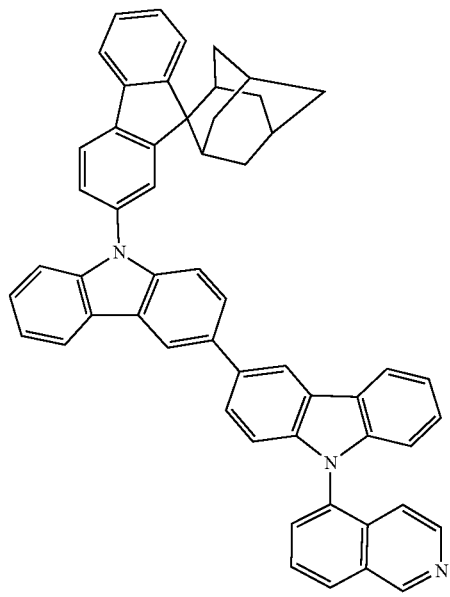
112
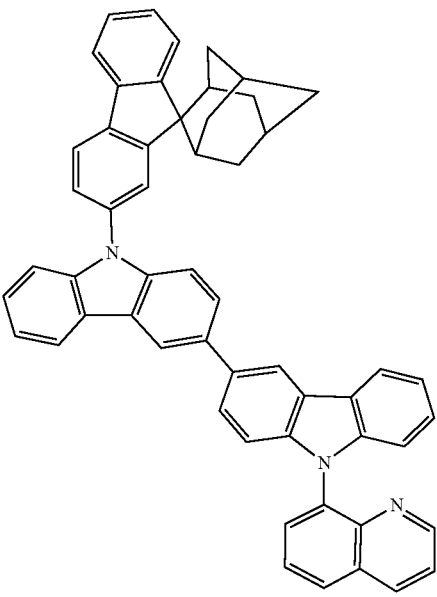
114
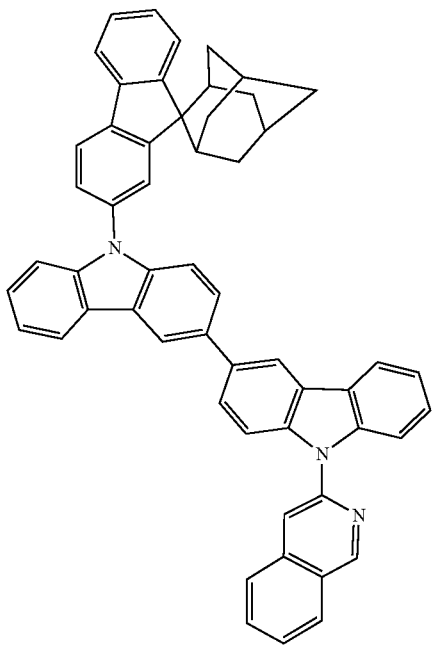
115

116
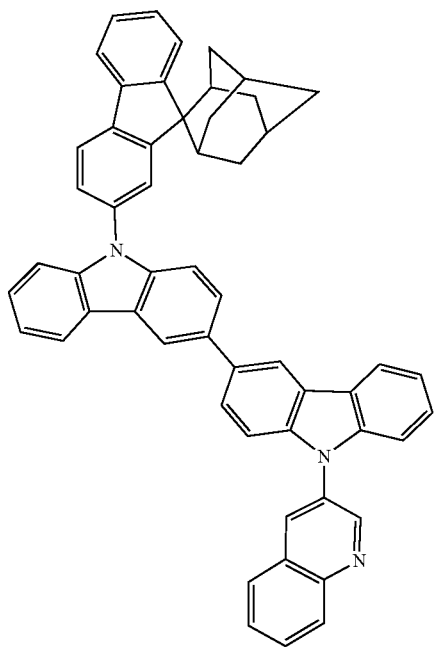
118
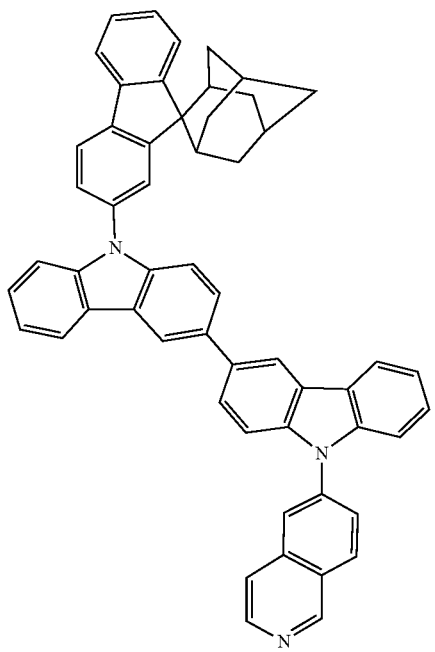
117
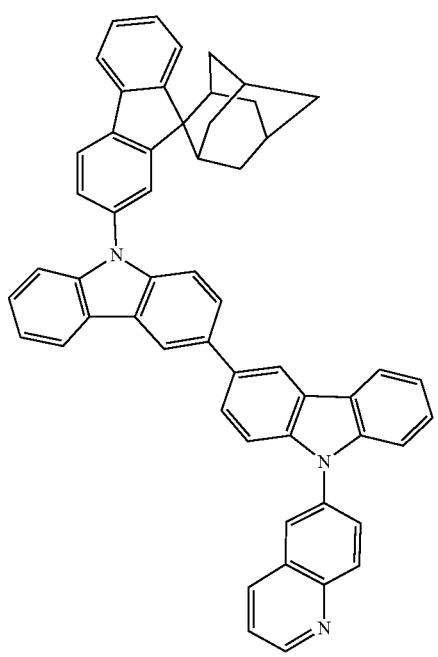
119
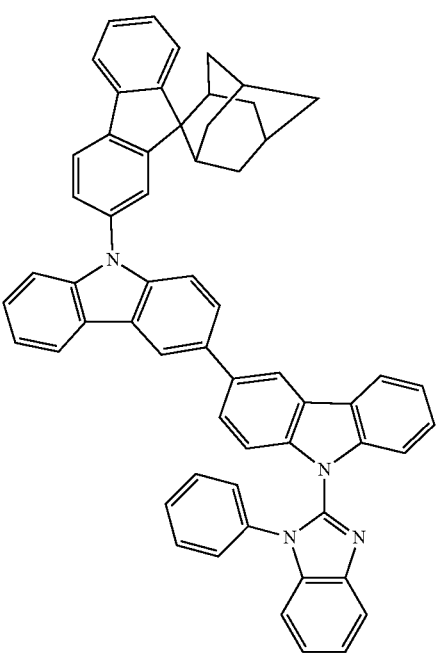

107
-continued
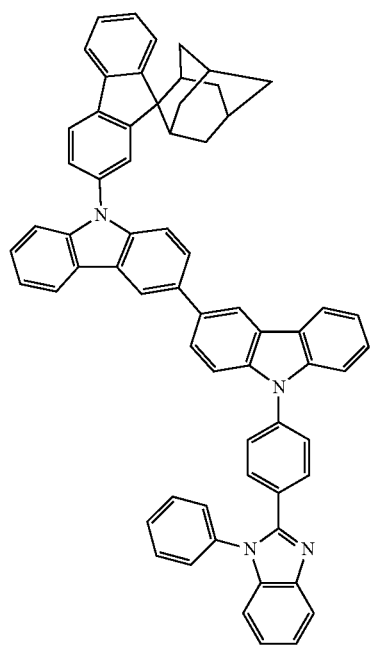
120
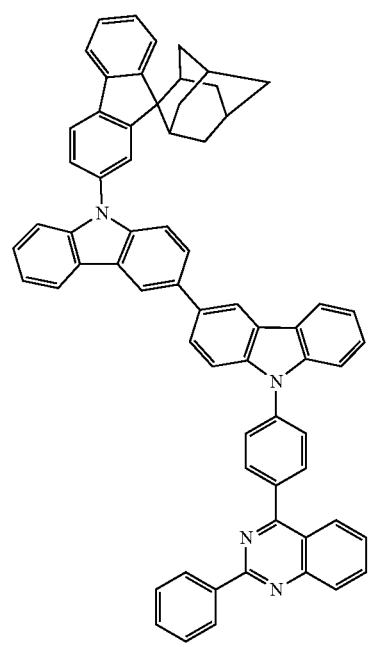
121
108
-continued
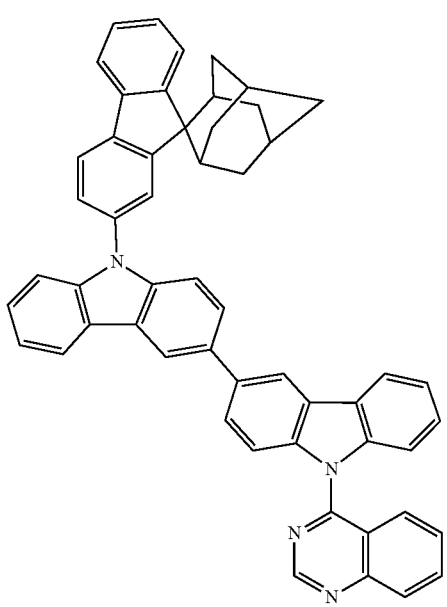
122
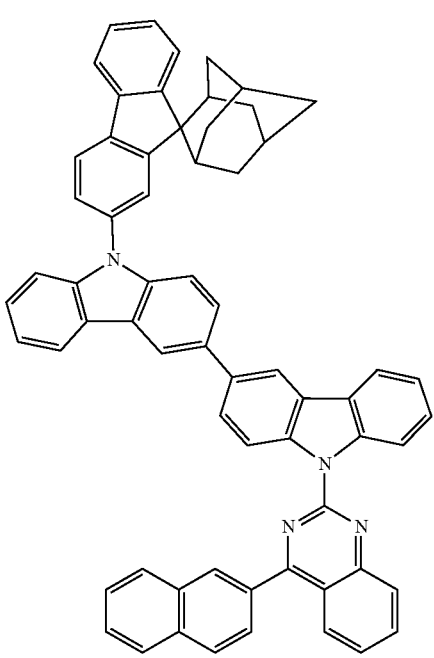
123

124
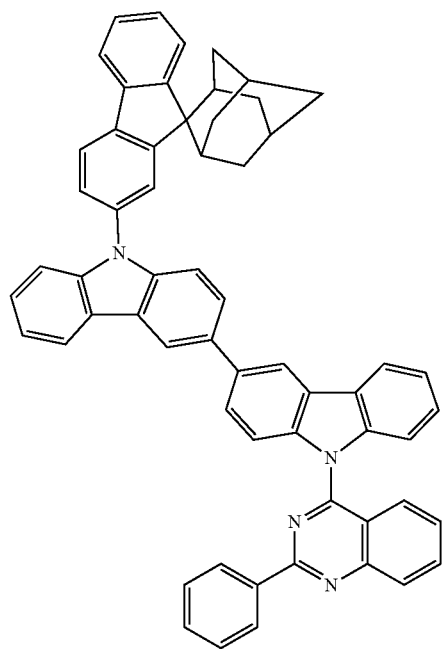
126
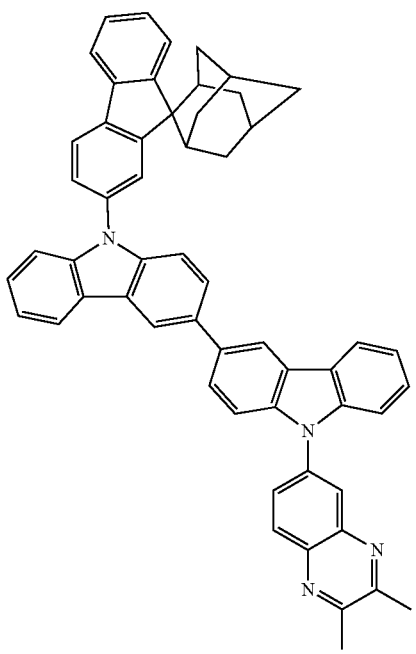
125
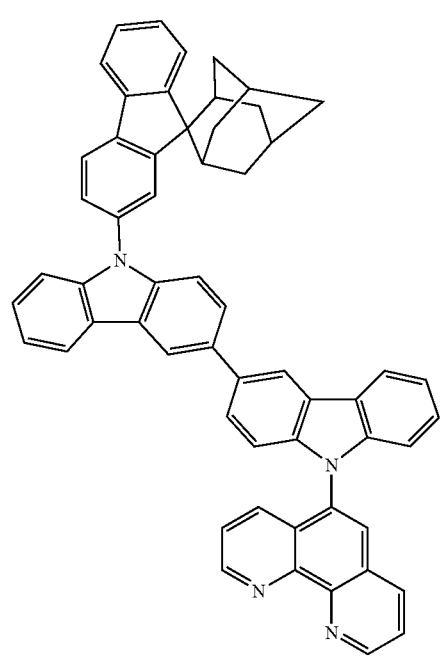
127
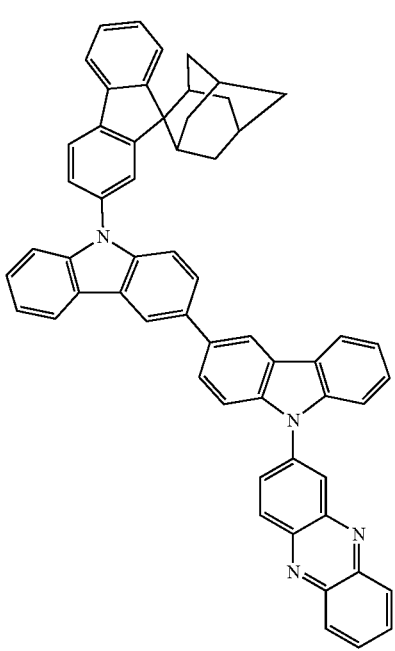

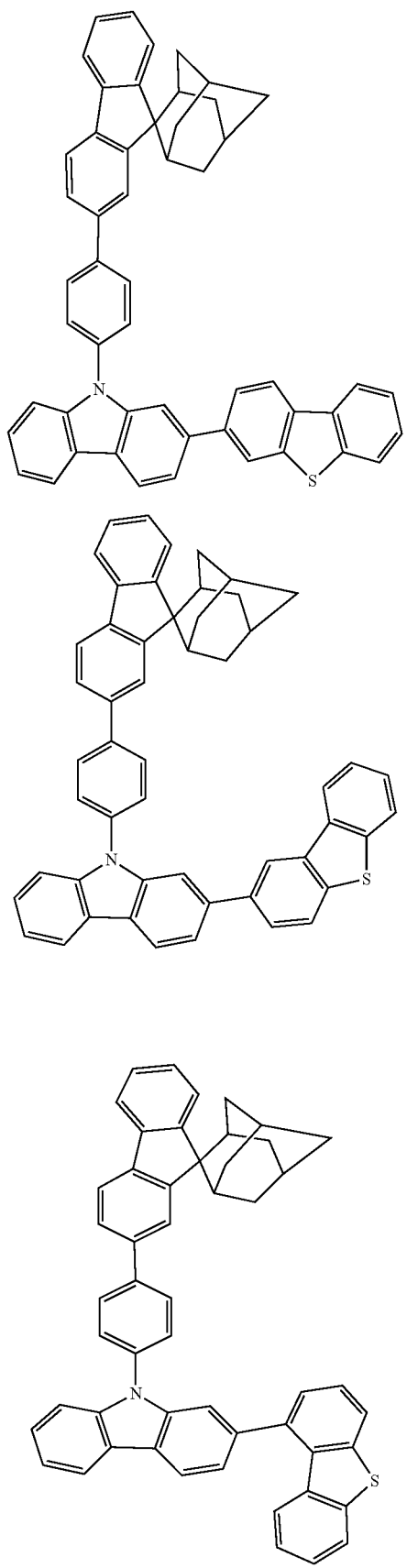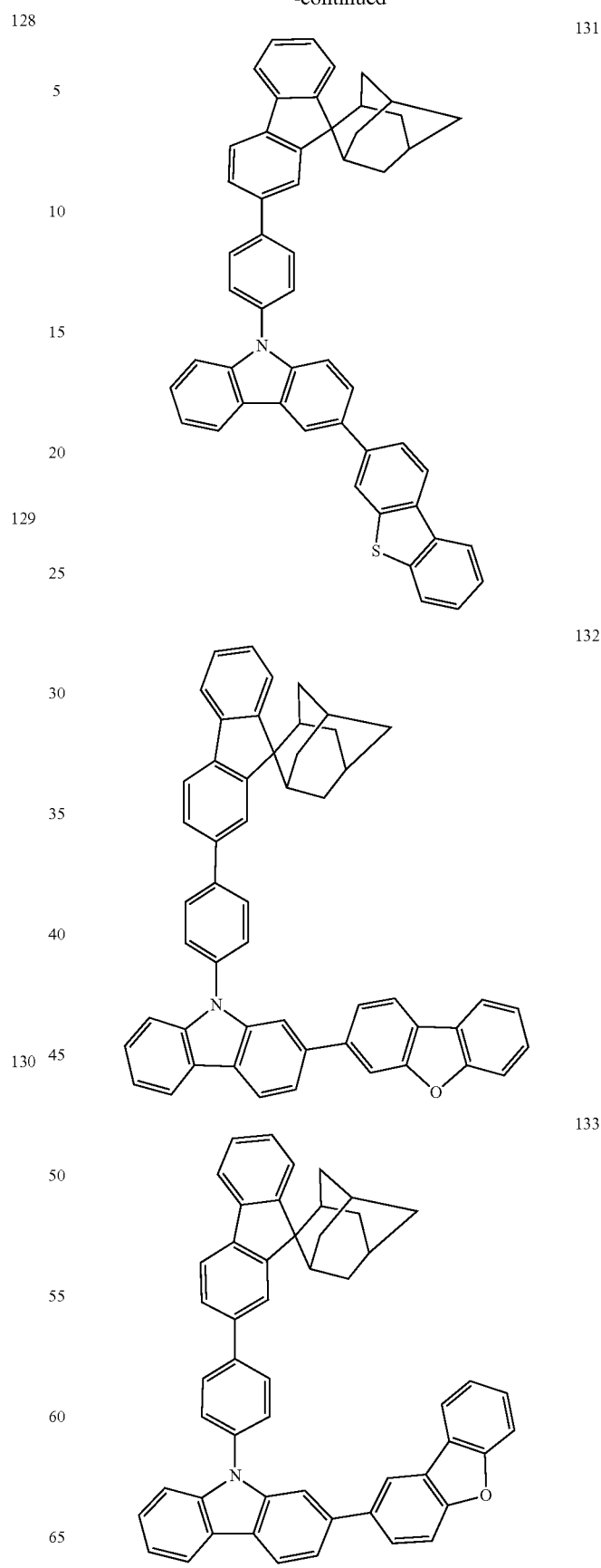

113 114
-continued -continued
134 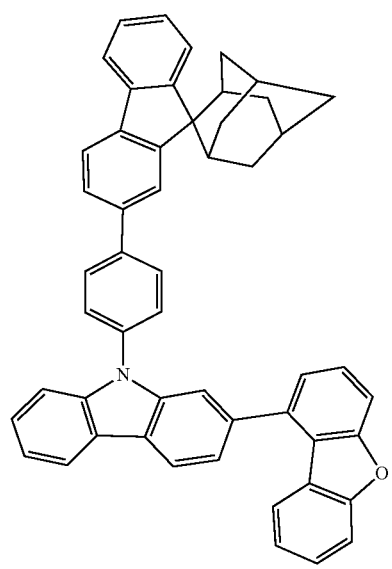
136 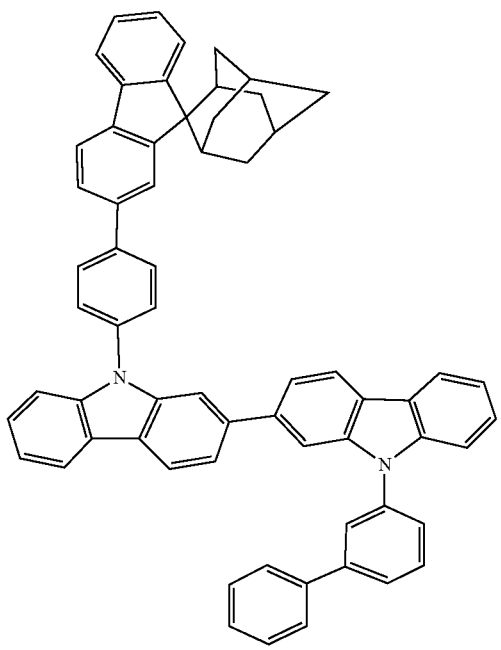
135 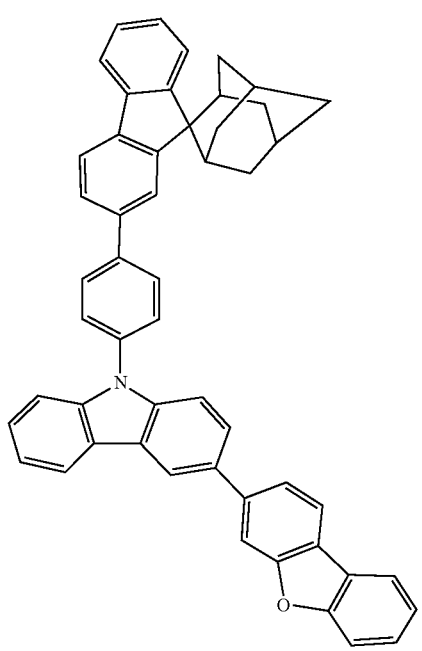
137 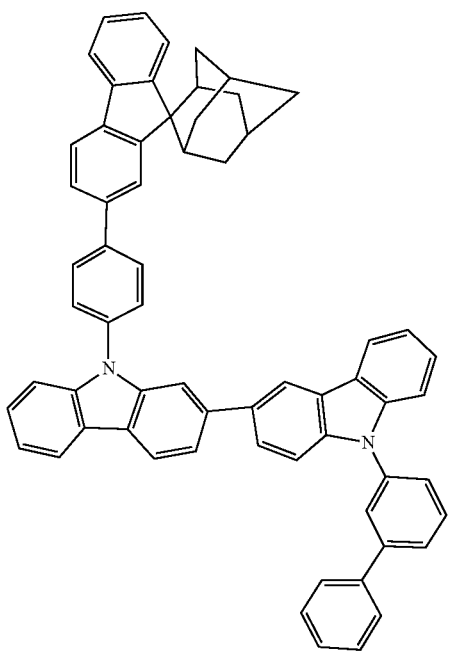

138
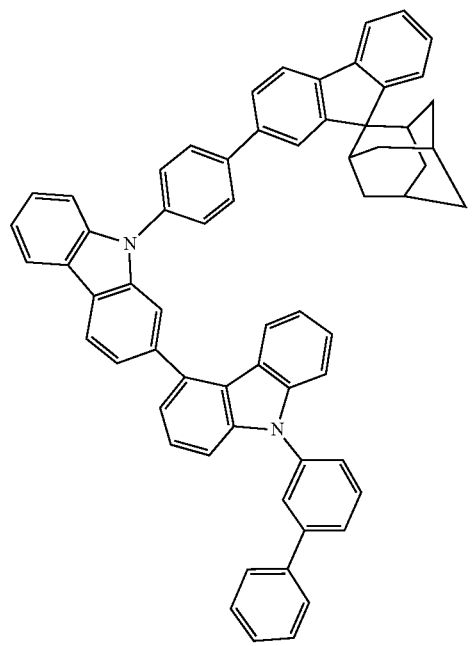
139
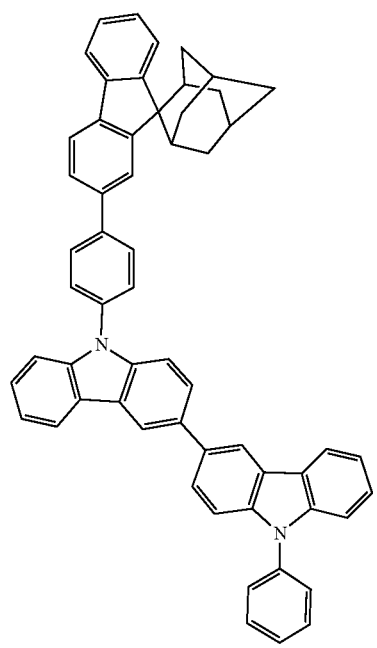
140
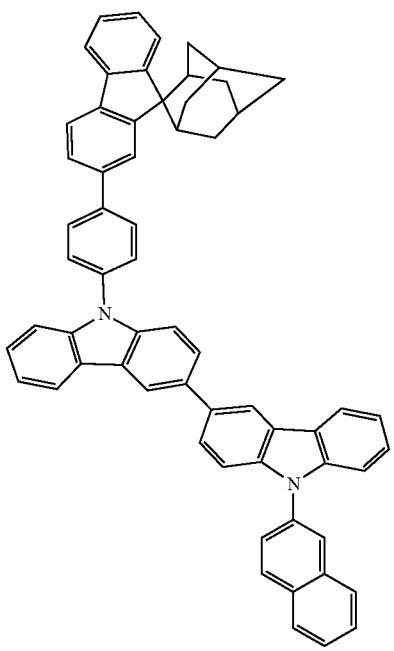
141
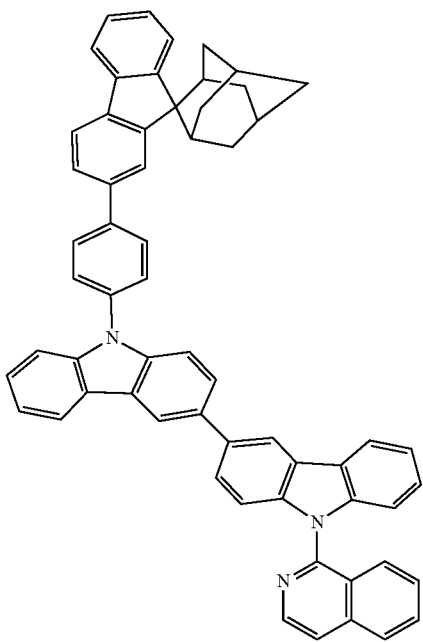

142
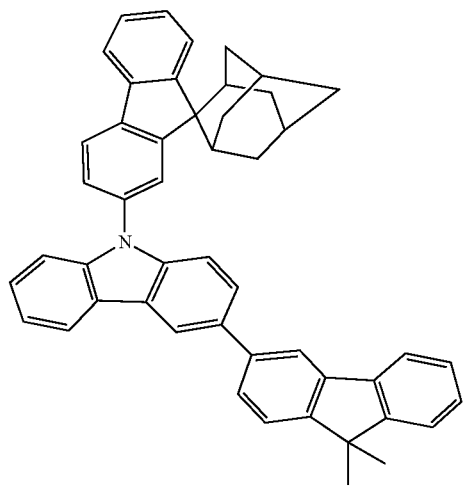
143
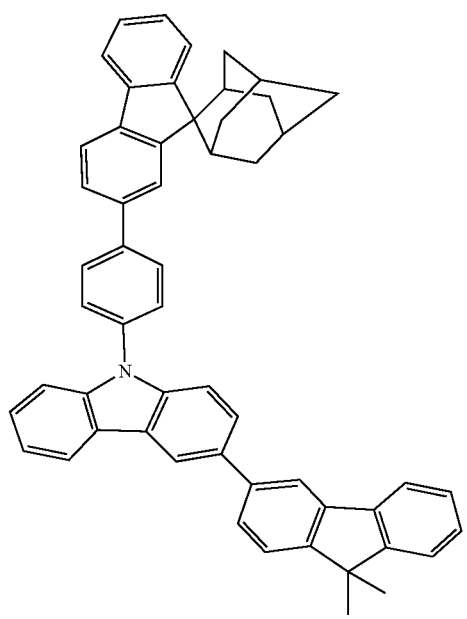
144
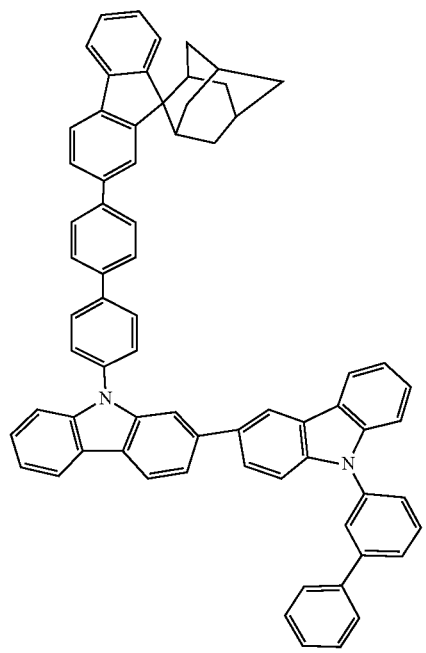
145
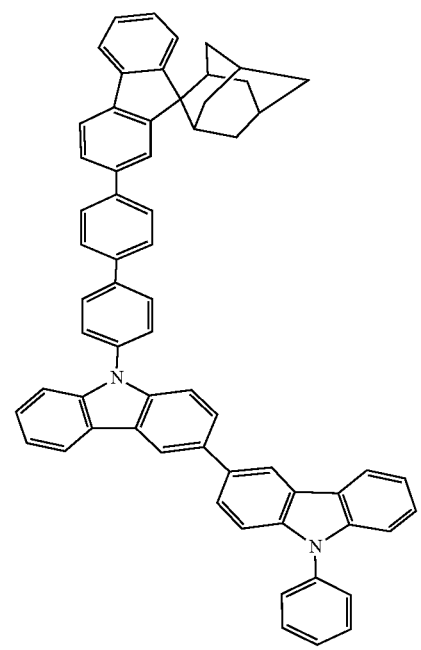

146
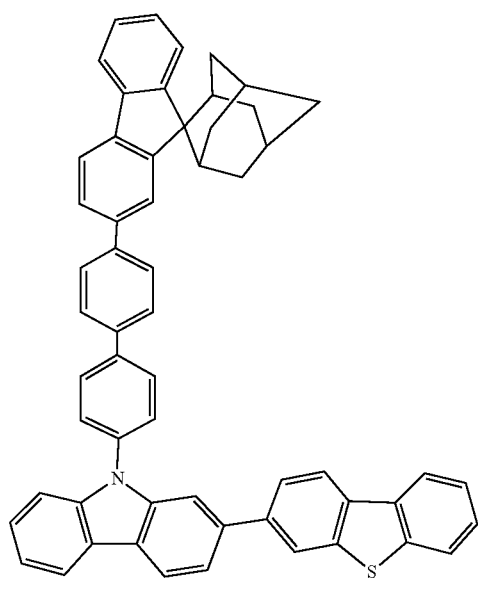
147
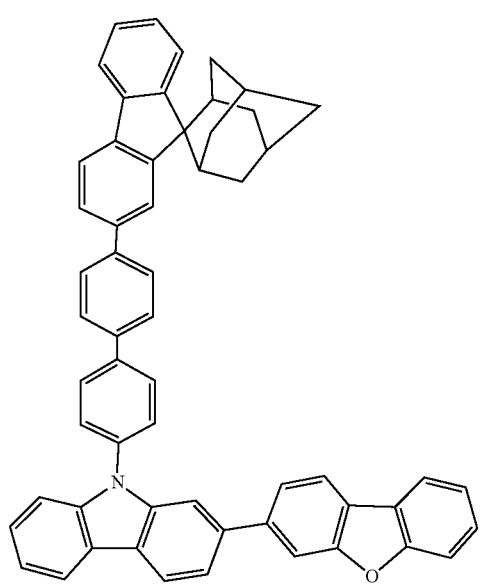
148
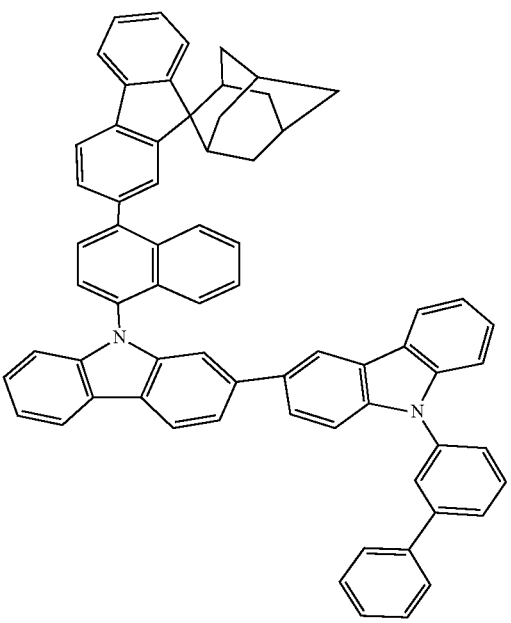
149
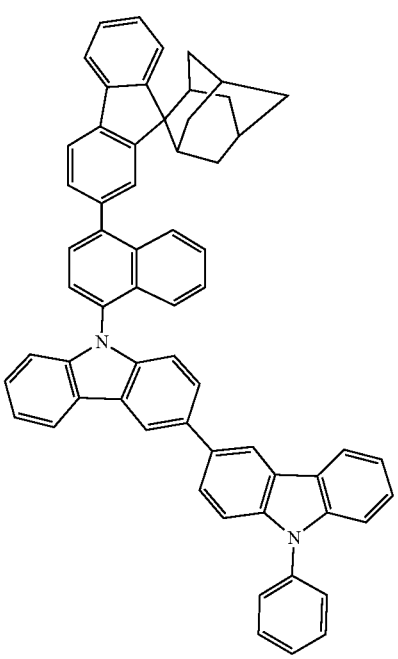

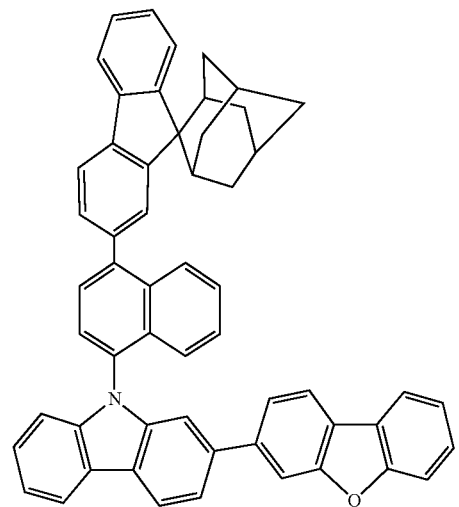
150
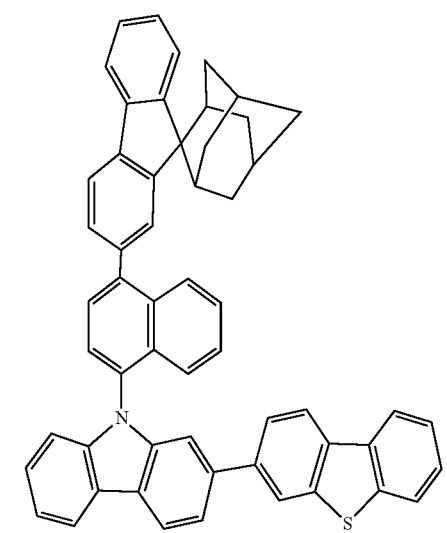
151
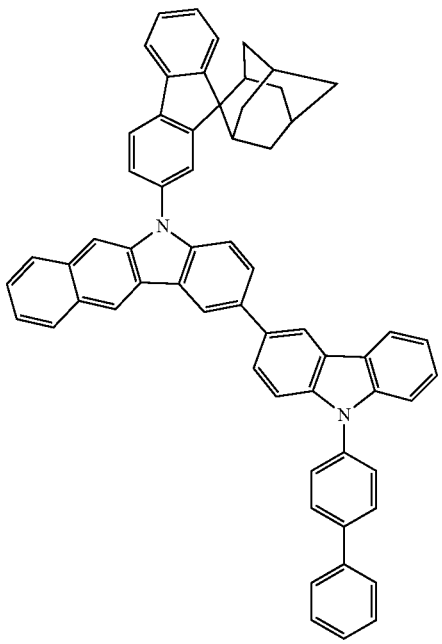
153
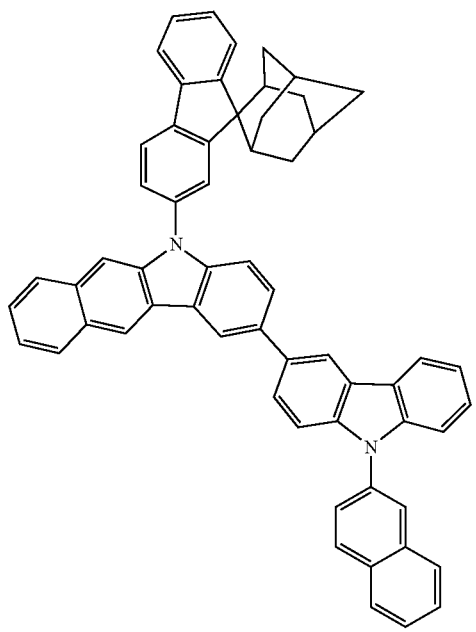
154

123
-continued
155
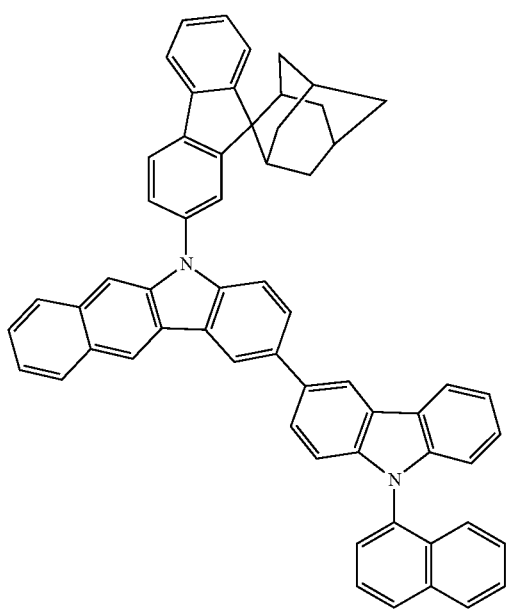
156
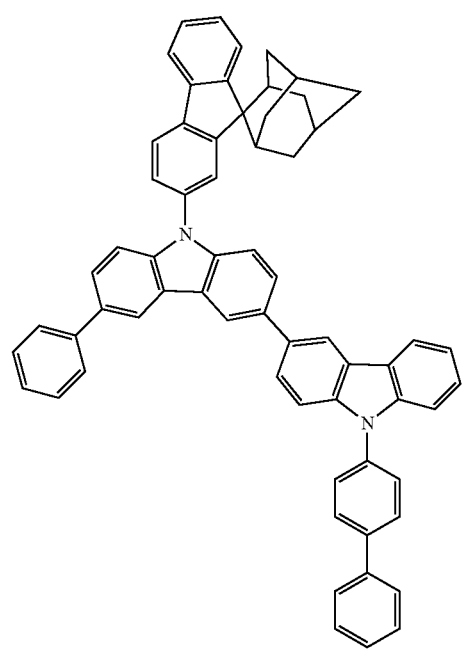
124
-continued
157
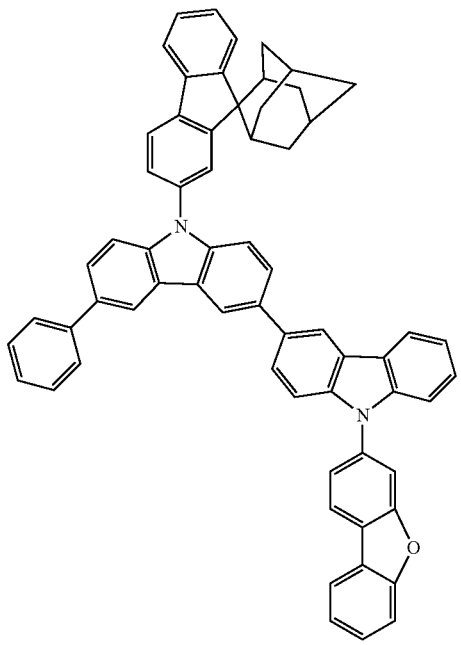
158
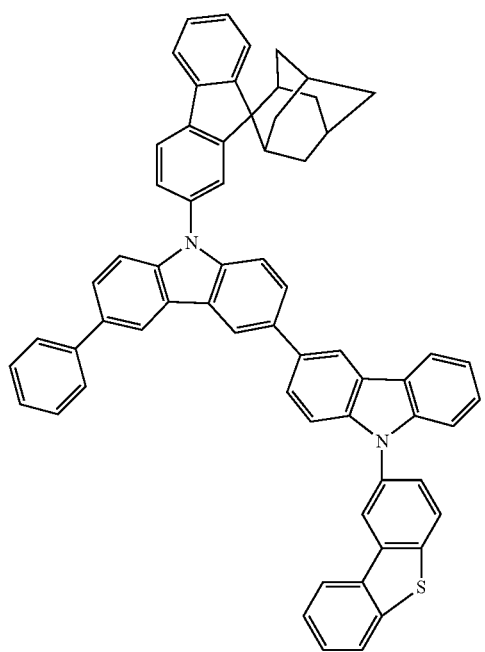

125
-continued
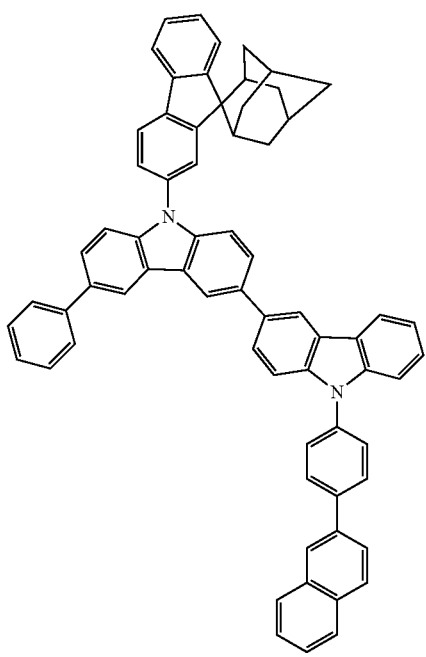
159
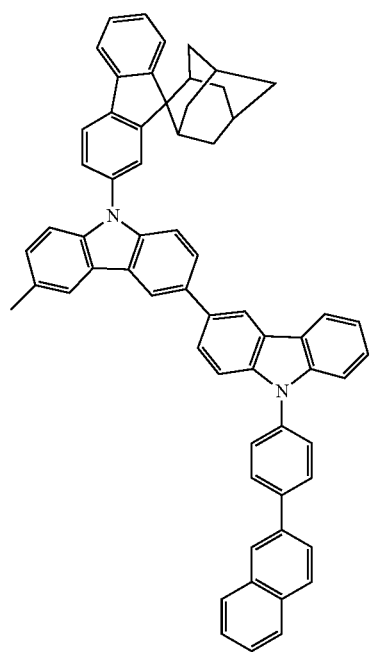
160
126
-continued
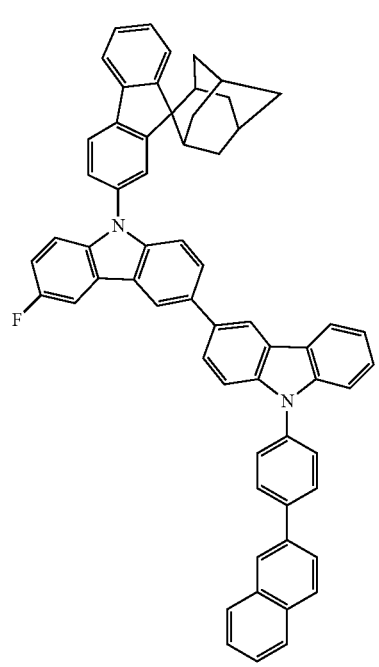
161
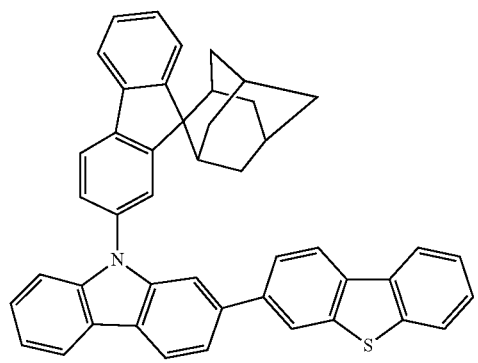
162
163

164
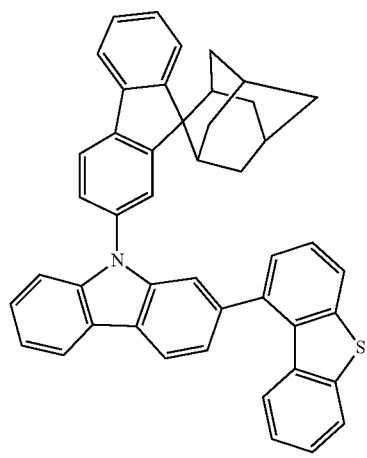
165
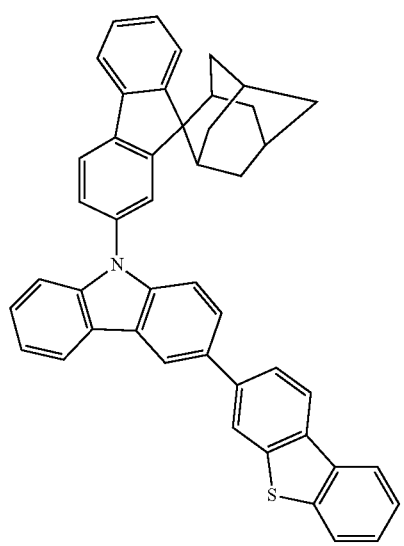
166
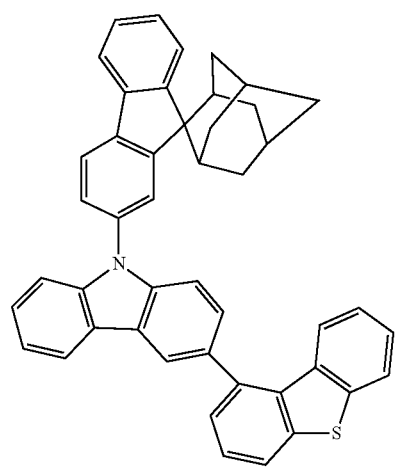
167
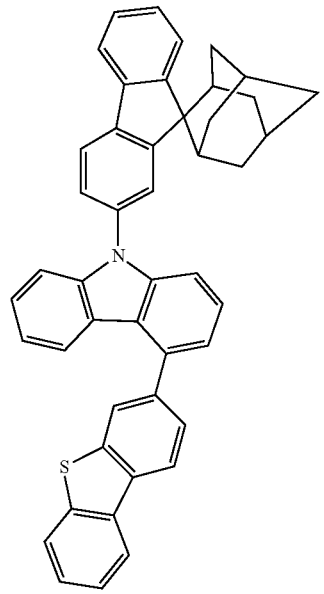
168
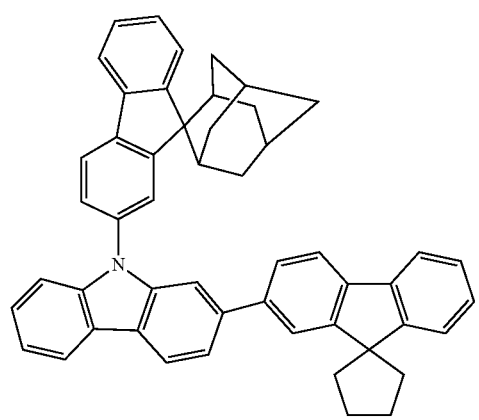
169
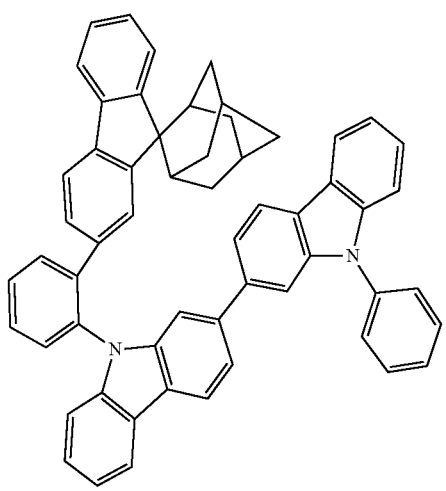

129 -continued
170
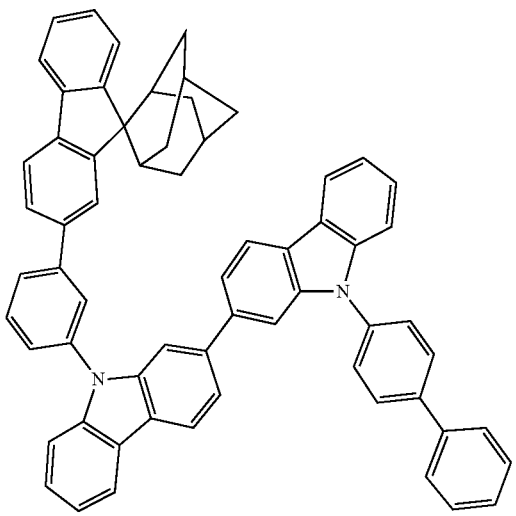
171
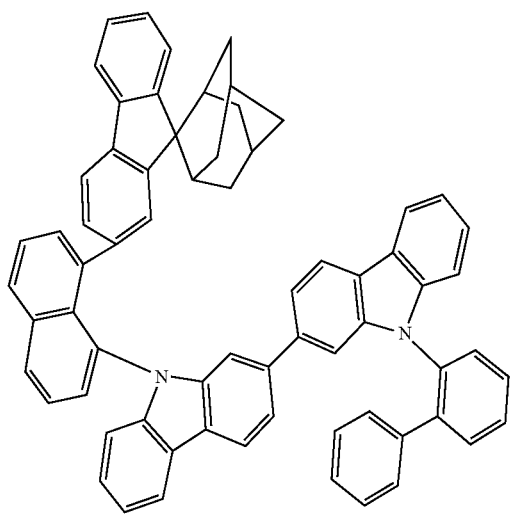
130 -continued
172
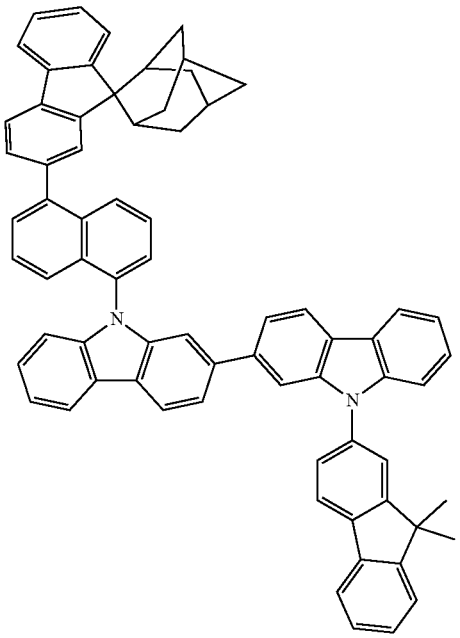
173
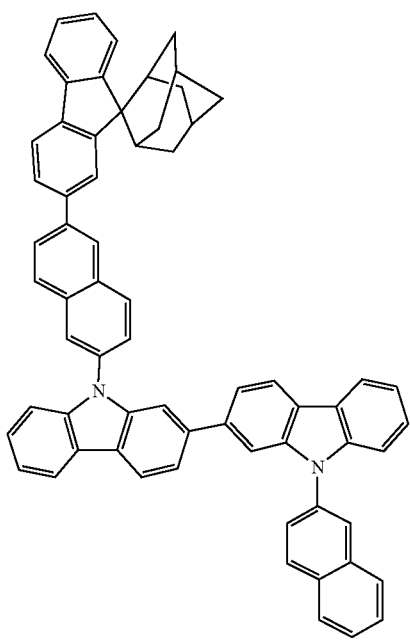

174
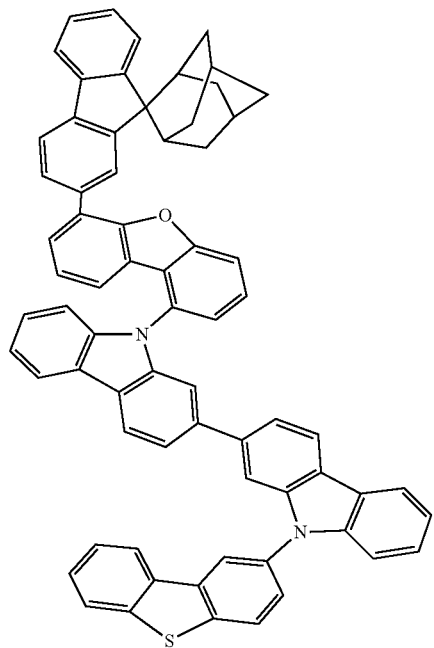
175
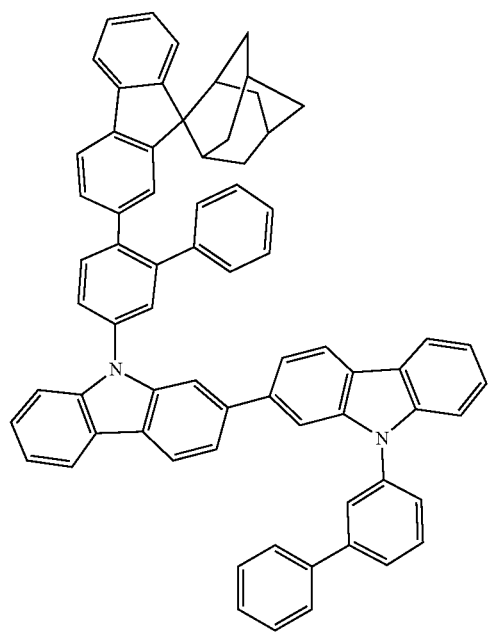
176
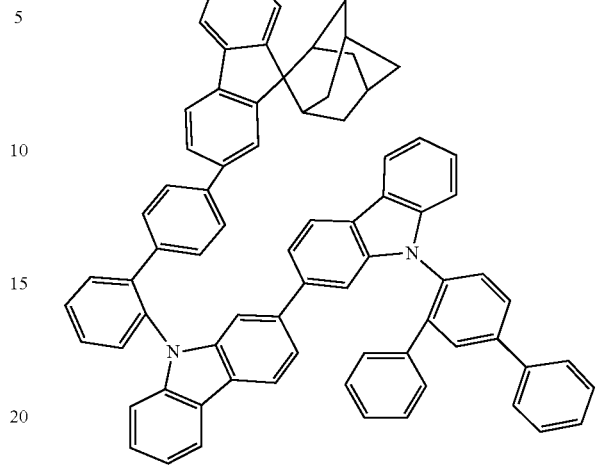
177
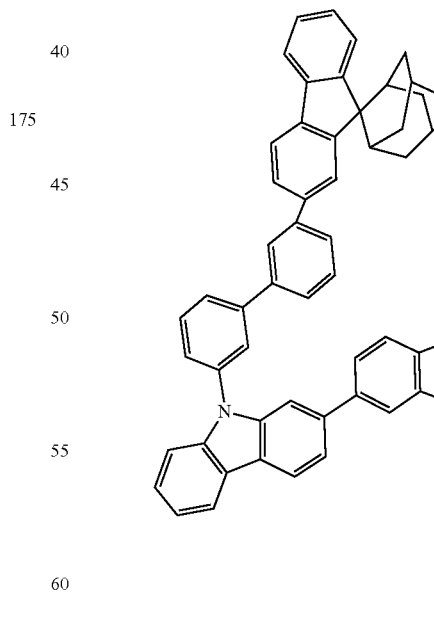

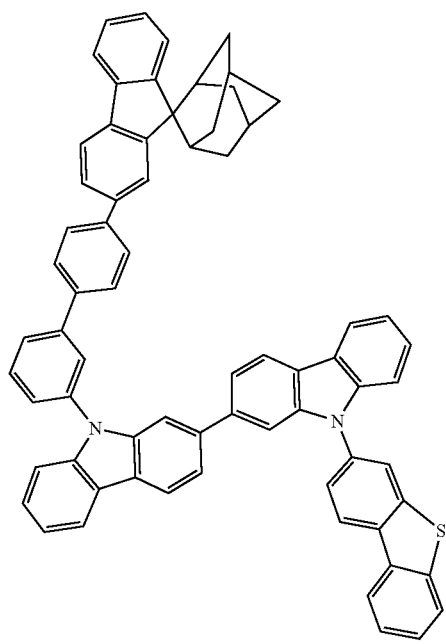
178
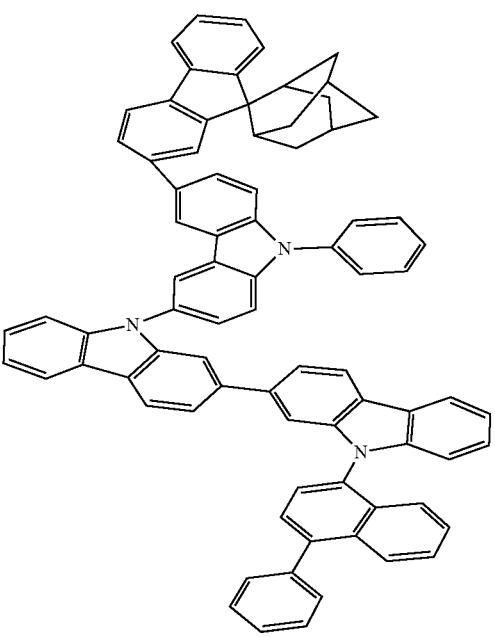
180
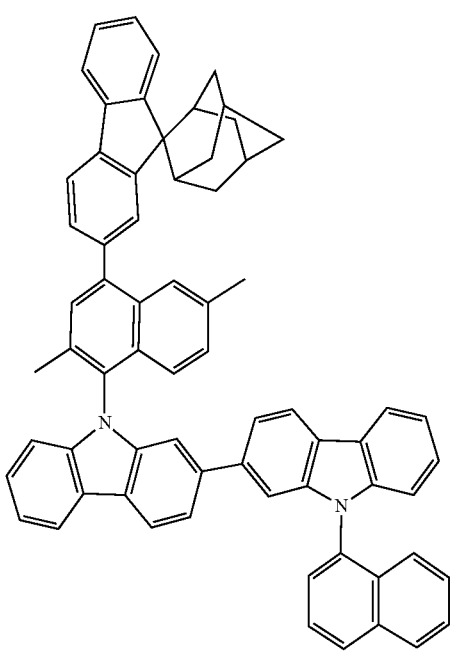
179
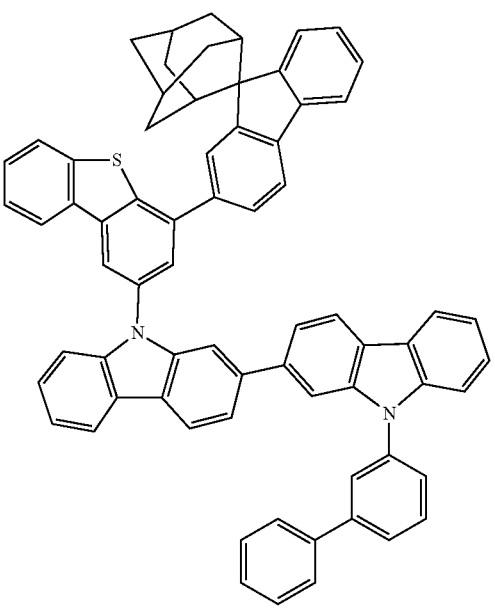
181

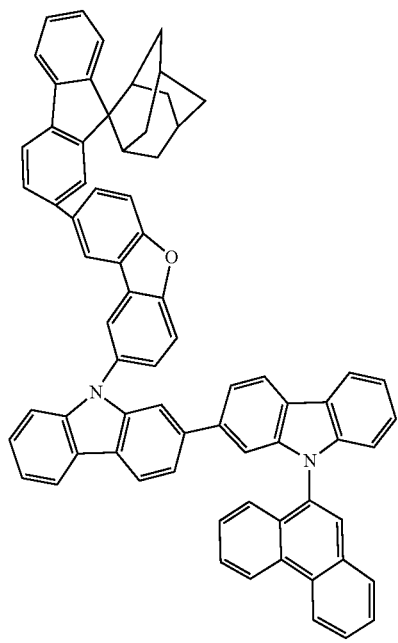
182
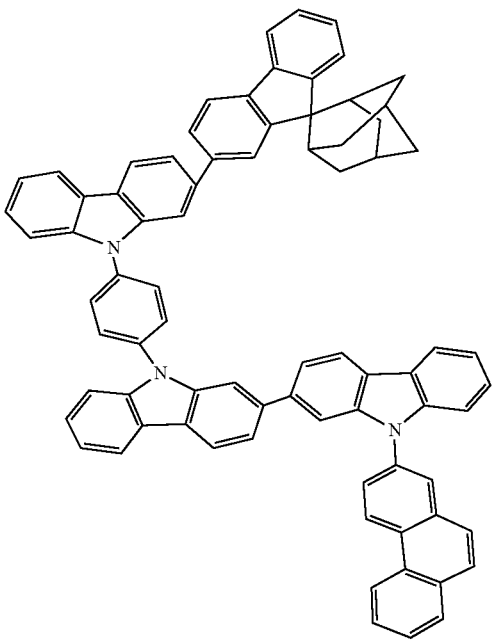
184
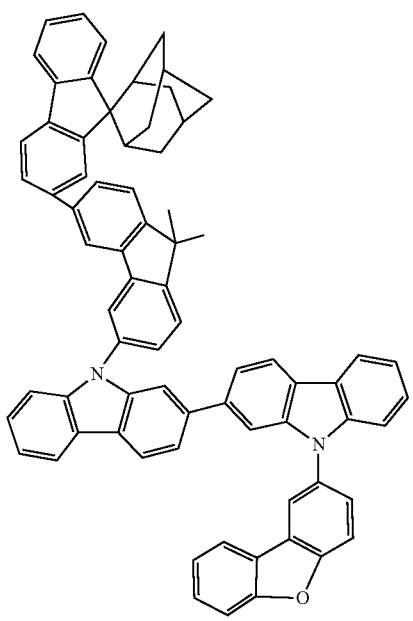
183
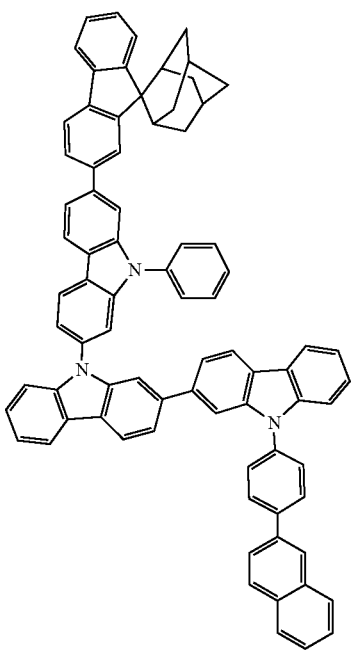
185

137
-continued
186
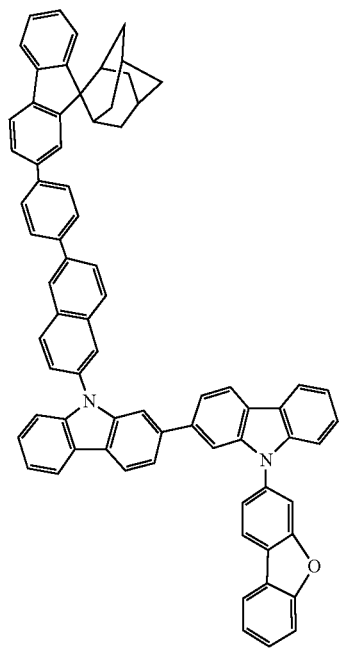
187
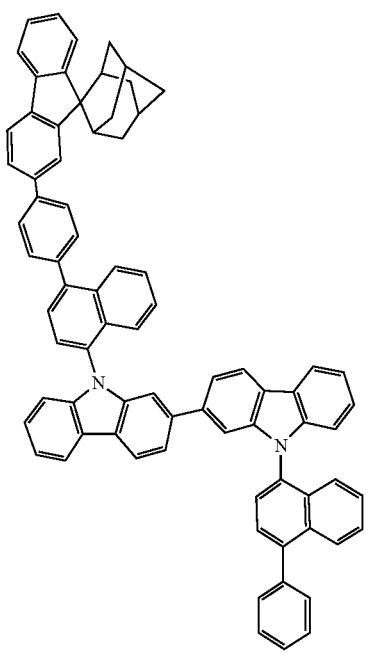
138
-continued
188
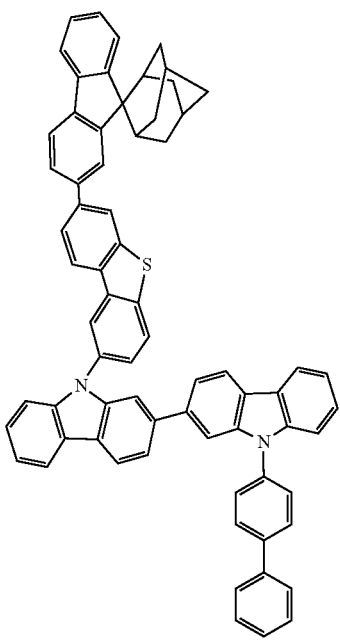
189
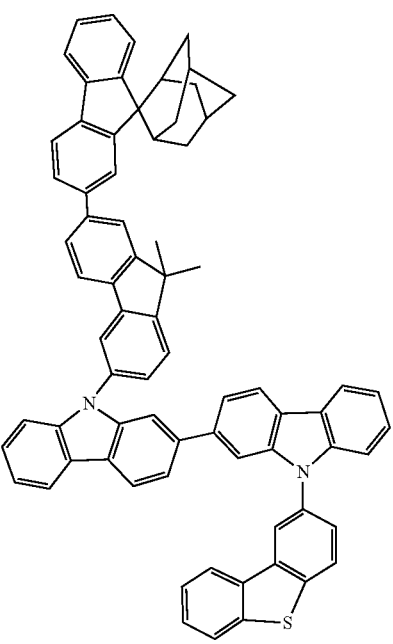

190
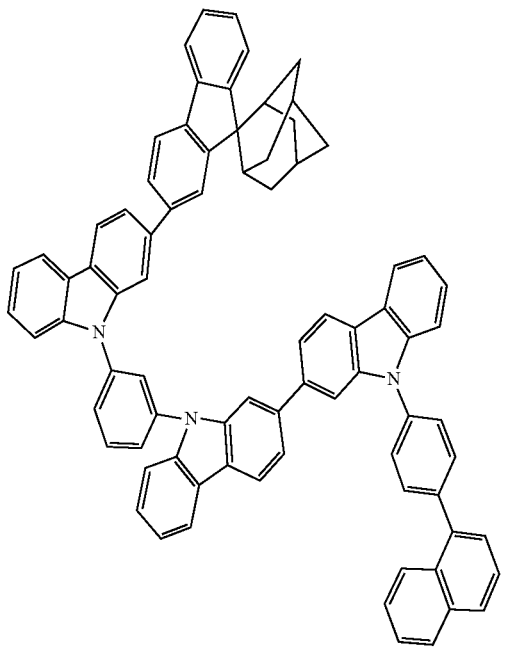
192
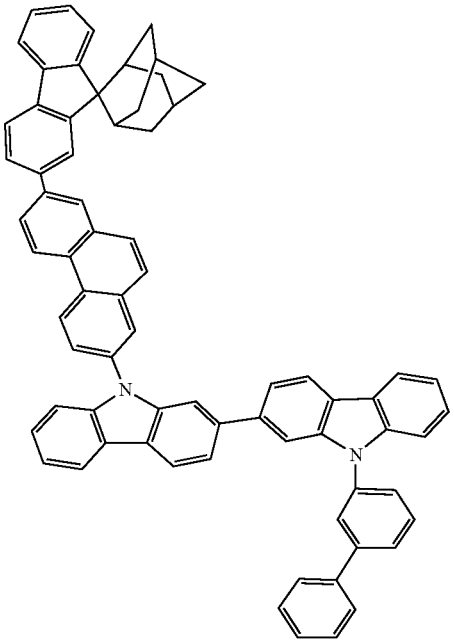
191
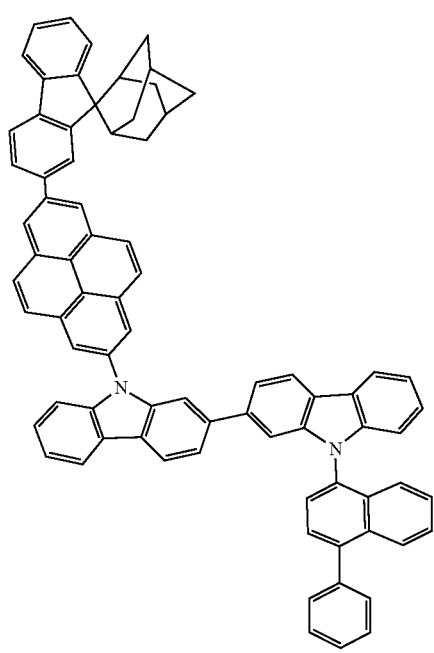
193
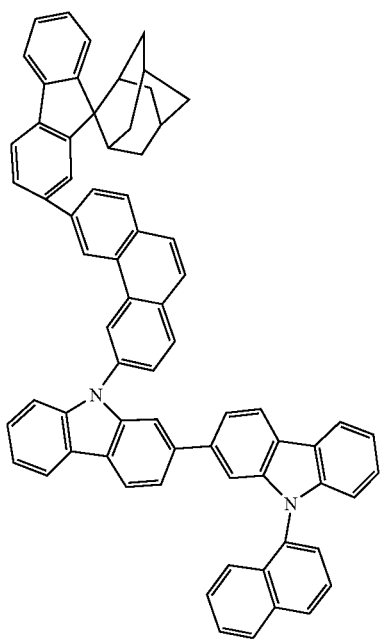

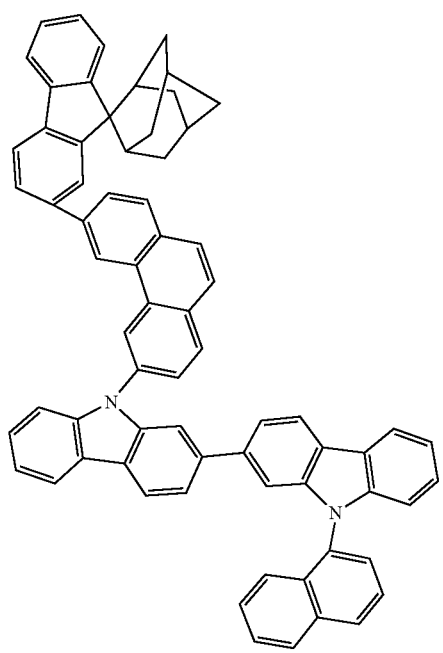
194
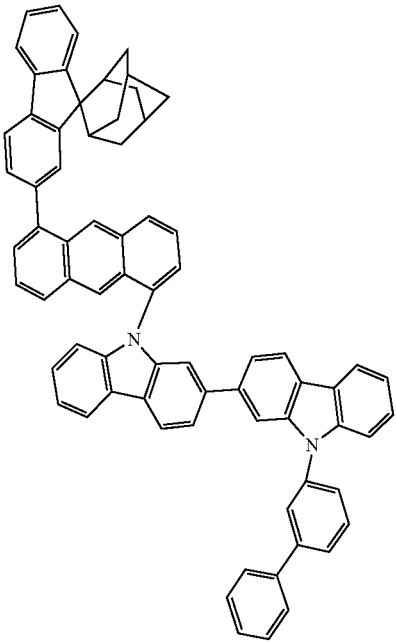
196
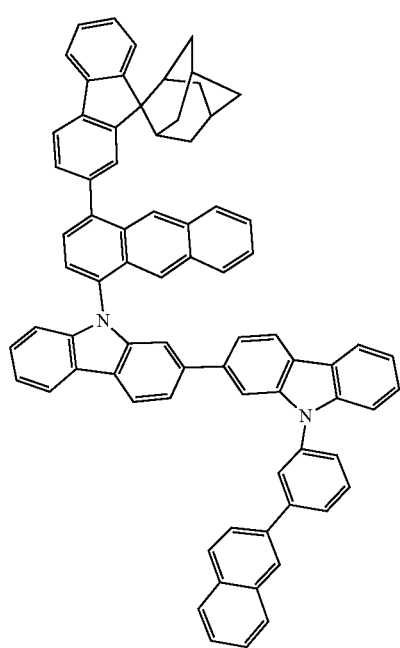
195
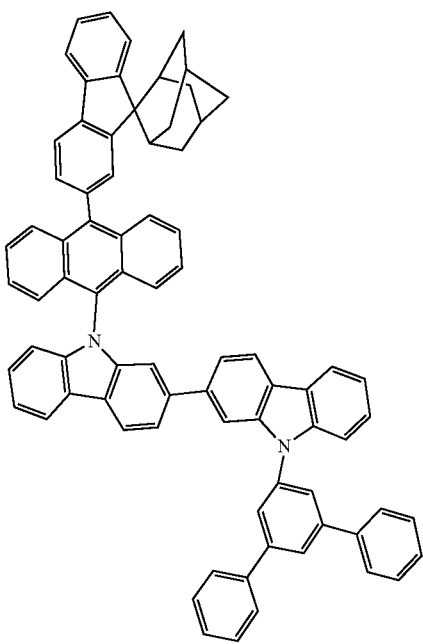
197

198
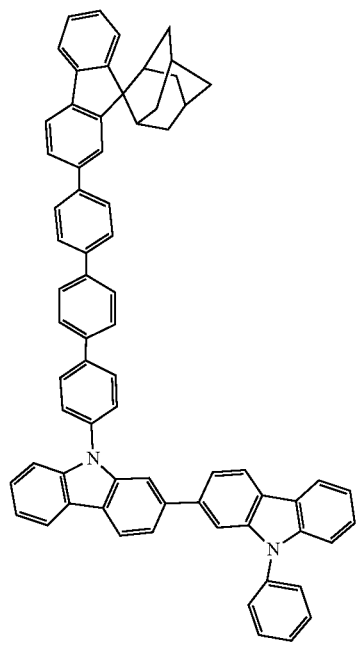
199
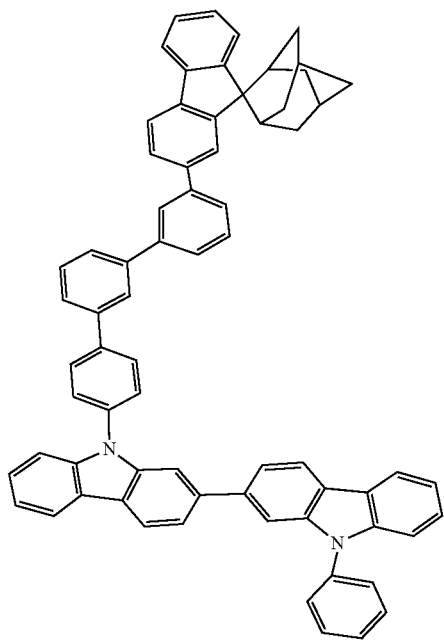
200
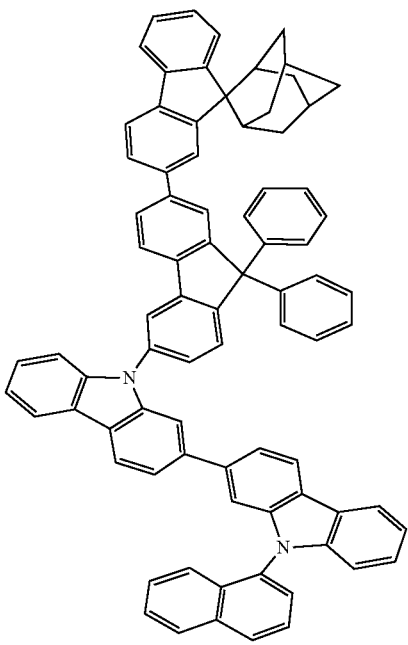
201
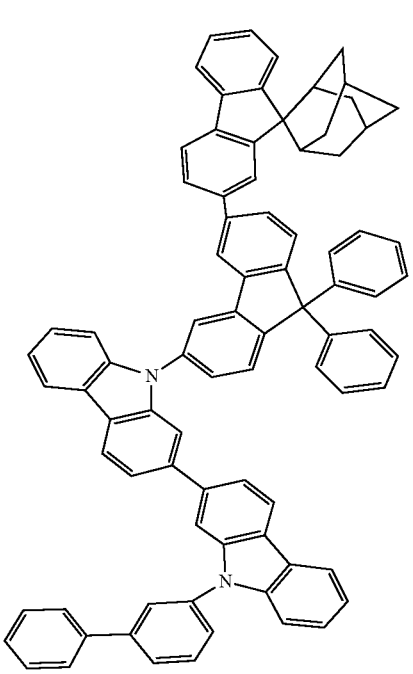

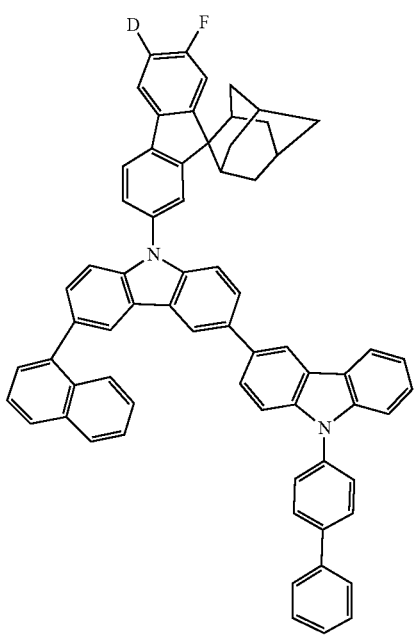
202
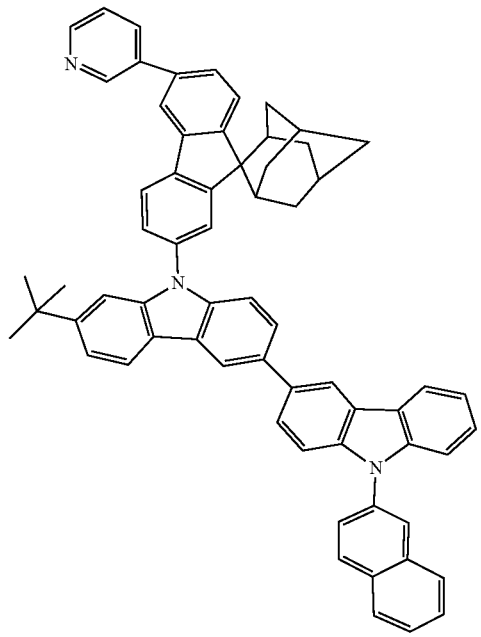
204
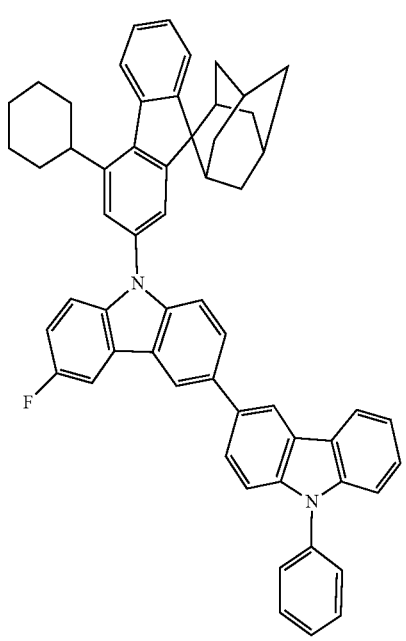
203
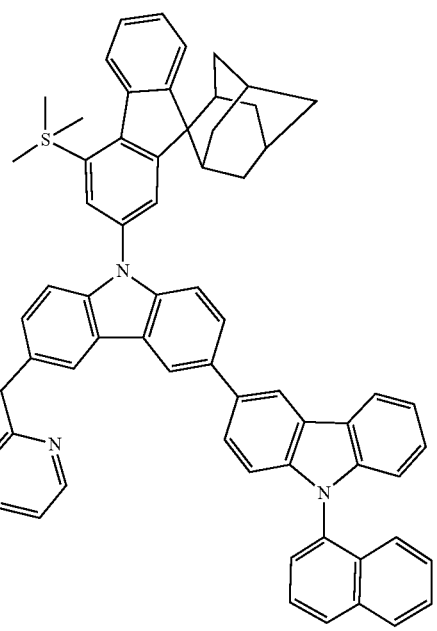
205

206
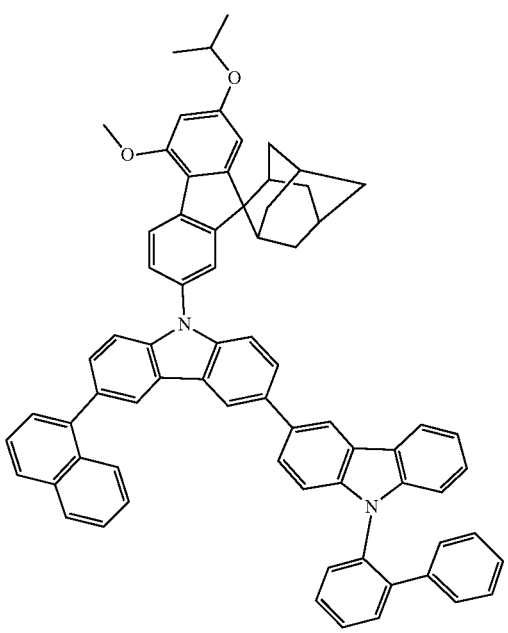
208
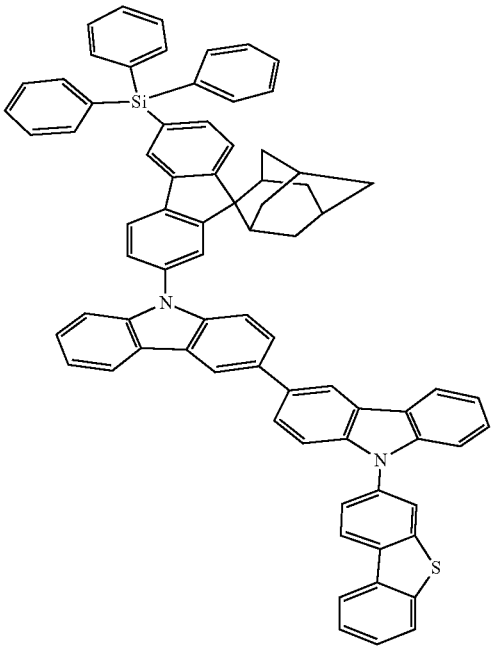
207
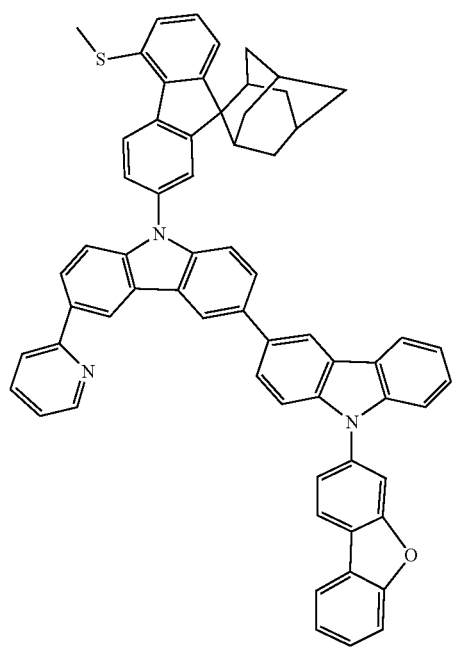
209
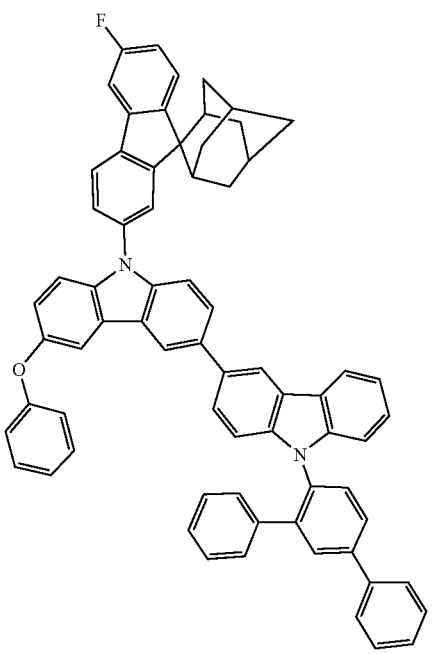

210
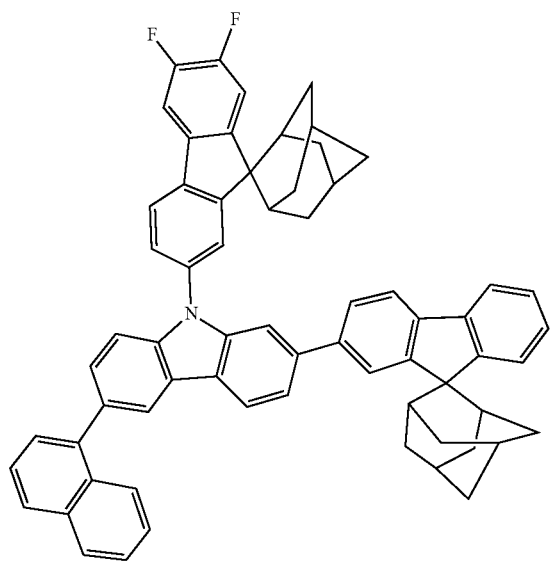
211
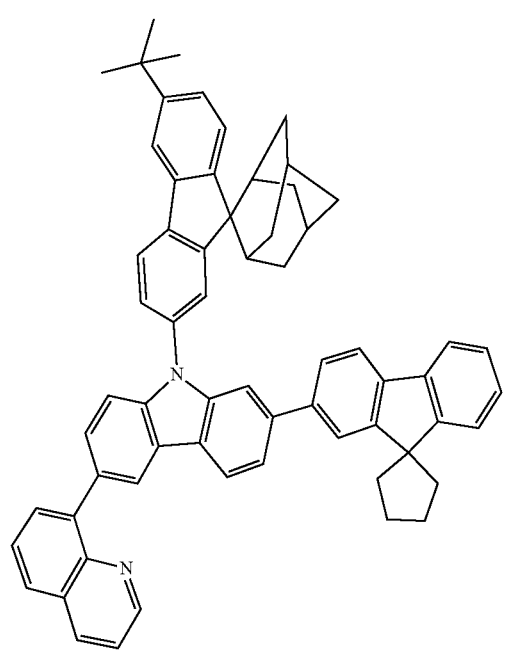
212
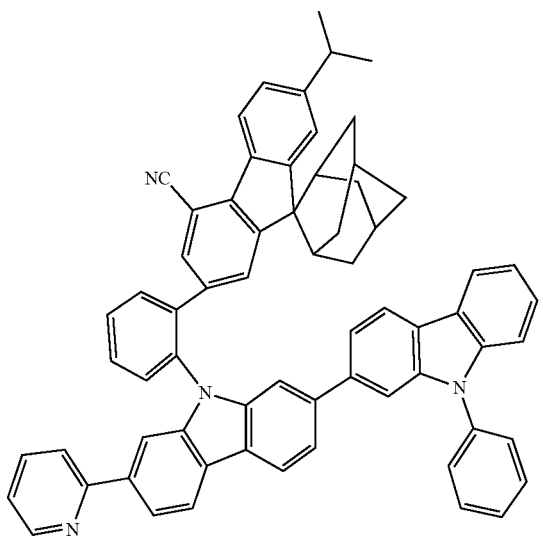
213
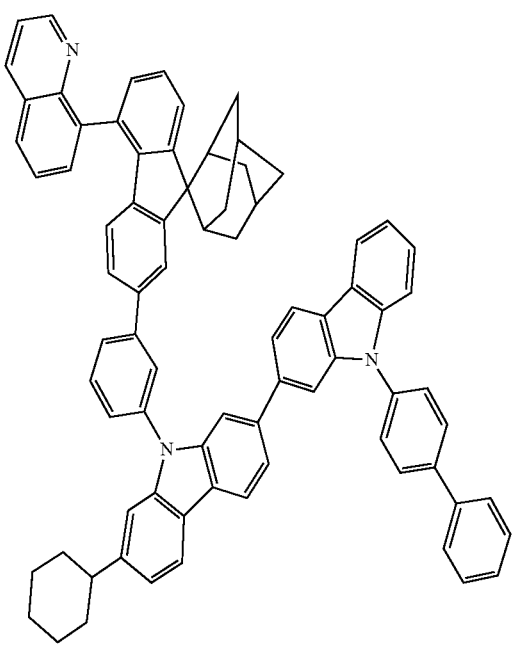

151
-continued
152
-continued
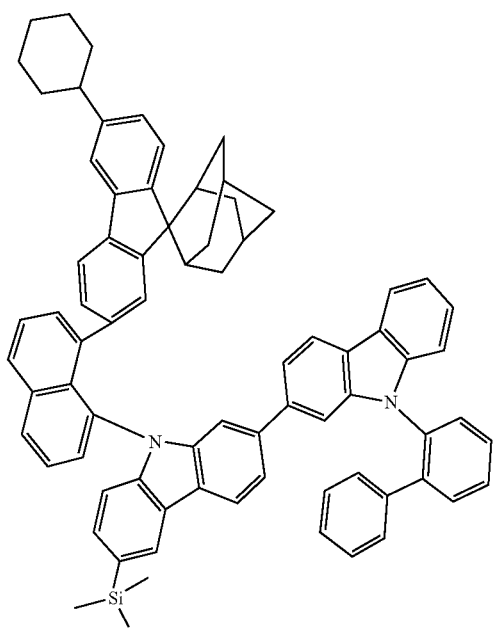
214
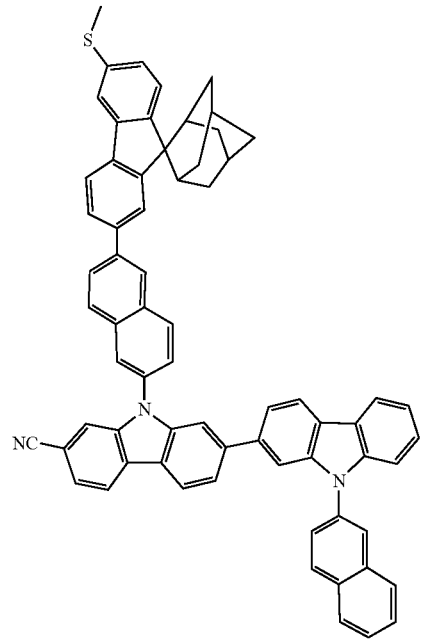
216
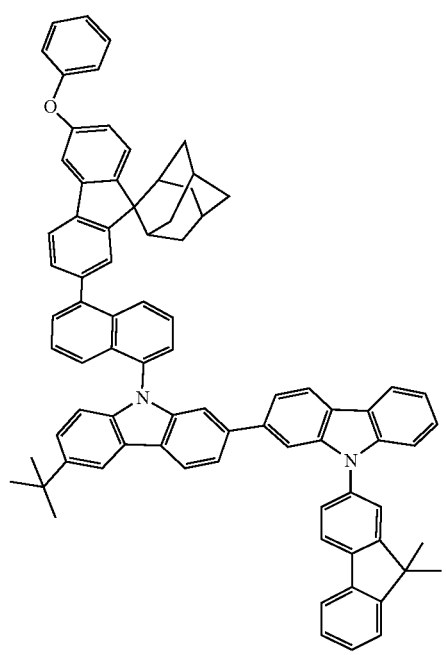
215
217

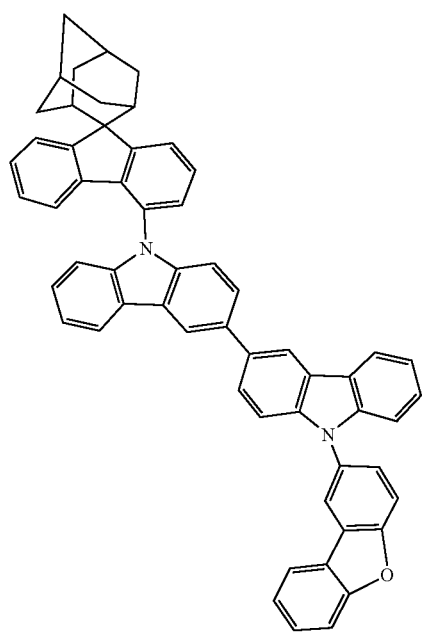
218
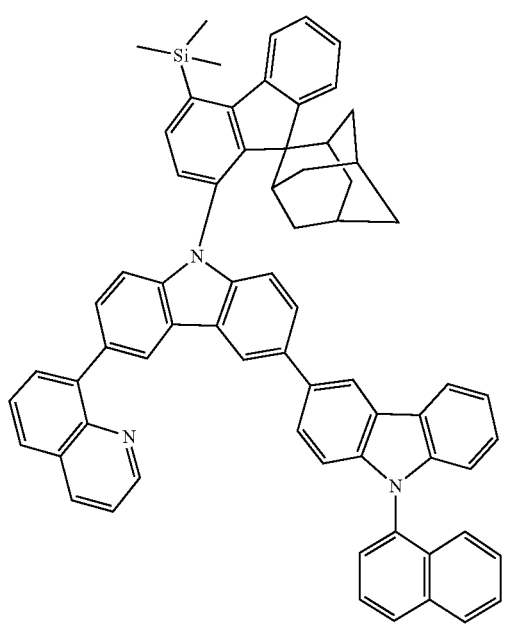
220
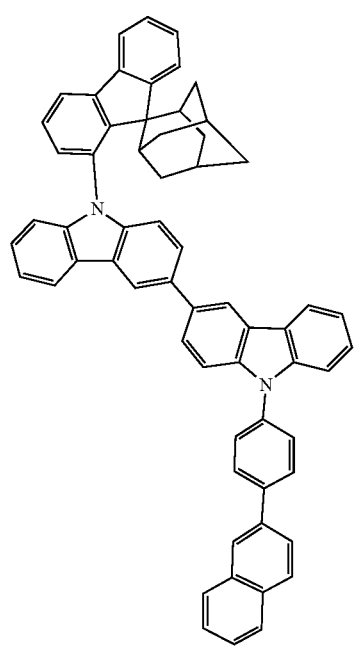
219
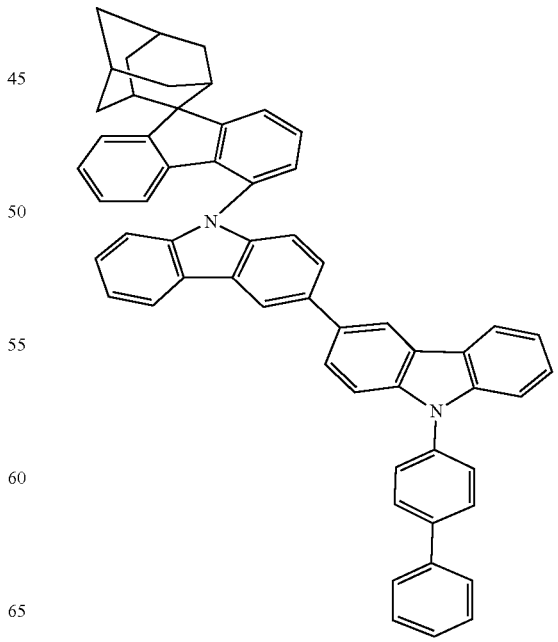
221

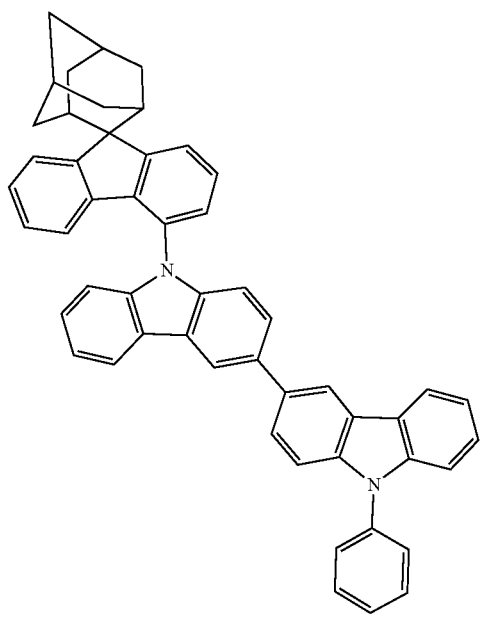
222
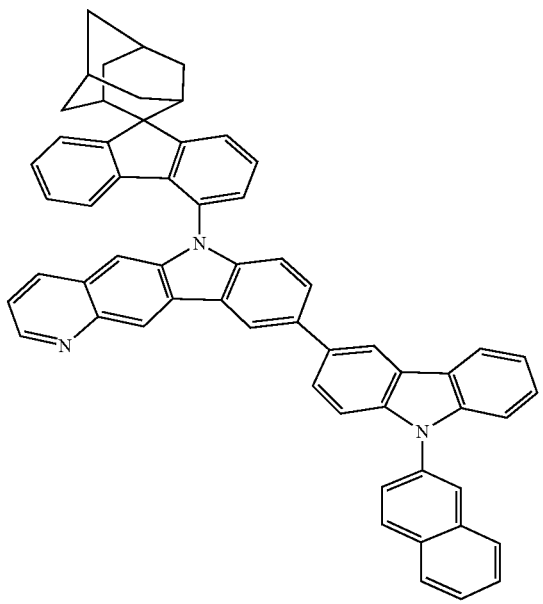
224
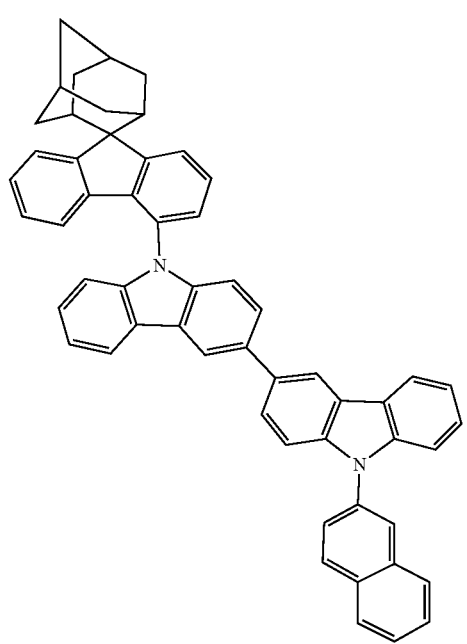
223
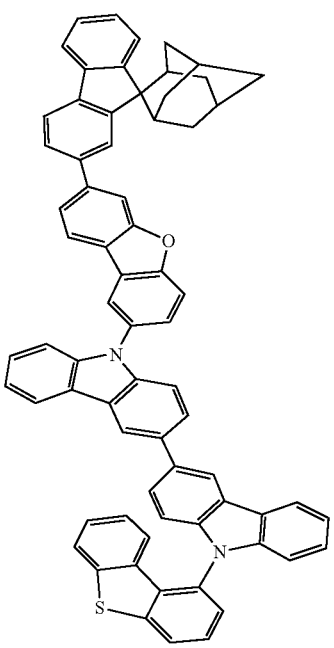
225

226
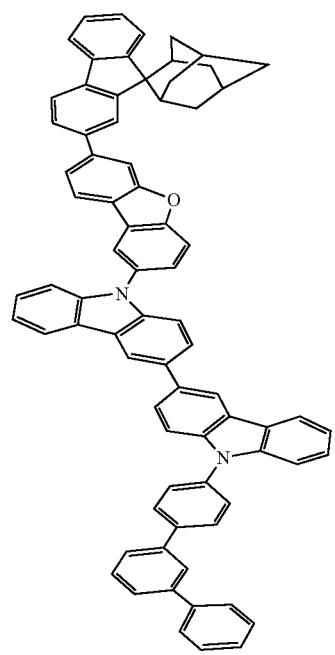
227
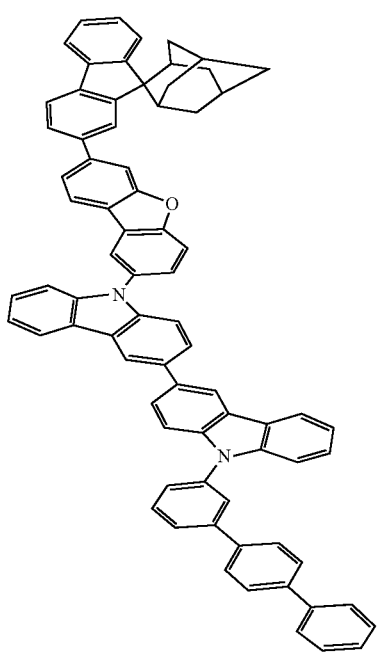
228
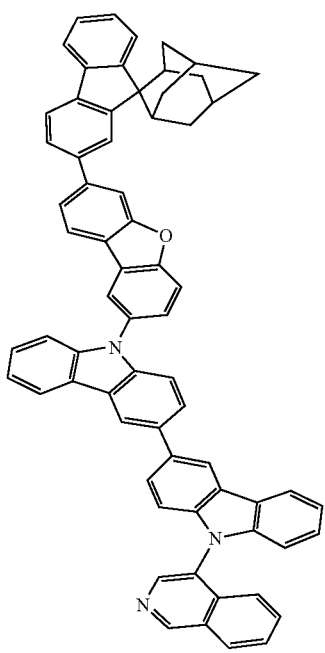
229
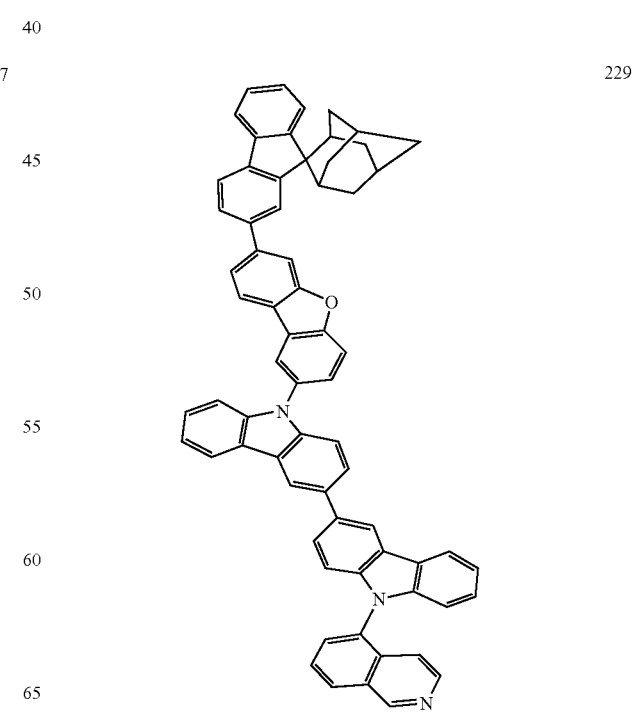

230
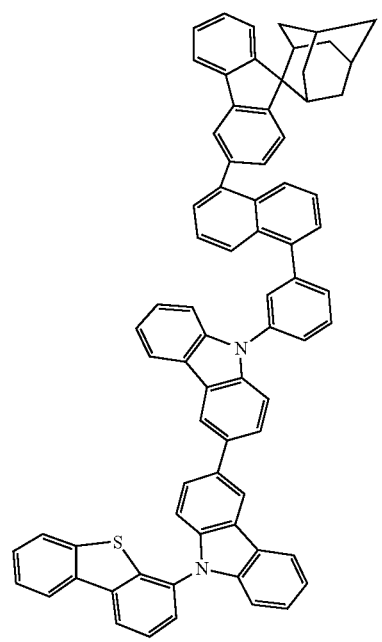
231
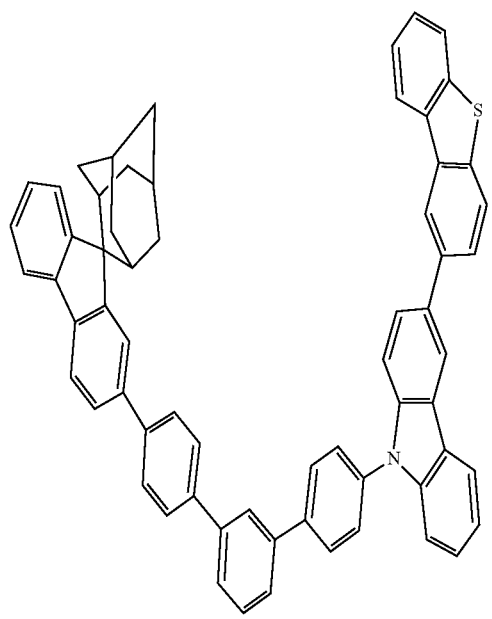
232
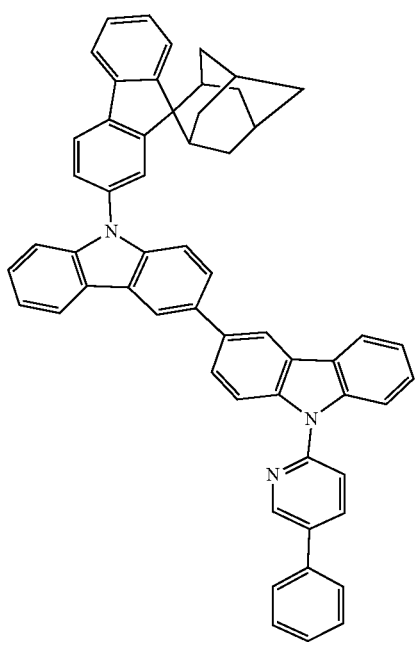
233
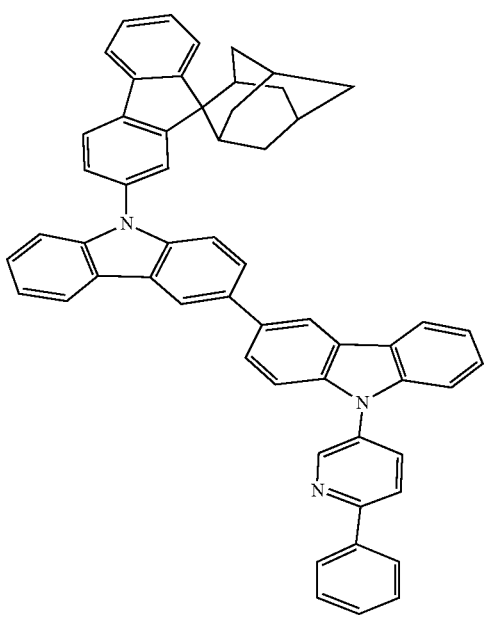

161
-continued
234
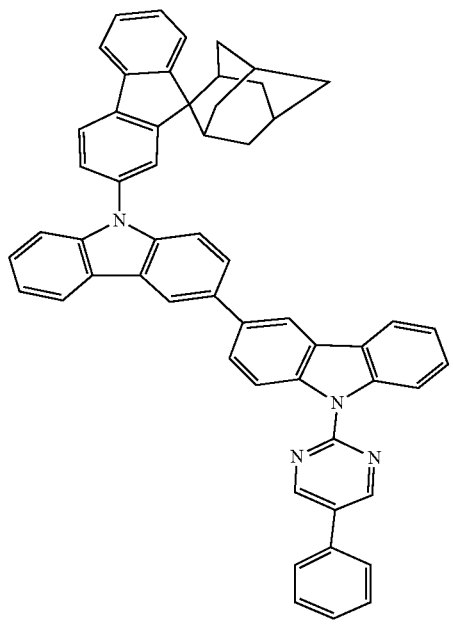
235
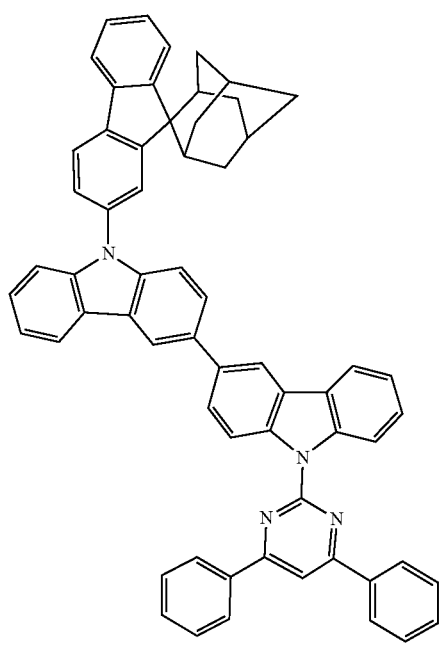
162
-continued
236
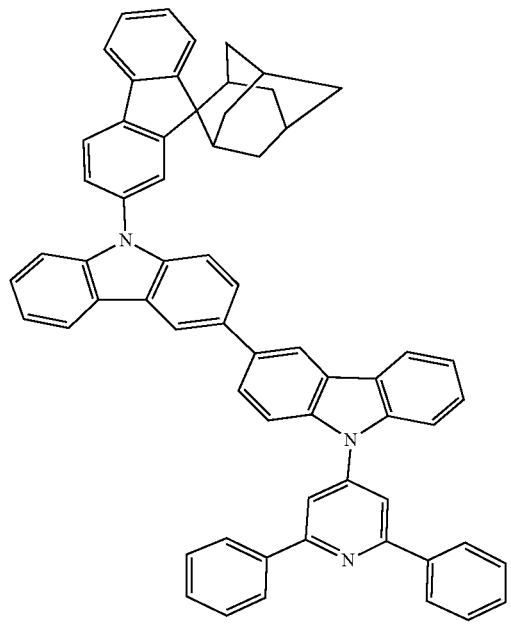
237
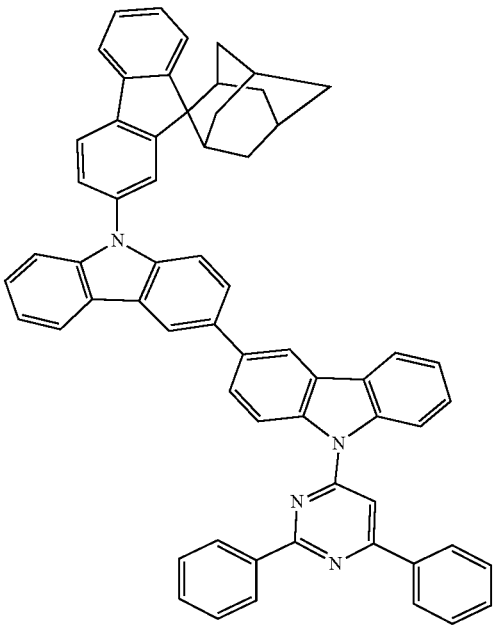

238
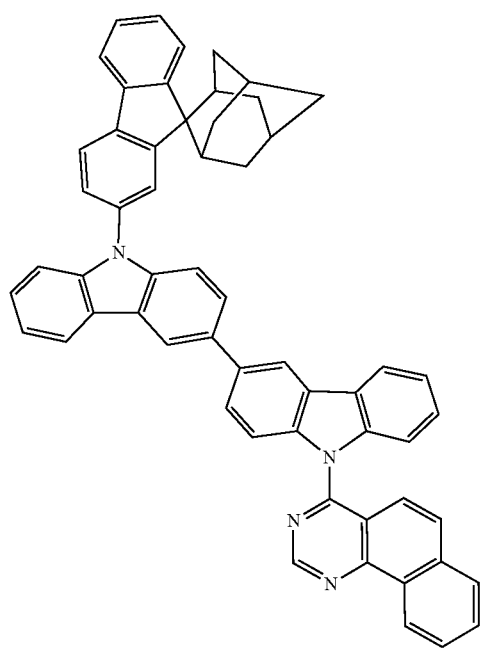
239
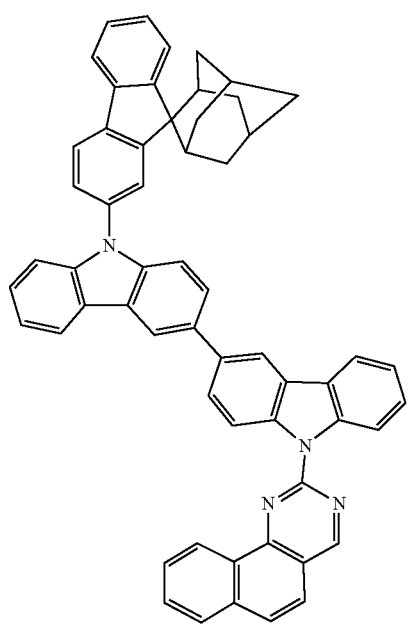
240
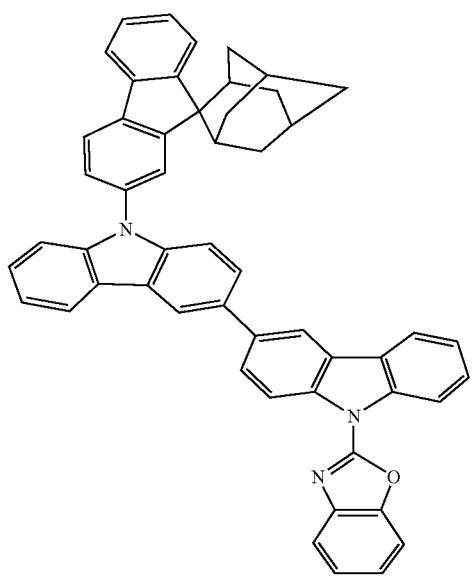
241
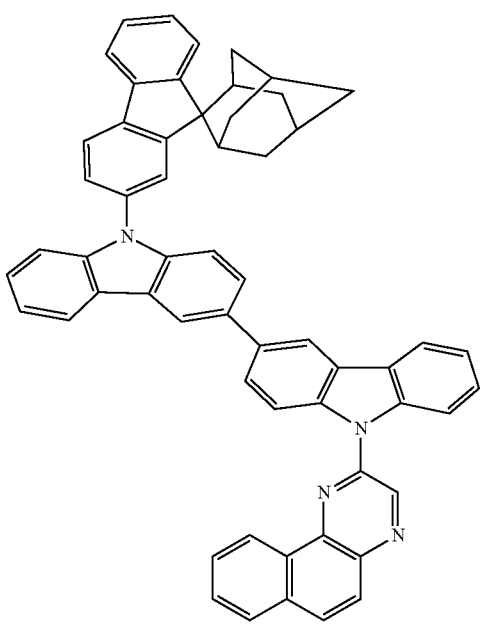

242
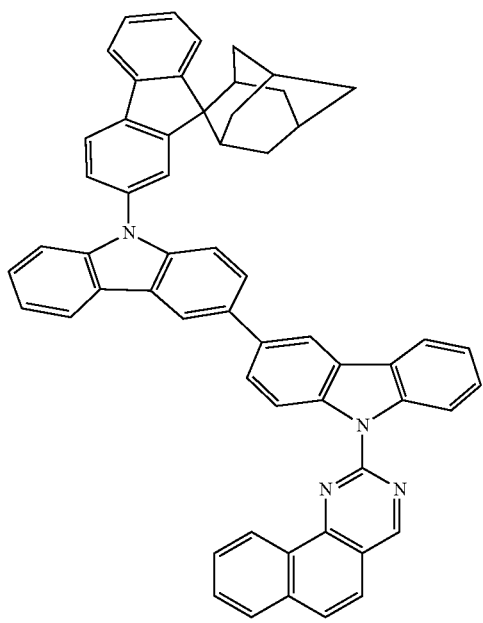
243
244
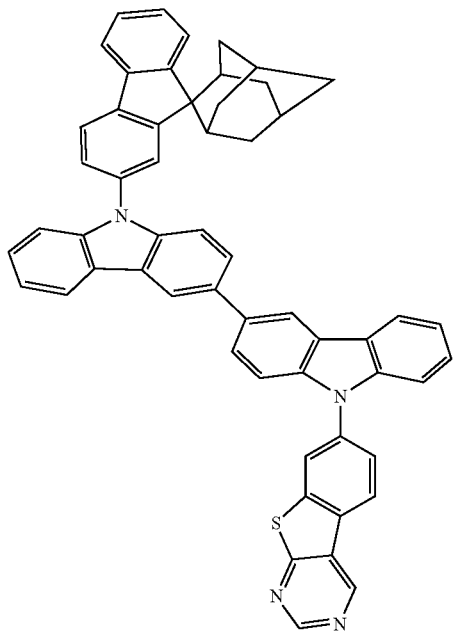
245

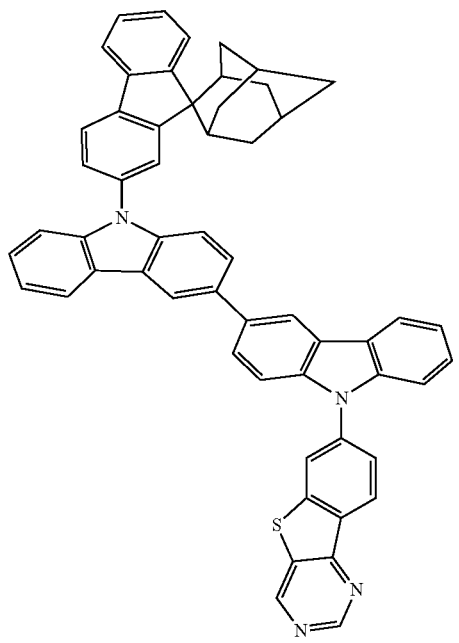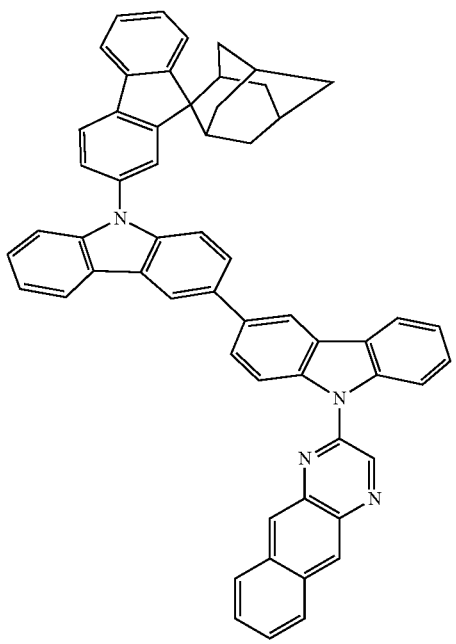

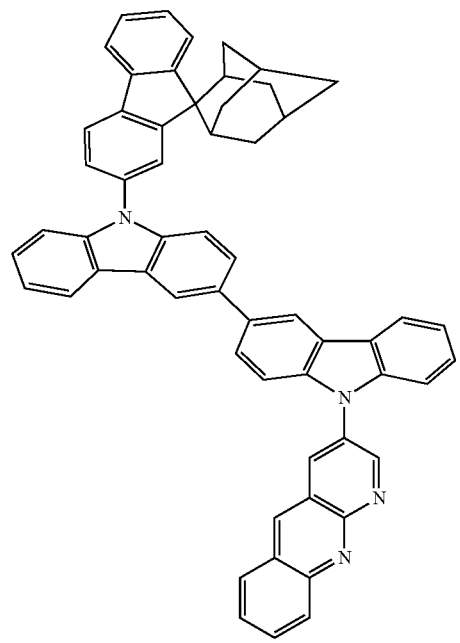
250
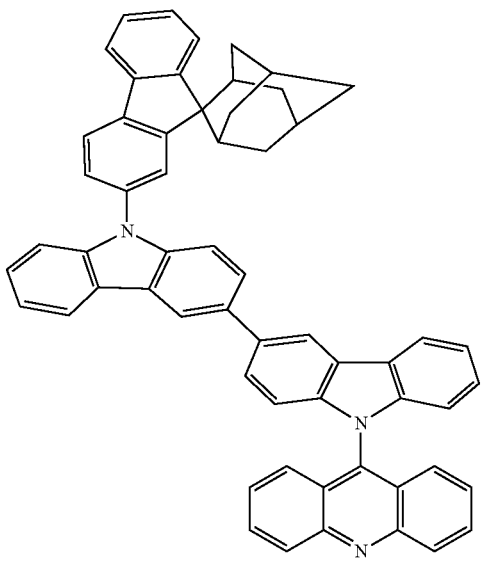
252
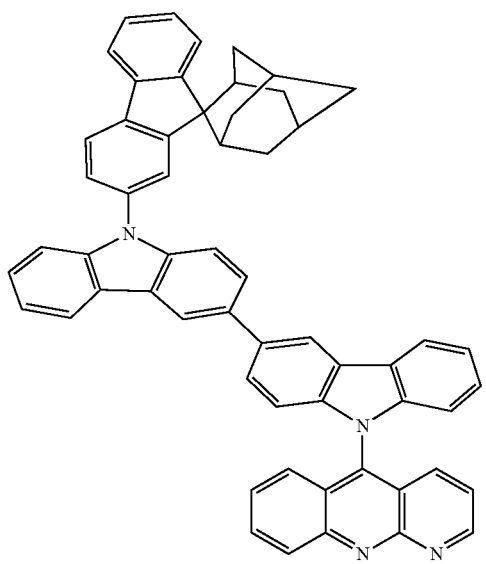
251
253

171
-continued
254
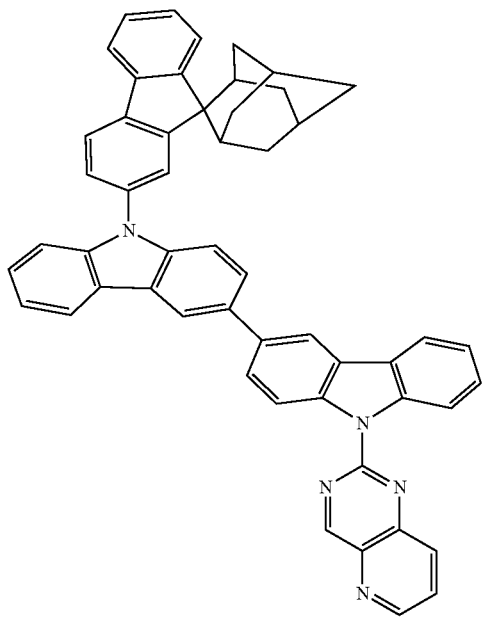
255
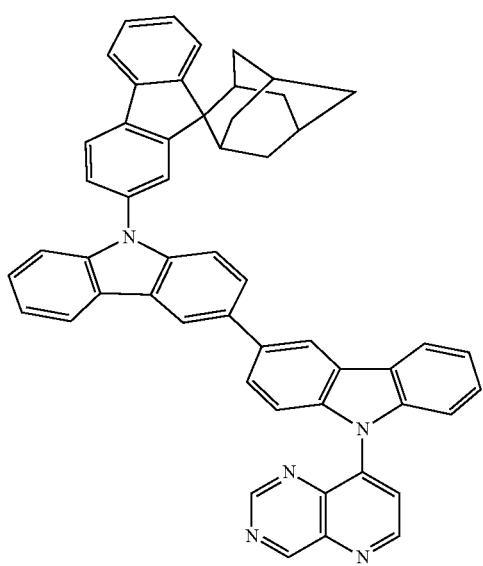
172
-continued
256
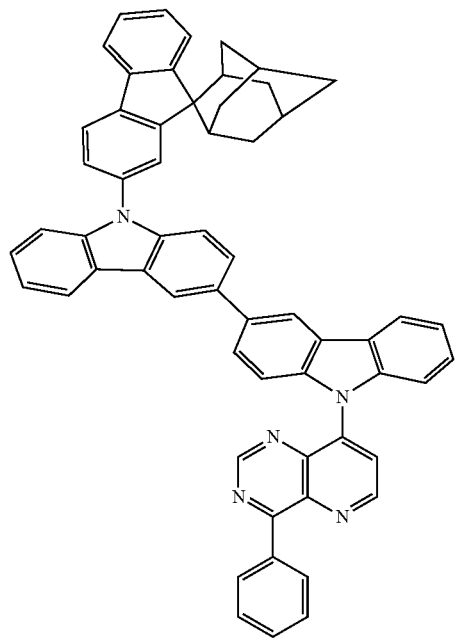
257
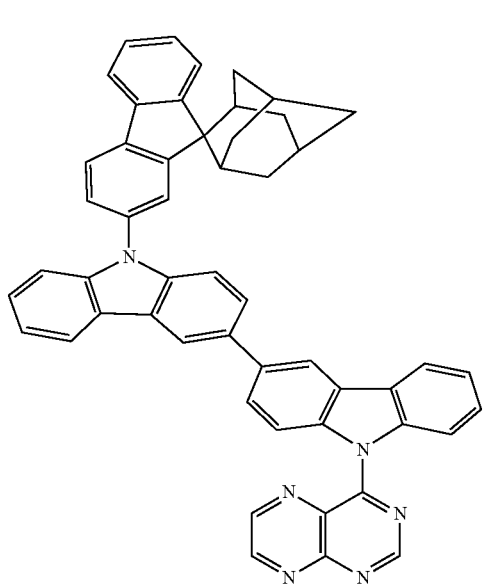

173
-continued
258
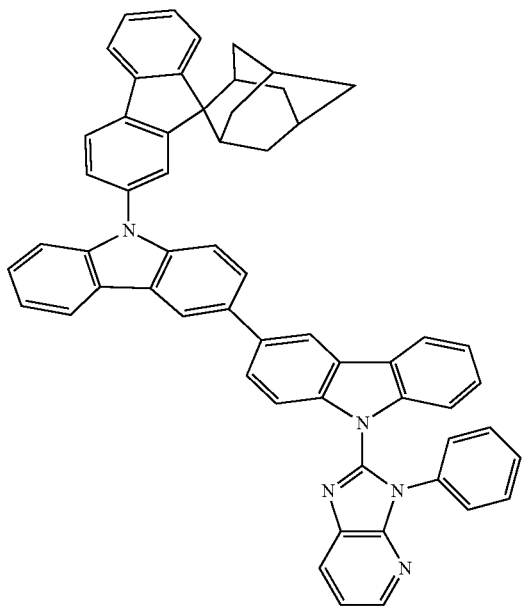
259
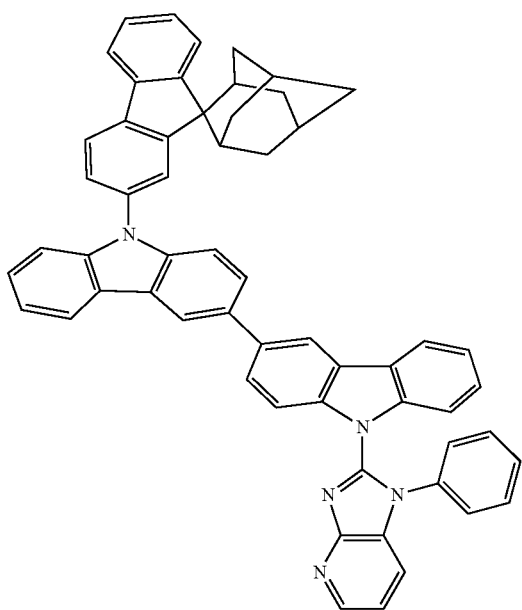
174
-continued
260
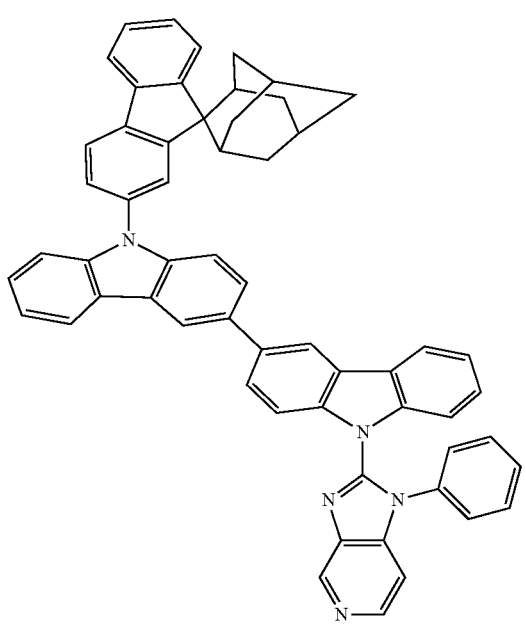
261
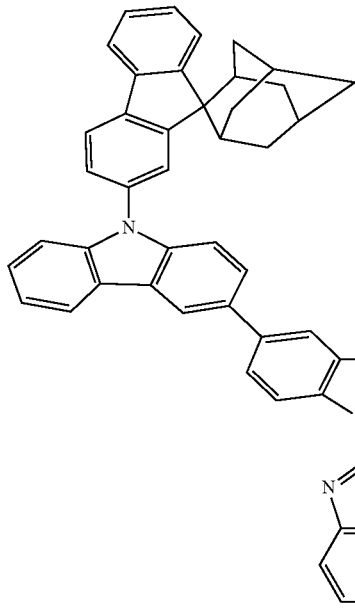

262
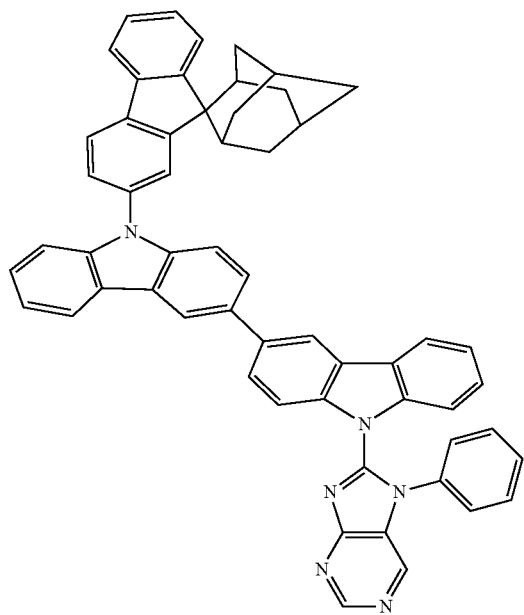
263
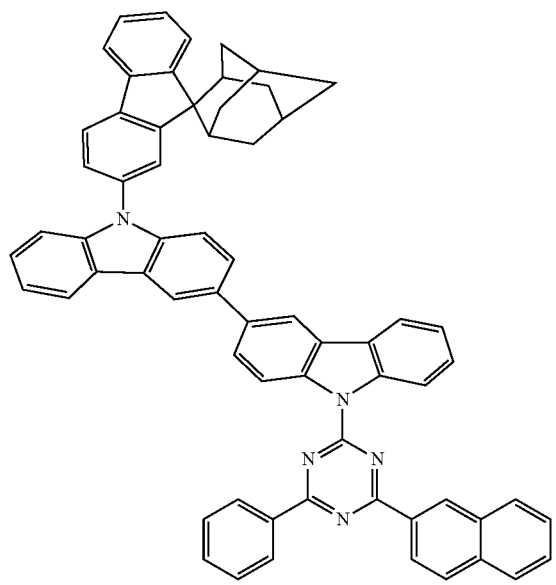
264
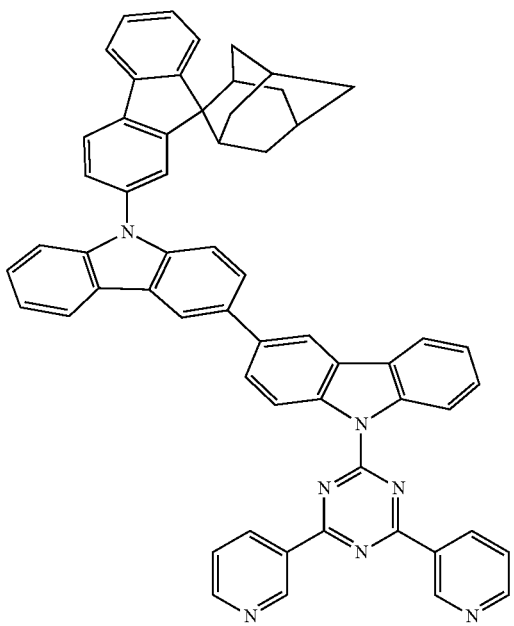
265
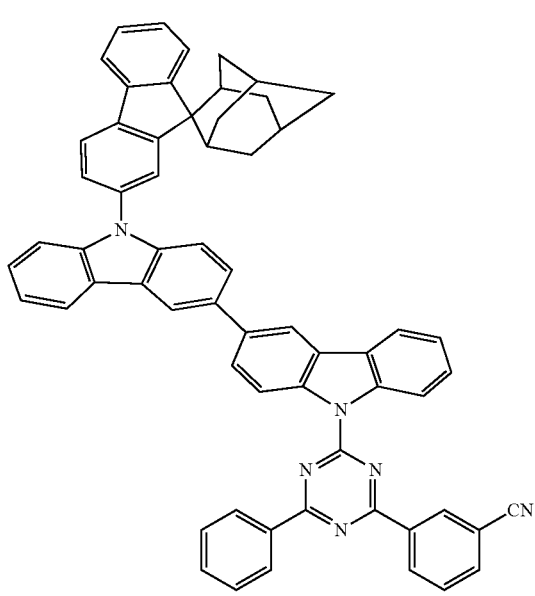

266
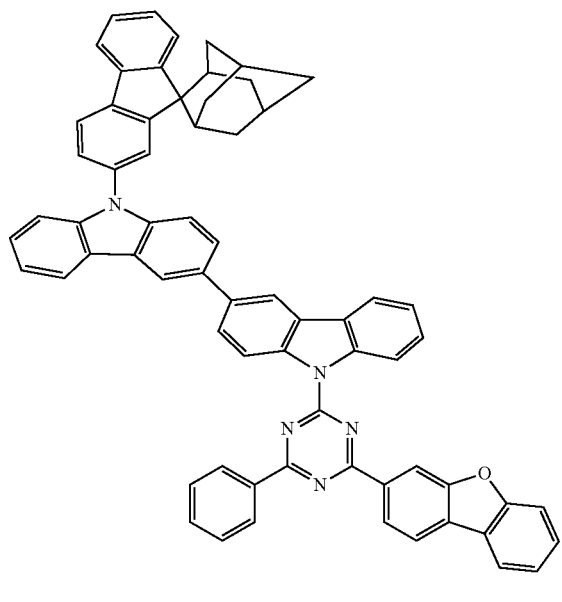
267
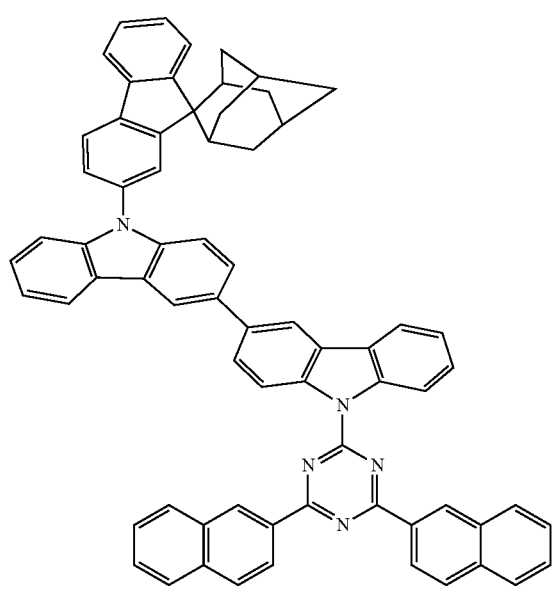
268
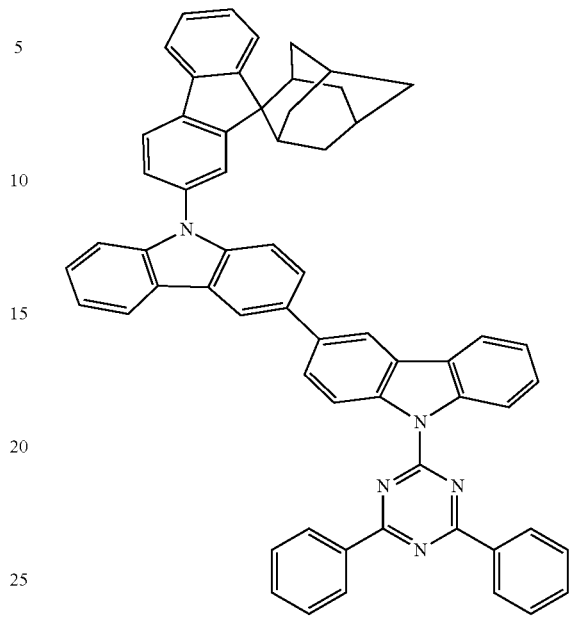
269
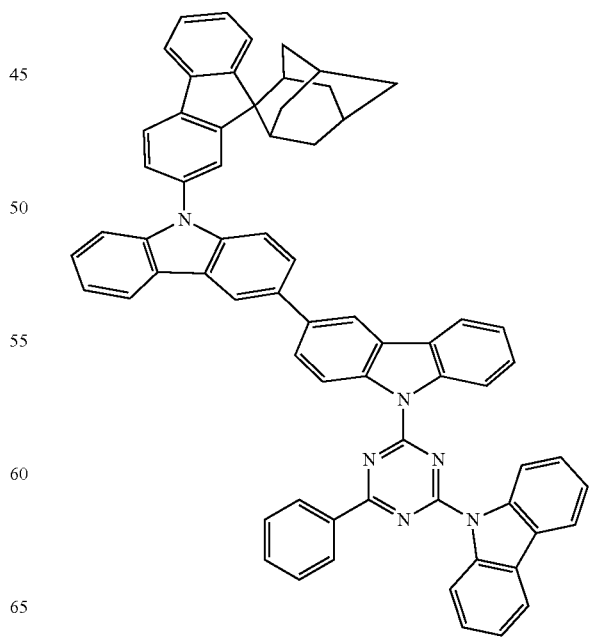

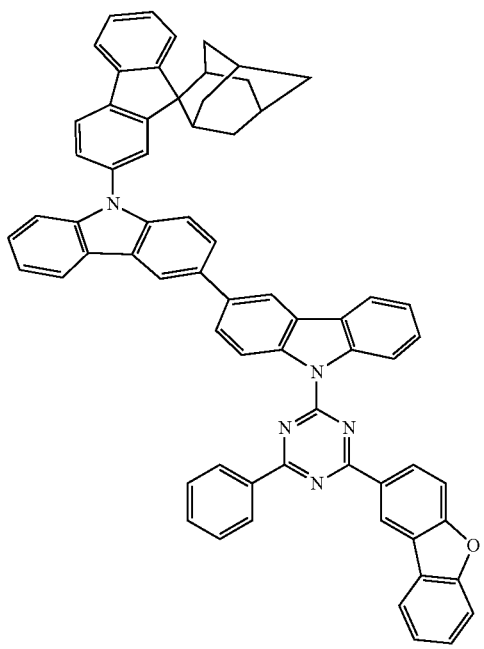
270

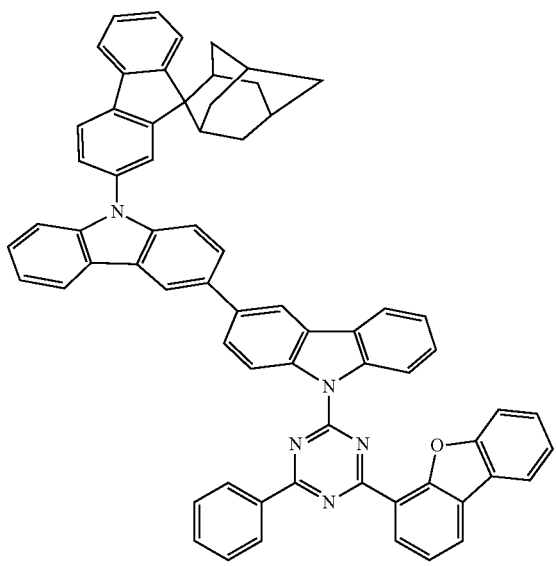
271

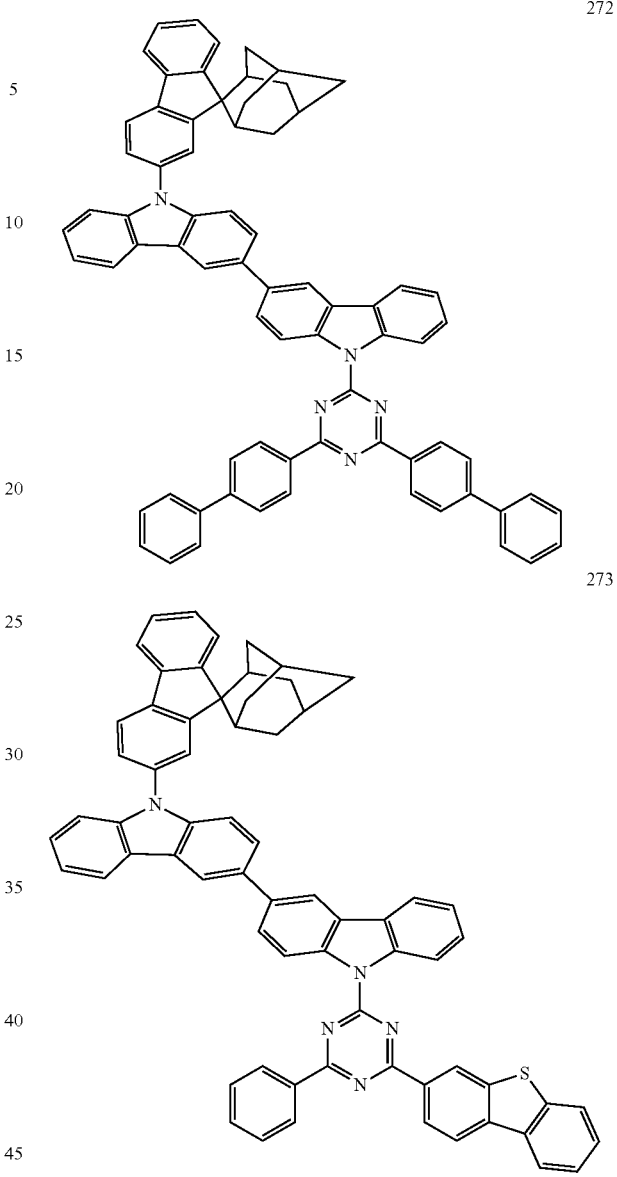
272

273

Also provided is an organic electroluminescent device, comprising an anode, a cathode arranged opposite the anode, and a functional layer arranged between the anode and the cathode; wherein the functional layer contains the above nitrogen-containing compounds to improve the voltage characteristic, efficiency characteristic and lifetime characteristic of the organic electroluminescent device.

Optionally, the functional layer comprises an organic light emitting layer, the organic light emitting layer comprises the above nitrogen-containing compound, in particular, the host material of the organic light emitting layer comprises the above nitrogen-containing compound.

For example, as shown in FIG. 1, the organic electroluminescent device may comprise an anode 100, a hole transport layer 321, an organic light emitting layer 330, an electron transport layer 340 and a cathode 200 which are stacked in turn. The nitrogen-containing compound provided in the disclosure can be applied to the organic light emitting layer 330 of the organic electroluminescent device to increase the lifetime of the organic electroluminescent device, improve the luminous efficiency of the organic electroluminescent device, or reduce the driving voltage of the organic electroluminescent device.

Optionally, the anode 100 comprises anode materials, which are optionally materials with great escape work (work function) that facilitates hole injection into the functional layer. Specific examples of anode materials include, but are not limited to: metals such as nickel, platinum, vanadium, chromium, copper, zinc and gold or alloys thereof; metal oxides such as zinc oxide, indium oxide, indium tin oxide (ITO) and indium zinc oxide (IZO); combined metals and oxides such as ZnO:Al or $SnO_2$:Sb; or conducting polymers such as poly (3-methylthiophene), poly [3,4-(ethylidene-1, 2-dioxyl) thiophene] (PEDT), polypyrrole and polyaniline. Optionally, the specific examples of anode materials include a transparent electrode containing indium tin oxide (ITO) as an anode.

Optionally, the hole transport layer 321 may comprise one or more hole transport materials. The hole transport materials may be selected from carbazole polymers, carbazole linked triarylamine compounds or other types of compounds, which are not specially defined herein.

Optionally, the organic light emitting layer 330 may comprise a host material and a dopant material, the holes injected into the organic light emitting layer 330 and the electrons injected into the organic light emitting layer 330 can be recombined at the organic light emitting layer 330 to generate excitons, the excitons transfer energy to the host material, and the host material transfers energy to the dopant material, so that the dopant material can emit light.

In one embodiment of the disclosure, the host material may consist of the nitrogen-containing compound of the disclosure, especially consisting of the nitrogen-containing compound containing an electron-deficient aromatic heterocycle on $Z^3$. Such nitrogen-containing compound can transport electrons and holes simultaneously and balance the transport efficiency of holes and electrons, and therefore, electrons and holes can be efficiently combined in the organic light emitting layer to improve the light emitting efficiency of the organic electroluminescent device.

In another embodiment of the disclosure, the host material may be a composite material, for example, it may include the nitrogen-containing compound and the host material of the electronic organic light emitting layer of the disclosure. The nitrogen-containing compound in the disclosure can transport holes effectively, so that the hole transport efficiency is balanced with the electron transport efficiency of the organic light emitting layer, and then the electrons and holes can be combined in the organic light emitting layer efficiently to improve the luminous efficiency of the organic electroluminescent device. For example, the host material may comprise the nitrogen-containing compound in the disclosure and GH-n1 or GH-n2.

In one embodiment of the disclosure, the host material may consist of the nitrogen-containing compound of the disclosure. Since the nitrogen-containing compound in the disclosure has high hole mobility, it can be used as a hole-type host material in the organic light emitting layer, so that holes can be transported in the organic light emitting layer effectively, so that the hole transport efficiency is balanced with the electron transport efficiency of the organic light emitting layer, and then the electrons and holes can be combined in the organic light emitting layer efficiently to improve the luminous efficiency of the organic electroluminescent device.

The dopant material of the organic light emitting layer 330 may be a compound with a condensed aryl ring or a derivative thereof, a compound with a heteroaryl ring or a derivative thereof, an aromatic amine derivative or other materials, which is not specially restricted herein. In one embodiment in the disclosure, the dopant material of the organic light emitting layer 330 may be $Ir(piq)_2(acac)$ and the like. In another embodiment in the disclosure, the dopant material of the organic light emitting layer 330 may be $Ir(ppy)_3$ and the like.

Optionally, the electron transport layer 340 is either a single-layer structure or a multi-layer structure. The electron transport layer 340 may comprise one or more electron transport materials. The electron transport material may be selected from, but is not limited to, benzimidazole derivatives, oxadiazole derivatives, quinoxaline derivatives or other electron transport materials.

Optionally, the cathode 200 may comprise cathode materials, which are materials with small escape work that facilitates electron injection into the functional layer. Specific examples of cathode materials include, but are not limited to: metals such as magnesium, calcium, sodium, potassium, titanium, indium, yttrium, lithium, gadolinium, aluminum, silver, tin and lead or alloys thereof; or multilayer materials such as LiF/Al, Liq/Al, $LiO_2$/Al, LiF/Ca, LiF/Al and $BaF_2$/Ca. Optionally, the specific examples of cathode materials include a Al-containing metal electrode as a cathode. In one embodiment in the disclosure, the material of the cathode 200 may be magnesium-silver alloy.

Optionally, as shown in FIG. 1, a hole injection layer 310 may also be arranged between the anode 100 and the hole transport layer 321 to enhance the capability of injecting holes into the first hole transport layer 321. Benzidine derivatives, starburst arylamine compounds, phthalocyanine derivatives or other materials are options for the hole injection layer 310, which is not specially restricted herein. For example, the hole injection layer 310 may consist of F4-TCNQ.

Optionally, as shown in FIG. 1, an electron blocking layer 322 can additionally be arranged between the hole transport layer 321 and the organic light emitting layer 330 to block the transport of electrons to the hole transport layer 321, improve the recombination rate of electrons and holes in the organic light emitting layer 330, and protect the hole transport layer 321 against electron impact. The material of the electron blocking layer 322 may be carbazole polymers, carbazole linked triarylamine compounds or other feasible structures.

Optionally, as shown in FIG. 1, an electron injection layer 350 may also be arranged between the cathode 200 and the electron transport layer 340 to enhance the capability of injecting electrons into the electron transport layer 340. The electron injection layer 350 may comprise either inorganic materials such as alkali sulfides and alkali halides, or a complex of alkali metal and organic substances. For example, the electron injection layer 350 may comprise LiQ.

Figure 2:
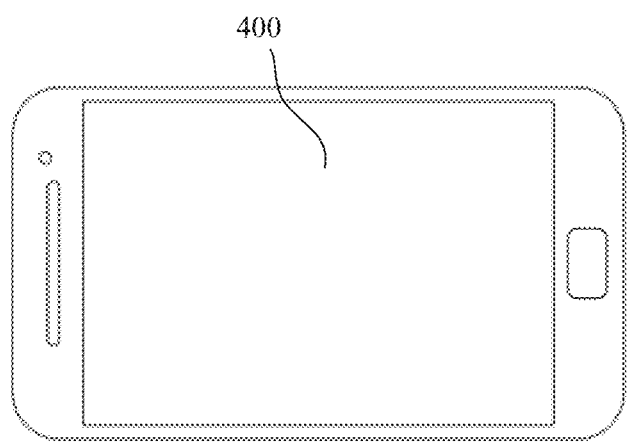
FIG. 2 illustrates a structural view of the electronic apparatus in accordance with the embodiment in the disclosure.

Also provided is an electronic apparatus 400, as shown in FIG. 2. The electronic apparatus 400 comprises any one organic electroluminescent device described in the above embodiments of the organic electroluminescent device. The electronic apparatus 400 may be display apparatus, lighting apparatus, optical communication apparatus or other types of electronic apparatuses, for example, including but not limited to computer screen, mobile phone screen, television, electronic paper, emergency lighting lamp, optical module and the like. The electronic apparatus 400 has any one organic electroluminescent device described in the above embodiments of the organic electroluminescent device, so it has the same beneficial effect, which will not be repeated herein.

SYNTHESIS EXAMPLES

The following synthesis examples and embodiments are used to further illustrate and explain the contents in the disclosure.

Generally, the nitrogen-containing compound in the disclosure can be prepared by the method described herein. Unless further described, the meaning of a substituent symbol herein is the same as that of the substituent symbol in the formula 1. Those skilled in the art will be aware of that: the chemical reactions described herein can be used to appropriately prepare many other nitrogen-containing compounds in the disclosure, and other methods for preparing the nitrogen-containing compounds in the disclosure are considered to fall within the scope of the present application. For example, those skilled in the art can synthesize other nitrogen-containing compounds in the disclosure by referring to or adequately modifying the preparation method provided in the disclosure, for example, they can have the aid of appropriate protecting groups, utilize other known reagents other than those described herein, modify reaction conditions and the like.

Unless otherwise stated, all the temperatures in the synthesis examples described below are in Celsius degree. Some reagents were purchased from commodity suppliers, such as Aldrich Chemical Company, Arco Chemical Company and Alfa Chemical Company, etc., and these reagents were not further purified in use unless otherwise stated. Some conventional reagents were purchased from Shantou Xilong Chemical Factory, Guangdong Guanghua Chemical Reagent Factory, Guangzhou Chemical Reagent Factory, Tianjin Haoyuyu Chemical Co., Ltd., Tianjin Fuchen Chemical Reagent Factory, Wuhan Xinhuayuan Technology Development Co., Ltd., Qingdao Tenglong Chemical Reagent Co., Ltd. and Qingdao Haiyang Chemical Factory.

Wherein anhydrous tetrahydrofuran, dioxane, toluene and ether were obtained by drying with reflux over sodium. Anhydrous dichloromethane and chloroform were obtained by drying with reflux over calcium hydride. Ethyl acetate, petroleum ether, n-hexane, N,N-dimethylacetamide and N,N-dimethylformamide were dried in advance with anhydrous sodium sulfate in use.

Unless otherwise stated, the following reactions are generally performed under positive pressure of nitrogen or argon, or a drying tube is installed to an anhydrous solvent; all reaction bottles were plugged with suitable rubber stoppers, and the substrate was injected into the reaction bottles through a syringe. Glassware was dried.

A silica gel column was used as a chromatographic column. Silica gel (100-200 meshes) was purchased from Qingdao Haiyang Chemical Factory. All the compounds of the synthesis methods not mentioned herein are commercially available raw materials.

$^1$H NMR spectra were recorded by a Bruker 400 MHz or 600 MHz NMR spectrometer. $^1$H NMR spectra use CDCl$_3$, CD$_2$Cl$_2$, D$_2$O, DMSO-d$_6$, CD$_3$OD or acetone-d$_6$ as solvents (in ppm), and TMS (0 ppm) or chloroform (7.26 ppm) is used as a reference standard. When multiplet appears, the following abbreviations will be used: s (singlet), d (doublet), t (triplet), m (multiplet), br (broadened), dd (doublet of doublets).

The measurement conditions of low resolution mass spectrometry (MS) data are: Agilent 6120 Quadrupoles HPLC-M (column model: Zorbax SB-C18, 2.1×30 mm, 3.5 microns, 6 min, flow rate 0.6 mL/min. Mobile phase: 5%-95% (the proportion of acetonitrile containing 0.1% formic acid in H$_2$O containing 0.1% formic acid), as detected by UV at 210 nm/254 nm using electrospray ionization (ESI).

Pure compounds were detected by UV at 210 nm/254 nm using Agilent 1260pre-HPLC or Calesep pump 250pre-HPLC (column model: NOVASEP 50/80 mm DAC).

Compound 1-Compound 2 were Synthesized by the Following Synthetic Route

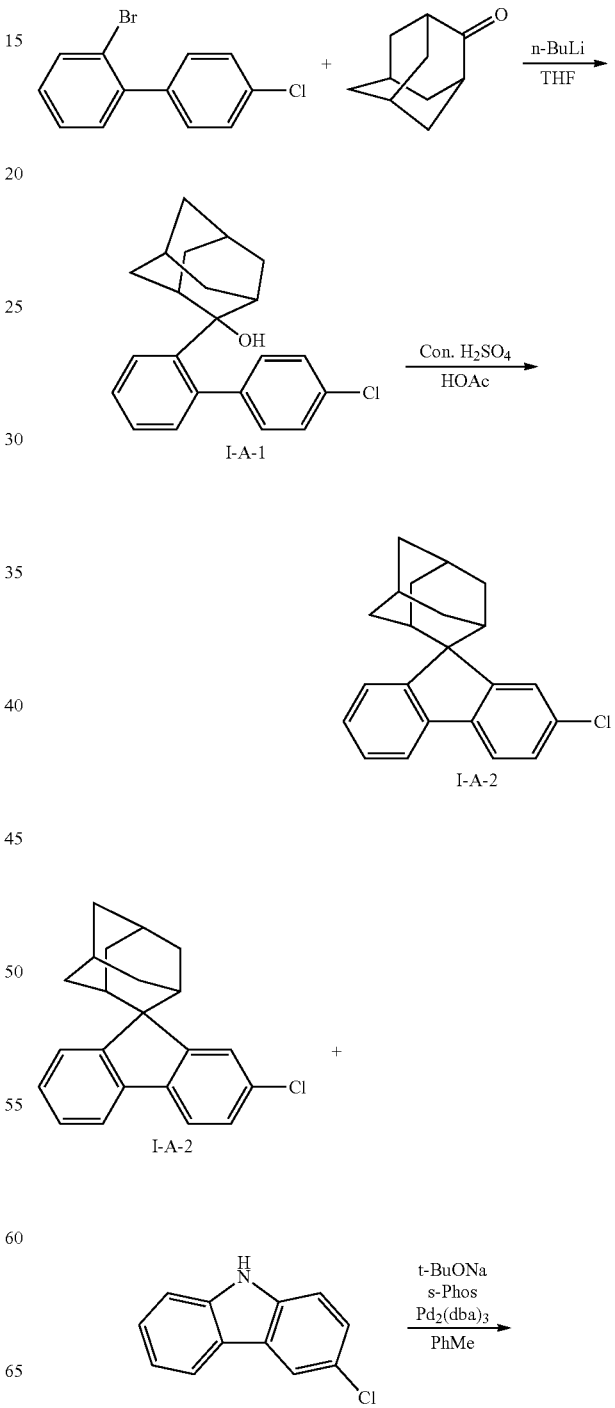

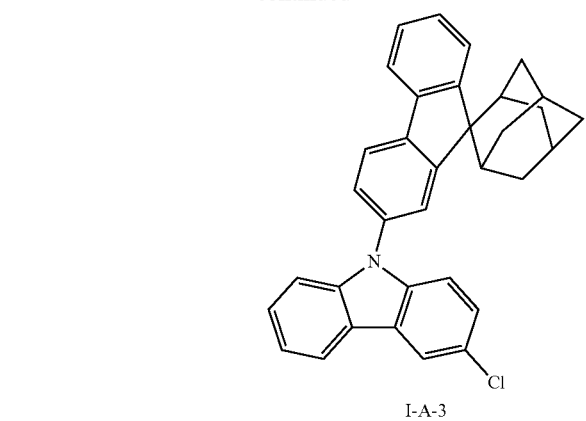
I-A-3
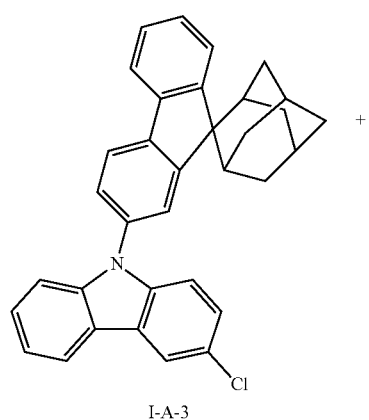
I-A-3
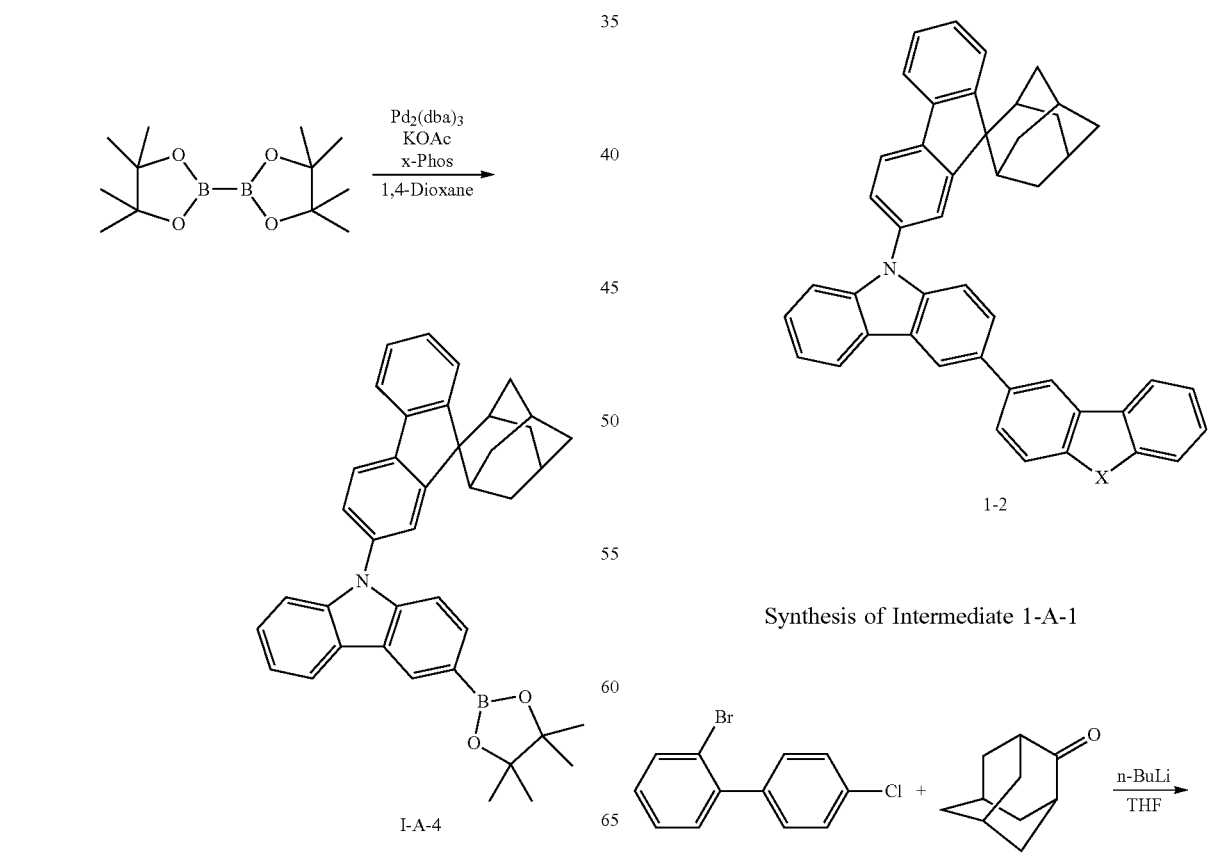
I-A-4
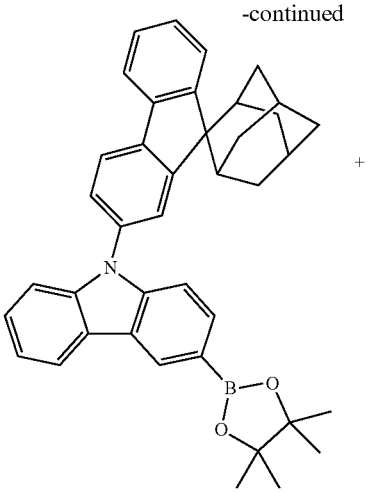
I-A-4
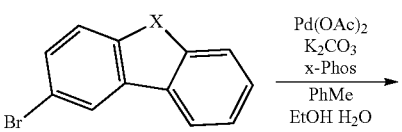
Synthesis of Intermediate 1-A-1

-continued

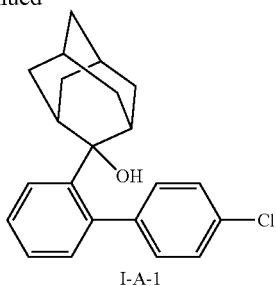
I-A-1

Under nitrogen atmosphere, 2-bromo-4-chlorobiphenyl (142 g, 530 mmol) and THF (852 mL) were added to a 2 L three-necked round-bottom flask. The mixture was stirred at −80° C. to −90° C. until they became clear. The solution of n-BuLi in THF (254.75 mL) was added dropwise into the reaction mixture slowly, and the resulted mixture was stirred at −80° C. to −90° C. for another 50 min. Then a solution of adamantanone (63.78 g, 42.45 mmol) in THF (260 mL) was added dropwise into the reaction system slowly at −80° C. to −90° C. for 1 h. After the reaction was completed, the reaction mixture was naturally raised to room temperature. Then 5% hydrochloric acid was poured into the reaction solution until pH<7, after the solution was fully stirred, DCM (dichloromethane) was added for extraction. The combined organic phases were, washed to neutral with water, dried over anhydrous magnesium sulfate and filtered. Then the filtrate was concentrated in a vacuuo to obtain an oil-like crude product. The crude product and n-heptane was added to a flask, the mixture was heated to reflux until a clear solution was obtained. The solution was cool down slowly and recrystallize at −20° C. to obtain the intermediate 1-A-1 (122 g, yield 68%) as a white solid.

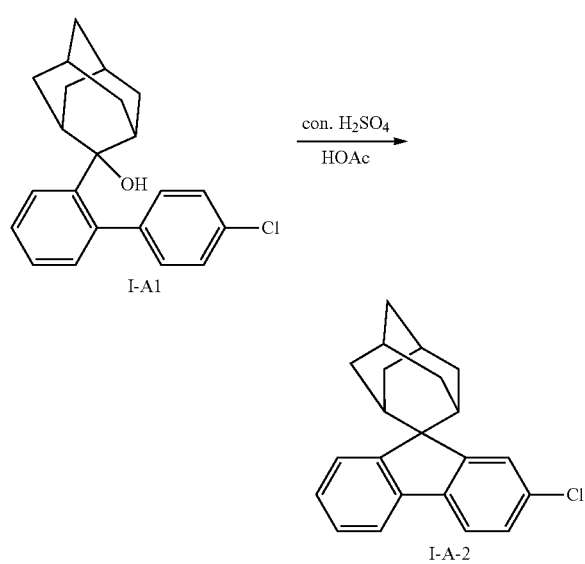

Under the nitrogen atmosphere, a mixture of intermediate I-A-1 (122 g, 360 mmol) and glacial acetic acid (1.5 L) was stirred at 50° C. to 60° C., after the reaction solution became completely clear, concentrated sulfuric acid (3.08 mL) was added dropwise. The reaction mixture was heated to 70° C.~80° C., and stirred for another 30 min. Then the reaction solution was cooled naturally to room temperature, and deionized water (2 L) was poured into the solution, the resulted mixture was stirred and filtered. The filter cake was drip washed to neutral with deionized water, and dried with a vacuum drying oven for 1 h to obtain the residue. The residue was dissolved in DCM (dichloromethane), and the solution was dried over anhydrous sodium sulfate for 30 min, filtered. The filtrate was concentrated in a vacuuo to obtain a crude product. Then, the crude product was purified by recrystallization using a mixture of n-heptane and distilled-off DCM, at −20° C. Filtered, the filter cake was collected and baked in the vacuum drying oven to obtain the intermediate 1-A-2 (104.8 g, yield 91%) as a white solid.

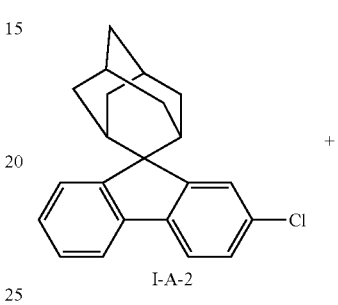
I-A-2

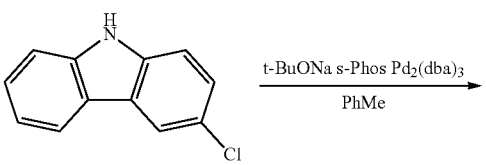

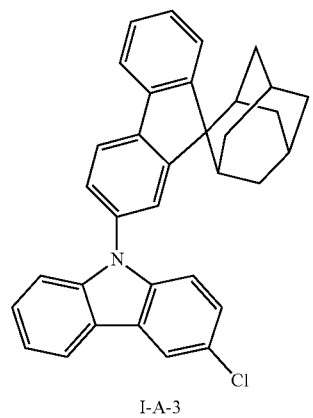
I-A-3

The intermediate 1-A-2 (104.8 g, 328 mmol), 3-chloro-carbazole (50 g, 249 mmol), tris (dibenzylidenacetone) dipalladium (2.63 g, 2.87 mmol), 2-dicyclohexylphosphino-2',6'-dimethoxybiphenyl (2.35 g, 5.74 mmol) and sodium tert-butoxide (41.4 g, 431 mmol) were added to toluene (800 mL), and the mixture was heated to 108° C. under the nitrogen atmosphere, and stirred for 3 h. Then the reaction solution was cooled to room temperature and washed with water, magnesium sulfate was added for drying, filtered. The filtrate was concentrated in a vacuuo to obtain a crude product. Then, the crude product was purified by recrystallization using toluene, to obtain intermediate 1-A-3 (97.6 g, yield 81%) as a white solid.

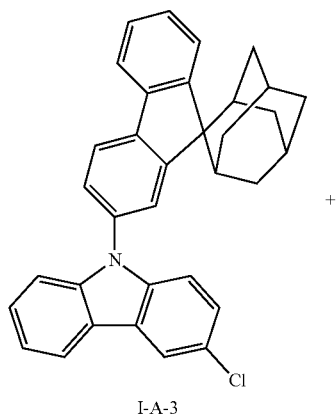

I-A-3

+

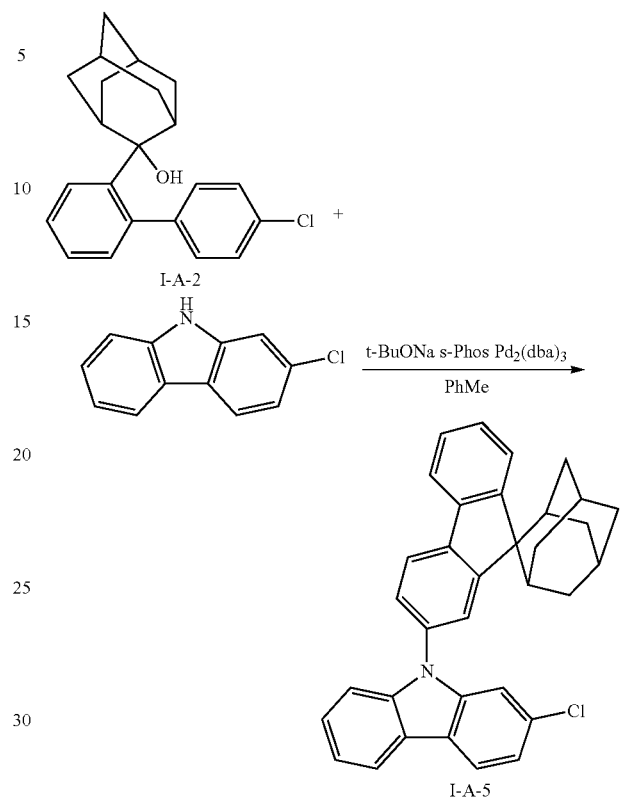

Synthesis of Intermediate I-A-5

I-A-2 t-BuONa s-Phos Pd$_2$(dba)$_3$
PhMe

I-A-5

The intermediate 1-A-2 (104.8 g, 328 mmol), 2-chloro-carbazole (50 g, 249 mmol), tris (dibenzylidenacetone) dipalladium (2.60 g, 2.84 mmol), 2-dicyclohexylphosphino-2',6'-dimethoxybiphenyl (2.28 g, 5.71 mmol) and sodium tert-butoxide (41.4 g, 431 mmol) were added to toluene (800 mL), the reaction mixture was heated to 108° C. under the nitrogen atmosphere, and stirred for 3 h. Then the reaction solution was cooled to room temperature, washed with water. The separated organic phase was dried over anhydrous magnesium sulfate, and then concentrated in a vacuuo to obtain a crude product. The crude product was purified by recrystallization using toluene to obtain intermediate 1-A-5 (97.0 g, yield 80%) as a white solid.

Synthesis of Intermediate 1-A-6

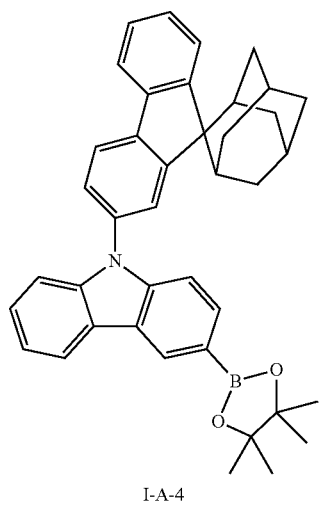

I-A-4

Pd$_2$(dba)$_3$ KOAc x-Phos
1,4-Dioxane

The intermediate 1-A-3 (97.6 g, 201 mmol), bis (pinacolato) diboron (61.3 g, 241.2 mmol), tris (dibenzylideneacetone) dipalladium (1.84 g, 2.01 mmol), 2-(dicyclohexylphosphino)-2',4',6'-triisopropylbiphenyl (0.96 g, 2.01 mmol) and potassium acetate (59.2 g, 603 mmol) were added into 1,4-dioxane (800 mL), and the reaction mixture was heated to 80° C. under nitrogen atmosphere, and stirred for 3 h; then the reaction solution was cooled to room temperature, washed with water. The separated organic phase was dried over anhydrous magnesium sulfate, and then concentrated in a vacuuo to obtain a crude product. The crude product was purified by recrystallization using toluene to obtain intermediate 1-A-4 (92.9 g, yield 80%) as a white solid.

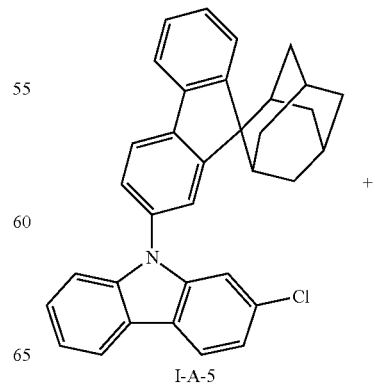

+

I-A-5

-continued

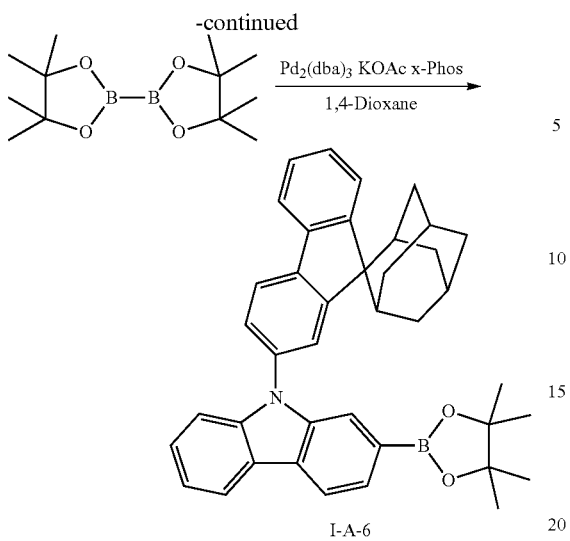

I-A-6

The intermediate 1-A-5 (97.0 g, 200 mmol), bis (pinacolato) diboron (61.3 g, 241.2 mmol), tris (dibenzylideneacetone) dipalladium (1.84 g, 2.01 mmol), 2-(dicyclohexylphosphino)-2',4',6'-triisopropylbiphenyl (0.94 g, 2.01 mmol) and potassium acetate (58.8 g, 601 mmol) were added into 1,4-dioxane (800 mL), the reaction mixture was heated to 80° C. under nitrogen atmosphere, and stirred for 3 h; then the reaction solution was cooled to room temperature, washed with water. The separated organic phase was dried over anhydrous magnesium sulfate, and then concentrated in a vacuuo to obtain a crude product. The crude product was purified by recrystallization using toluene to obtain intermediate 1-A-6 (92.0 g, yield 78.5%) as a white solid.

Synthesis of Compound 1

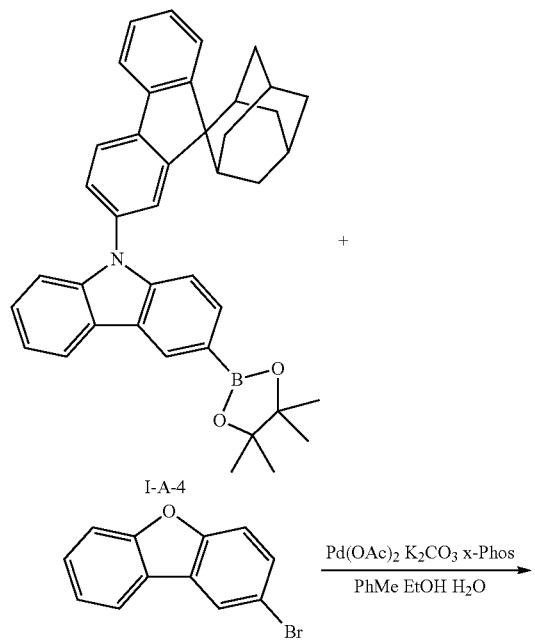

-continued

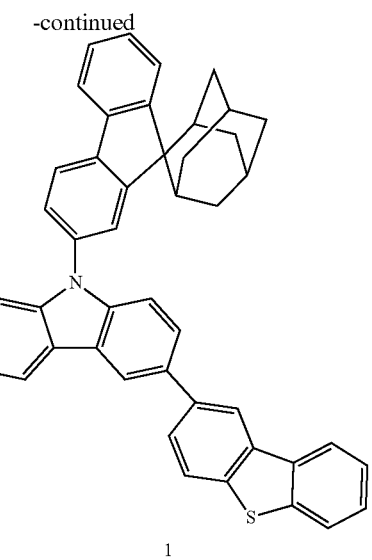

1

The intermediate 1-A-4 (6 g, 10.4 mmol), 2-bromo-dibenzothiophene (2.28 g, 8.6 mmol), palladium acetate (0.0965 g, 0.43 mmol), 2-(dicyclohexylphosphino)-2',4',6'-triisopropylbiphenyl (0.205 g, 0.43 mmol) and potassium carbonate (3.56 g, 25.8 mmol) were added into a solution of toluene (80 mL), absolute ethanol (40 mL) and deionized water (20 mL), the resulted mixture was heated to 80° C. under nitrogen atmosphere, and stirred for 2 h; then the reaction solution was cooled to room temperature, washed with water. The separated organic phase was dried over anhydrous magnesium sulfate, and then concentrated in a vacuuo to obtain a crude product. The crude product was purified by recrystallization using a mixture of dichloromethane and n-heptane to obtain compound 1 (3.7 g, yield 68%) as a light yellow solid. LC-MS (ESI, pos. ion) m/z: 633.95 [M+H]$^+$.

Compound 1 $^1$H NMR (CD$_2$Cl$_2$, 400 MHz) δ: 8.60 (d, 1H), 8.45 (d, 1H), 8.30 (d, 2H), 8.24-8.10 (m, 6H), 8.08-7.81 (m, 6H), 7.65-7.30 (m, 3H), 7.26-7.06 (m, 2H), 2.91 (d, 2H), 2.61 (d, 2H), 2.16 (s, 1H), 1.90 (s, 3H), 1.77 (d, 2H), 1.69 (d, 2H), 1.60 (s, 2H) ppm.

Synthesis of Compound 2

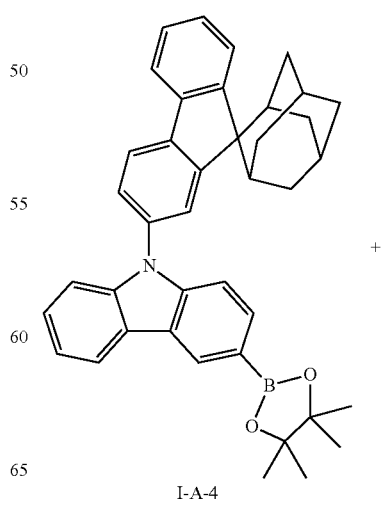

I-A-4

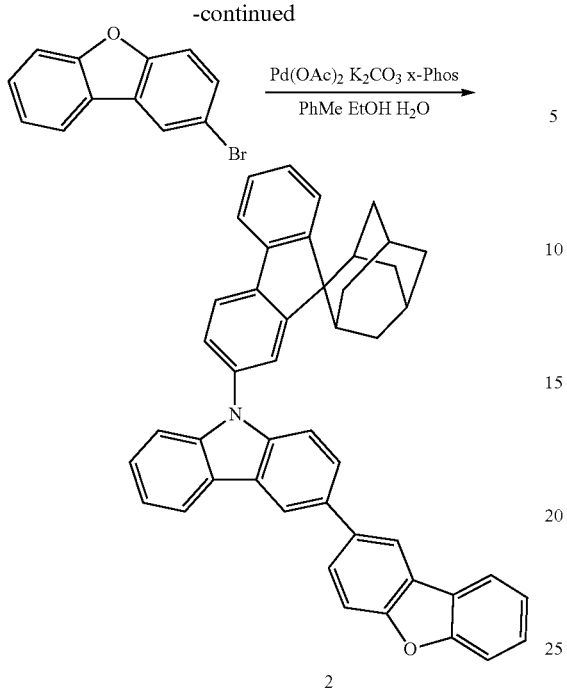

2

The intermediate 1-A-4 (6 g, 10.4 mmol), 2-bromodibenzofuran (2.12 g, 8.6 mmol), palladium acetate (0.0965 g, 0.43 mmol), 2-(dicyclohexylphosphino)-2',4',6'-triisopropylbiphenyl (0.205 g, 0.43 mmol) and potassium carbonate (3.56 g, 25.8 mmol) were added into a mixture of toluene (80 mL), absolute ethanol (40 mL) and deionized water (20 mL), the reaction mixture was heated to 80° C. under nitrogen atmosphere, and stirred for 2 h; then the reaction solution was cooled to room temperature, washed with water. The separated organic phase was dried over anhydrous magnesium sulfate, and then concentrated in a vacuuo to obtain a crude product. The crude product was purified by recrystallization using a mixture of dichloromethane and n-heptane to obtain compound 2 (3.45 g, yield 65%) as a solid. LC-MS (ESI, pos. ion) m/z: 617.97 [M+H]$^+$.

The compound 3 to compound 18, compound 119, compound 120, compound 121, compound 124, compound 233, compound 246, compound 252 and compound 268 were synthesized by the following synthetic route.

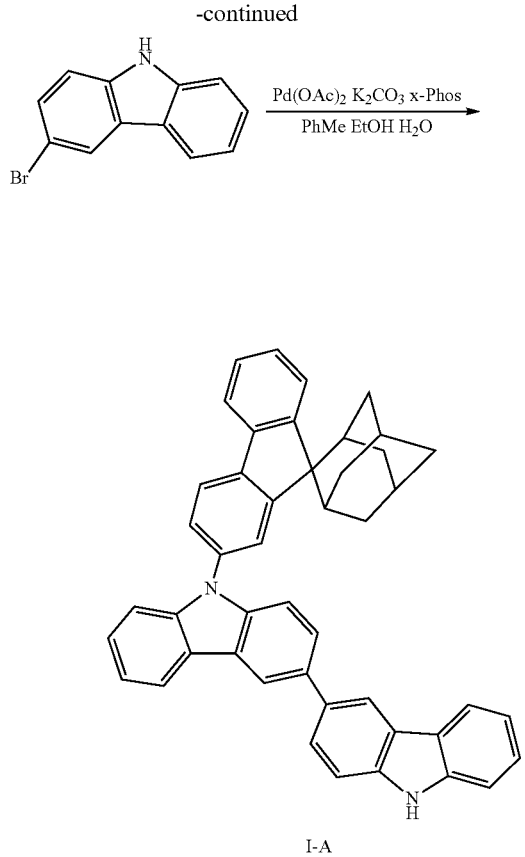

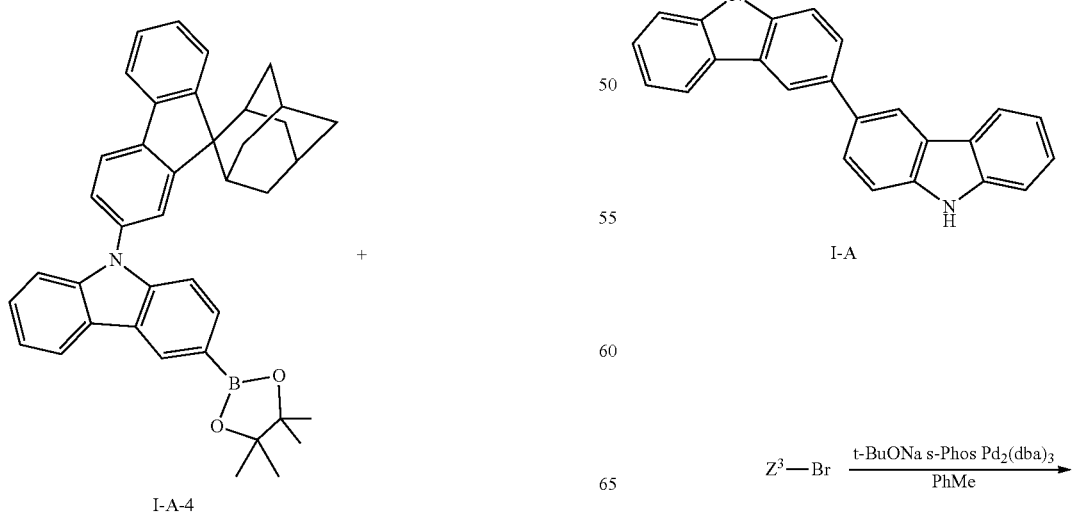

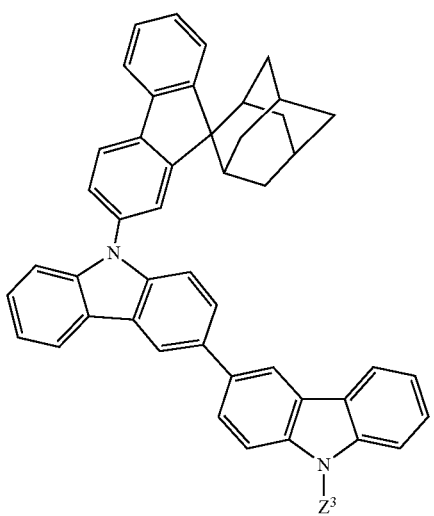

3-18

Wherein Z³ has the definition stated herein.

Synthesis of Intermediate 1-A

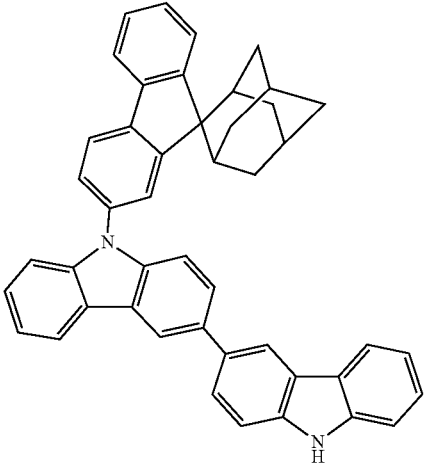

I-A

The intermediate 1-A-4 (92.9 g, 161 mmol), 3-bromocarbazole (33 g, 134 mmol), palladium acetate (1.5 g, 6.7 mmol), 2-(dicyclohexylphosphino)-2',4',6'-triisopropylbiphenyl (3.2 g, 6.7 mmol) and potassium carbonate (40.7 g, 294.8 mmol) were added into a mixture of toluene (80 mL), absolute ethanol (40 mL) and deionized water (20 mL), the reaction mixture was heated to 80° C. under nitrogen atmosphere, and stirred for 2 h; then the reaction solution was cooled to room temperature, washed with water. The separated organic phase was dried over anhydrous magnesium sulfate, and then concentrated in a vacuuo to obtain a crude product. The crude product was purified by recrystallization using a mixture of dichloromethane and n-heptane to obtain intermediate 1-A (57.8 g, yield 70%) as a solid.

Synthesis of Intermediate VI

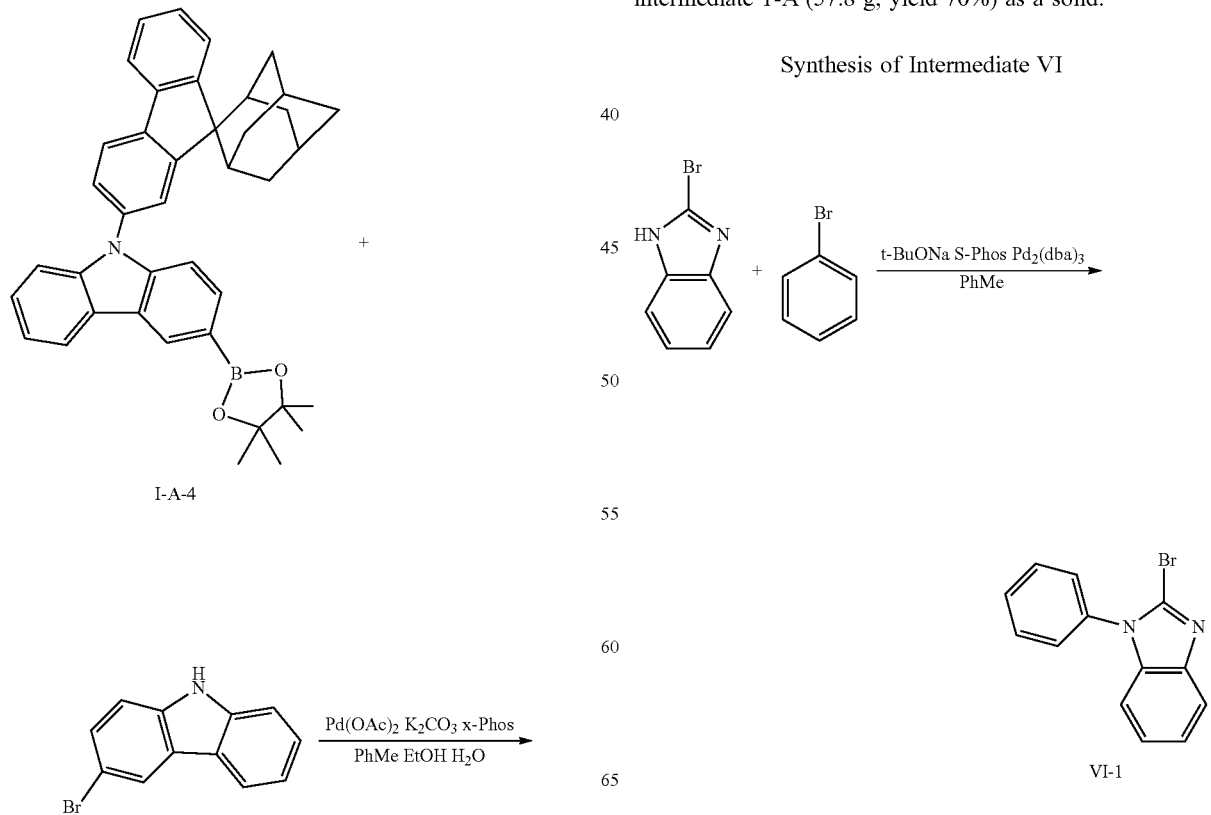

2-bromobenzimidazole (3.6 g, 18 mmol), bromobenzene (2.8 g, 18 mmol), tris (dibenzylidenacetone) dipalladium (0.16 g, 0.18 mmol), 2-dicyclohexylphosphino-2',6'-dimethoxybiphenyl (0.15 g, 0.36 mmol) and sodium tert-butoxide (2.6 g, 27 mmol) were added to toluene (80 mL), the reaction mixture was heated to 108° C. under the nitrogen atmosphere, and stirred for 3 h; then the reaction solution was cooled to room temperature, washed with water. The separated organic phase was dried over anhydrous magnesium sulfate, and then concentrated in a vacuuo to obtain a crude product. The crude product was purified by recrystallization using toluene to obtain intermediate VI-1 (3.9 g, yield 80%).

Synthesis of Compound 3

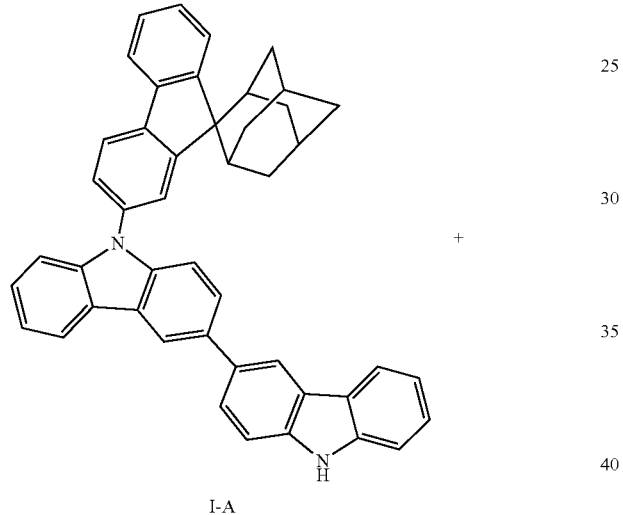

I-A

+

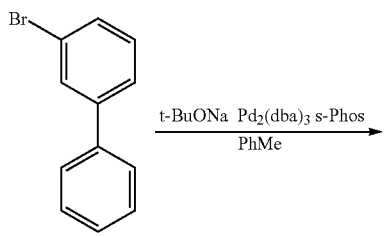

t-BuONa  Pd$_2$(dba)$_3$  s-Phos
PhMe

-continued

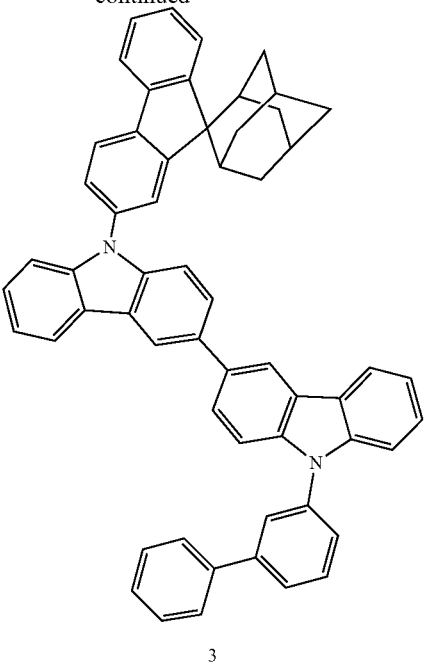

3

The intermediate 1-A (6 g, 9.7 mmol), 3-bromobiphenyl (1.13 g, 4.8 mmol), tris (dibenzylidenacetone) dipalladium (0.044 g, 0.048 mmol), 2-dicyclohexylphosphino-2',6'-dimethoxybiphenyl (0.039 g, 0.096 mmol) and sodium tert-butoxide (0.692 g, 7.2 mmol) were added to toluene (80 mL), the reaction mixture was heated to 108° C. under the nitrogen atmosphere, and stirred for 3 h; then the reaction solution was cooled to room temperature, washed with water. The separated organic phase was dried over anhydrous magnesium sulfate, and then concentrated in a vacuuo to obtain a crude product. The crude product was purified by recrystallization using toluene to obtain compound 3 (2.55 g, yield 69%) as a white solid. LC-MS (ESI, pos. ion) m/z: 769.05 [M+H]$^+$.

Compound 3 $^1$H NMR (CD$_2$Cl$_2$, 400 MHz) δ: 8.55 (d, 2H), 8.30 (s, 1H), 8.24-8.10 (m, 3H), 8.08-7.81 (m, 11H), 7.65-7.30 (m, 7H), 7.26-7.06 (m, 6H), 2.91 (d, 2H), 2.61 (d, 2H), 2.16 (s, 1H), 1.90 (s, 3H), 1.77 (d, 2H), 1.69 (d, 2H), 1.60 (s, 2H) ppm.

The compound 4 to compound 18, compound 119, compound 120, compound 121, compound 124, compound 233, compound 246, compound 252 and compound 268 were prepared by reference to the synthesis method of compound 3 using a raw material 2 instead of 3-bromobiphenyl. Wherein the numbers, structures, raw materials, synthesis yield in the last step, characterization data and the like of the compound 4 to compound 18, compound 119, compound 120, compound 121, compound 233, compound 124, compound 246, compound 252 and compound 268 are shown in Table 1:

TABLE 1
Structures, Preparation and Characterization Data of Compounds
| Compound Number | Intermediate Number | Raw material 2 | Compound Structure | Yield (%) | Mass spectrum (m/z) (M + H)+ |
|---|---|---|---|---|---|
| 4 | Intermediate 1-A | 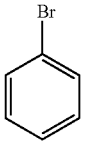 | 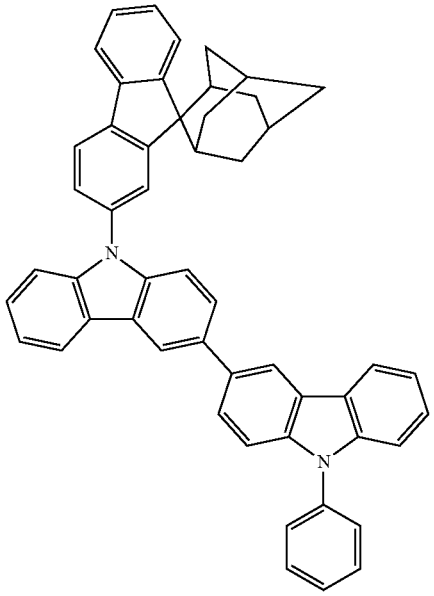 [SMILES: c1ccc(-n2c3ccccc3c3cc(-c4ccc5c(c4)c4ccccc4n5-c4ccc5c(c4)C4(c6ccccc6-5)C5CC6CC(C5)CC4C6)ccc32)cc1] | 70% | 693.02 |
| 5 | Intermediate 1-A | 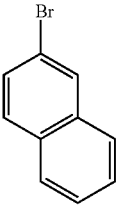 | 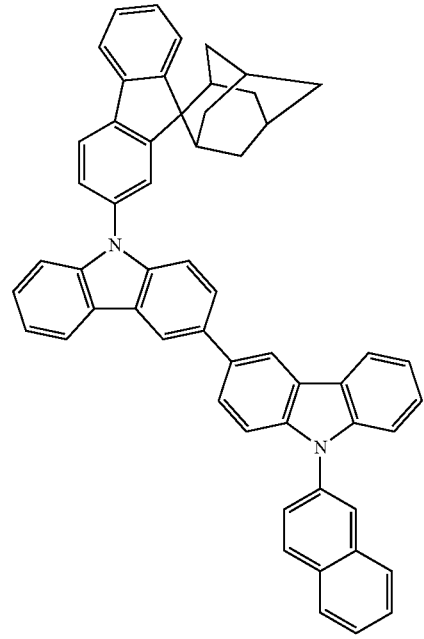 [SMILES: c1ccc2c(c1)-c1ccc(-n3c4ccccc4c4cc(-c5ccc6c(c5)c5ccccc5n6-c5ccc6ccccc6c5)ccc43)cc1C21C2CC3CC(C2)CC1C3] | 68% | 743.03 |

TABLE 1-continued
Structures, Preparation and Characterization Data of Compounds
| Compound Number | Intermediate Number | Raw material 2 | Compound Structure | Yield (%) | Mass spectrum (m/z) (M + H)+ |
|---|---|---|---|---|---|
| 6 | Intermediate 1-A | 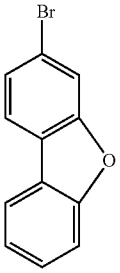 [SMILES: Brc1ccc2c(c1)oc1ccccc12] | 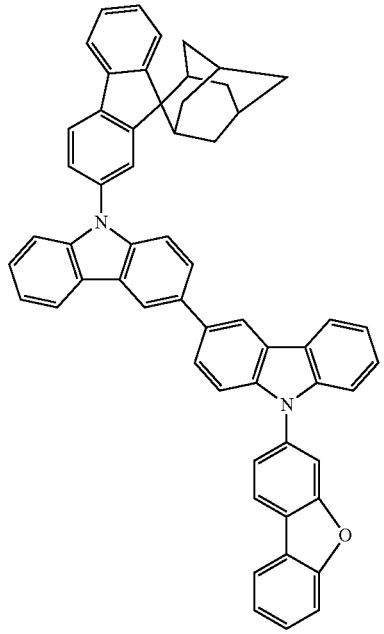 [SMILES: c1ccc2c(c1)-c1ccc(-n3c4ccccc4c4cc(-c5ccc6c(c5)c5ccccc5n6-c5ccc6c(c5)oc5ccccc56)ccc43)cc1C21C2CC3CC(C2)CC1C3] | 65% | 743.03 |
| 7 | Intermediate 1-A | 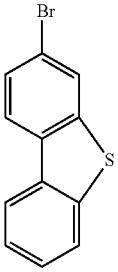 [SMILES: Brc1ccc2c(c1)sc1ccccc12] | 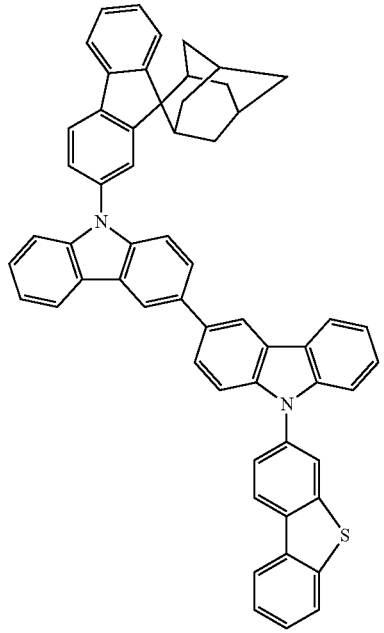 [SMILES: c1ccc2c(c1)-c1ccc(-n3c4ccccc4c4cc(-c5ccc6c(c5)c5ccccc5n6-c5ccc6c(c5)sc5ccccc56)ccc43)cc1C21C2CC3CC(C2)CC1C3] | 71% | 799.01 |

TABLE 1-continued

Structures, Preparation and Characterization Data of Compounds

| Compound Number | Intermediate Number | Raw material 2 | Compound Structure | Yield (%) | Mass spectrum (m/z) (M + H)+ |
|---|---|---|---|---|---|
| 8 | Intermediate 1-A | | 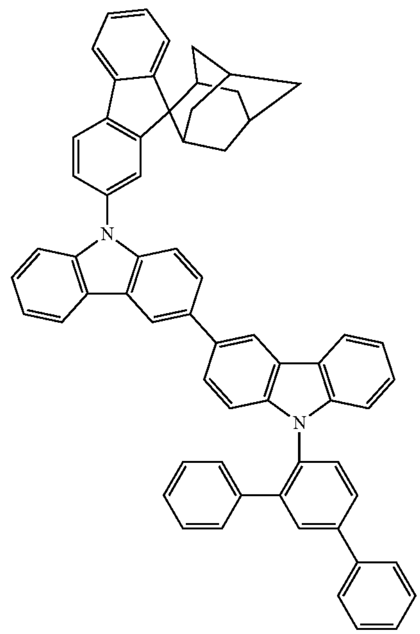 [SMILES: c1ccc(-c2ccc(-n3c4ccccc4c4cc(-c5ccc6c(c5)c5ccccc5n6-c5ccc6c(c5)C5(c7ccccc7-6)C6CC7CC(C6)CC5C7)ccc43)c(-c3ccccc3)c2)cc1] | 70% | 845.08 |
| 9 | Intermediate 1-A | | 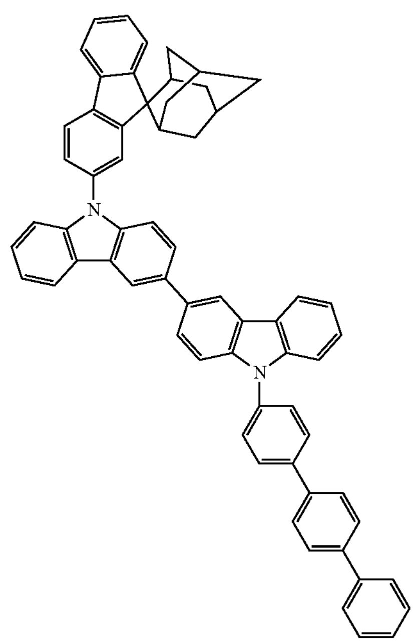 [SMILES: c1ccc(-c2ccc(-c3ccc(-n4c5ccccc5c5cc(-c6ccc7c(c6)c6ccccc6n7-c6ccc7c(c6)C6(c8ccccc8-7)C7CC8CC(C7)CC6C8)ccc54)cc3)cc2)cc1] | 65% | 845.08 |

TABLE 1-continued

Structures, Preparation and Characterization Data of Compounds

| Compound Number | Intermediate Number | Raw material 2 | Compound Structure | Yield (%) | Mass spectrum (m/z) (M + H)+ |
|---|---|---|---|---|---|
| 10 | Intermediate 1-A | 4-bromophenyl-naphthalene | 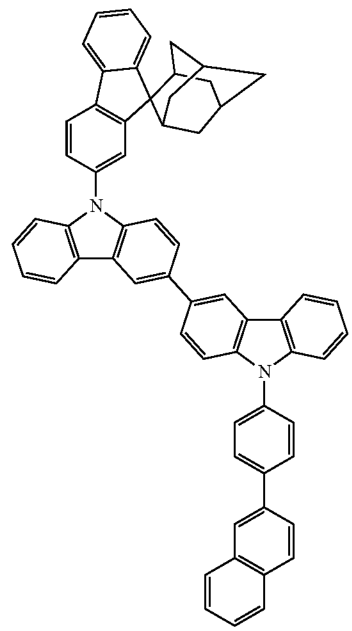 [SMILES: c1ccc2c(c1)-c1ccc(-n3c4ccccc4c4cc(-c5ccc6c(c5)c5ccccc5n6-c5ccc(-c6ccc7ccccc7c6)cc5)ccc43)cc1C21C2CC3CC(C2)CC1C3] | 63% | 819.07 |
| 11 | Intermediate 1-A | 2-bromophenanthrene | 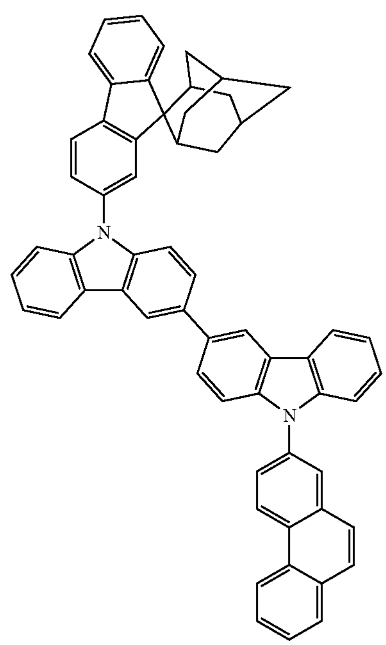 [SMILES: c1ccc2c(c1)-c1ccc(-n3c4ccccc4c4cc(-c5ccc6c(c5)c5ccccc5n6-c5ccc6c(ccc7ccccc76)c5)ccc43)cc1C21C2CC3CC(C2)CC1C3] | 59% | 793.05 |

TABLE 1-continued

Structures, Preparation and Characterization Data of Compounds

| Compound Number | Intermediate Number | Raw material 2 | Compound Structure | Yield (%) | Mass spectrum (m/z) $(M + H)^+$ |
|---|---|---|---|---|---|
| 12 | Intermediate 1-A | 1-bromo-4-phenylnaphthalene | (structure) | 75% | 819.07 |
| 13 | Intermediate 1-A | 1-(3-bromophenyl)naphthalene | (structure) | 72% | 819.07 |

TABLE 1-continued

Structures, Preparation and Characterization Data of Compounds

| Compound Number | Intermediate Number | Raw material 2 | Compound Structure | Yield (%) | Mass spectrum (m/z) (M + H)+ |
|---|---|---|---|---|---|
| 14 | Intermediate 1-A | (structure) | (structure) | 48% | 847.07 |
| 15 | Intermediate 1-A | (structure) | (structure) | 45% | 894.01 |

TABLE 1-continued
Structures, Preparation and Characterization Data of Compounds
| Compound Number | Intermediate Number | Raw material 2 | Compound Structure | Yield (%) | Mass spectrum (m/z) (M + H)+ |
|---|---|---|---|---|---|
| 16 | Intermediate 1-A | 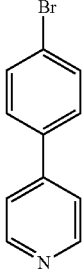 [SMILES: Brc1ccc(-c2ccncc2)cc1] | 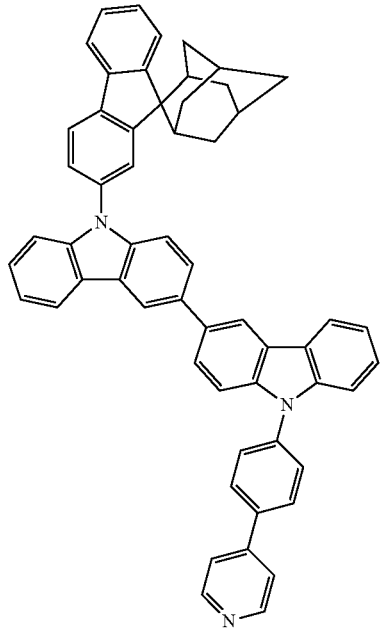 [SMILES: c1ccc2c(c1)-c1ccc(-n3c4ccccc4c4cc(-c5ccc6c(c5)c5ccccc5n6-c5ccc(-c6ccncc6)cc5)ccc43)cc1C21C2CC3CC(C2)CC1C3] | 51% | 770.05 |
| 17 | Intermediate 1-A | 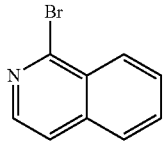 [SMILES: Brc1nccc2ccccc12] | 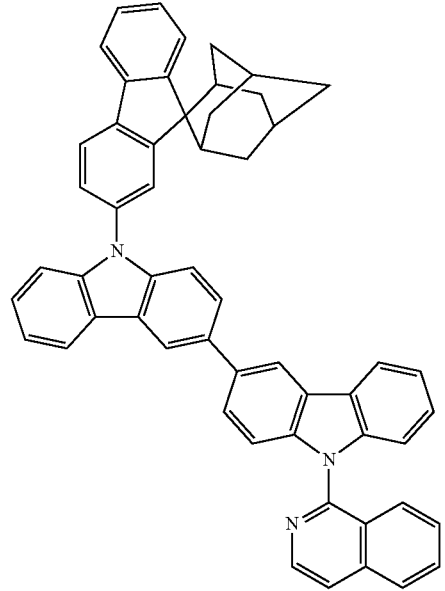 [SMILES: c1ccc2c(c1)-c1ccc(-n3c4ccccc4c4cc(-c5ccc6c(c5)c5ccccc5n6-c5nccc6ccccc56)ccc43)cc1C21C2CC3CC(C2)CC1C3] | 53% | 744.03 |

TABLE 1-continued

Structures, Preparation and Characterization Data of Compounds

| Compound Number | Intermediate Number | Raw material 2 | Compound Structure | Yield (%) | Mass spectrum (m/z) (M + H)+ |
|---|---|---|---|---|---|
| 18 | Intermediate 1-A | Br-phenanthrene | (structure) | 69% | 793.05 |
| 119 | Intermediate 1-A | VI-1 (2-bromo-1-phenylbenzimidazole) | (structure) | 65% | 809.36 |

TABLE 1-continued

Structures, Preparation and Characterization Data of Compounds

| Compound Number | Intermediate Number | Raw material 2 | Compound Structure | Yield (%) | Mass spectrum (m/z) (M + H)+ |
|---|---|---|---|---|---|
| 120 | Intermediate 1-A | | 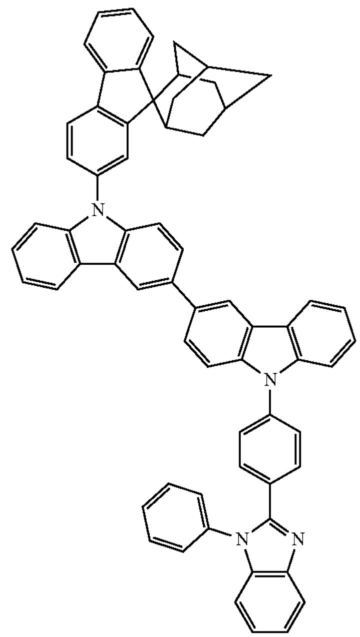 [SMILES: c1ccc(-n2c(-c3ccc(-n4c5ccccc5c5cc(-c6ccc7c(c6)c6ccccc6n7-c6ccc7c(c6)C6(c8ccccc8-7)C7CC8CC(C7)CC6C8)ccc54)cc3)nc3ccccc32)cc1] | 63% | 885.39 |
| 121 | Intermediate 1-A | | 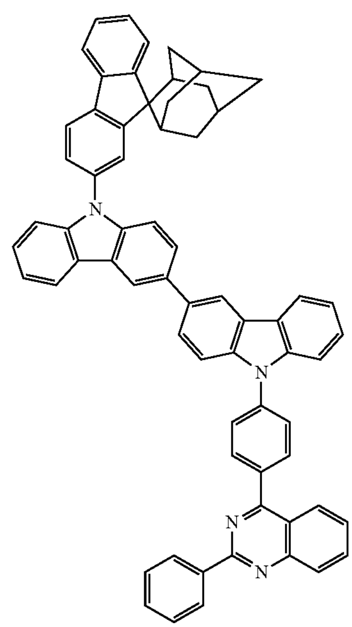 [SMILES: c1ccc(-c2nc(-c3ccc(-n4c5ccccc5c5cc(-c6ccc7c(c6)c6ccccc6n7-c6ccc7c(c6)C6(c8ccccc8-7)C7CC8CC(C7)CC6C8)ccc54)cc3)c3ccccc3n2)cc1] | 61% | 897.39 |

TABLE 1-continued
Structures, Preparation and Characterization Data of Compounds
| Compound Number | Intermediate Number | Raw material 2 | Compound Structure | Yield (%) | Mass spectrum (m/z) (M + H)+ |
|---|---|---|---|---|---|
| 124 | Intermediate 1-A | 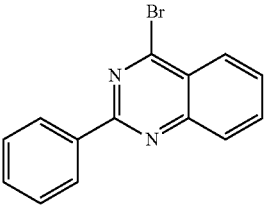 [SMILES: Brc1nc(-c2ccccc2)nc2ccccc12] | 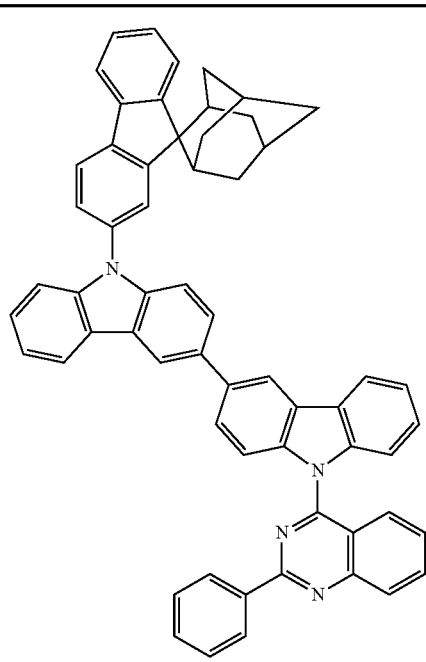 | 65% | 822.36 |
| 233 | Intermediate 1-A | 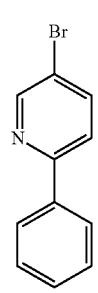 | 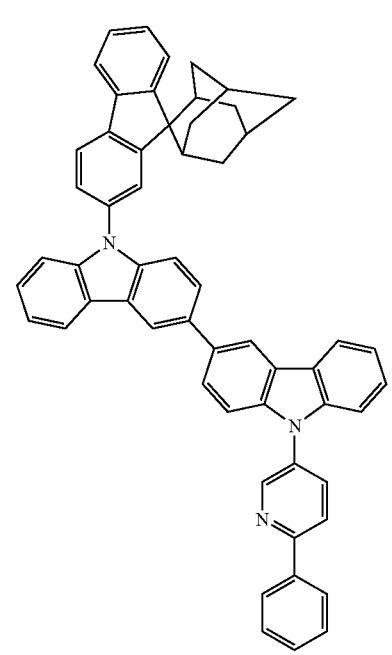 [SMILES: c1ccc(-c2ccc(-n3c4ccccc4c4cc(-c5ccc6c(c5)c5ccccc5n6-c5ccc6c(c5)C5(c7ccccc7-6)C6CC7CC(C6)CC5C7)ccc43)cn2)cc1] | 75% | 770.35 |

TABLE 1-continued

Structures, Preparation and Characterization Data of Compounds

| Compound Number | Intermediate Number | Raw material 2 | Compound Structure | Yield (%) | Mass spectrum (m/z) (M + H)+ |
|---|---|---|---|---|---|
| 246 | Intermediate 1-A | | 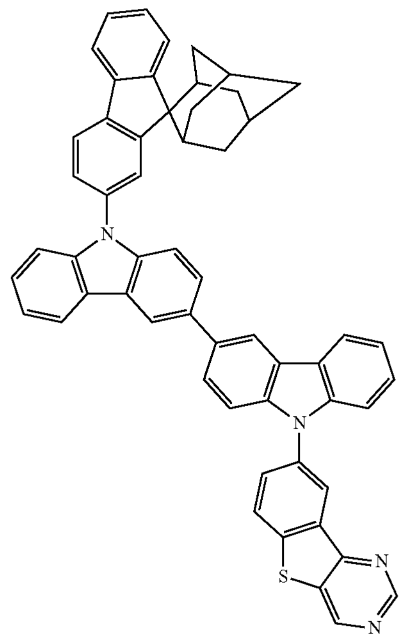 [SMILES: c1ccc2c(c1)-c1ccc(-n3c4ccccc4c4cc(-c5ccc6c(c5)c5ccccc5n6-c5ccc6sc7cncnc7c6c5)ccc43)cc1C21C2CC3CC(C2)CC1C3] | 68% | 801.30 |
| 252 | Intermediate 1-A | | 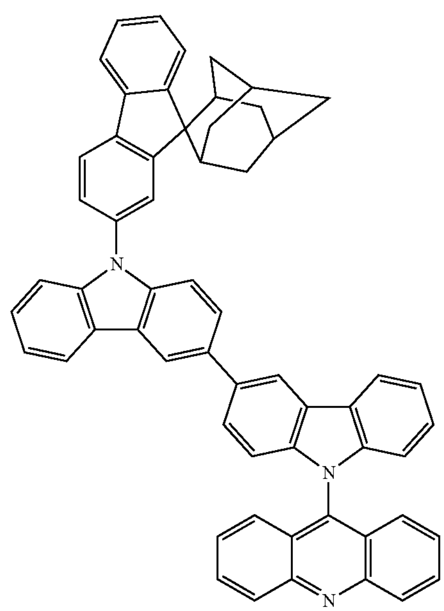 [SMILES: c1ccc2c(c1)-c1ccc(-n3c4ccccc4c4cc(-c5ccc6c(c5)c5ccccc5n6-c5c6ccccc6nc6ccccc56)ccc43)cc1C21C2CC3CC(C2)CC1C3] | 73% | 794.35 |

TABLE 1-continued

Structures, Preparation and Characterization Data of Compounds

| Compound Number | Intermediate Number | Raw material 2 | Compound Structure | Yield (%) | Mass spectrum (m/z) (M + H)+ |
|---|---|---|---|---|---|
| 268 | Intermediate 1-A | 2-bromo-4,6-diphenyl-1,3,5-triazine | (structure shown) | 75% | 848.37 |

Nuclear magnetic data of some compounds in the table above are shown in Table 2 below:

TABLE 2

| Compound | Structure | Nuclear magnetic data 1H NMR(CD$_2$Cl$_2$, 400 MHz) |
|---|---|---|
| Compound 4 | (structure shown) | δ: 8.54(d, 2H), 8.33(s, 1H), 8.28-8.25 (m, 2H), 8.20(d, 1H), 8.05(d, 1H), 7.91 (d, 1H), 7.84(t, 2H), 7.68-7.62(m, 5H), 7.58(d, 1H), 7.54-7.50(m, 3H), 7.48-7.43(m, 4H), 7.37-7.31(m, 3H), 3.00(d, 2H), 2.86(d, 2H), 2.22(s, 1H), 2.07(s, 1H), 1.97(s, 2H), 1.85(d, 4H), 1.74(s, 2H) ppm |

TABLE 2-continued
| Compound | Structure | Nuclear magnetic data 1H NMR(CD$_2$Cl$_2$, 400 MHz) |
|---|---|---|
| Compound 5 | 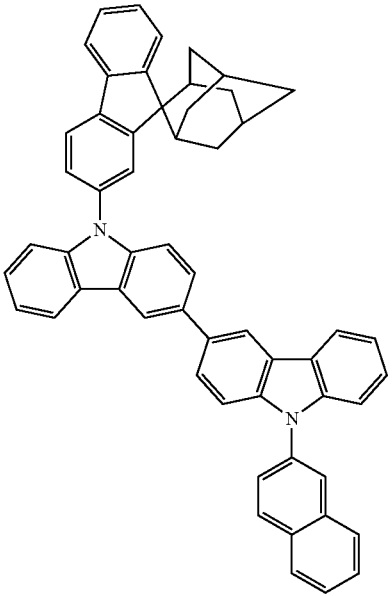 [SMILES: c1ccc2c(c1)-c1ccc(-n3c4ccccc4c4cc(-c5ccc6c(c5)c5ccccc5n6-c5ccc6ccccc6c5)ccc43)cc1C21C2CC3CC(C2)CC1C3] | δ: 8.28(d, 2H), 8.22(d, 2H), 7.87(d, 2H), 7.75(d, 4H), 7.67(s, 1H), 7.65(m, 1H), 7.55(m, 2H), 7.40(m, 3H), 7.30(m, 6H), 7.17(m, 1H), 7.11(d, 1H), 7.06(d, 1H), 7.01(m, 2H), 2.91 (d, 2H), 2.61 (d, 2H), 2.16 (s, 1H), 1.90 (s, 3H), 1.77 (d, 2H), 1.69 (d, 2H), 1.60 (s, 2H) ppm. |
| Compound 6 | 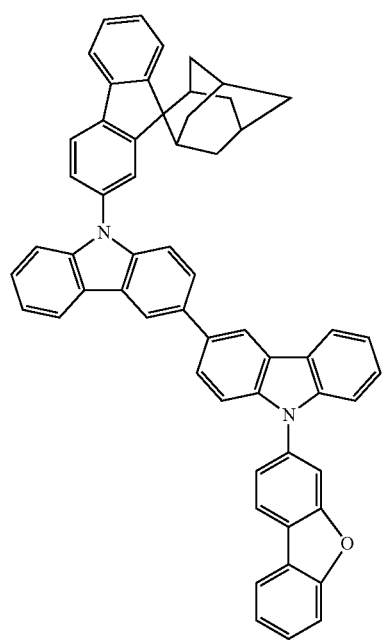 [SMILES: c1ccc2c(c1)-c1ccc(-n3c4ccccc4c4cc(-c5ccc6c(c5)c5ccccc5n6-c5ccc6c(c5)oc5ccccc56)ccc43)cc1C21C2CC3CC(C2)CC1C3] | δ: 8.26(d, 1H), 8.11(d, 2H), 8.00(t, 3H), 7.64-7.48(m, 7H), 7.34(m, 4H), 7.24(m, 7H), 7.09(m, 2H), 7.01(m, 2H), 2.91 (d, 2H), 2.61 (d, 2H), 2.16 (s, 1H), 1.90 (s, 3H), 1.77 (d, 2H), 1.69 (d, 2H), 1.60 (s, 2H) ppm |

TABLE 2-continued

| Compound | Structure | Nuclear magnetic data 1H NMR(CD$_2$Cl$_2$, 400 MHz) |
|---|---|---|
| Compound 124 | 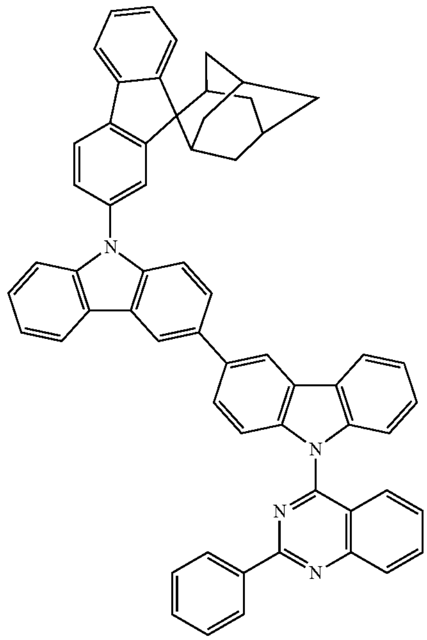 [SMILES: c1ccc(-c2nc(-n3c4ccccc4c4cc(-c5ccc6c(c5)c5ccccc5n6-c5ccc6c(c5)C5(c7ccccc7-6)C6CC7CC(C6)CC5C7)ccc43)c3ccccc3n2)cc1] | δ: 8.38(d, 2H), 8.20(d, 1H), 8.11(d, 2H), 8.06(d, 1H), 8.00(t, 2H), 7.88(m, 3H), 7.69(m, 1H), 7.65-7.57(m, 3H), 7.50(m, 5H), 7.38-7.30(m, 2H), 7.27-7.22(m, 5H), 7.18-6.97(m, 3H), 2.91 (d, 2H), 2.61 (d, 2H), 2.16 (s, 1H), 1.90 (s, 3H), 1.77 (d, 2H), 1.69 (d, 2H), 1.60 (s, 2H) ppm |
| Compound 268 | 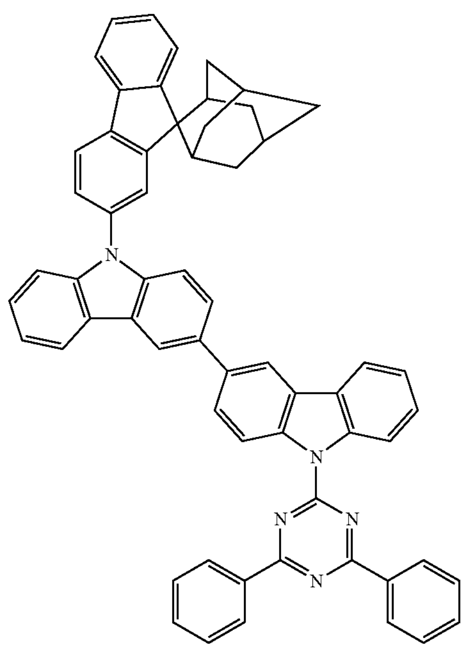 [SMILES: c1ccc(-c2nc(-c3ccccc3)nc(-n3c4ccccc4c4cc(-c5ccc6c(c5)c5ccccc5n6-c5ccc6c(c5)C5(c7ccccc7-6)C6CC7CC(C6)CC5C7)ccc43)n2)cc1] | δ: 8.52(t, 4H), 8.34(d, 1H), 8.22-8.18(d, 3H), 8.03(m, 2H), 7.8(m, 1H), 7.58-7.51(m, 10H), 7.42-7.34(m, 2H), 7.29-7.18(m, 5H), 7.08-7.01(m, 3H), 2.91 (d, 2H), 2.61 (d, 2H), 2.16 (s, 1H), 1.90 (s, 3H), 1.77 (d, 2H), 1.69 (d, 2H), 1.60 (s, 2H) ppm |

Compound 19-Compound 20 were Synthesized by the Following Synthetic Route
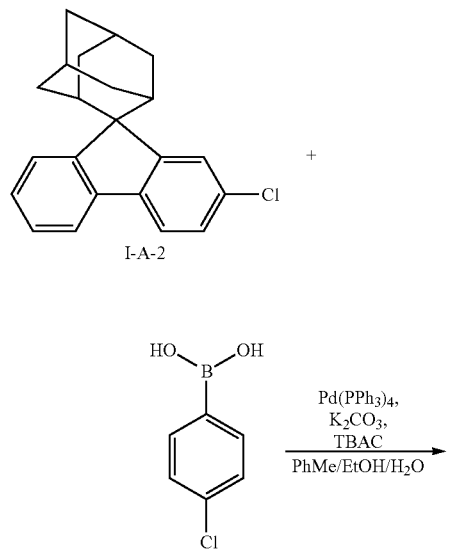
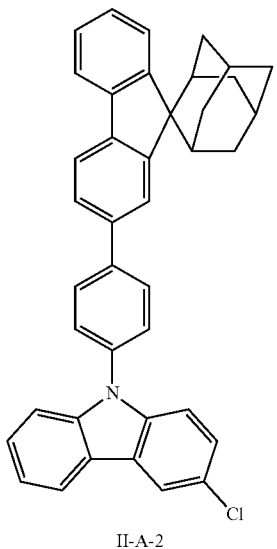
-continued
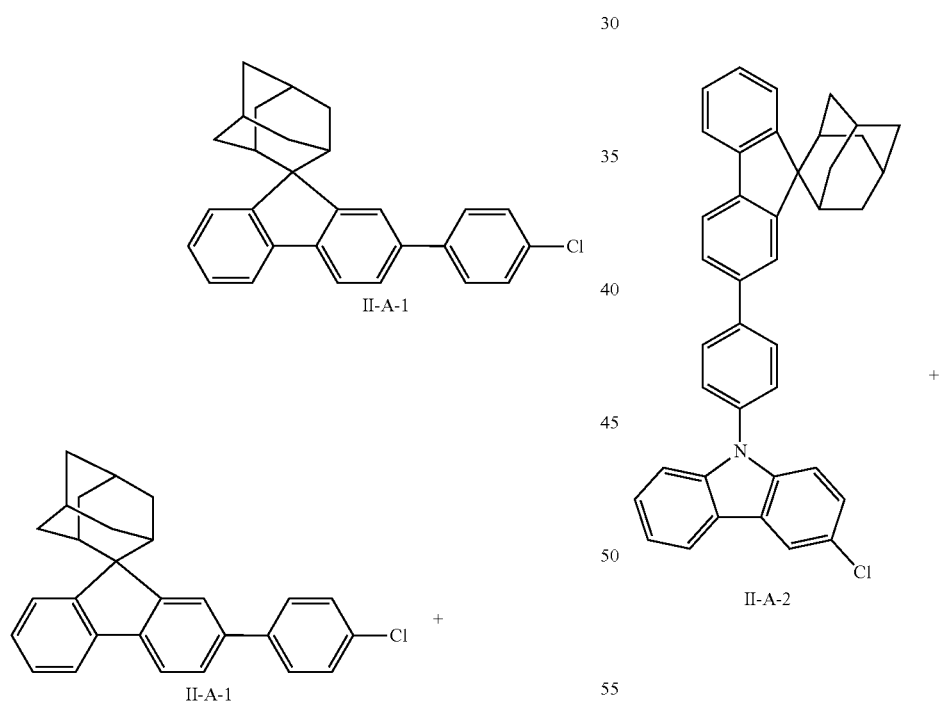
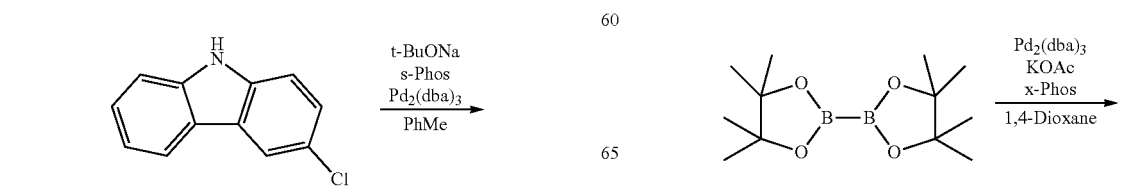

-continued
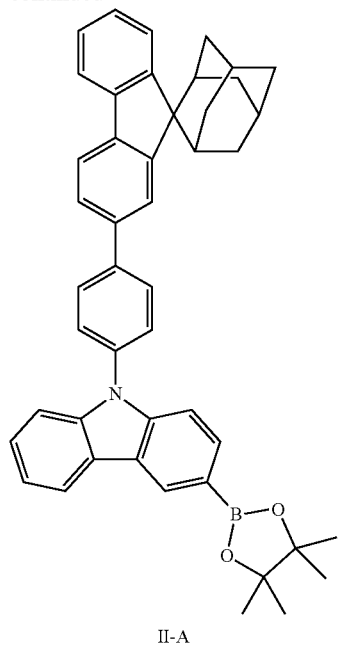
II-A
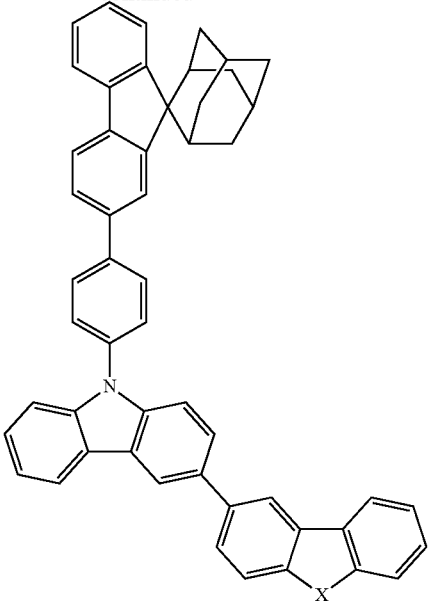
19 or 20
Wherein X has the definition stated herein.
Synthesis of Intermediate II-A
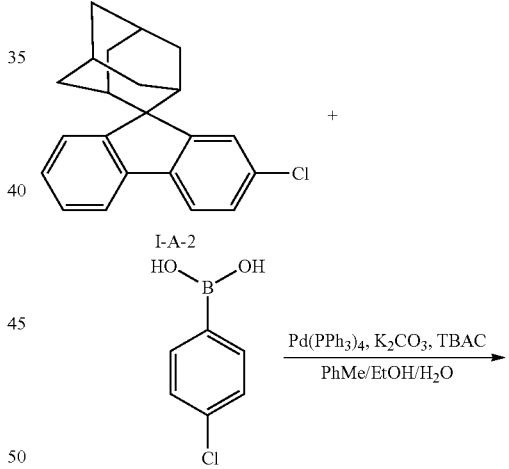
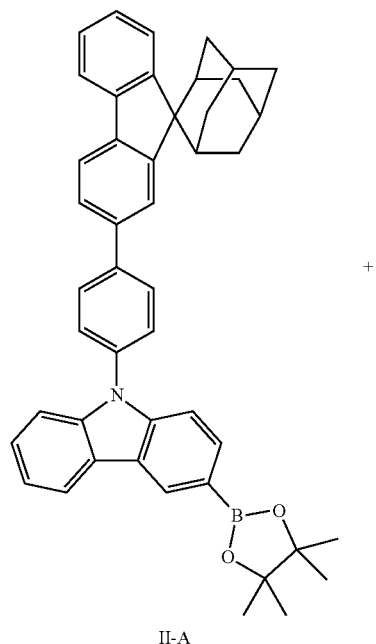
II-A
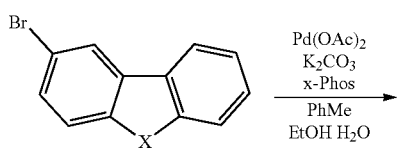
The intermediate I-A-2 (20 g, 62.34 mmol), 4-chlorophenylboronic acid (9.75 g, 62.34 mmol), tetrakis (triphenylphosphine) palladium (0.72 g, 0.62 mmol), potassium carbonate (17.2 g, 124.6 mmol), tetrabutyl ammonium chloride (0.34 g, 1.25 mmol), methylbenzene (160 mL), ethanol (40 mL) and deionized water (40 mL) were added into a round-bottom flask, and the reaction mixture was heated to 78° C. under the nitrogen atmosphere and stirred for 8 hours; the reaction solution was cooled to room temperature. Methylbenzene (100 mL) was added for extraction, the combined organic phases were dried over anhydrous magnesium sulfate, and then concentrated in a vacuuo to obtain a residue. The residue was purified by silica gel column chromatography and eluted with n-heptane. The obtained crude product was purified by recrystallization using a mixture of dichloromethane and ethanol, to obtain compound intermediate II-A-1 (18.6 g, yield 75%) as a white solid.

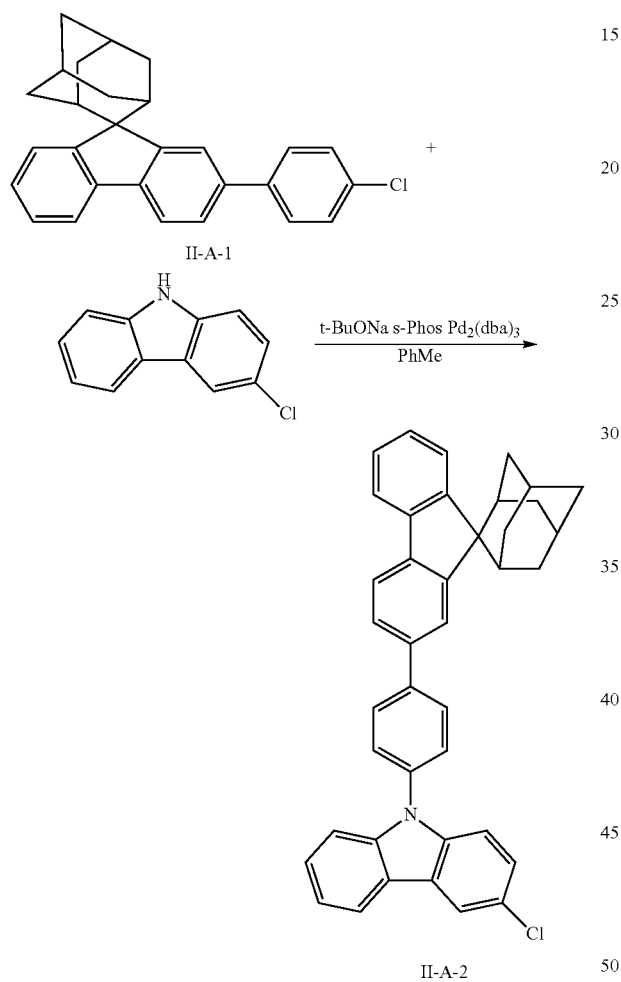

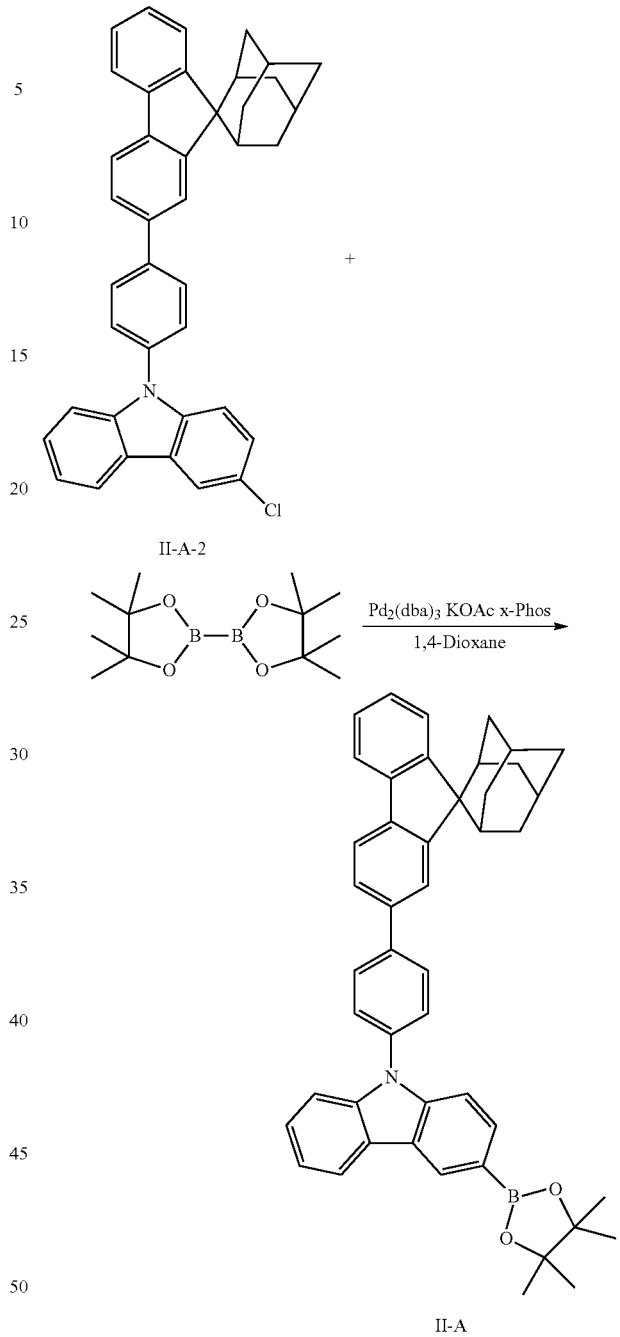

The intermediate II-A-1 (18.6 g, 46.9 mmol), 3-chlorocarbazole (8.2 g, 40.8 mmol), tris (dibenzylidenacetone) dipalladium (0.37 g, 0.41 mmol), 2-dicyclohexylphosphino-2',6'-dimethoxybiphenyl (0.34 g, 0.82 mmol) and sodium tert-butoxide (5.89 g, 61.2 mmol) were added to toluene (160 mL), the reaction mixture was heated to 108° C. under the nitrogen atmosphere, and stirred for 3 h; then the reaction solution was cooled to room temperature, washed with water. The separated organic phase was dried over anhydrous magnesium sulfate, and then concentrated in a vacuuo to obtain a crude product. The crude product was purified by recrystallization using toluene to obtain intermediate II-A-2 (16 g, yield 70%) as a white solid compound.

The intermediate II-A-2 (16 g, 29.2 mmol), bis (pinacolato) diboron (8.9 g, 30.1 mmol), tris (dibenzylideneacetone) dipalladium (0.267 g, 0.292 mmol), 2-(dicyclohexylphosphino)-2',4',6'-triisopropylbiphenyl (0.139 g, 0.292 mmol) and potassium acetate (8.59 g, 603 mmol) were added into 1,4-dioxane (128 mL), the reaction mixture was heated to 80° C. under nitrogen atmosphere, and stirred for 3 h; then the reaction solution was cooled to room temperature, washed with water. The separated organic phase was dried over anhydrous magnesium sulfate, and then concentrated in a vacuuo to obtain a crude product. The crude product was purified by recrystallization using toluene to obtain intermediate II-A (13.3 g, yield 70%) as a white solid.

Synthesis of Compound 19

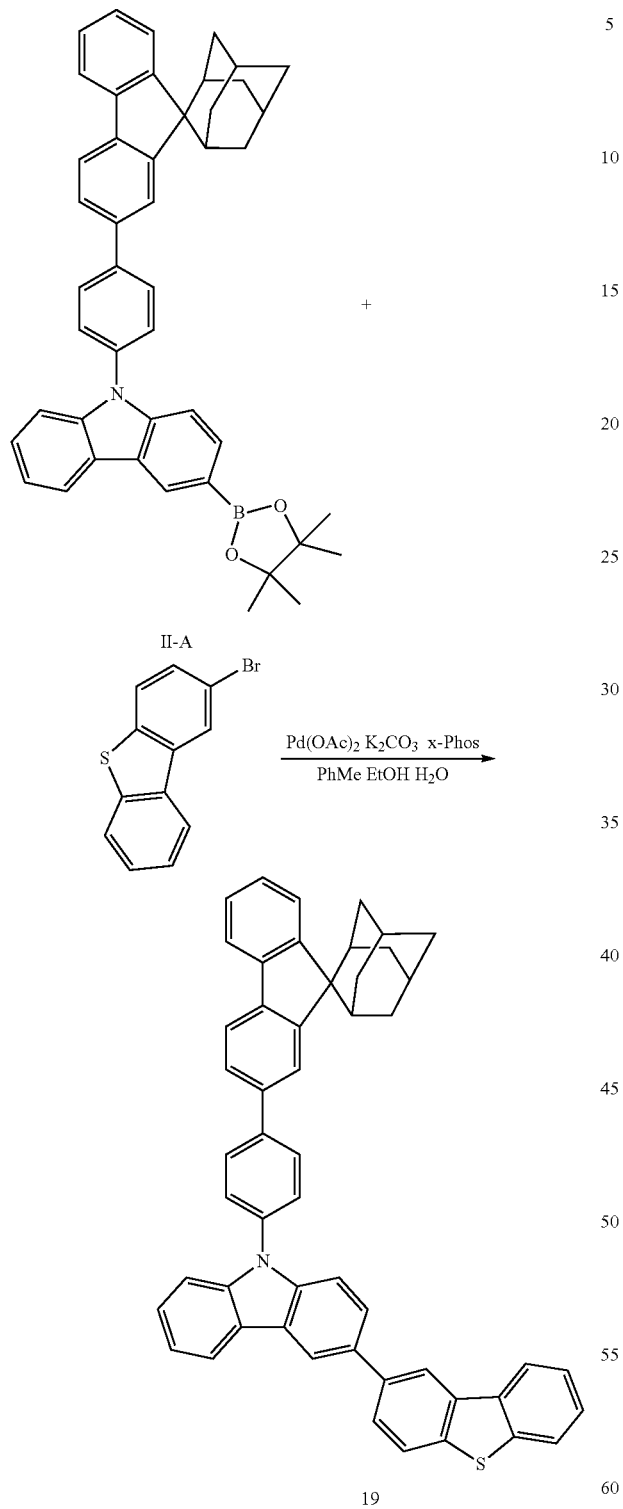

The intermediate II-A (6 g, 9.1 mmol), 2-bromo-dibenzothiophene (2.2 g, 9.1 mmol), palladium acetate (0.11 g, 0.45 mmol), 2-(dicyclohexylphosphino)-2',4',6'-triisopropylbiphenyl (0.215 g, 0.45 mmol) and potassium carbonate (2.76 g, 20 mmol) were added into a mixture of toluene (48 mL), absolute ethanol (24 mL) and deionized water (12 mL), the reaction mixture was heated to 80° C. under nitrogen protection, and stirred for 2 h; then the reaction solution was cooled to room temperature, washed with water. The separated organic phase was dried over anhydrous magnesium sulfate, and then concentrated in a vacuuo to obtain a crude product. The crude product was purified by recrystallization using a mixture of dichloromethane and n-heptane to obtain compound 19 (4.8 g, yield 75%) as a light yellow solid. LC-MS (ESI, pos. ion) m/z: 709.98 [M+H]$^+$.

Synthesis of Compound 20

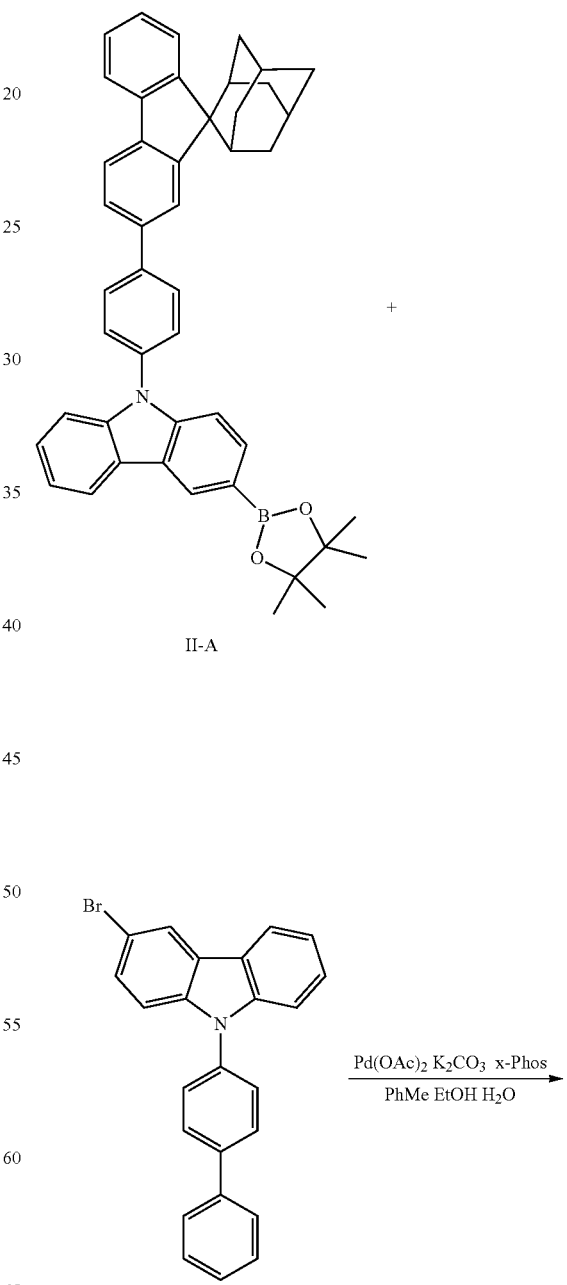

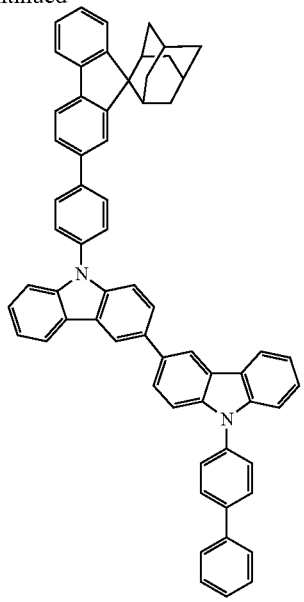

20

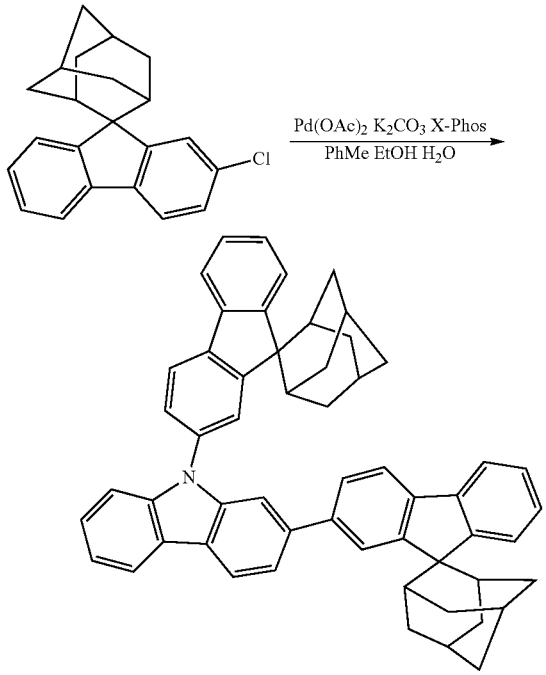

21

The intermediate II-A (6 g, 9.1 mmol), 9-[1,1'-biphenyl-4-yl]-3-bromo-9H-carbazole (3.6 g, 9.1 mmol), palladium acetate (0.11 g, 0.45 mmol), 2-(dicyclohexylphosphino)-2',4',6'-triisopropylbiphenyl (0.215 g, 0.45 mmol) and potassium carbonate (2.76 g, 20 mmol) were added into a mixture of toluene (48 mL), absolute ethanol (24 mL) and deionized water (12 mL), the reaction mixture was heated to 80° C. under nitrogen atmosphere, and stirred for 2 h; then the reaction solution was cooled to room temperature, washed with water, dried over anhydrous sodium sulfate, filtered. The filtrate was concentrated in a vacuuo to obtain a crude product. The crude product was purified by recrystallization using a mixture of dichloromethane and n-heptane to obtain compound 20 (5.23 g, yield 68%) as a white solid. LC-MS (ESI, pos. ion) m/z: 845.08 [M+H]$^+$.

Compound 20 $^1$H NMR (CD$_2$Cl$_2$, 400 MHz) δ: 8.11 (d, 2H), 7.97 (m, 2H), 7.63 (d, 1H), 7.59 (t, 2H), 7.57 (m, 2H), 7.53 (t, 5H), 7.43 (d, 3H), 7.35 (m, 7H), 7.32-7.18 (m, 8H), 7.11 (m, 2H), 2.91 (d, 2H), 2.61 (d, 2H), 2.16 (s, 1H), 1.90 (s, 3H), 1.77 (d, 2H), 1.69 (d, 2H), 1.60 (s, 2H) ppm.

Synthesis of Compound 21

The intermediate I-A-6 (6 g, 10.4 mmol), intermediate I-A-2 (3.3 g, 10.4 mmol), palladium acetate (0.0965 g, 0.43 mmol), 2-(dicyclohexylphosphino)-2',4',6'-triisopropylbiphenyl (0.205 g, 0.43 mmol) and potassium carbonate (3.56 g, 25.8 mmol) were added into a mixture of toluene (80 mL), absolute ethanol (40 mL) and deionized water (20 mL), the reaction mixture was heated to 80° C. under nitrogen atmosphere, and stirred for 2 h; then the reaction solution was cooled to room temperature, washed with water. The separated organic phase was dried over anhydrous magnesium sulfate, and then concentrated in a vacuuo to obtain a crude product. The crude product was purified by recrystallization using a mixture of dichloromethane and n-heptane to obtain compound 21 (4.2 g, yield 55%) as a white solid. LC-MS (ESI, pos. ion) m/z: 736.39[M+H]$^+$.

Compound 21 $^1$H NMR (CD$_2$Cl$_2$, 400 MHz) δ: 8.05 (d, 1H), 7.82 (d, 2H), 7.64 (d, 1H), 7.55 (m, 4H), 7.50 (d, 2H), 7.43-7.34 (m, 4H), 7.27 (m, 3H), 7.20-7.05 (m, 4H), 2.91 (d, 4H), 2.61 (d, 4H), 2.16 (s, 2H), 1.90 (s, 6H), 1.77 (d, 4H), 1.69 (d, 4H), 1.60 (s, 4H) ppm.

Synthesis of Compound 22-Compound 25

Synthesis of Intermediate III-A-1

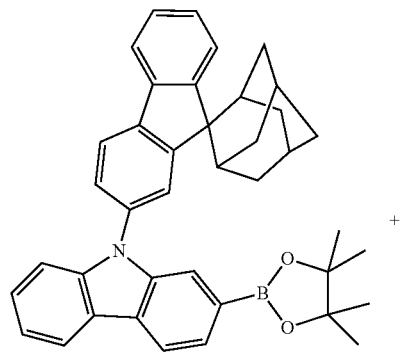

+

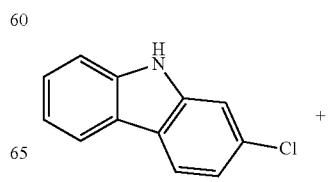

+

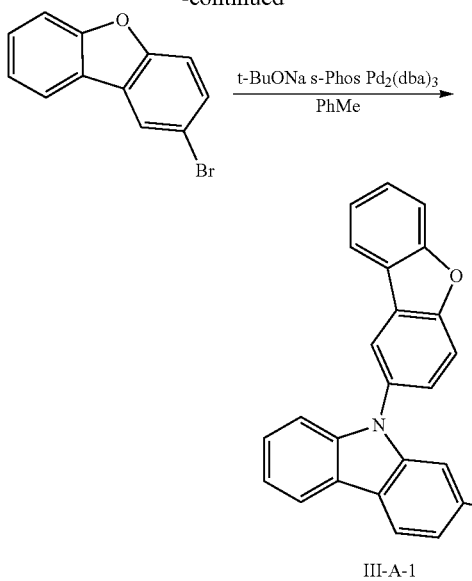

III-A-1

2-chlorocarbazole (10 g, 49.7 mmol), 2-bromodibenzofuran (12 g, 49.7 mmol), tris (dibenzylidenacetone) dipalladium (0.455 g, 0.49 mol), 2-dicyclohexylphosphino-2',6'-dimethoxybiphenyl (0.40 g, 0.98 mmol) and sodium tert-butoxide (7.16 g, 74.5 mmol) were added to toluene (80 mL), the reaction mixture was heated to 108° C. under the nitrogen atmosphere, and stirred for 3 h; then the reaction solution was cooled to room temperature, washed with water. The separated organic phase was dried over anhydrous magnesium sulfate, and then concentrated in a vacuuo to obtain a crude product. The crude product was purified by recrystallization using toluene to obtain intermediate III-A-1 (9 g, yield 50%) as a white solid.

The intermediate III-B-1, intermediate III-C-1 and intermediate III-D-1 were prepared by reference to the synthesis method of the intermediate III-A-1 using the raw material 2A in Table 3 instead of 2-bromodibenzofuran. Wherein the numbers, structures, raw materials, synthesis yield and the like of the intermediate III-B-1, intermediate III-C-1 and intermediate III-D-1 are shown in Table 3:

TABLE 3

Intermediate Number, Structure and Raw Material

| Intermediate Number | Raw material 2A | Intermediate Structure | Yield (%) |
|---|---|---|---|
| Intermediate III-B-1 | [structure: 4-bromophenyl-1-naphthalene] | [structure: 2-chloro-9-(4-(naphthalen-1-yl)phenyl)-9H-carbazole] | 61% |
| Intermediate III-C-1 | [structure: bromobenzene] | [structure: 2-chloro-9-phenyl-9H-carbazole] | 75% |

TABLE 3-continued

Intermediate Number, Structure and Raw Material

| Intermediate Number | Raw material 2A | Intermediate Structure | Yield (%) |
|---|---|---|---|
| Intermediate III-D-1 | Br-(dibenzothiophene) | Cl-carbazole-N-(dibenzothiophene) | 71% |

Synthesis of Intermediate III-A-2

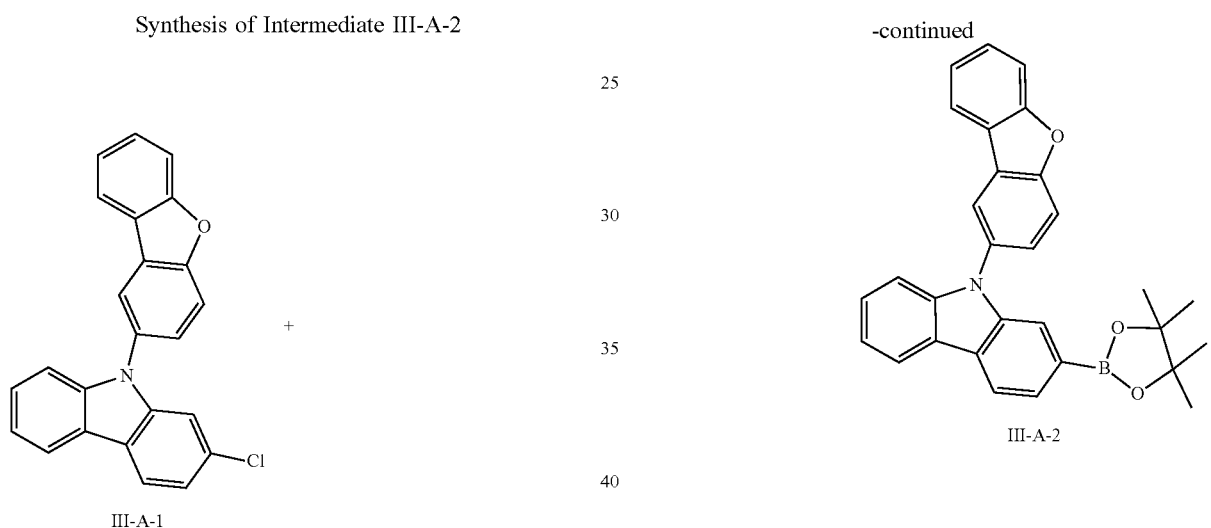

III-A-2

The intermediate III-A-1 (9 g, 24.4 mmol), bis (pinacolato) diboron (6.2 g, 24.4 mmol), tris (dibenzylideneacetone) dipalladium (0.4395 g, 0.48 mmol), 2-(dicyclohexylphosphino)-2',4',6'-triisopropylbiphenyl (0.1159 g, 0.244 mmol) and potassium acetate (3.9 g, 36.6 mmol) were added into 1,4-dioxane (80 mL), the reaction mixture was heated to 80° C. under nitrogen atmosphere, and stirred for 3 h; then the reaction solution was cooled to room temperature, washed with water. The separated organic phase was dried over anhydrous magnesium sulfate, and then concentrated in a vacuuo to obtain a crude product. The crude product was purified by recrystallization using toluene to obtain intermediate III-A-2 (8 g, yield 71%) as a white solid.

The intermediate III-B-2, intermediate III-C-2 and intermediate III-D-2 were prepared by reference to the synthesis method of the intermediate III-A-2 using the raw material 2B instead of the intermediate III-A-1. Wherein the numbers, structures, raw materials, synthesis yield and the like of the intermediate III-B-2, intermediate III-C-2 and intermediate III-D-2 are as shown in Table 4:

TABLE 4
Intermediate Number, Structure and Raw Material
| Intermediate Number | Raw material 2B | Intermediate Structure | Yield (%) |
|---|---|---|---|
| Intermediate III-B-2 | 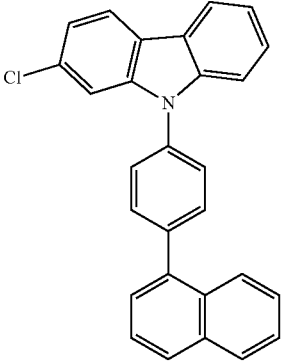 [SMILES: Clc1ccc2c3ccccc3n(-c3ccc(-c4cccc5ccccc45)cc3)c2c1] | 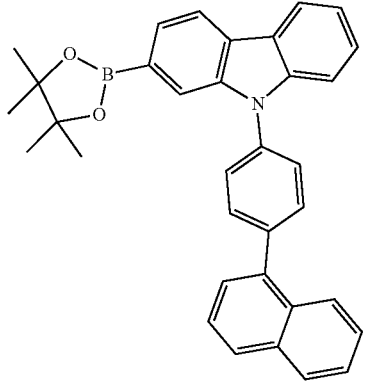 [SMILES: CC1(C)OB(c2ccc3c4ccccc4n(-c4ccc(-c5cccc6ccccc56)cc4)c3c2)OC1(C)C] | 58% |
| Intermediate III-C-2 | 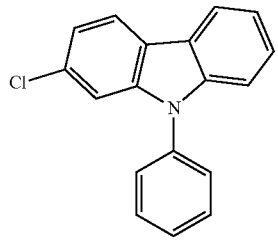 [SMILES: Clc1ccc2c3ccccc3n(-c3ccccc3)c2c1] | 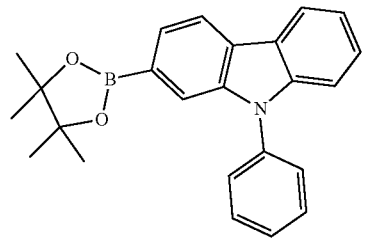 [SMILES: CC1(C)OB(c2ccc3c4ccccc4n(-c4ccccc4)c3c2)OC1(C)C] | 68% |
| Intermediate III-D-2 | 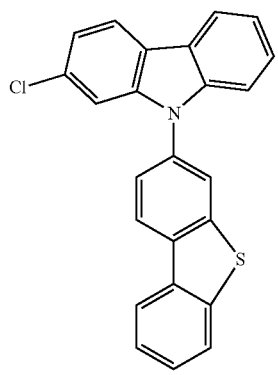 [SMILES: Clc1ccc2c3ccccc3n(-c3ccc4c(c3)sc3ccccc34)c2c1] | 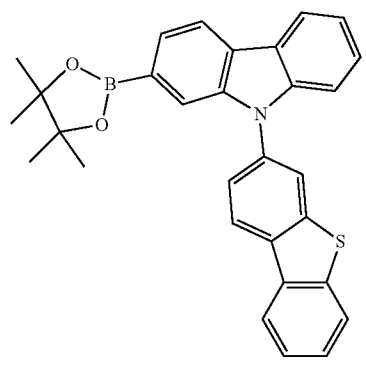 [SMILES: CC1(C)OB(c2ccc3c4ccccc4n(-c4ccc5c(c4)sc4ccccc45)c3c2)OC1(C)C] | 75% |

Synthesis of Intermediate III-A-3

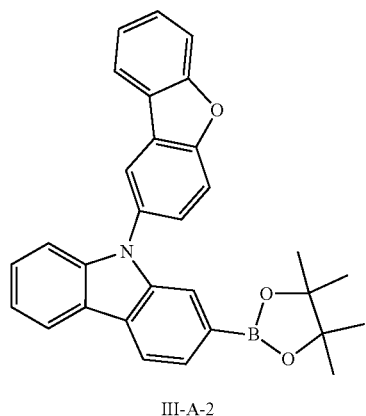

III-A-2

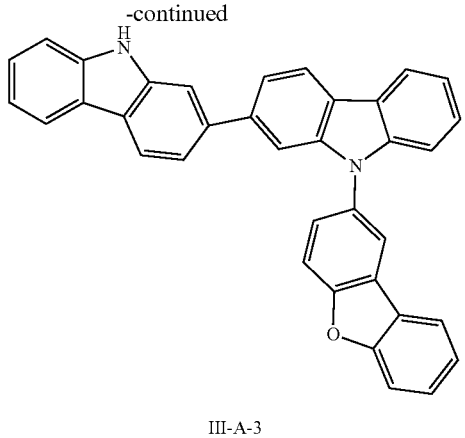

III-A-3

The intermediate III-A-2 (8 g, 17.4 mmol), 2-chlorocarbazole (3.5 g, 17.4 mmol), palladium acetate (0.1593 g, 0.174 mmol), 2-(dicyclohexylphosphino)-2',4',6'-triisopropylbiphenyl (0.1653 g, 0.348 mmol) and potassium carbonate (3.56 g, 25.8 mmol) were added into a mixture of toluene (80 mL), absolute ethanol (40 mL) and deionized water (20 mL), the reaction mixture was heated to 80° C. under nitrogen atmosphere, and stirred for 2 h; then the reaction solution was cooled to room temperature, washed with water. The separated organic phase was dried over anhydrous magnesium sulfate, and then concentrated in a vacuuo to obtain a crude product. The crude product was purified by recrystallization using a mixture of dichloromethane and n-heptane to obtain intermediate III-A-3 (6 g, yield 68.9%) as a white solid.

The intermediate III-B-3, intermediate III-C-3 and intermediate III-D-3 were prepared by reference to the synthesis method of the intermediate III-A-3 using the raw material 2C instead of the intermediate III-A-2. Wherein the numbers, structures, raw materials, synthesis yield and the like of the intermediate III-B-3, intermediate III-C-3 and intermediate III-D-3 are as shown in Table 5:

TABLE 5

Intermediate Number, Structure and Raw Material

| Intermediate Number | Raw material 2C | Intermediate Structure | Yield (%) |
|---|---|---|---|
| Intermediate III-B-3 | *(structure shown)* | *(structure shown)* | 70% |

TABLE 5-continued

Intermediate Number, Structure and Raw Material

| Intermediate Number | Raw material 2C | Intermediate Structure | Yield (%) |
|---|---|---|---|
| Intermediate III-C-3 | | | 65% |
| Intermediate III-D-3 | | | 59% |

Synthesis of Intermediate III-A-4

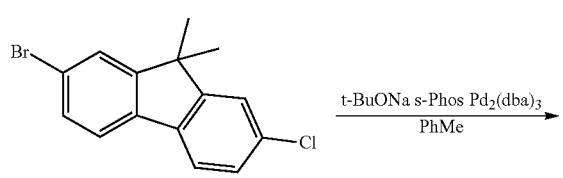

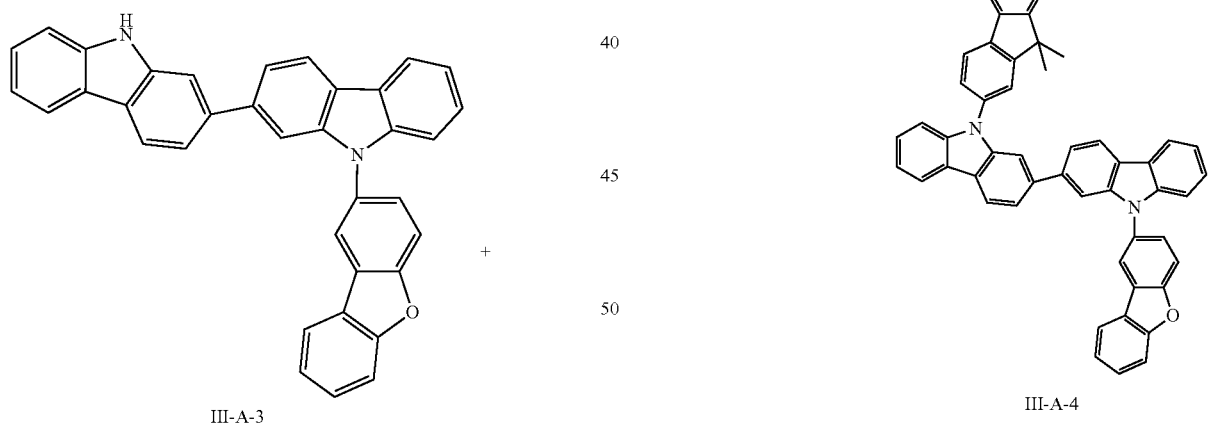

III-A-3 (6 g, 12.03 mmol), 2,7-dibromo-9,9-dimethyl-fluorene (4.45 g, 12.6 mmol), tris (dibenzylidenacetone) dipalladium (0.1098 g, 0.12 mol), 2-dicyclohexylphosphino-2',6'-dimethoxybiphenyl (0.098 g, 0.24 mmol) and sodium tert-butoxide (1.73 g, 18 mmol) were added to toluene (60 mL), the reaction mixture was heated to 108° C. under the nitrogen atmosphere, and stirred for 3 h; then the reaction solution was cooled to room temperature, washed with water. The separated organic phase was dried over anhydrous magnesium sulfate, and then concentrated in a vacuuo to obtain a crude product. The crude product was purified by recrystallization using toluene to obtain intermediate III-A-4 (6.46 g, yield 70%) as a white solid.

The intermediate III-B-4, intermediate III-C-4 and intermediate III-D-4 were prepared by reference to the synthesis method of the intermediate III-A-4 using the raw material 2D instead of the intermediate III-A-3 and the raw material 2E instead of 2,7-dibromo-9,9-dimethylfluorene. Wherein the numbers, structures, raw materials, synthesis yield and the like of the intermediate III-B-4 intermediate III-C-4 and intermediate III-D-4 are as shown in Table 6:

TABLE 6

Intermediate Number, Structure and Raw Material

| Intermediate Number | Raw material 2D | Raw material 2E | Intermediate Structure | Yield (%) |
|---|---|---|---|---|
| Intermediate III-B-4 | ![structure] | ![structure] | ![structure] | 75% |
| Intermediate III-C-4 | ![structure] | ![structure] | ![structure] | 80% |

TABLE 6-continued

Intermediate Number, Structure and Raw Material

| Intermediate Number | Raw material 2D | Raw material 2E | Intermediate Structure | Yield (%) |
|---|---|---|---|---|
| Intermediate III-D-4 | (structure) | (structure) | (structure) | 79% |

Synthesis of Intermediate III-A-5

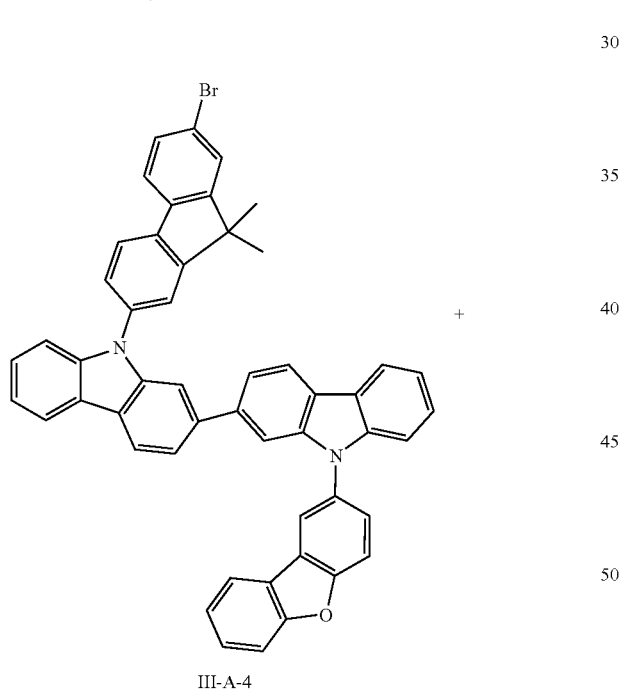

III-A-4

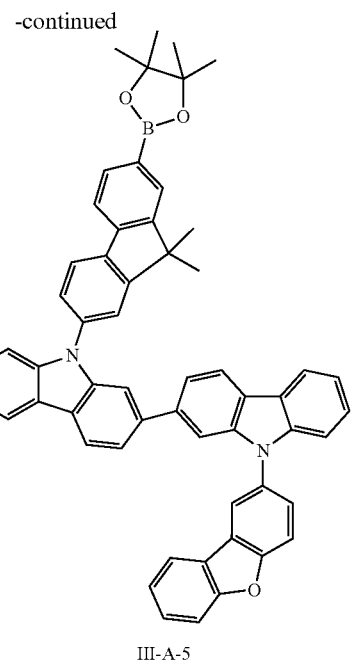

III-A-5

The intermediate III-A-4 (6.46 g, 8.1 mmol), bis (pinacolato) diboron (2.06 g, 8.1 mmol), tris (dibenzylideneacetone) dipalladium (0.741 g, 0.081 mmol), 2-(dicyclohexylphosphino)-2',4',6'-triisopropylbiphenyl (0.0769 g, 0.162 mmol) and potassium acetate (1.17 g, 12 mmol) were added into 1,4-dioxane (60 mL), the reaction mixture was heated to 80° C. under nitrogen atmosphere, and stirred for 3 h; then the reaction solution was cooled to room temperature, washed with water. The separated organic phase was dried over anhydrous magnesium sulfate, and then concentrated in a vacuuo to obtain a crude product. The crude product was purified by recrystallization using toluene to obtain intermediate III-A-5 (4.8 g, yield 71%) as a white solid.

The intermediate III-B-5, intermediate III-C-5 and intermediate III-D-5 were prepared by reference to the synthesis method of the intermediate III-A-5 using the raw material 2F instead of the intermediate III-A-4. Wherein the numbers, structures, raw materials, synthesis yield and the like of the intermediate III-B-5, intermediate III-C-5 and intermediate III-D-5 are as shown in Table 7:

TABLE 7

| Intermediate Number, Structure and Raw Material | | | |
|---|---|---|---|
| Intermediate Number | Raw material 2F | Intermediate Structure | Yield (%) |
| Intermediate III-B-5 | 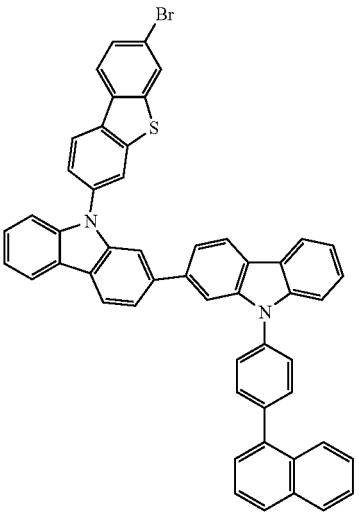 [SMILES: Brc1ccc2c(c1)sc1cc(-n3c4ccccc4c4ccc(-c5ccc6c7ccccc7n(-c7ccc(-c8cccc9ccccc89)cc7)c6c5)cc43)ccc12] | 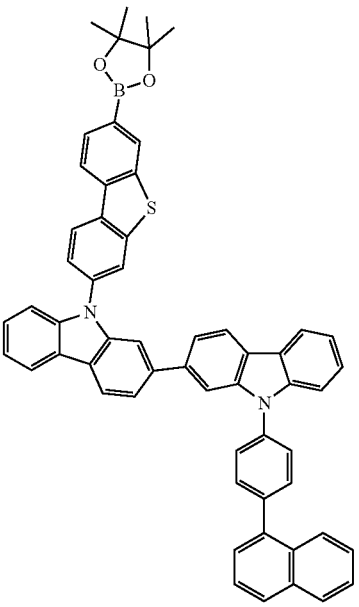 [SMILES: CC1(C)OB(c2ccc3c(c2)sc2cc(-n4c5ccccc5c5ccc(-c6ccc7c8ccccc8n(-c8ccc(-c9cccc%10ccccc9%10)cc8)c7c6)cc54)ccc23)OC1(C)C] | 69% |
| Intermediate III-C-5 | 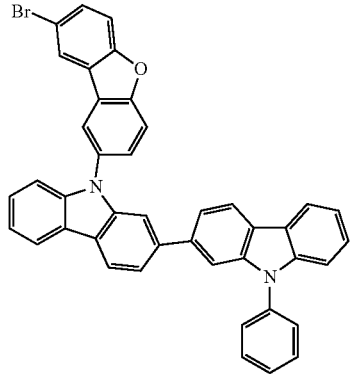 [SMILES: Brc1ccc2oc3ccc(-n4c5ccccc5c5ccc(-c6ccc7c8ccccc8n(-c8ccccc8)c7c6)cc54)cc3c2c1] | 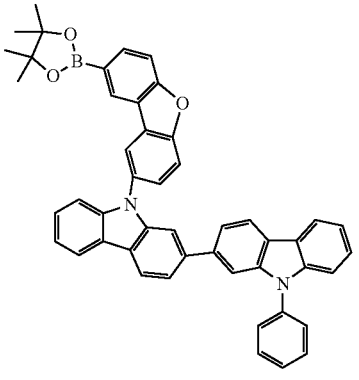 [SMILES: CC1(C)OB(c2ccc3oc4ccc(-n5c6ccccc6c6ccc(-c7ccc8c9ccccc9n(-c9ccccc9)c8c7)cc65)cc4c3c2)OC1(C)C] | 76% |

TABLE 7-continued
Intermediate Number, Structure and Raw Material
| Intermediate Number | Raw material 2F | Intermediate Structure | Yield (%) |
|---|---|---|---|
| Intermediate III-D-5 | | | 82% |
Synthesis of Compound 22
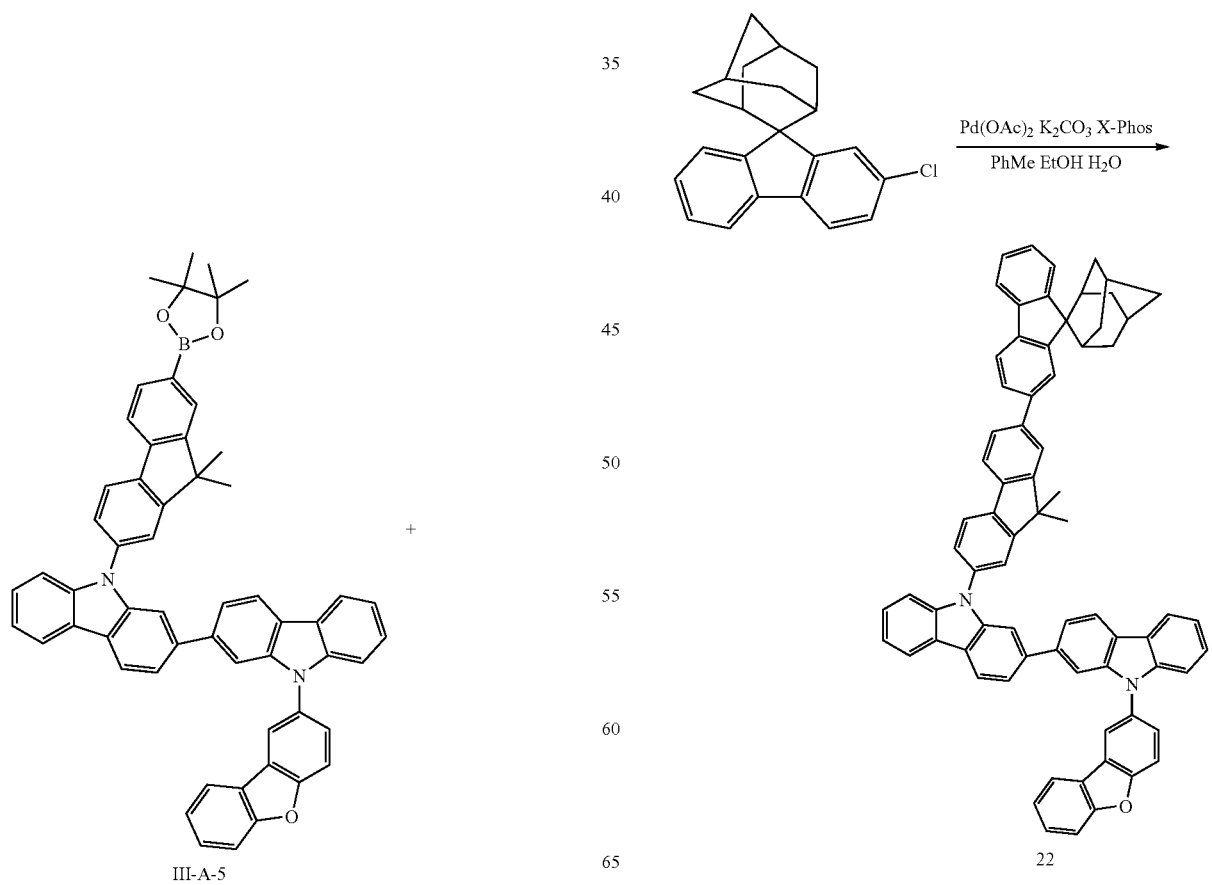

The intermediate III-A-5 (4.8 g, 5.9 mmol), intermediate I-A-1 (1.9 g, 5.9 mmol), palladium acetate (0.0133 g, 0.059 mmol), 2-(dicyclohexylphosphino)-2',4',6'-triisopropylbiphenyl (0.0561 g, 0.118 mmol) and potassium carbonate (0.85 g, 8.8 mmol) were added into a mixture of toluene (40 mL), absolute ethanol (20 mL) and deionized water (10 mL), the reaction mixture was heated to 80° C. under nitrogen atmosphere, and stirred for 2 h; then the reaction solution was cooled to room temperature, washed with water. The separated organic phase was dried over anhydrous magnesium sulfate, and then concentrated in a vacuuo to obtain a crude product. The crude product was purified by recrystallization using a mixture of dichloromethane and n-heptane to obtain compound 22 (4.6 g, yield 80%) as a white solid, LC-MS (ESI, pos. ion) m/z: 975.42 [M+H]$^+$.

The compound 23, compound 24 and compound 25 were prepared by reference to the synthesis method of compound 22 using the raw material 2G instead of the intermediate III-A-5. Wherein the structures, raw materials, synthesis yield, characterization data and the like of the compound 23, compound 24 and compound 25 are as shown in Table 8:

TABLE 8

| Numbers, Structures, Raw Materials and Characterization of Compounds | | | | |
|---|---|---|---|---|
| Compound Number | Raw material 2G | Compound Structure | Yield (%) | Mass spectrum (m/z) [M + H]$^+$ |
| Compound 23 | | | 69% | 1001.39 |
| Compound 24 | | | 76% | 859.36 |

TABLE 8-continued

Numbers, Structures, Raw Materials and Characterization of Compounds

| Compound Number | Raw material 2G | Compound Structure | Yield (%) | Mass spectrum (m/z) [M + H]+ |
|---|---|---|---|---|
| Compound 25 | | 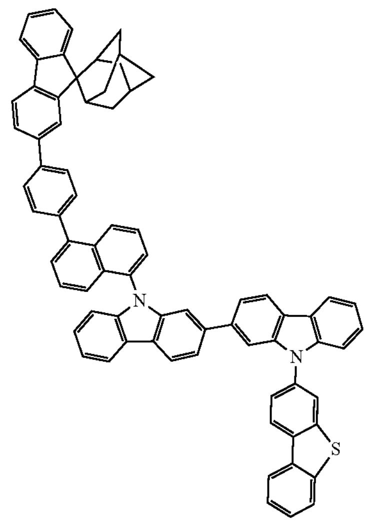 [SMILES: c1ccc2c(c1)-c1ccc(-c3ccc(-c4cccc5c(-n6c7ccccc7c7ccc(-c8ccc9c%10ccccc%10n(-c%10ccc%11c(c%10)sc%10ccccc%10%11)c9c8)cc76)cccc45)cc3)cc1C21C2CC3CC(C2)CC1C3] | 82% | 1001.39 |

Nuclear magnetic data of the compound 23 in Table 8 above is as shown below:

$^1$H NMR (CD$_2$Cl$_2$, 400 MHz) δ: 8.39 (d, 1H), 8.10 (m, 3H), 8.04 (d, 2H), 7.99 (d, 1H), 7.94-7.86 (m, 4H), 7.78-7.72 (m, 4H), 7.64 (m, 3H), 7.54 (m, 2H), 7.47-7.18 (m, 18H), 2.91 (d, 2H), 2.61 (d, 2H), 2.16 (s, 1H), 1.90 (s, 3H), 1.77 (d, 2H), 1.69 (d, 2H), 1.60 (s, 2H) ppm.

Synthesis of Compound 26

Synthesis of Intermediate IV-A-1

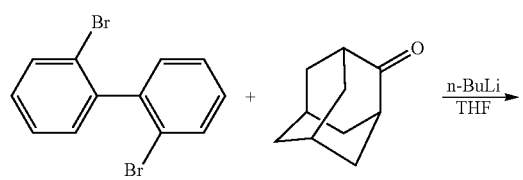

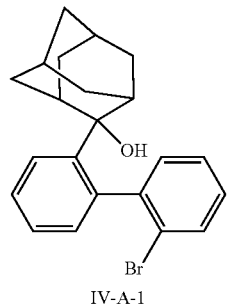

IV-A-1

Under the nitrogen atmosphere, 2,2'-dibromo-1,1'-biphenyl (14.2 g, 53 mmol) and THF (85.2 mL) were added to a 250 L three-necked round-bottom flask and heated to −80° C. to −90° C. until they became clear. A solution of n-BuLi (31.8 mL, 2.5 mol/L) in THF was added dropwise into the reaction system slowly, and the resulted mixture was stirred at −80° C. to −90° C. for another 50 min. Then a solution of adamantanone (6.378 g, 42.45 mmol) in THF (26 mL) was added dropwise into the reaction system slowly at −80° C. to −90° C. for 1 h. After the reaction was completed, the temperature was naturally raised to room temperature. Then 5% hydrochloric acid was poured into the reaction solution until pH=6 to 7, after the solution was fully stirred, DCM was added for extraction. The combined organic phases were washed to neutral with water, dried over anhydrous magnesium sulfate and filtered. Then the filtrate was concentrated in a vacuuo to obtain an oil-like crude product. The crude product and n-heptane was added to a flask, the mixture was heated for reflux until a clear solution was obtained. The solution was cool down slowly and recrystallize at −20° C. to obtain the intermediate IV-A-1 (12 g, 68%) as a white solid.

Synthesis of Intermediate IV-A-2

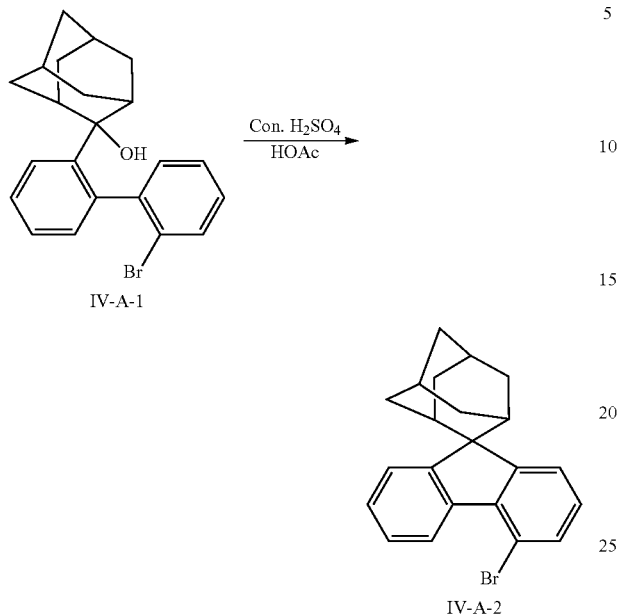

IV-A-1

IV-A-2

Under the nitrogen atmosphere, a mixture of intermediate 1V-A-1 (12.2 g, 36 mmol) and glacial acetic acid (150 mL) was stirred at 50° C. to 60° C., after the reaction solution became completely clear, concentrated sulfuric acid (0.308 mL) was added dropwise. The reaction mixture was heated to 70° C.~80° C., and stirred for another 30 min. Then the reaction solution was cooled naturally to room temperature, and deionized water (200 L) was poured into the solution, the resulted mixture was stirred and filtered. The filter cake was drip washed to neutral with deionized water, and dried with a vacuum drying oven for 1 h to obtain the residue. The residue was dissolved in DCM, and the solution was dried over anhydrous sodium sulfate for 30 min, filtered. The filtrate was concentrated in a vacuuo to obtain a crude product. Then, the crude product was purified by recrystallization using a mixture of n-heptane and distilled-off DCM, at −20° C. Filtered, the filter cake was collected and baked in the vacuum drying oven to obtain the intermediate 1V-A-2 (10.48 g, yield 91%) as a white solid.

Synthesis of Intermediate IV-A-3

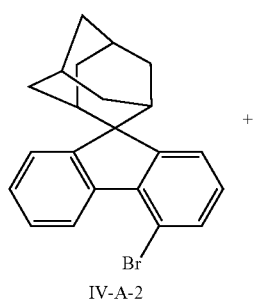

IV-A-2

+

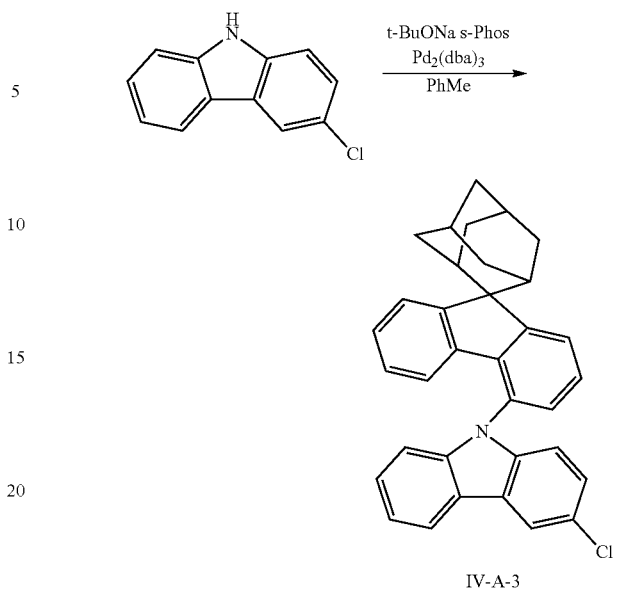

IV-A-3

The intermediate 1V-A-2 (10.48 g, 32.8 mmol), 3-chlorocarbazole (5 g, 24.9 mmol), tris (dibenzylidenacetone) dipalladium (0.263 g, 0.287 mmol), 2-dicyclohexylphosphino-2',6'-dimethoxybiphenyl (0.235 g, 0.574 mmol) and sodium tert-butoxide (4.14 g, 0.431 mmol) were added to toluene (80 mL), and the mixture was heated to 108° C. under the nitrogen atmosphere, and stirred for 3 h. Then the reaction solution was cooled to room temperature, and washed with water. The separated organic phase was dried over magnesium sulfate, filtered. The filtrate was concentrated in a vacuuo to obtain a crude product. The crude product was purified by recrystallization using toluene to obtain intermediate 1V-A-3 (9.76 g, yield 81.3%) as a white solid.

Synthesis of Intermediate IV-A-4

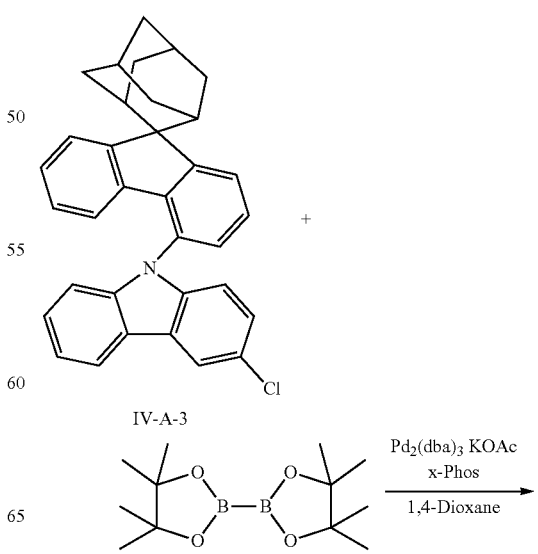

IV-A-3

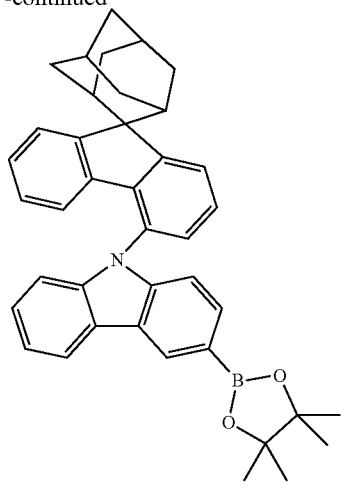

IV-A-4

The intermediate 1-A-3 (9.76 g, 20.1 mmol), bis (pinacolato) diboron (6.13 g, 24.12 mmol), tris (dibenzylideneacetone) dipalladium (0.184 g, 0.201 mmol), 2-(dicyclohexylphosphino)-2',4',6'-triisopropylbiphenyl (0.096 g, 0.201 mmol) and potassium acetate (5.92 g, 60.3 mmol) were added into 1,4-dioxane (80 mL), and the reaction mixture was heated to 80° C. under nitrogen atmosphere, and stirred for 3 h; then the reaction solution was cooled to room temperature, washed with water. The separated organic phase was dried over anhydrous magnesium sulfate, and then concentrated in a vacuuo to obtain a crude product. The crude product was purified by recrystallization using toluene to obtain intermediate 1V-A-4 (9.29 g, yield 80%) as a white solid.

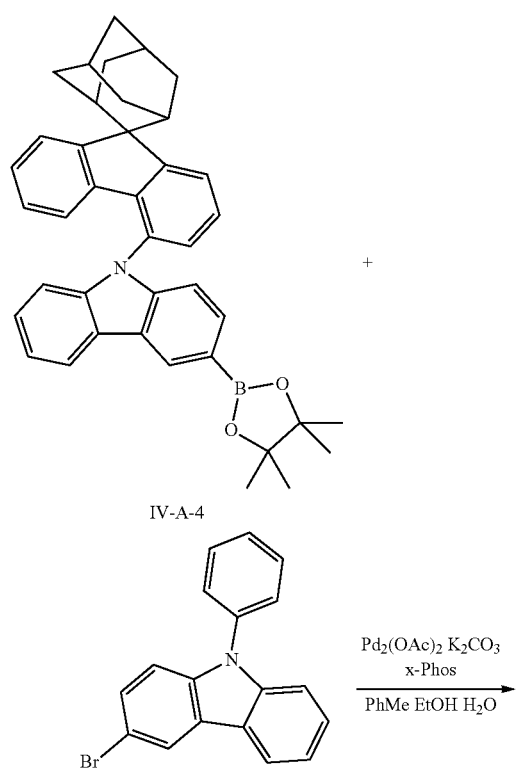

IV-A-4

26

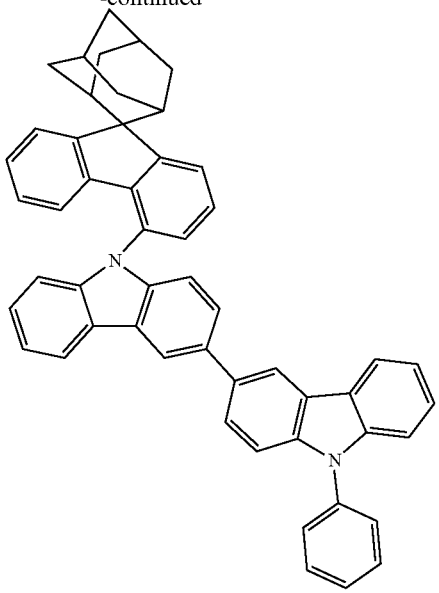

The intermediate 1V-A-4 (6 g, 10.4 mmol), 3-bromo-9-phenylcarbazole (2.28 g, 8.6 mmol), palladium acetate (0.0965 g, 0.43 mmol), 2-(dicyclohexylphosphino)-2',4',6'-triisopropylbiphenyl (0.205 g, 0.43 mmol) and potassium carbonate (3.56 g, 25.8 mmol) were added into a mixture of toluene (80 mL), absolute ethanol (40 mL) and deionized water (20 mL). The reaction mixture was heated to 80° C. under nitrogen atmosphere, and stirred for 2 h; then the reaction solution was cooled to room temperature, washed with water. The separated organic phase was dried over anhydrous magnesium sulfate, and then concentrated in a vacuuo to obtain a crude product. The crude product was purified by recrystallization using a mixture of dichloromethane and n-heptane to obtain compound 26 (3.7 g, yield 65%) as a white solid. LC-MS (ESI, pos. ion) m/z: 693.32 [M+H]⁺.

Synthesis of Compound 82

Synthesis of Intermediate V-A-1

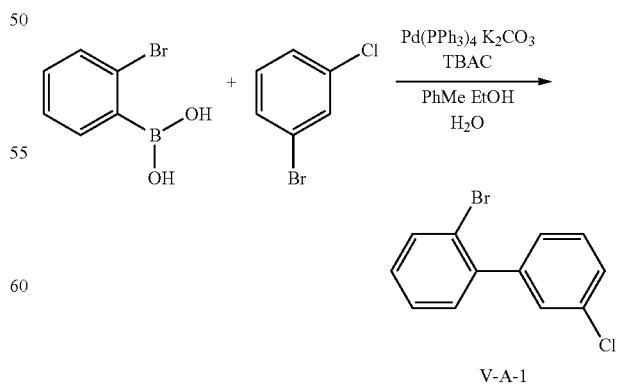

V-A-1

2-bromophenylboronic acid (10 g, 50 mmol), 3-bromochlorobenzene (9.57 g, 50 mmol), tetrakis (triphenylphosphine) palladium (0.58 g, 0.5 mmol), potassium carbonate (7.35 g, 75 mmol), tetrabutyl ammonium chloride (0.278 g, 1 mmol), methylbenzene (80 mL), ethanol (20 mL) and deionized water (20 mL) were added into a round-bottom flask, and the reaction mixture was heated to 78° C. under the nitrogen atmosphere and stirred for 8 hours. Then the reaction solution was cooled to room temperature, and methylbenzene (50 mL) was added for extraction. The combined organic phases were dried over anhydrous magnesium sulfate, and then concentrated in a vacuuo to obtain a residue. The residue was purified by silica gel column chromatography and eluted with n-heptane to obtain the crude product, the obtained crude product was purified by recrystallization using a mixture of toluene and n-heptane to obtain intermediate V-A-1 (16.8 g, 80%) as a white solid.

Synthesis of Intermediate V-A-2

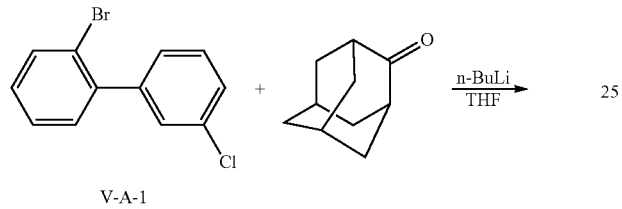

V-A-1

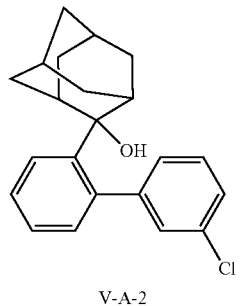

V-A-2

Under the nitrogen atmosphere, the intermediate V-A-1 (16.8 g, 62.8 mmol) and THF (852 mL) were added to a 2 L three-necked round-bottom flask. The mixture was stirred at −80° C. to −90° C. until they became clear. A solution of n-BuLi (37.7 mL, 2.5 mol/L) in THF was added dropwise into the reaction mixture slowly, and the resulted mixture was stirred at −80° C. to −90° C. for another 50 min. Then a solution of adamantanone (9.43 g, 62.8 mmol) in THF (160 mL) was added dropwise into the reaction mixture and slowly at −80° C. to 90° C. for 1 h. After the reaction was completed, the reaction mixture was naturally raised to room temperature. Then 5% hydrochloric acid was poured into the reaction solution until pH<7, after the solution was fully stirred, DCM was added for extraction. The combined organic phases were, washed to neutral with water, dried with anhydrous magnesium sulfate and filtered. Then the filtrate was concentrated in a vacuuo to obtain an oil-like crude product. The crude product and n-heptane was added to a flask, the mixture was heated for reflux until a clear solution was obtained. The solution was cool down slowly and recrystallize at −20° C. to obtain the intermediate V-A-2 (14.9 g, 70%) as a white solid.

Synthesis of Intermediate V-A-3

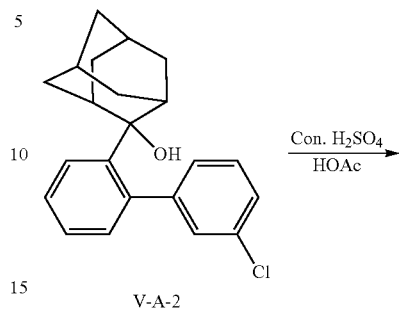

V-A-2

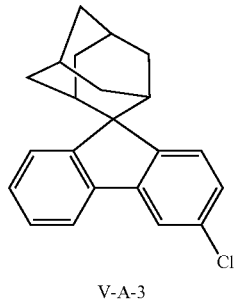

V-A-3

Under the nitrogen atmosphere, a mixture of an intermediate V-A-2 (14.9 g, 43.9 mmol) and glacial acetic acid (150 L) was stirred at 50° C. to 60° C., after the reaction solution became completely clear, concentrated sulfuric acid (0.5 mL) was added dropwise. The reaction mixture was heated to 70° C. to 80° C., after the solution was stirred for 30 min, the reaction solution was cooled naturally to room temperature, and deionized water (200 mL) was poured into the solution, the resulted mixture was full stirred and filtered. The filter cake was drip washed to neutral with deionized water, and dried with a vacuum drying oven for 1 h to obtain the residue. The residue was dissolved in DCM (dichloromethane), and the solution was dried over anhydrous sodium sulfate for 30 min, filtered. The filtrate was concentrated in a vacuuo to obtain a crude product. Then, the crude product was purified by recrystallization using a mixture of n-heptane and distilled-off DCM, at −20° C. Filtered, the filter cake was collected and baked in the vacuum drying oven to obtain intermediate V-A-3 (14 g, yield 90%) as a white solid.

Synthesis of Intermediate V-A-4

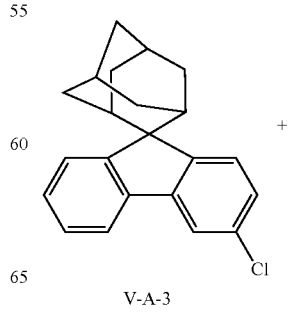

V-A-3

-continued

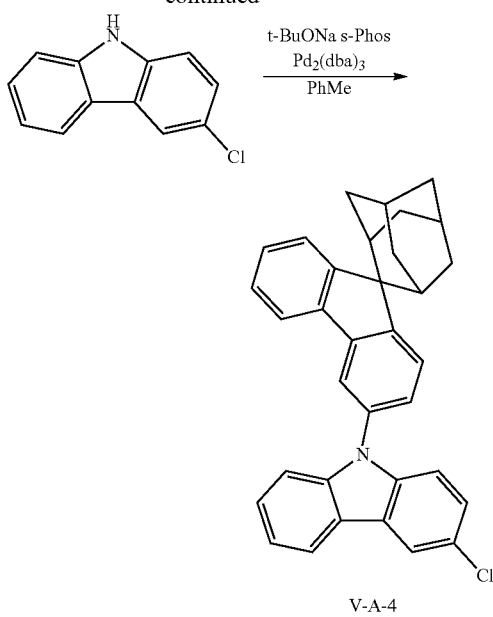

V-A-4

The intermediate V-A-3 (14 g, 43.8 mmol), 3-chlorocarbazole (8.8 g, 43.8 mmol), tris (dibenzylidenacetone) dipalladium (0.401 g, 0.438 mmol), 2-dicyclohexylphosphino-2',6'-dimethoxybiphenyl (0.3592 g, 0.876 mmol) and sodium tert-butoxide (6.1 g, 67 mmol) were added to toluene (140 mL), and the mixture was heated to 108° C. under the nitrogen atmosphere, and stirred for 3 h. Then the reaction solution was cooled to room temperature, and washed with water, magnesium sulfate was added for drying, then filtered. The filtrate was concentrated in a vacuuo to obtain a crude product. Then, the crude product was purified by recrystallization using toluene, to obtain intermediate V-A-4 (14.9 g, yield 70%) as a white solid.

Synthesis of Intermediate V-A-5

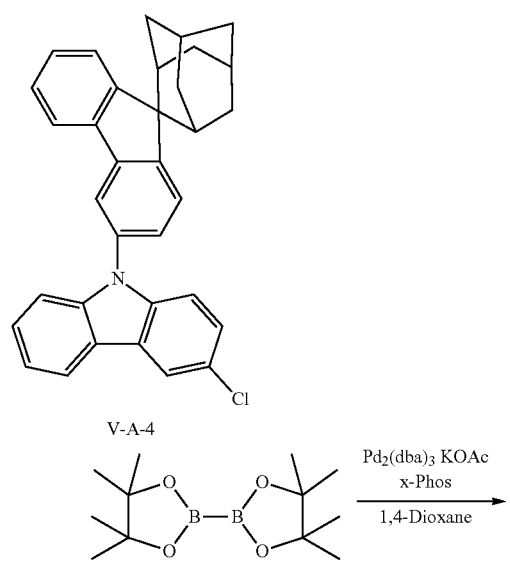

V-A-5

The intermediate V-A-4 (14.9 g, 30.7 mmol), bis (pinacolato) diboron (7.78 g, 30.7 mmol), tris (dibenzylideneacetone) dipalladium (0.2811 g, 0.307 mmol), 2-(dicyclohexylphosphino)-2',4',6'-triisopropylbiphenyl (0.2917 g, 0.614 mmol) and potassium acetate (6.02 g, 61.4 mmol) were added into 1,4-dioxane (150 mL), and the reaction mixture was heated to 80° C. under nitrogen atmosphere, and stirred for 3 h; then the reaction solution was cooled to room temperature, washed with water. The separated organic phase was dried over anhydrous magnesium sulfate, and then concentrated in a vacuuo to obtain a crude product. The crude product was purified by recrystallization using toluene to obtain intermediate V-A-5 (12.4 g, yield 80%) as a white solid.

Synthesis of Intermediate V-A

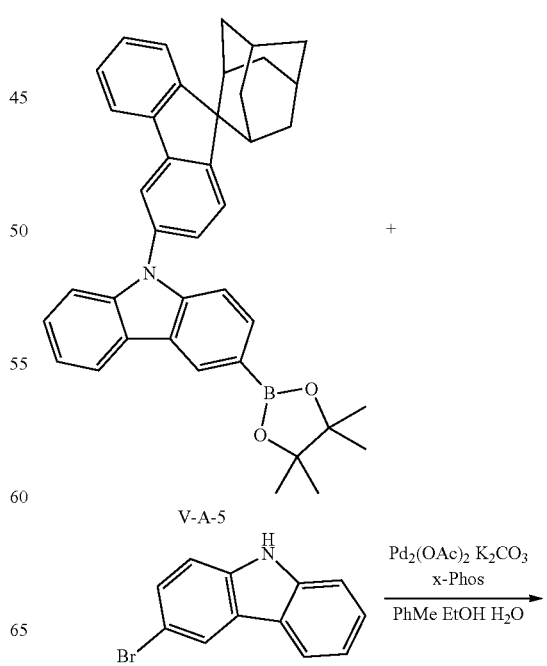

-continued

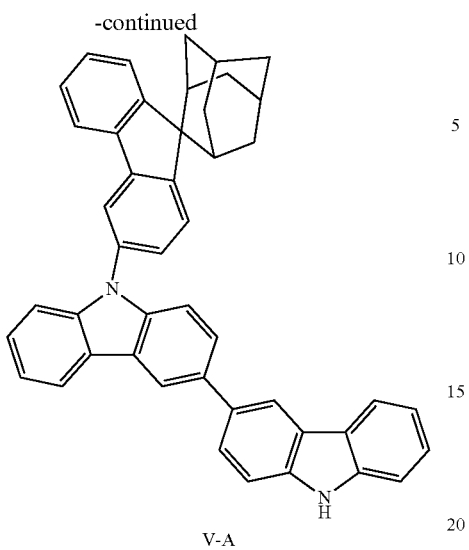

V-A

The intermediate 1-A-5 (12.4 g, 21.5 mmol), 3-bromocarbazole (5.3 g, 21.5 mmol), palladium acetate (0.0483 g, 0.215 mmol), 2-(dicyclohexylphosphino)-2',4',6'-triisopropylbiphenyl (0.1995 g, 0.42 mmol) and potassium carbonate (4.116 g, 42 mmol) were added into a mixture of toluene (40 mL), absolute ethanol (20 mL) and deionized water (20 mL), the reaction mixture was heated to 80° C. under nitrogen atmosphere, and stirred for 2 h. Then the reaction solution was cooled to room temperature, washed with water. The separated organic phase was dried over anhydrous magnesium sulfate, and then concentrated in a vacuuo to obtain a crude product. The crude product was purified by recrystallization using a mixture of dichloromethane and n-heptane to obtain intermediate V-A (9.27 g, yield 70%) as a solid.

Synthesis of Compound 82

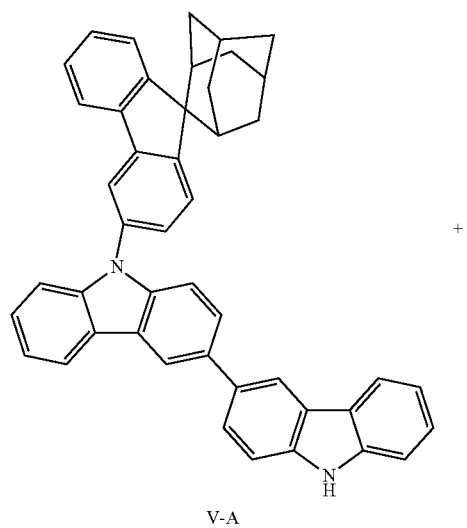

V-A

+

-continued

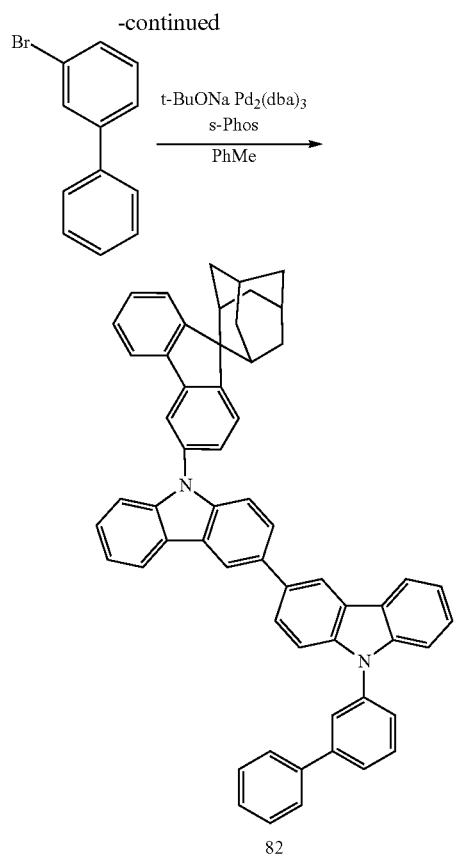

82

The intermediate V-A (6 g, 9.7 mmol), 3-bromobiphenyl (1.13 g, 4.8 mmol), tris (dibenzylidenacetone) dipalladium (0.044 g, 0.048 mmol), 2-dicyclohexylphosphino-2',6'-dimethoxybiphenyl (0.039 g, 0.096 mmol) and sodium tert-butoxide (0.692 g, 7.2 mmol) were added to toluene (80 mL), the resulted mixture was heated to 108° C. under the nitrogen atmosphere, and stirred for 3 h; then the reaction solution was cooled to room temperature, washed with water. The separated organic phase was dried over anhydrous magnesium sulfate, and then concentrated in a vacuuo to obtain a crude product. The crude product was purified by recrystallization using toluene to obtain compound 82 (2.55 g, yield 69%) as a white solid. LC-MS (ESI, pos. ion) m/z: 769.35 [M+H]$^+$.

Preparation and Performance Evaluation of Organic Electroluminescent Device

Example 1: Green Organic Electroluminescent Device

The anode was prepared through the following process: a substrate (manufactured by Corning) with an ITO thickness of 1500 Å was cut into the dimension of 40 mm×40 mm×0.7 mm, the substrate was prepared into an experimental substrate having a cathode, an anode and insulation layer patterns by a photoetching procedure, and surface treatment was performed by ultraviolet ozone and $O_2$:$N_2$ plasma to increase the work function of the anode (experimental substrate) and remove scum.

F4-TCNQ was vacuum deposited on the experimental substrate (anode) to form a hole injection layer (HIL) with a thickness of 100 Å, and the NPB was deposited on the hole injection layer to form a first hole transport layer with a thickness of 800 Å.

PAPB was vacuum deposited on the first hole transport layer to form a second hole transport layer with a thickness of 300 Å.

Compounds 1:GH-n1:Ir(ppy)$_3$ were jointly deposited at the ratio of 50%:45%:5% (deposition rate) on the second hole transport layer to form a green organic light emitting layer (EML) with a thickness of 400 Å.

ET-06 and LiQ were mixed at the weight ratio of 1:1 and deposited to form an electron transport layer (ETL) with a thickness of 300 Å, LiQ was deposited on the electron transport layer to form an electron injection layer (EIL) with a thickness of 10 Å, then magnesium (Mg) and silver (Ag) were mixed at a deposition rate of 1:9 and vacuum deposited on the electron injection layer to form a cathode with a thickness of 105 Å.

CP-05 with a thickness of 650 Å was deposited on the cathode, an organic capping layer (CPL) was formed, so that the manufacturing of the organic light emitting device was completed.

Example 2 to Example 27

When the organic light emitting layer was formed, the compound 1 in Embodiment 1 was replaced by the compound shown in the compound X column in Table 9, and the organic electroluminescent device was fabricated by the same method as Example 1. For example, in Example, the compound 1 in Example 1 was replaced by the compound 2, and the organic electroluminescent device was prepared by the same method as Example 1. It is understood that in the organic light emitting layer of the prepared organic electroluminescent device, compound X:GH-n1:Ir(ppy)$_3$=50%:45%:5%.

Example 28

As shown in Embodiment 1, the light emitting layer material is changed only when the organic light emitting layer is formed, and compound 1:GH-n1:Ir(ppy)$_3$ in Embodiment 1 were jointly deposited in the ratio of 50%:45%:5% (deposition rate), which was changed to that GH-n2:compound 119:Ir(ppy)$_3$ were jointly deposited in the ratio of 50%:45%:5% (deposition rate), so that a green organic light emitting layer (EML) with a thickness of 400 Å was formed. Other parts of the device were not altered.

Example 29 to Example 35

When the organic light emitting layer was formed, the compound 119 in Example 28 was replaced by the compound shown in the compound Y column in Table 9, and the organic electroluminescent device was fabricated by the same method as Example 28.

Comparative Example 1

Refer to Table 9, the compound 1 in Embodiment 1 was replaced by the compound A, and the organic electroluminescent device was prepared by the same method as Example 1. It is understood that in the organic light emitting layer of the prepared organic electroluminescent device, compound A:GH-n1:Ir(ppy)$_3$=50%:45%:5%.

Comparative Example 2

Refer to Table 9, the compound 1 in Embodiment 1 was replaced by the compound B, and the organic electroluminescent device was prepared by the same method as Example 1. It is understood that in the organic light emitting layer of the prepared organic electroluminescent device, compound B:GH-n1:Ir(ppy)$_3$=50%:45%:5%.

Comparative Examples 3 to 5

Refer to Table 9, the compound 1 in Example 1 was replaced by the compound C, compound D and compound F, and the organic electroluminescent device was prepared by the same method as Embodiment 1. It is understood that in the organic light emitting layer of the prepared organic electroluminescent device, compound C (D or F):GH-n1:Ir(ppy)$_3$=50%:45%:5%.

Comparative Example 6

Refer to Table 9, the compound 119 in Example 28 was replaced by the compound C, and the organic electroluminescent device was prepared by the same method as Example 28. It is understood that in the organic light emitting layer of the prepared organic electroluminescent device, GH-n2:compound D:Ir(ppy)$_3$=50%:45%:5%.

Comparative Example 7

Refer to Table 8, the compound 119 in Example 28 was replaced by the compound E, and the organic electroluminescent device was prepared by the same method as Embodiment 28. It is understood that in the organic light emitting layer of the prepared organic electroluminescent device, GH-n2:compound E:Ir(ppy)$_3$=50%:45%:5%.

Comparative Example 8

Refer to Table 9, the compound 119 in Example 28 was replaced by the compound F, and the organic electroluminescent device was prepared by the same method as Embodiment 28. It is understood that in the organic light emitting layer of the prepared organic electroluminescent device, GH-n2:compound F:Ir(ppy)$_3$=50%:45%:5%.

In Examples 1 to 35 and Comparative Examples 1 to 8, the structural formulas of all materials in use are as follows:

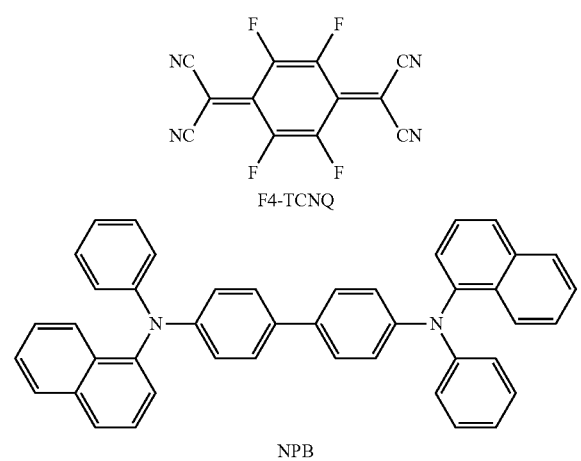

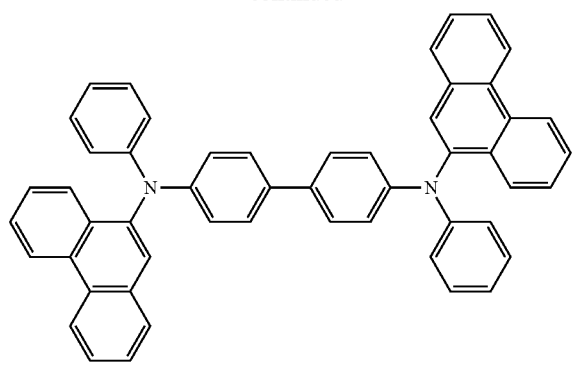
PAPB
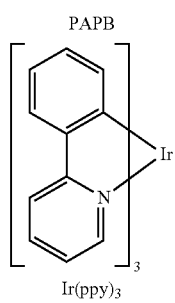
Ir(ppy)₃
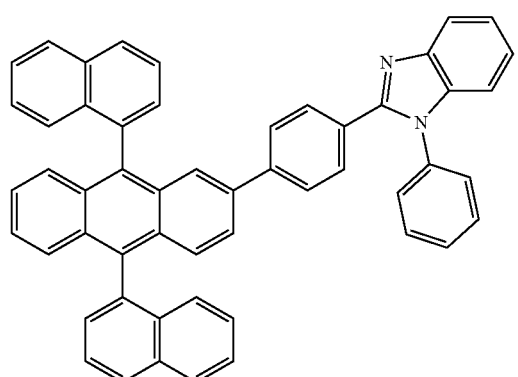
ET-06
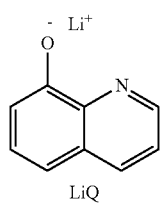
LiQ
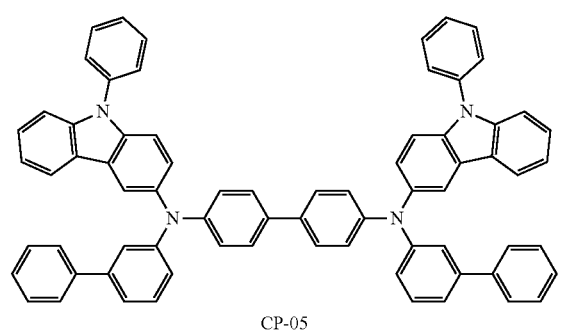
CP-05
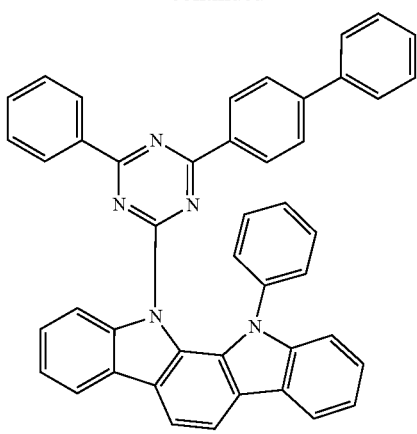
GH-n1
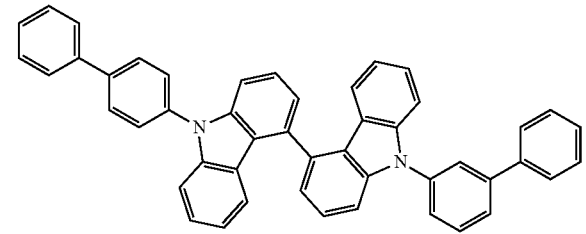
GH-n2
Compound A
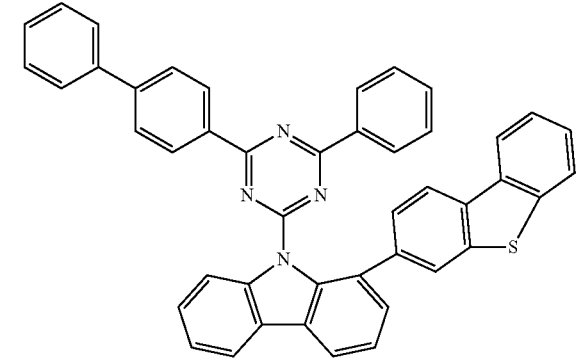
Compound B
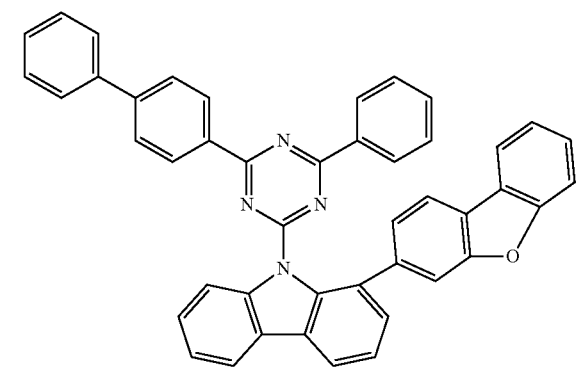

-continued

Compound C
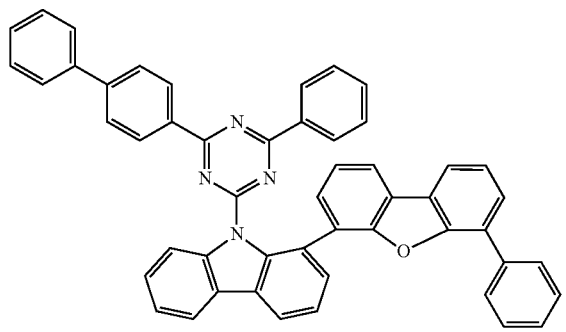

Compound E
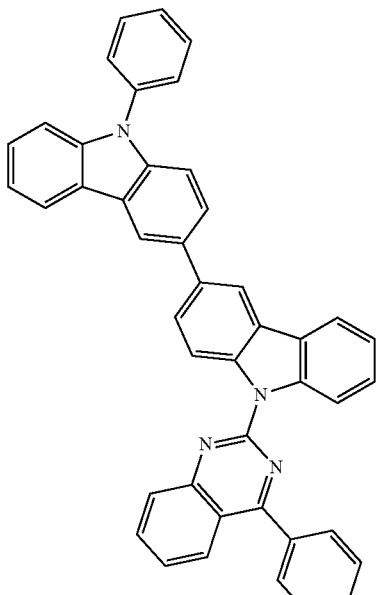

Compound D

Compound F
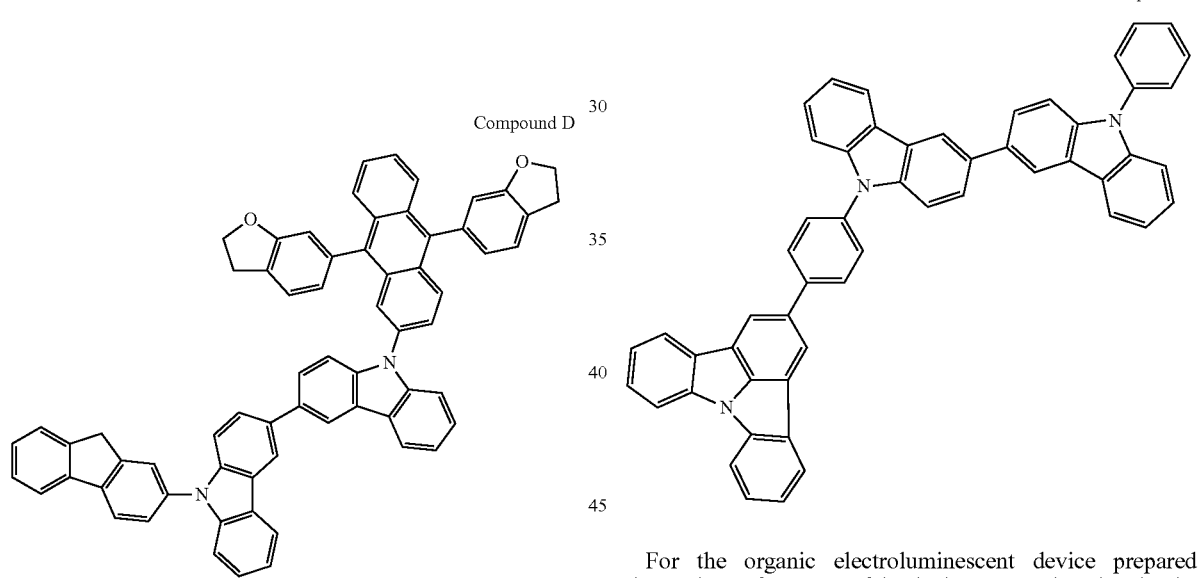

For the organic electroluminescent device prepared above, the performance of the device was analyzed under the condition of 20 mA/cm$^2$, and the results are as shown in Table 9 below:

TABLE 9

Performance Test Results of Organic Electroluminescent Device

| Example Number | Compound X: Compound Y: Ir(ppy)$_3$ 50%: 45%: 5% | | | Driving voltage (V) | Current efficiency (Cd/A) | Power efficiency (lm/W) | Chromaticity coordinates CIEx | Chromaticity coordinates CIEy | External quantum efficiency EQE (%) | T95 lifetime (h) |
| --- | --- | --- | --- | --- | --- | --- | --- | --- | --- | --- |
| | Compound X | Compound Y | G-dopant | | | | | | | |
| Example 1 | Compound 1 | GH-n1 | Ir(ppy)$_3$ | 3.85 | 74.1 | 60.5 | 0.22 | 0.73 | 19.6 | 266 |
| Example 2 | Compound 2 | GH-n1 | Ir(ppy)$_3$ | 3.80 | 72.9 | 60.2 | 0.23 | 0.73 | 19.9 | 250 |
| Example 3 | Compound 3 | GH-n1 | Ir(ppy)$_3$ | 3.81 | 72.2 | 59.5 | 0.22 | 0.74 | 19.1 | 295 |
| Example 4 | Compound 4 | GH-n1 | Ir(ppy)$_3$ | 3.87 | 70.5 | 57.3 | 0.23 | 0.72 | 19.2 | 287 |
| Example 5 | Compound 5 | GH-n1 | Ir(ppy)$_3$ | 3.87 | 77.0 | 62.5 | 0.24 | 0.75 | 20.1 | 258 |
| Example 6 | Compound 6 | GH-n1 | Ir(ppy)$_3$ | 3.87 | 75.2 | 61.1 | 0.22 | 0.73 | 20.2 | 257 |
| Example 7 | Compound 7 | GH-n1 | Ir(ppy)$_3$ | 3.94 | 74.3 | 59.3 | 0.23 | 0.73 | 19.6 | 258 |

TABLE 9-continued

Performance Test Results of Organic Electroluminescent Device

| Example Number | Compound X | Compound Y | G-dopant | Driving voltage (V) | Current efficiency (Cd/A) | Power efficiency (lm/W) | Chromaticity coordinates CIEx | Chromaticity coordinates CIEy | External quantum efficiency EQE (%) | T95 lifetime (h) |
|---|---|---|---|---|---|---|---|---|---|---|
| Example 8 | Compound 8 | GH-n1 | Ir(ppy)₃ | 3.84 | 77.5 | 63.4 | 0.23 | 0.73 | 21.3 | 291 |
| Example 9 | Compound 9 | GH-n1 | Ir(ppy)₃ | 3.94 | 71.8 | 57.2 | 0.22 | 0.74 | 20.7 | 265 |
| Example 10 | Compound 10 | GH-n1 | Ir(ppy)₃ | 3.90 | 79.1 | 63.7 | 0.22 | 0.73 | 20.1 | 250 |
| Example 11 | Compound 11 | GH-n1 | Ir(ppy)₃ | 3.92 | 73.9 | 59.2 | 0.23 | 0.74 | 20.8 | 281 |
| Example 12 | Compound 12 | GH-n1 | Ir(ppy)₃ | 3.84 | 77.9 | 63.8 | 0.22 | 0.73 | 19.7 | 286 |
| Example 13 | Compound 13 | GH-n1 | Ir(ppy)₃ | 3.80 | 73.8 | 61.0 | 0.22 | 0.73 | 20.2 | 258 |
| Example 14 | Compound 14 | GH-n1 | Ir(ppy)₃ | 3.82 | 70.3 | 57.8 | 0.24 | 0.72 | 20.4 | 272 |
| Example 15 | Compound 15 | GH-n1 | Ir(ppy)₃ | 3.88 | 71.7 | 58.1 | 0.22 | 0.73 | 21.4 | 275 |
| Example 16 | Compound 16 | GH-n1 | Ir(ppy)₃ | 3.82 | 74.2 | 61.0 | 0.23 | 0.72 | 19.6 | 286 |
| Example 17 | Compound 17 | GH-n1 | Ir(ppy)₃ | 3.93 | 74.2 | 59.3 | 0.22 | 0.73 | 19.5 | 278 |
| Example 18 | Compound 18 | GH-n1 | Ir(ppy)₃ | 3.87 | 74.4 | 60.4 | 0.23 | 0.74 | 21.2 | 253 |
| Example 19 | Compound 19 | GH-n1 | Ir(ppy)₃ | 3.82 | 72.3 | 59.5 | 0.23 | 0.74 | 20.8 | 260 |
| Example 20 | Compound 20 | GH-n1 | Ir(ppy)₃ | 3.80 | 75.8 | 62.6 | 0.25 | 0.74 | 19.6 | 260 |
| Example 21 | Compound 21 | GH-n1 | Ir(ppy)₃ | 3.91 | 78.9 | 63.1 | 0.22 | 0.73 | 20.8 | 278 |
| Example 22 | Compound 22 | GH-n1 | Ir(ppy)₃ | 3.94 | 78.8 | 63.2 | 0.22 | 0.73 | 20.9 | 289 |
| Example 23 | Compound 23 | GH-n1 | Ir(ppy)₃ | 3.89 | 79.0 | 64.2 | 0.24 | 0.72 | 21.0 | 276 |
| Example 24 | Compound 24 | GH-n1 | Ir(ppy)₃ | 3.90 | 77.9 | 63.9 | 0.22 | 0.73 | 20.7 | 287 |
| Example 25 | Compound 25 | GH-n1 | Ir(ppy)₃ | 3.88 | 79.2 | 64.9 | 0.23 | 0.72 | 20.8 | 293 |
| Example 26 | Compound 26 | GH-n1 | Ir(ppy)₃ | 3.94 | 78.5 | 64.8 | 0.22 | 0.73 | 21.2 | 289 |
| Example 27 | Compound 82 | GH-n1 | Ir(ppy)₃ | 3.80 | 79.2 | 64.9 | 0.226 | 0.724 | 20.8 | 292 |
| Example 28 | GH-n2 | Compound 119 | Ir(ppy)₃ | 3.95 | 77.8 | 61.9 | 0.220 | 0.730 | 18.7 | 275 |
| Example 29 | GH-n2 | Compound 120 | Ir(ppy)₃ | 3.93 | 79.4 | 63.5 | 0.220 | 0.730 | 19.1 | 260 |
| Example 30 | GH-n2 | Compound 121 | Ir(ppy)₃ | 3.93 | 77.5 | 61.9 | 0.220 | 0.730 | 18.6 | 272 |
| Example 31 | GH-n2 | Compound 124 | Ir(ppy)₃ | 3.98 | 77.8 | 61.4 | 0.220 | 0.730 | 18.7 | 280 |
| Example 32 | GH-n2 | Compound 233 | Ir(ppy)₃ | 3.91 | 82.2 | 66.0 | 0.220 | 0.730 | 19.7 | 282 |
| Example 33 | GH-n2 | Compound 246 | Ir(ppy)₃ | 3.94 | 83.2 | 66.3 | 0.220 | 0.730 | 20.0 | 283 |
| Example 34 | GH-n2 | Compound 252 | Ir(ppy)₃ | 3.94 | 81.5 | 65.0 | 0.220 | 0.730 | 19.6 | 282 |
| Example 35 | GH-n2 | Compound 268 | Ir(ppy)₃ | 3.94 | 76.7 | 61.1 | 0.220 | 0.730 | 18.4 | 277 |
| Comparative Example 1 | Compound A | GH-n1 | Ir(ppy)₃ | 3.89 | 62.9 | 50.8 | 0.220 | 0.730 | 17.0 | 198 |
| Comparative Example 2 | Compound B | GH-n1 | Ir(ppy)₃ | 3.91 | 64.9 | 52.1 | 0.220 | 0.730 | 17.5 | 185 |
| Comparative Example 3 | Compound C | GH-n1 | Ir(ppy)₃ | 3.89 | 63.5 | 51.3 | 0.220 | 0.730 | 17.1 | 197 |
| Comparative Example 4 | Compound D | GH-n1 | Ir(ppy)₃ | 3.98 | 64.5 | 52.0 | 0.220 | 0.730 | 17.6 | 188 |
| Comparative Example 5 | Compound F | GH-n1 | Ir(ppy)₃ | 3.95 | 64.7 | 53.1 | 0.220 | 0.730 | 17.4 | 183 |
| Comparative Example 6 | GH-n2 | Compound C | Ir(ppy)₃ | 4.08 | 64.5 | 52.0 | 0.220 | 0.730 | 14.3 | 154 |
| Comparative Example 7 | GH-n2 | Compound E | Ir(ppy)₃ | 4.13 | 64.2 | 51.8 | 0.220 | 0.730 | 15.4 | 188 |
| Comparative Example 8 | GH-n2 | Compound F | Ir(ppy)₃ | 4.08 | 60.1 | 46.2 | 0.220 | 0.730 | 14.4 | 157 |

According to the results in Table 9, compared with Comparative Examples 1 to 5, the current efficiency (Cd/A) of the organic electroluminescent device prepared in Embodiments 1 to 27 is increased by at least 9%, the power efficiency (lm/W) is increased by at least 7.7%, the external quantum efficiency is increased by at least 8.5%, and the lifetime is increased to 26.3%. Compared with Comparative Examples 6 to 8, the current efficiency (Cd/A) of the organic electroluminescent device prepared in Examples 28 to 35 is increased by at least 18%, the power efficiency (lm/W) is increased by at least 17%, the external quantum efficiency is increased by at least 19%, and the lifetime is increased to 38%.

Therefore, when the nitrogen-containing compound of the disclosure is used as the host material of the organic electroluminescent device, the luminous efficiency and lifetime of the organic electroluminescent device can be improved whether the nitrogen-containing compound is used as a hole-type host material or an electronic host material.

The invention claimed is:

1. A nitrogen-containing compound, wherein the structural formula of the nitrogen-containing compound is as shown in formula 1:

Formula 1

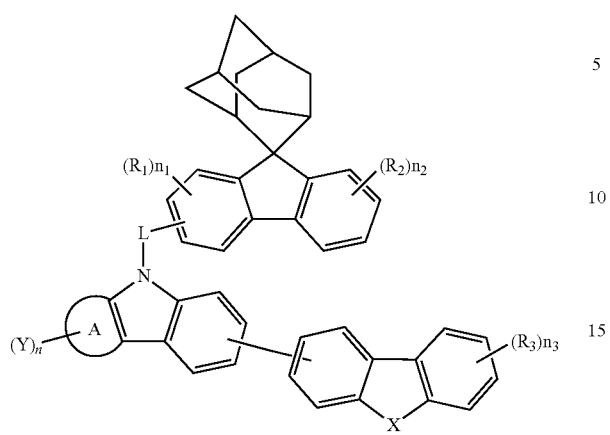

wherein ring A is benzene ring;

X is selected from C ($Z^1Z^2$), N($Z^3$), O or S;

$Z^1$ and $Z^2$ are the same or different, and are each independently selected from: methyl, or substituted or unsubstituted aryl with 6 to 30 carbon atoms, or substituted or unsubstituted heteroaryl with 3 to 30 carbon atoms, or alternatively, $Z^1$ and $Z^2$ are connected with each other to form saturated or unsaturated 5- to -13-membered rings together with the atoms to which they are jointly connected;

$Z^3$ is selected from substituted or unsubstituted aryl with 6 to 30 carbon atoms, or substituted or unsubstituted heteroaryl with 3 to 30 carbon atoms;

the substituents of the $Z^1$, $Z^2$ and $Z^3$ are the same or different from each other, and are each independently selected from: deuterium, fluorine, chlorine, bromine, cyano, methyl, aryl with 6 to 20 carbon atoms, or heteroaryl with 6 to 18 carbon atoms;

Y, $R_1$, $R_2$ and $R_3$ are the same or different, and are each independently selected from: deuterium, fluorine, chlorine, bromine, or cyano;

n and $n_3$ are the same or different, and are each independently selected from 0, 1, 2, 3 or 4; $n_1$ and $n_2$ are the same or different, and are each independently selected from 0, 1, 2 or 3;

when n is 2, 3 or 4, any two Y are the same or different; when $n_1$ is 2 or 3, any two $R_1$ are the same or different; when $n_2$ is 2 or 3, any two $R_2$ are the same or different; when $n_3$ is 2, 3 or 4, any two $R_3$ are the same or different;

L is selected from: single bond or unsubstituted $T_1$ or substituted $T_1$, wherein unsubstituted $T_1$ is selected from the group consisting of the following substituents:

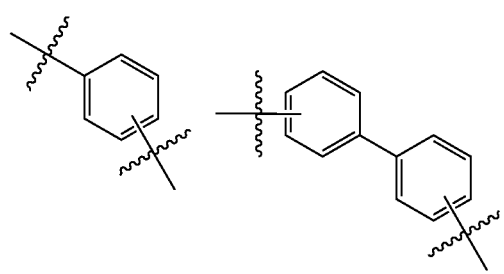

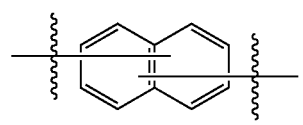

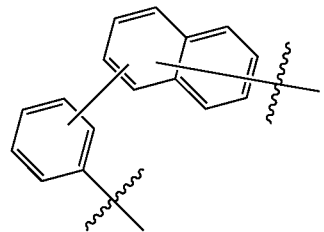

substituted $T_1$ is a group formed by substituting the unsubstituted $T_1$ by one or more substituent(s) selected from deuterium, fluorine, chlorine, cyano and methyl and when a plurality of substituents are included on the substituted $T_1$ any two substituents are the same or different.

2. The nitrogen-containing compound according to claim 1, wherein L is selected from: single bond or unsubstituted $T_2$ or substituted $T_2$, wherein the unsubstituted $T_2$ is selected from the group consisting of the following substituents:

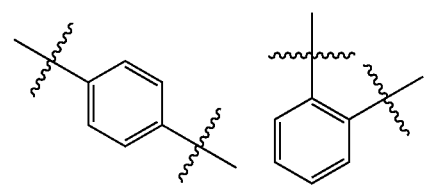

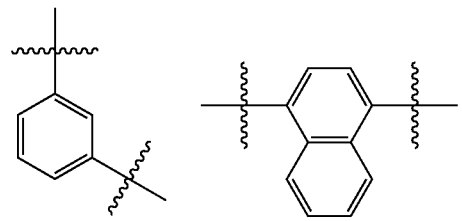

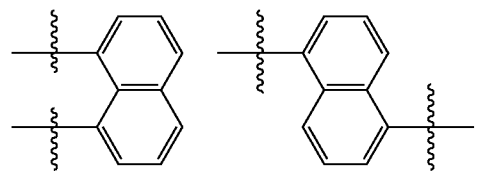

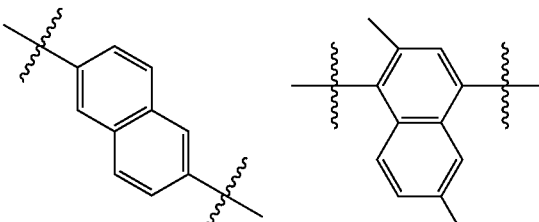

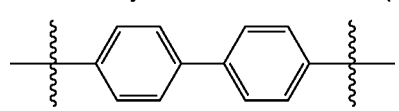

-continued

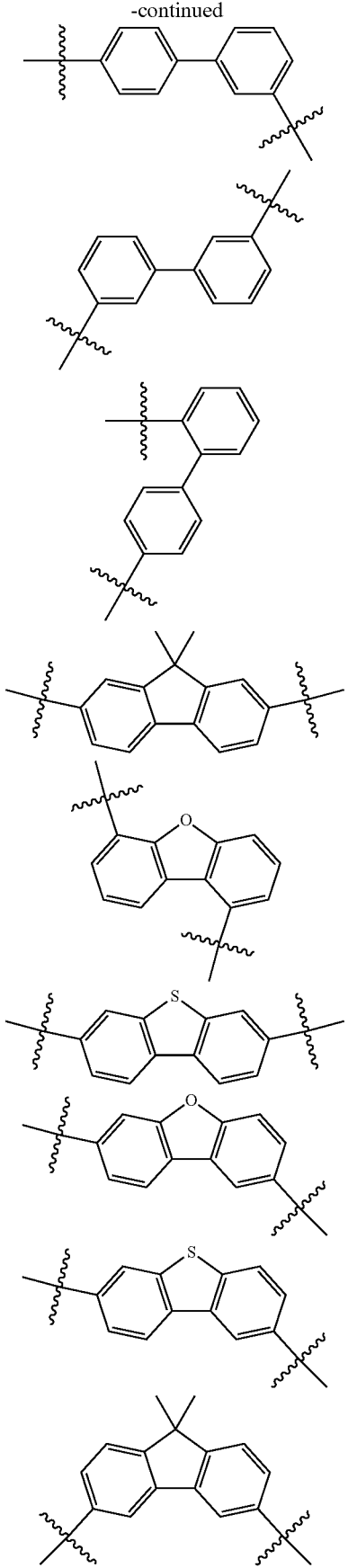

-continued

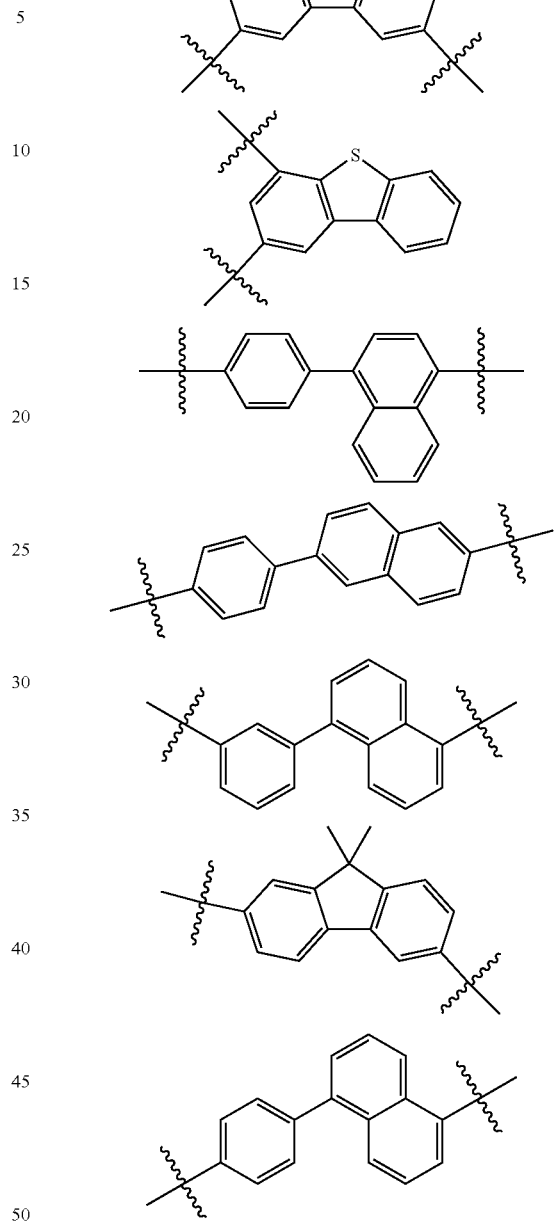

substituted $T_2$ is a group formed by substituting the unsubstituted $T_2$ by one or more substituent(s) selected from deuterium, fluorine, chlorine, cyano and methyl, and when a plurality of substituents are included on the substituted $T_2$, any two substituents are the same or different.

3. The nitrogen-containing compound according to claim 1, wherein $Z^1$ and $Z^2$ are each independently selected from methyl and phenyl, or alternatively, $Z^1$ and $Z^2$ are connected with each other to form 5- to 10-membered cycloalkyl together with the atoms to which they are jointly connected; and $Z^3$ is selected from substituted or unsubstituted $T_3$;

wherein unsubstituted $T_3$ is selected from the group consisting of the following substituents:

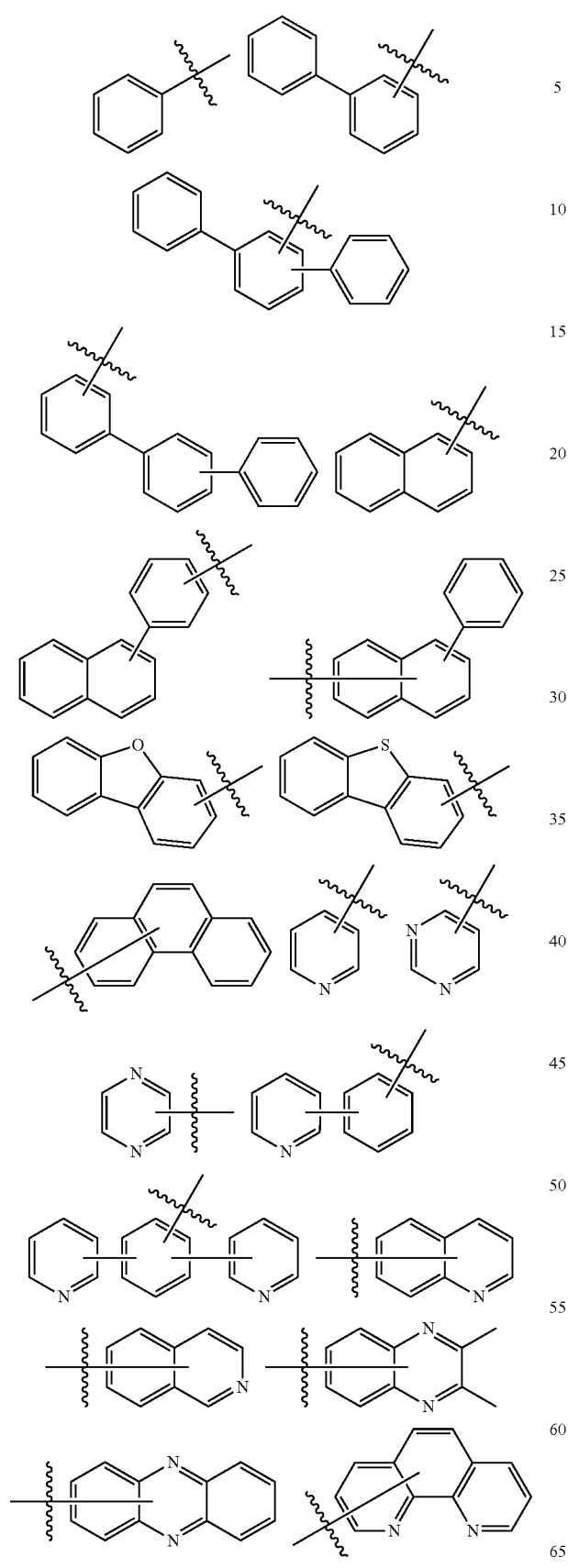

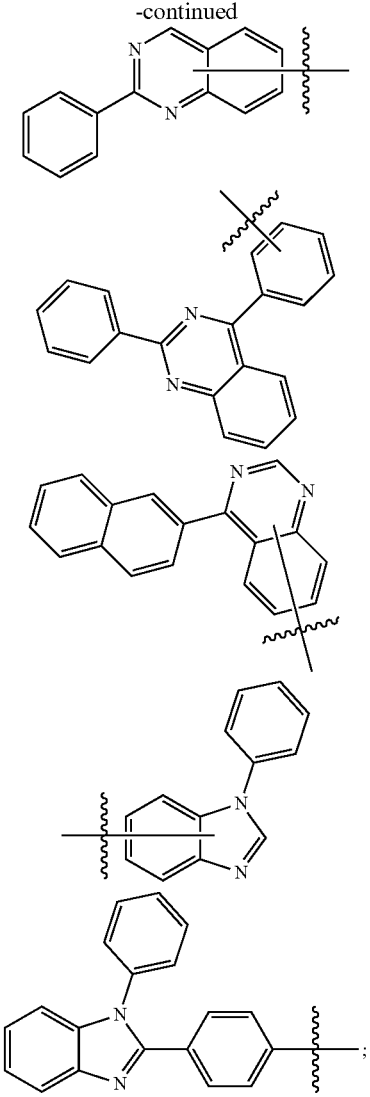

substituted $T_3$ is a group formed by substituting the unsubstituted $T_3$ by one or more substituent(s) selected from deuterium, fluorine, chlorine, cyano, methyl, aryl with 6 to 13 carbon atoms and heteroaryl with 12 carbon atoms, and when a plurality of substituents are included on the substituted $T_3$, any two substituents are the same or different.

4. The nitrogen-containing compound according to claim 1, wherein the $Z^3$ is independently selected from substituted or unsubstituted $T_6$, wherein unsubstituted $T_6$ is independently selected from the groups as shown below:

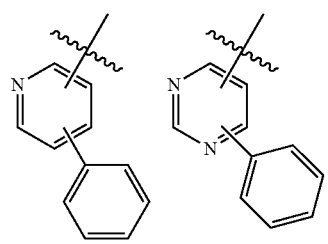

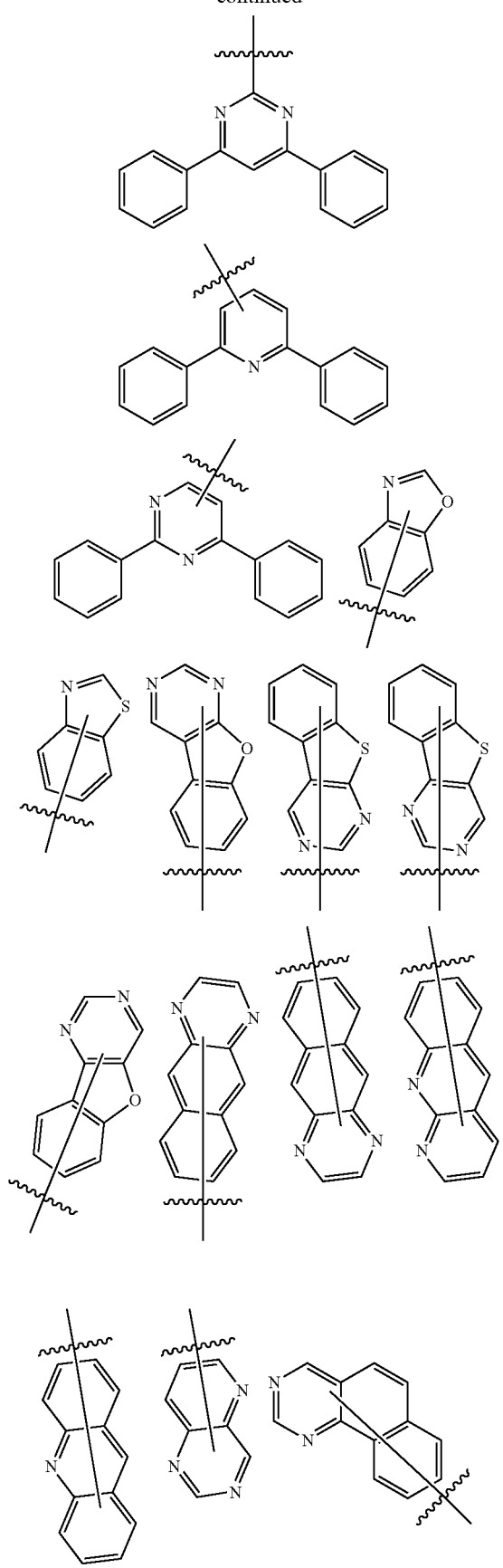
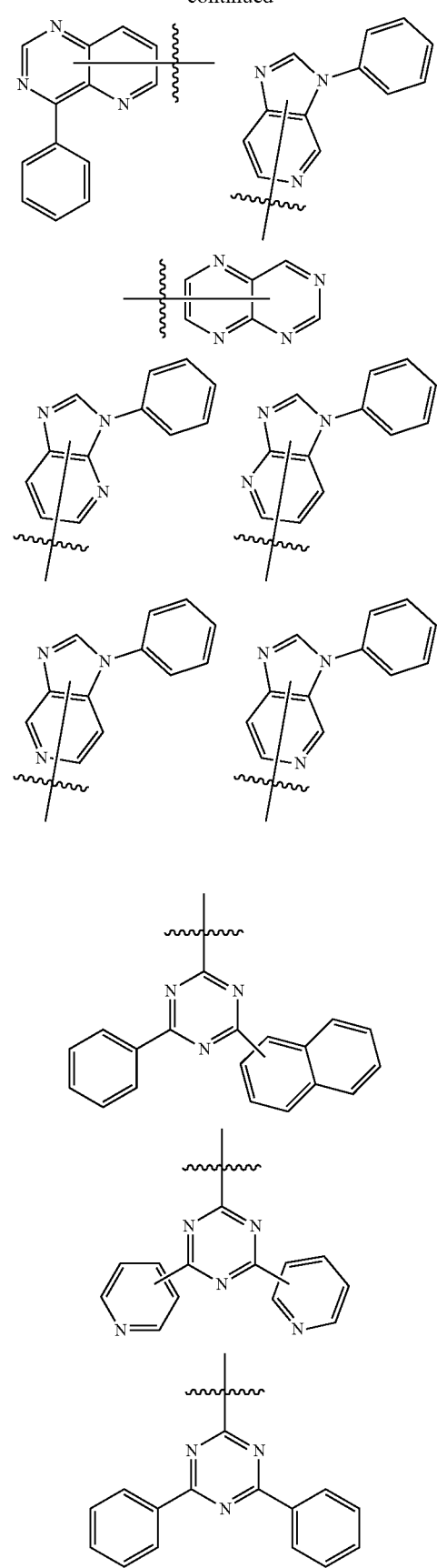

-continued

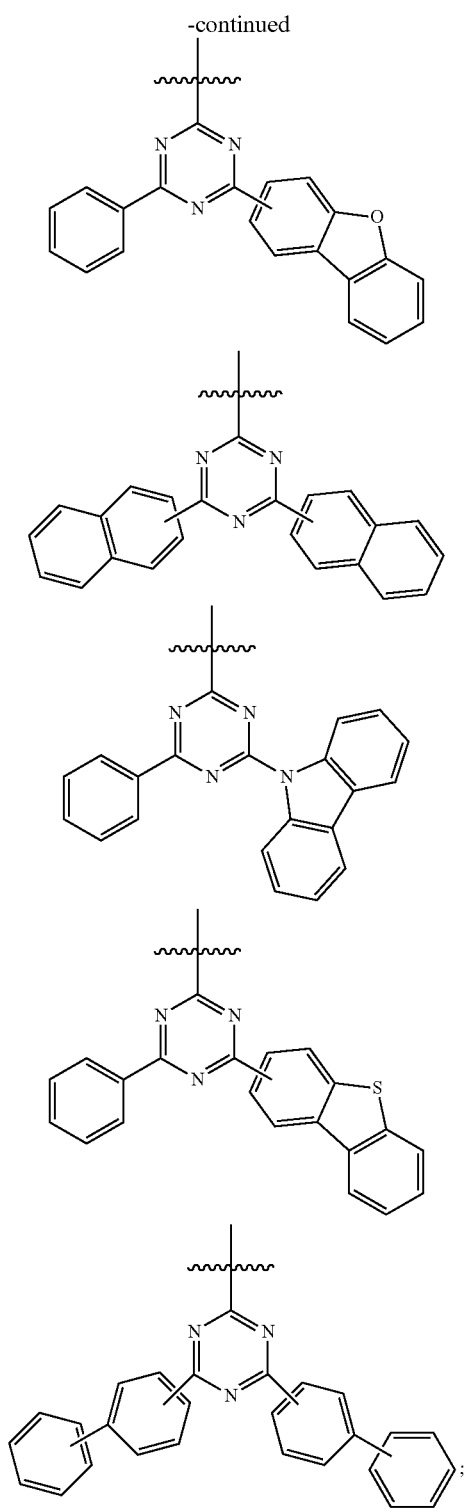

substituted $T_6$ is a group formed by substituting the unsubstituted $T_6$ by one or more substituent(s) selected from deuterium, fluorine, chlorine, cyano, methyl, aryl with 6 to 13 carbon atoms and heteroaryl with 12 carbon atoms, and when a plurality of substituents are included on the substituted $T_6$, any two substituents are the same or different.

5. The nitrogen-containing compound according to claim 1, wherein $Z^1$ and $Z^2$ are each independently selected from methyl and phenyl, or alternatively, $Z^1$ and $Z^2$ are connected with each other to form cyclopentyl, cyclohexyl or adamantyl together with the atoms to which they are jointly connected; and $Z^3$ is selected from substituted or unsubstituted $T_4$;

wherein unsubstituted $T_4$ is selected from the group consisting of the following substituents:

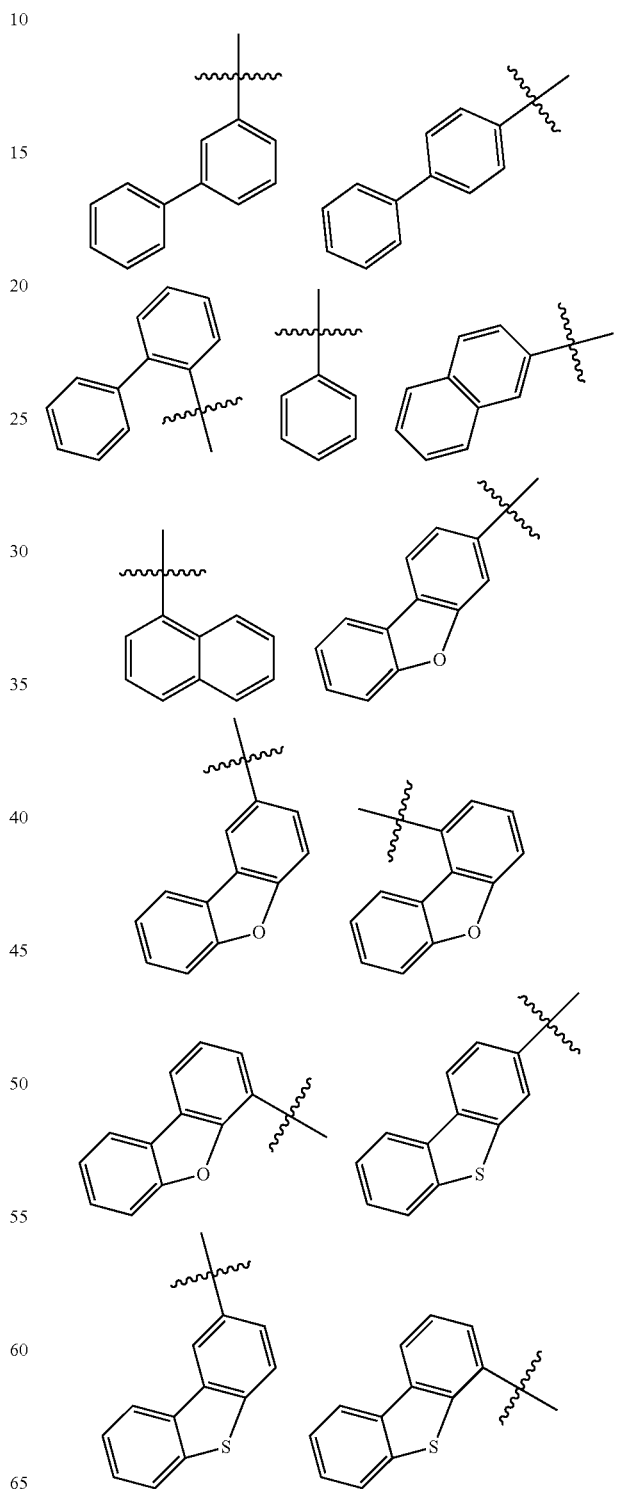

287
-continued
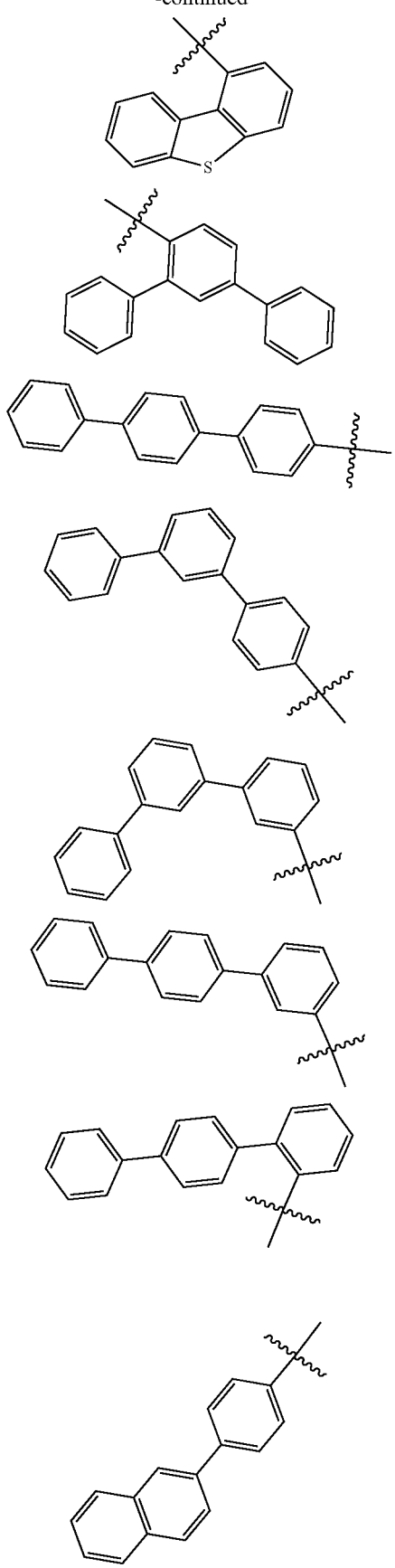
288
-continued
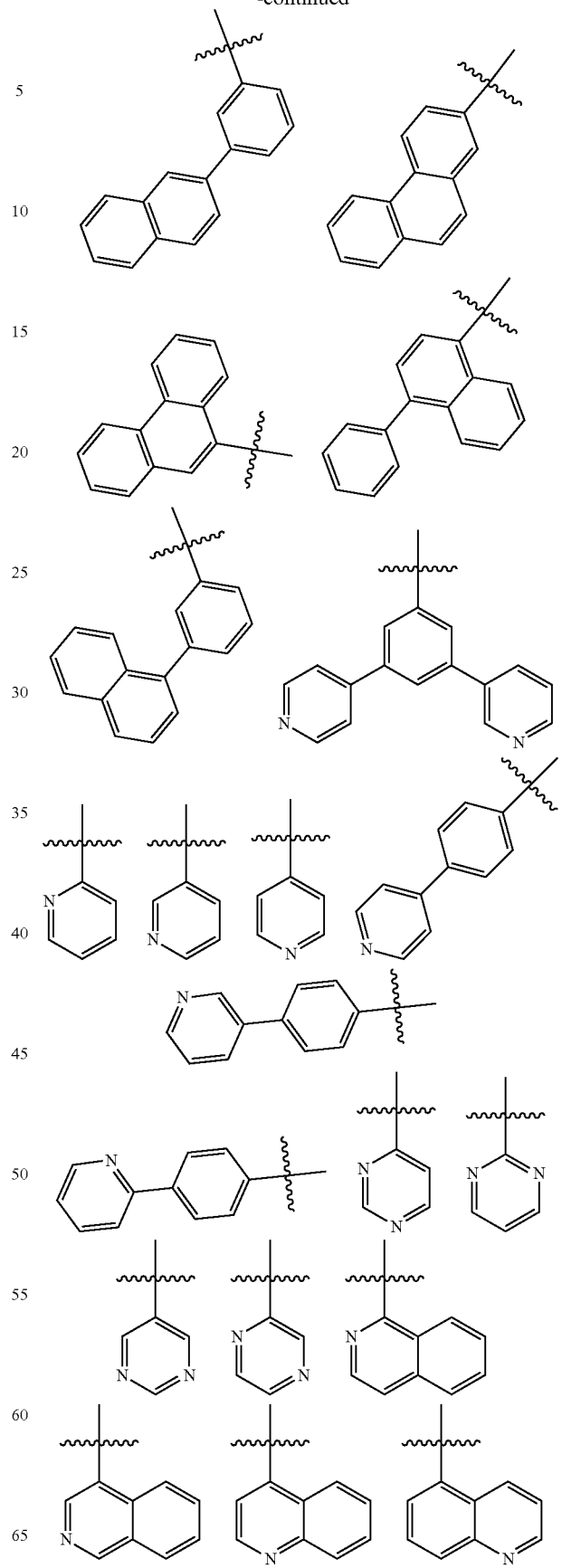

-continued

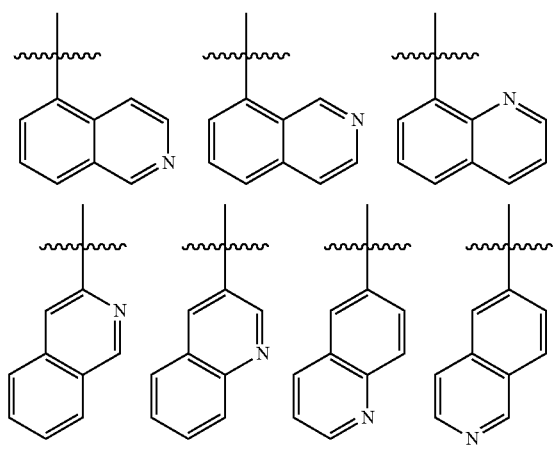

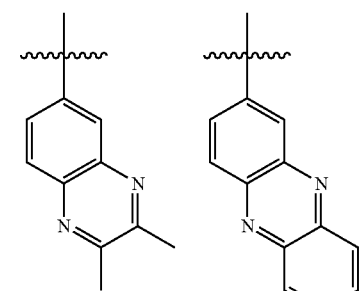

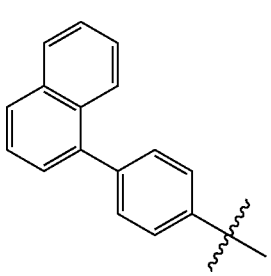

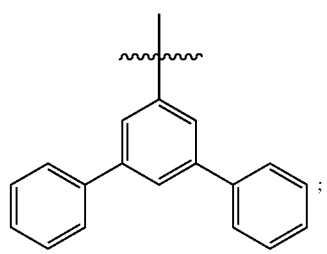

substituted $T_4$ is a group formed by substituting the unsubstituted $T_4$ by one or more substituent(s) selected from deuterium, fluorine, chlorine, cyano, methyl, phenyl, naphthyl, dibenzothiophenyl and dibenzofuranyl, and when a plurality of substituents are included on the substituted $T_4$, any two substituents are the same or different.

6. The nitrogen-containing compound according to claim 1, wherein the $Z^3$ is independently selected from substituted or unsubstituted $T_7$, wherein unsubstituted $T_7$ is independently selected from the groups as shown below:

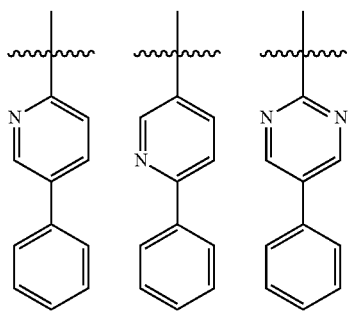

-continued
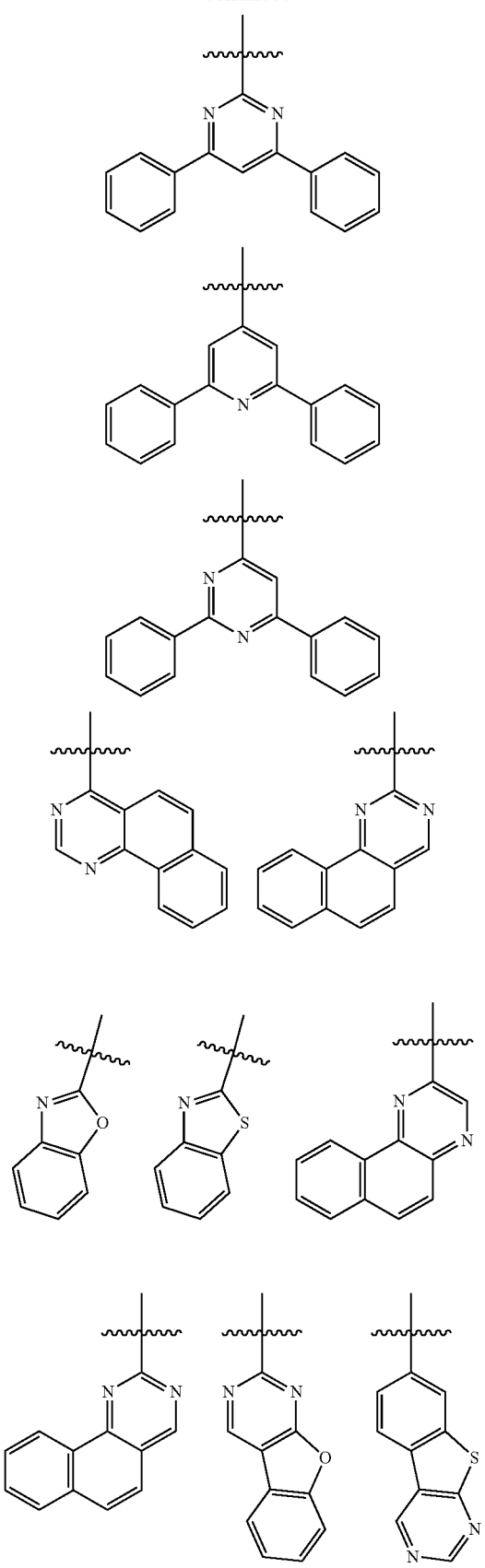
-continued
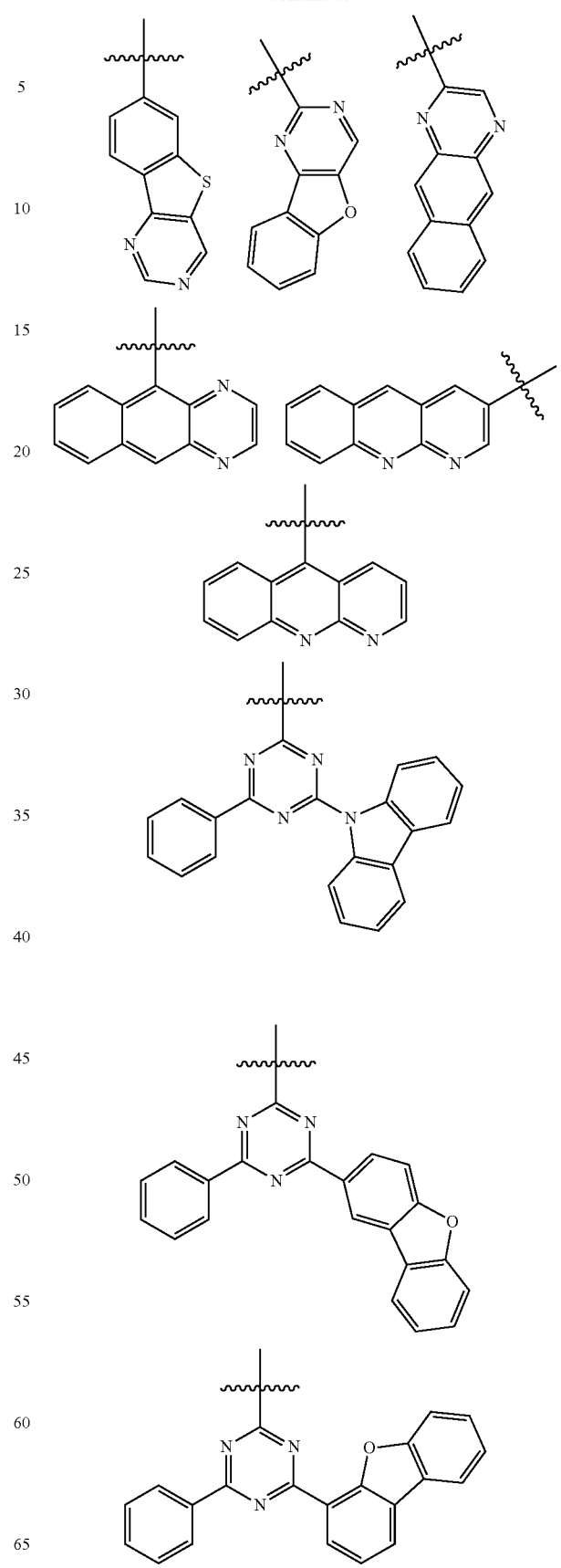

293
-continued
294
-continued
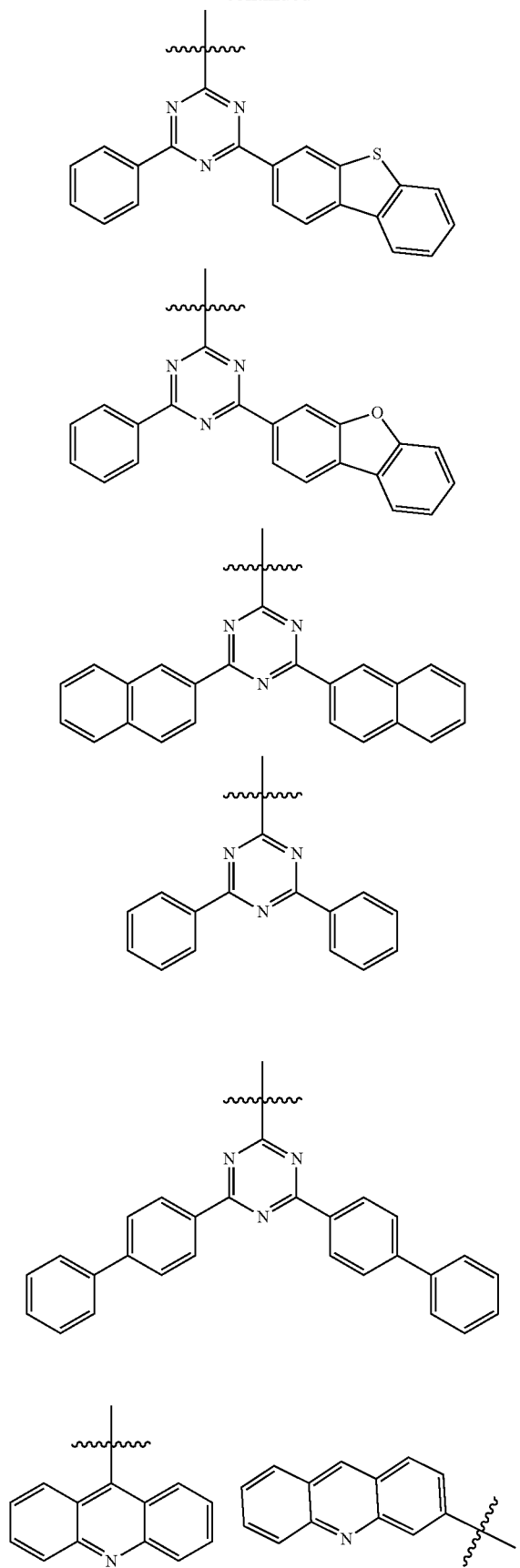
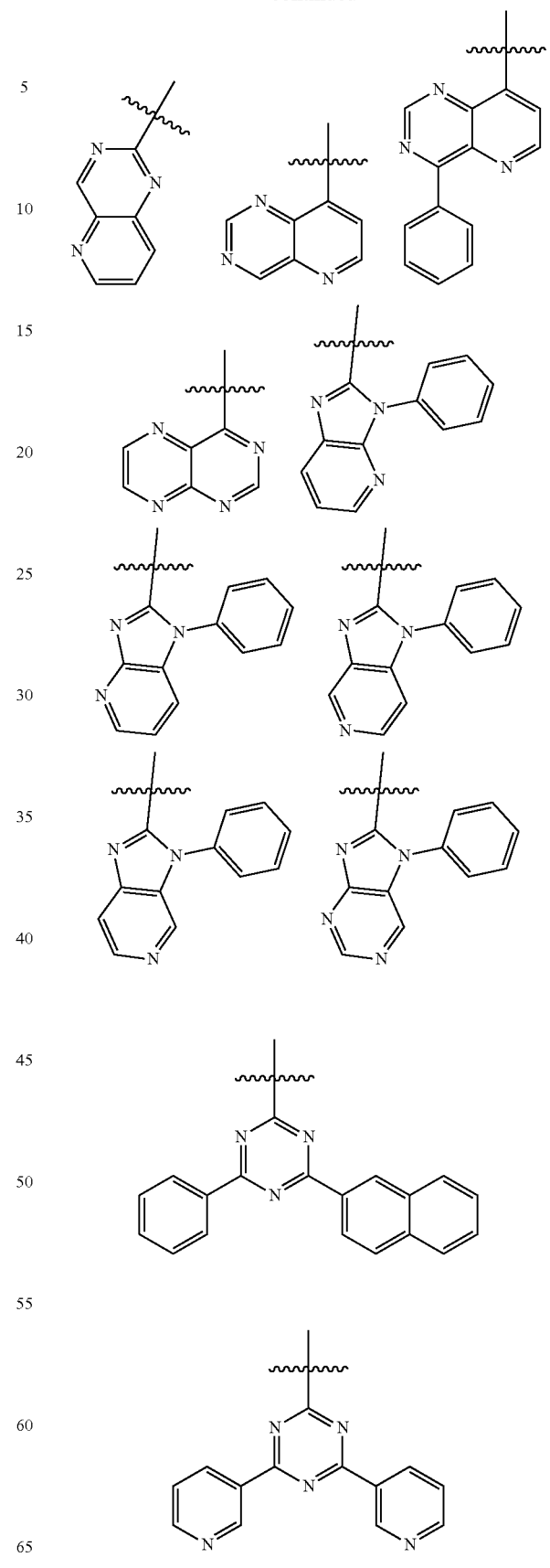

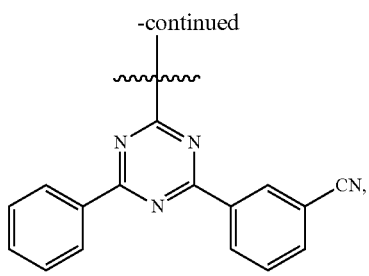

substituted $T_7$ is a group formed by substituting the unsubstituted $T_7$ by one or more substituent(s) selected from deuterium, fluorine, chlorine, cyano, methyl, phenyl, naphthyl, dibenzothiophenyl and dibenzofuranyl, and when a plurality of substituents are included on the substituted $T_7$, any two substituents are the same or different.

7. The nitrogen-containing compound according to claim 1, wherein

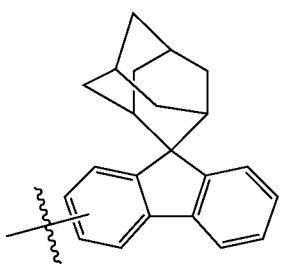

is selected from

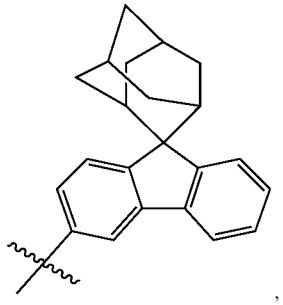

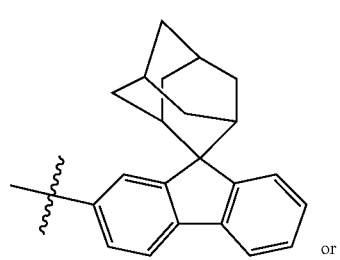

or

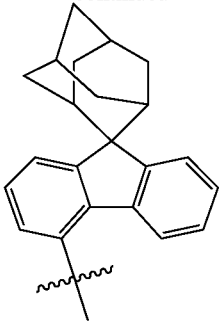

8. The nitrogen-containing compound according to claim 1, which has the structure as shown in any one of formula 2-4 to formula 2-19 below:

Formula 2-4

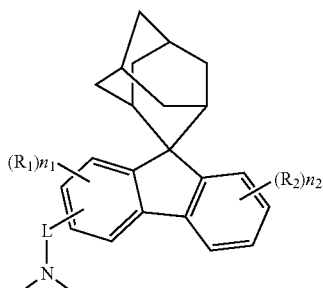

Formula 2-5

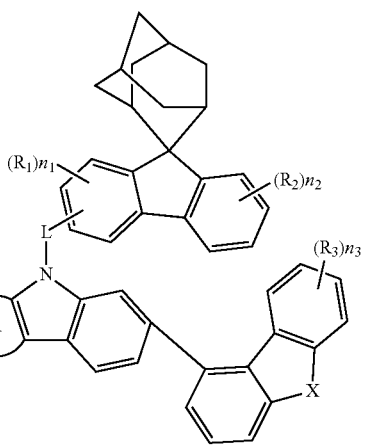

Formula 2-6
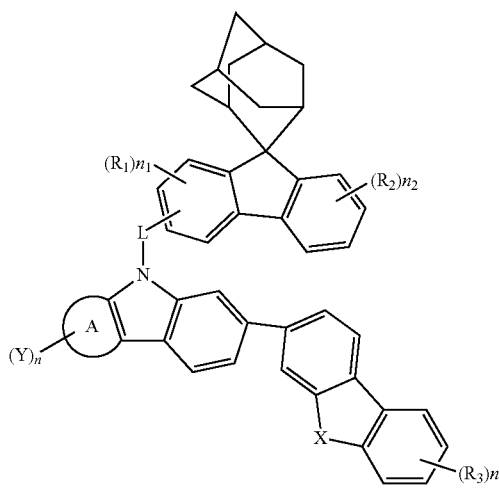
Formula 2-7
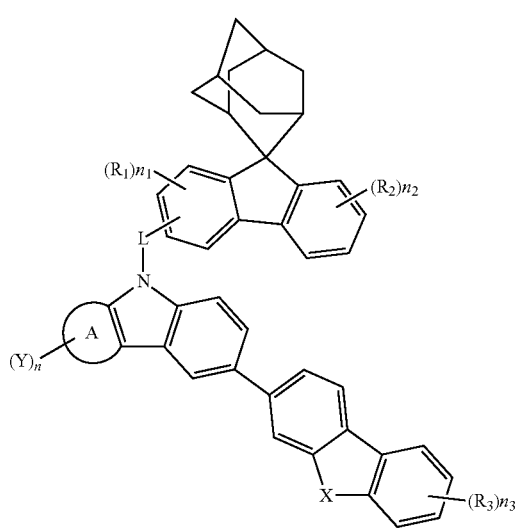
Formula 2-8
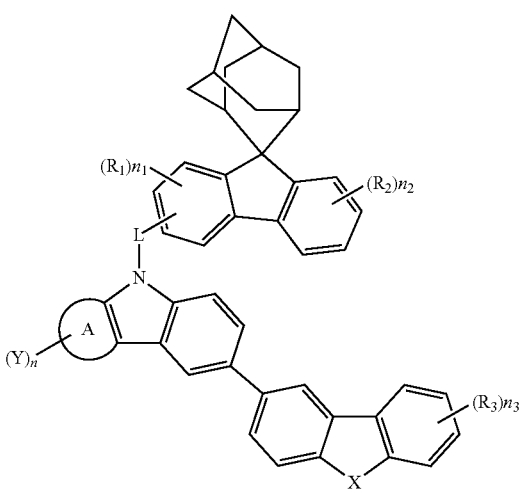
Formula 2-9
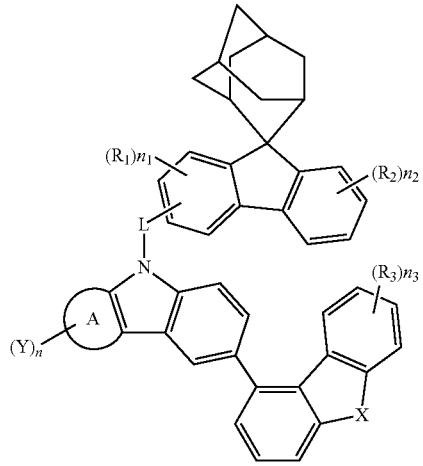
Formula 2-10
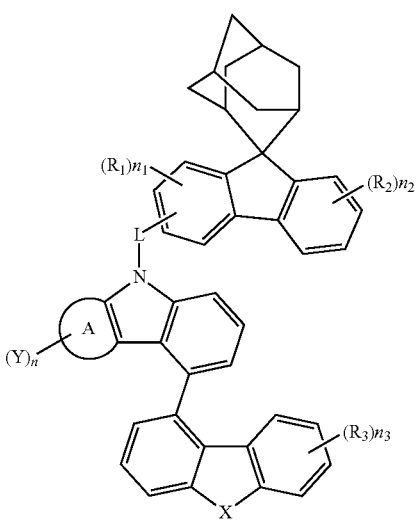
Formula 2-11
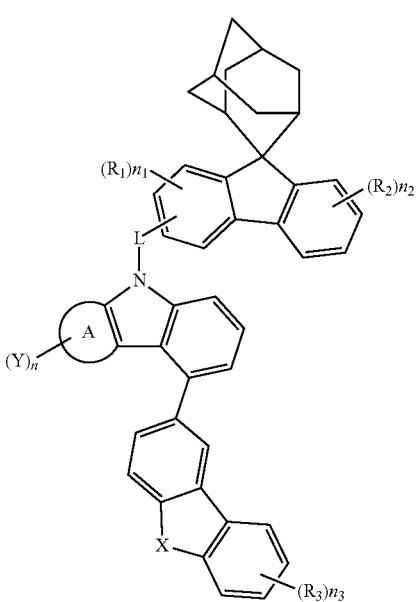

Formula 2-12
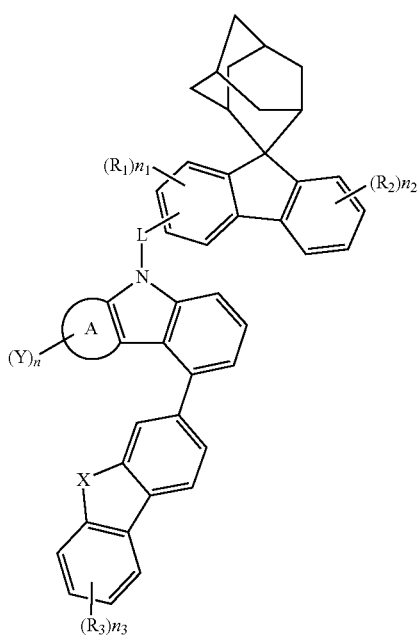
Formula 2-13
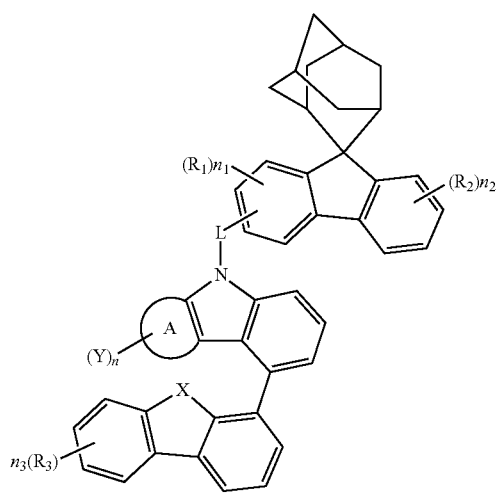
Formula 2-14
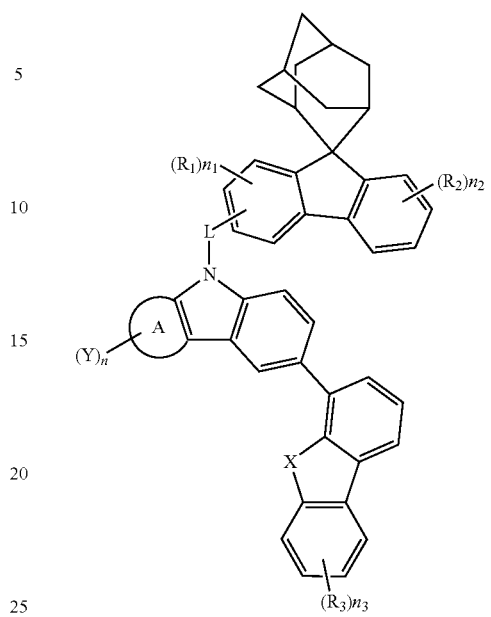
Formula 2-15
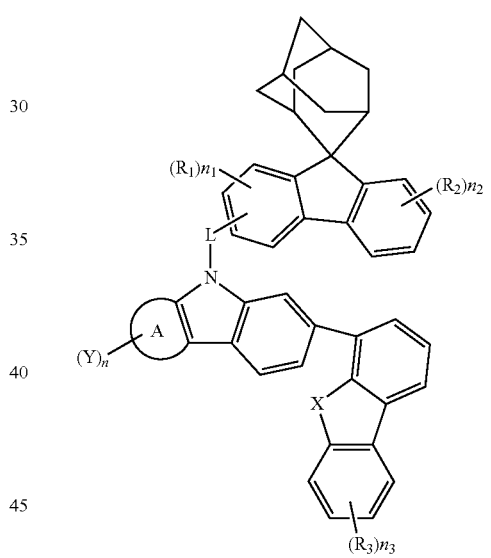
Formula 2-16
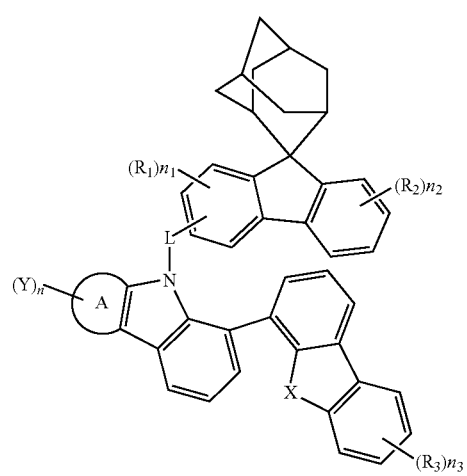

301
-continued
Formula 2-17
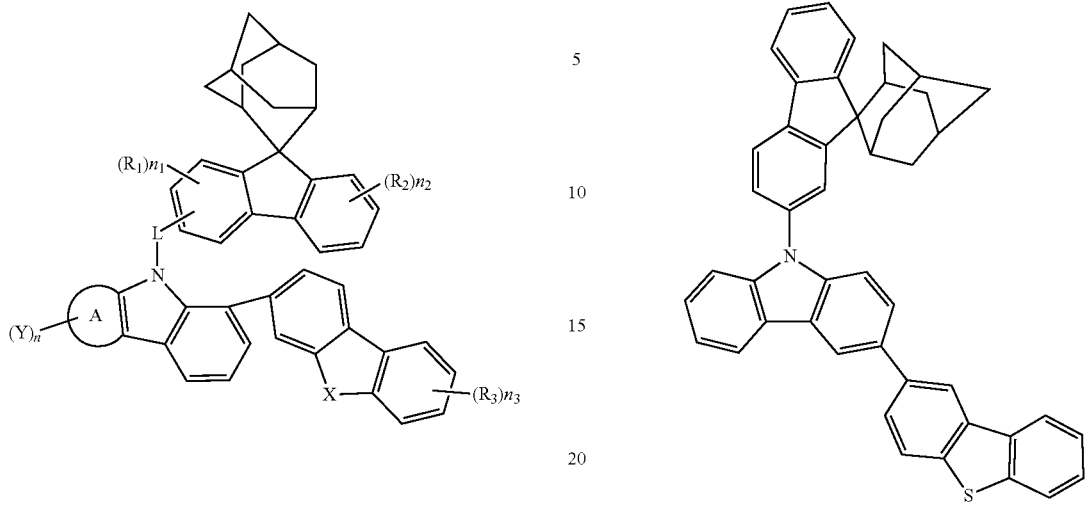
Formula 2-18
Formula 2-19
302
9. The nitrogen-containing compound according to claim 1, wherein the nitrogen-containing compound is selected from the group consisting of the following compounds:
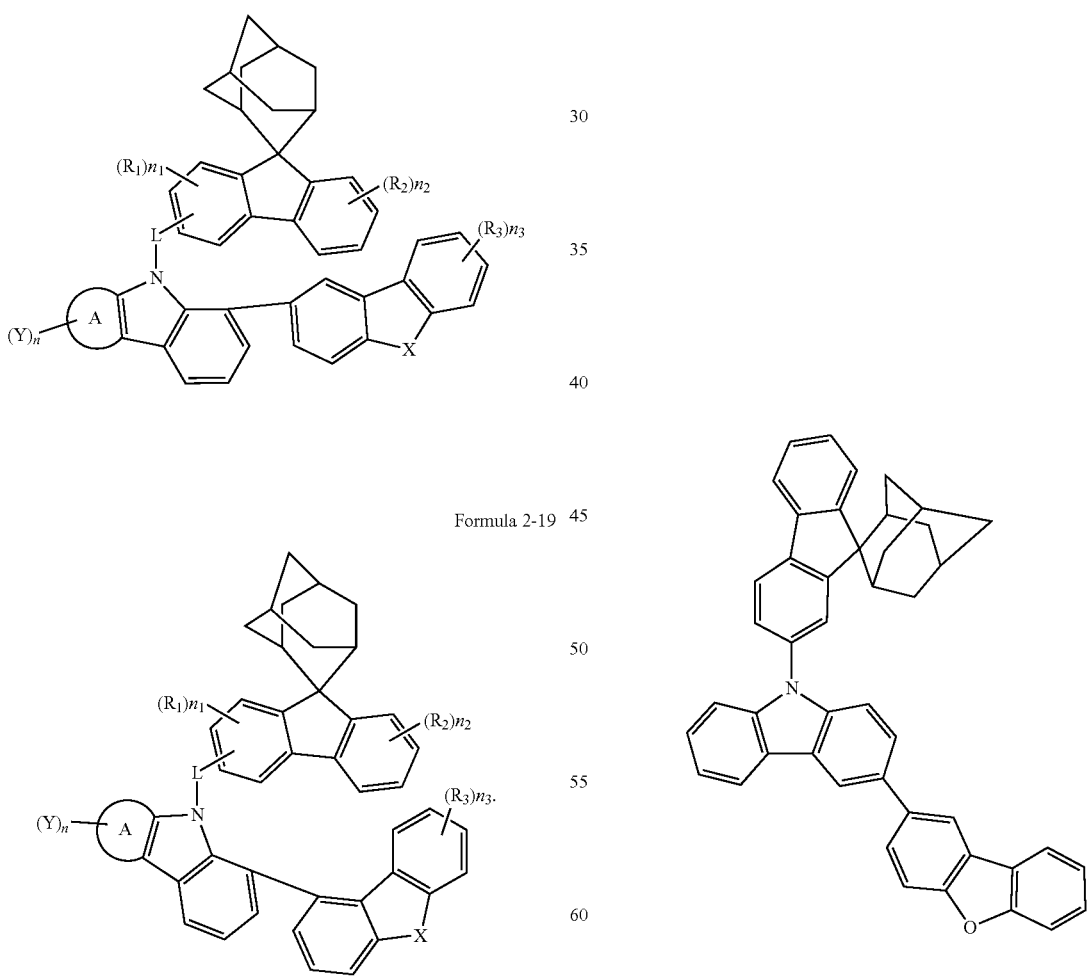

303
-continued
3
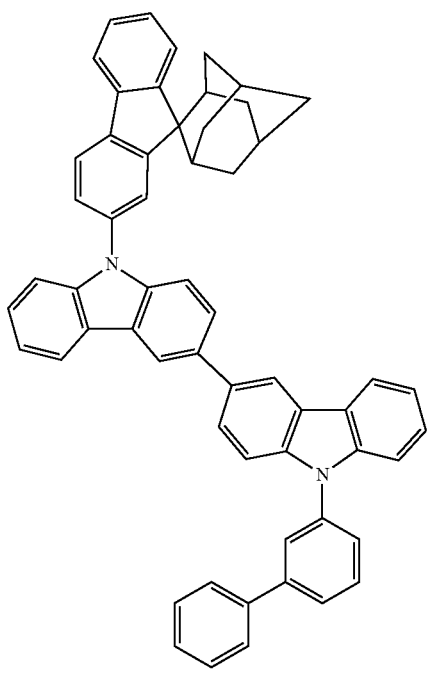
4
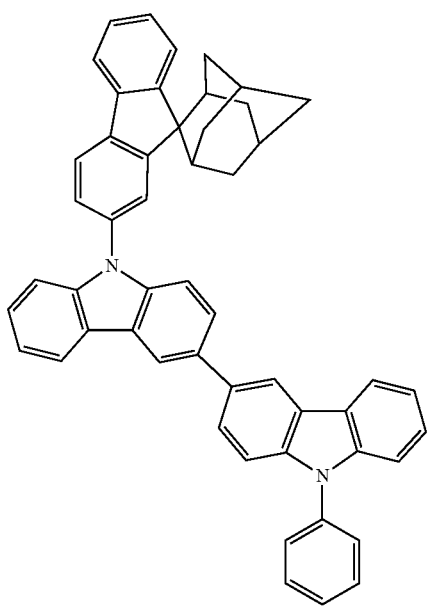
304
-continued
5
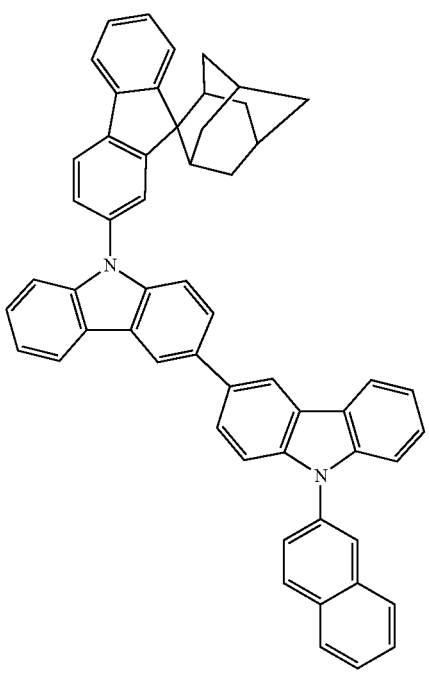
6
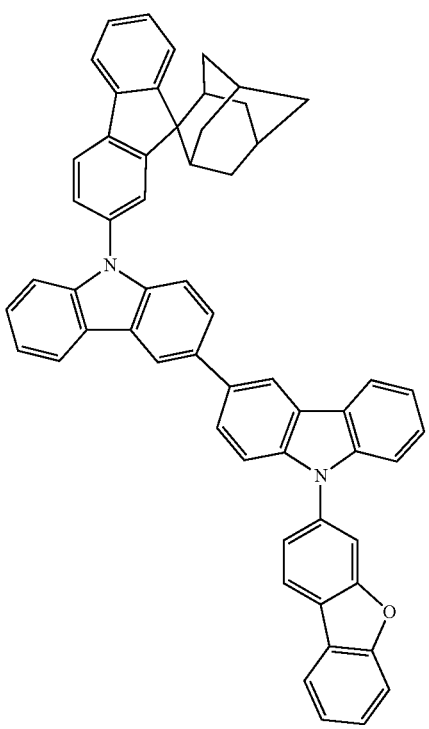

305
-continued
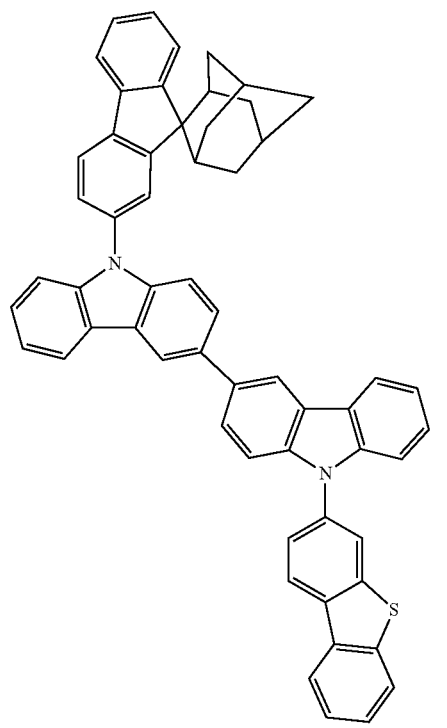
7
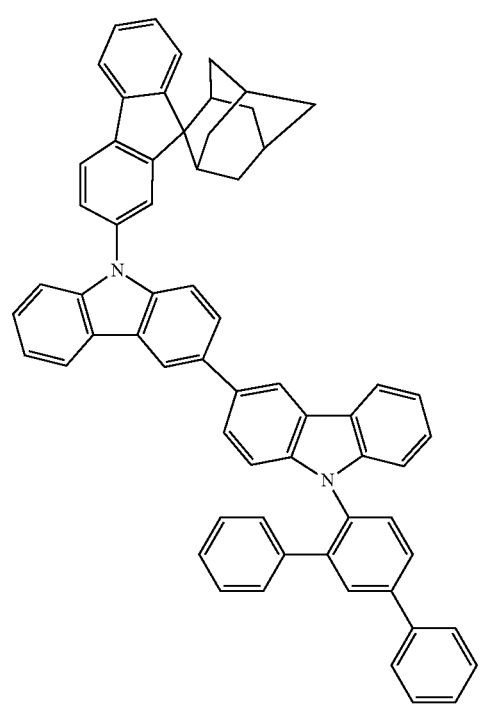
306
-continued
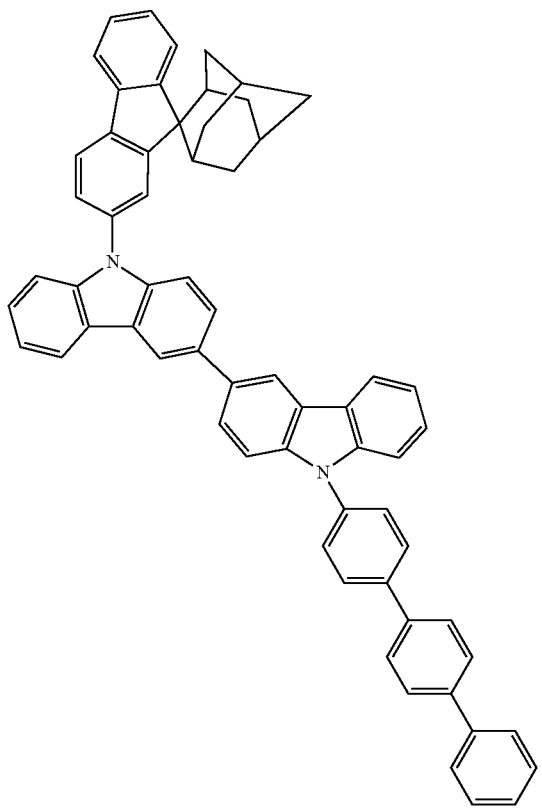
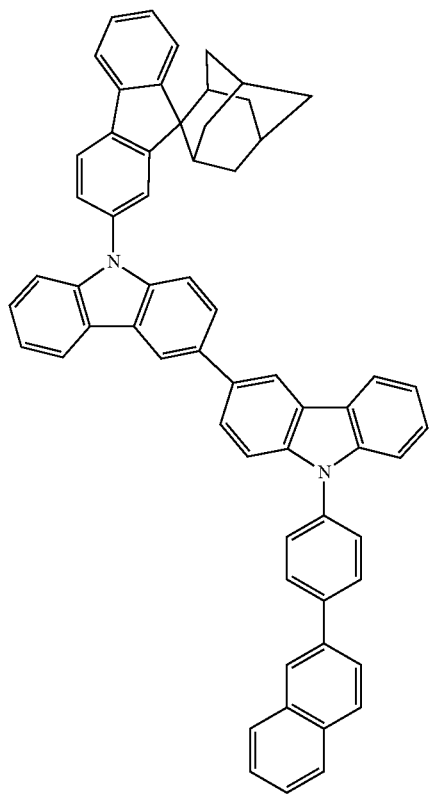

307
-continued
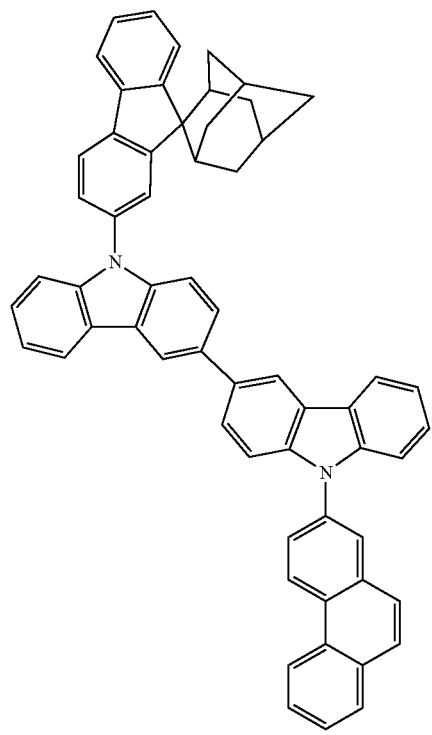
308
-continued
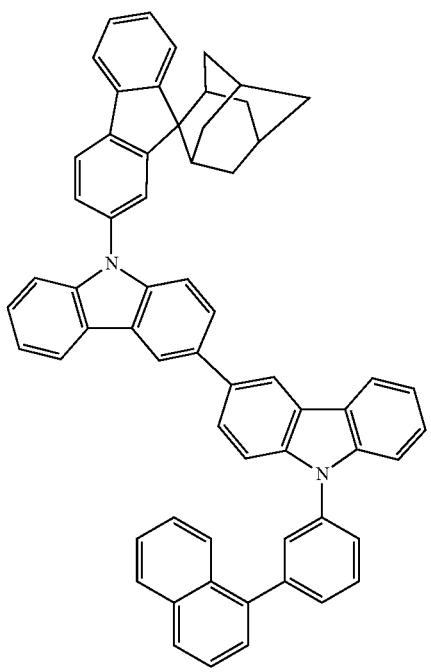
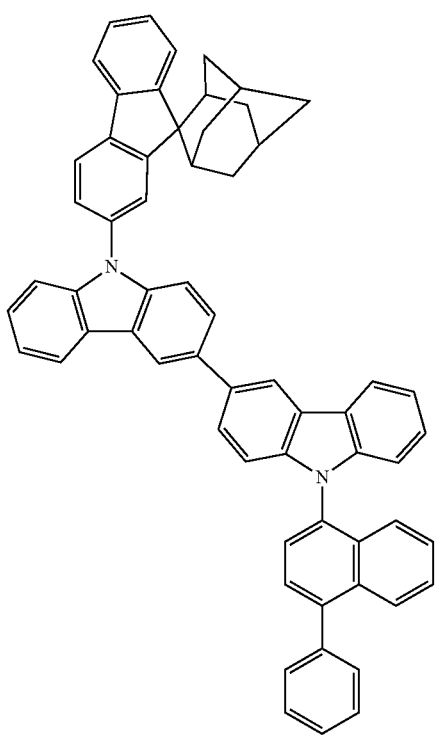

309
-continued
15
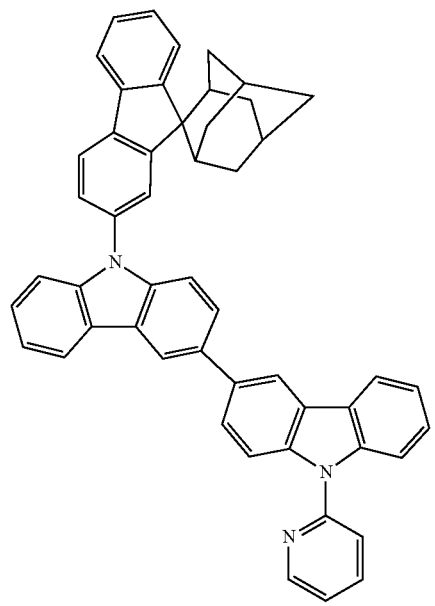
16
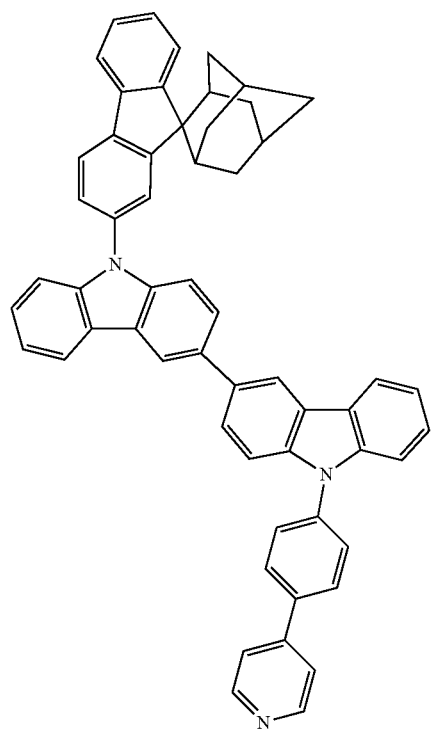
310
-continued
17
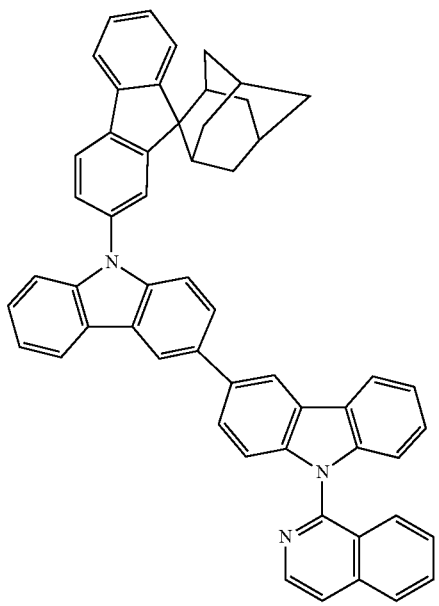
18
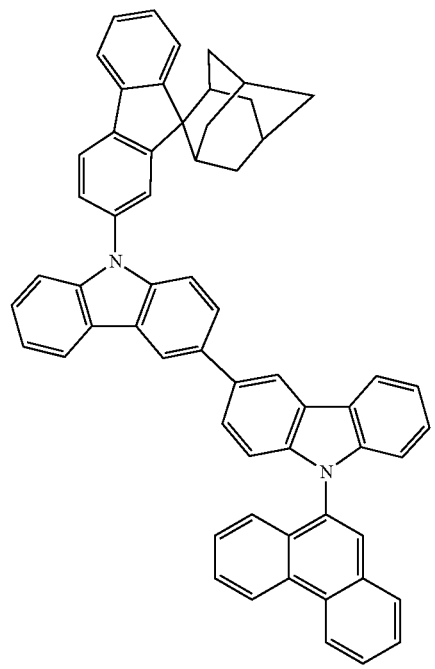

311
-continued
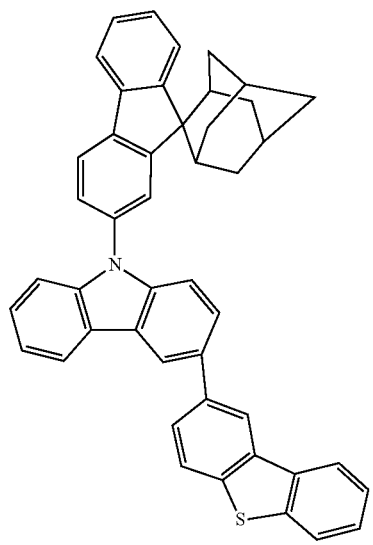
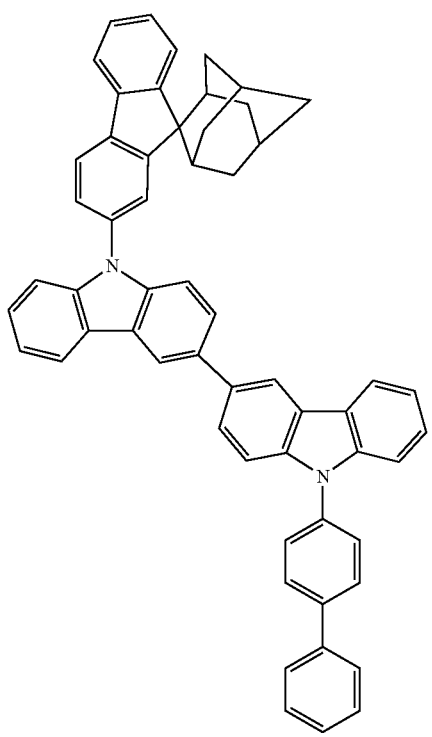
312
-continued
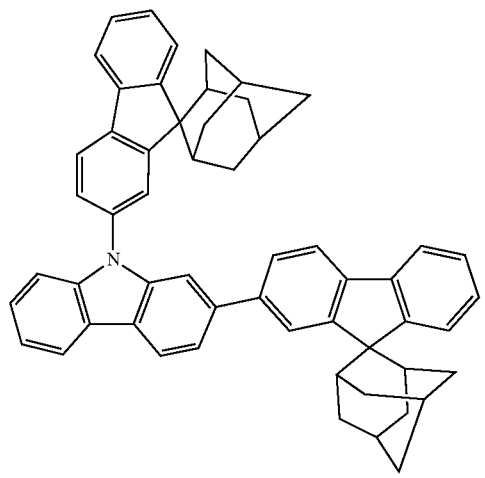
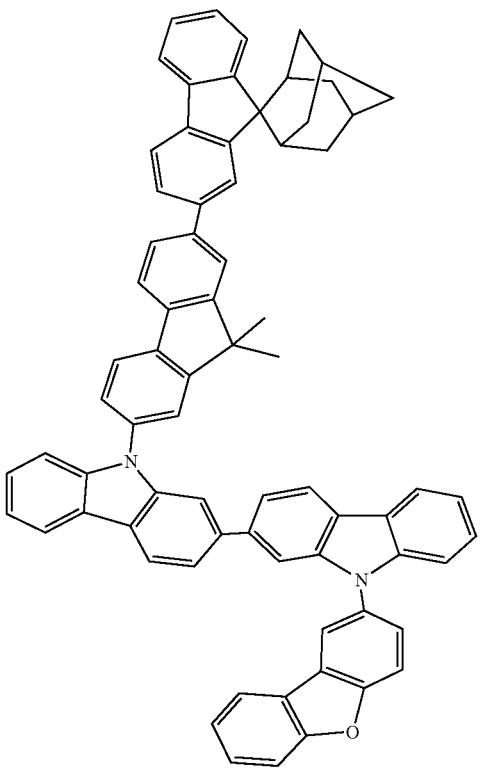

313
-continued
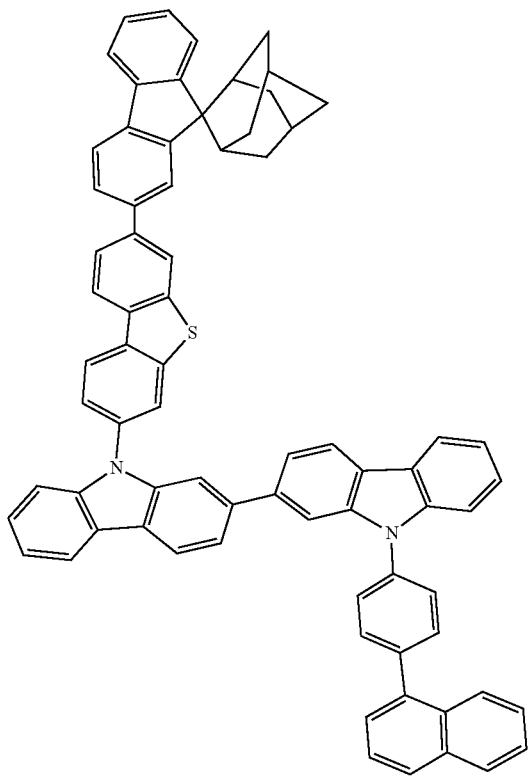
314
-continued
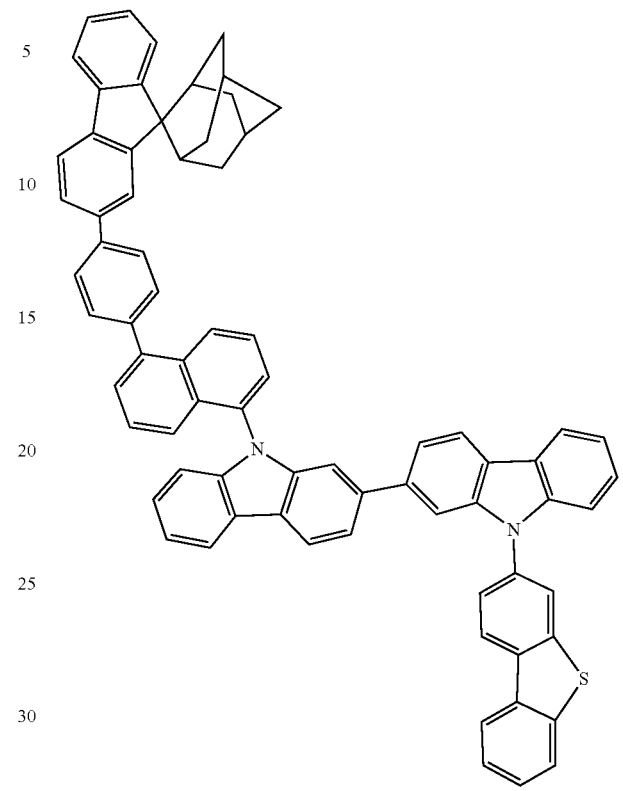
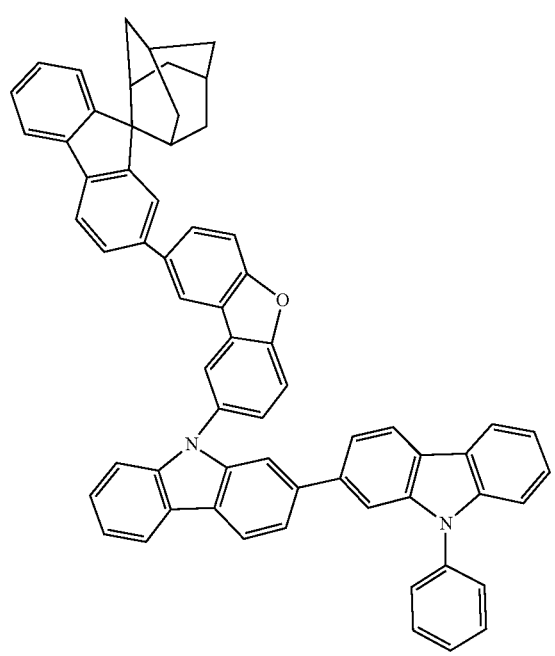
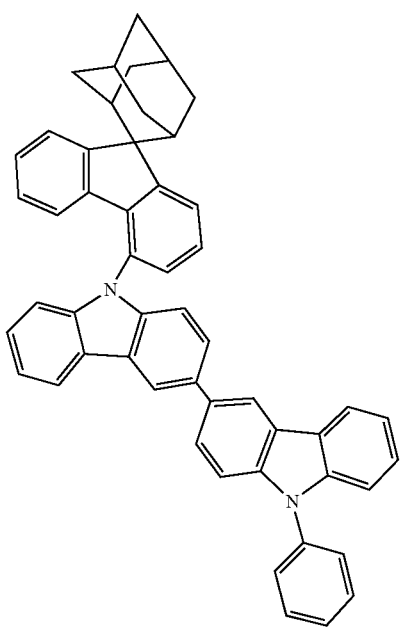

27
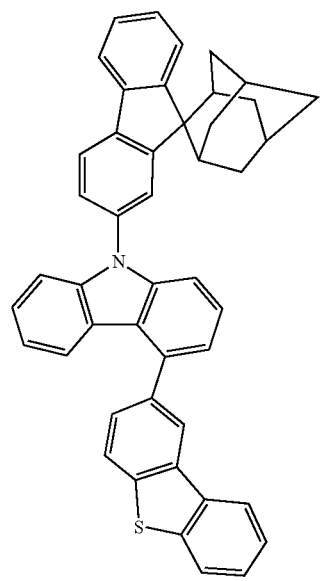
28
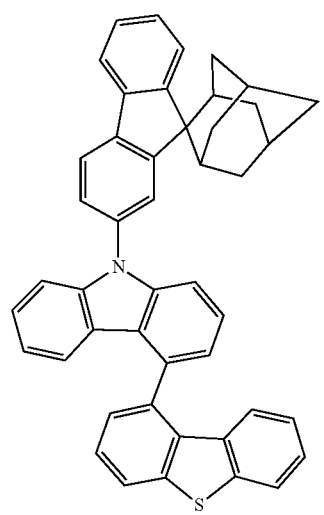
29
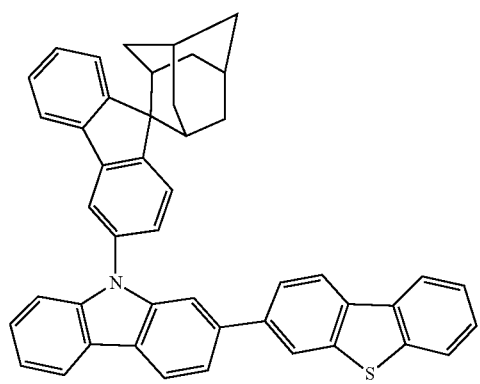
30
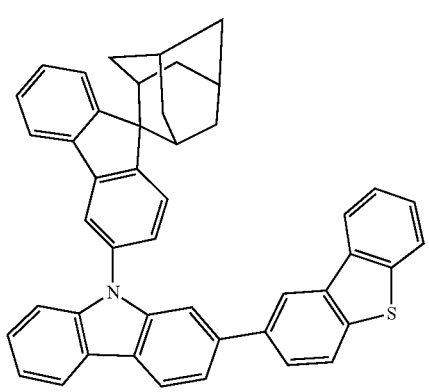
31
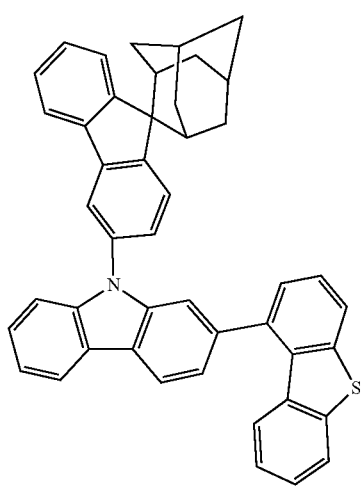
32
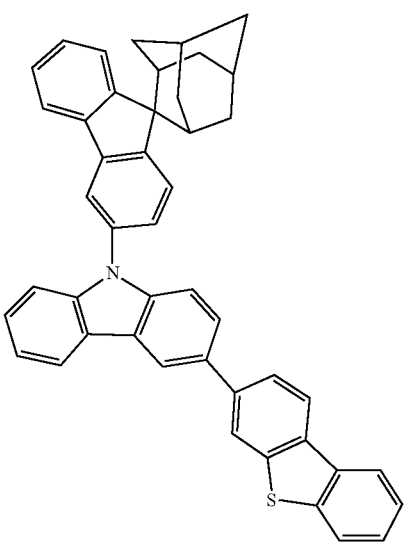

-continued
33
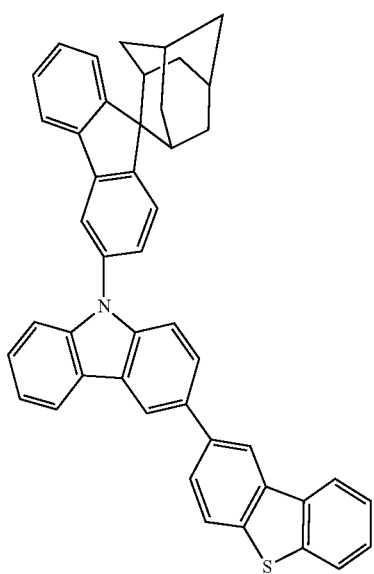
34
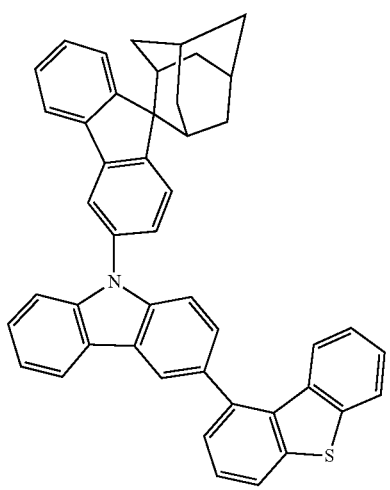
35
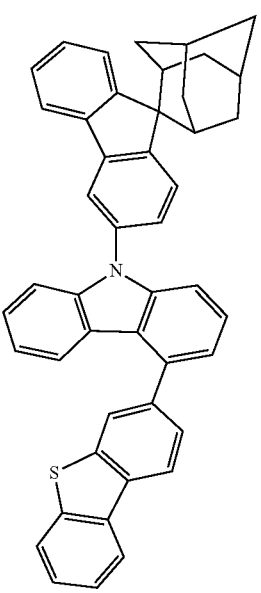
-continued
36
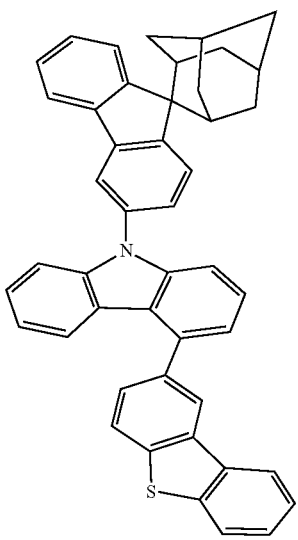
37
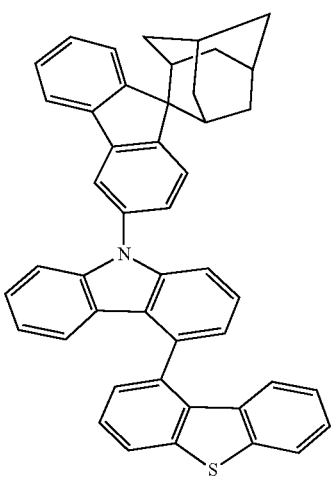
38
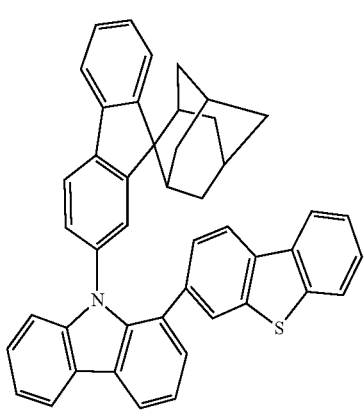

39
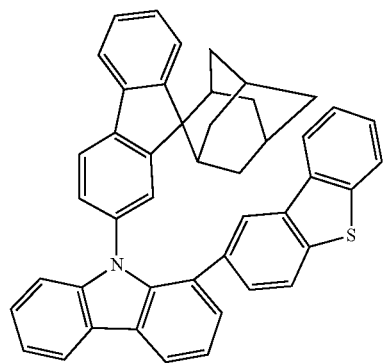
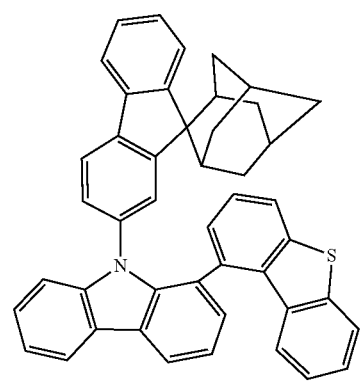
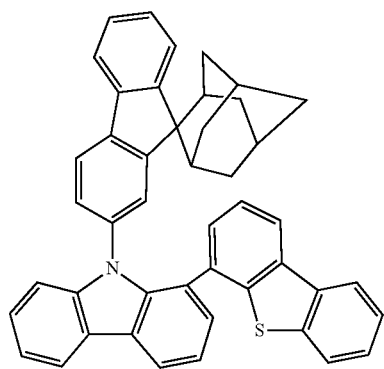
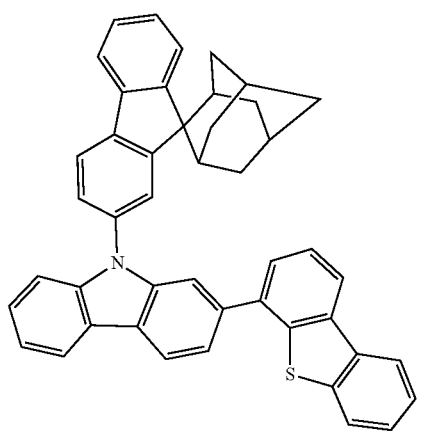
43
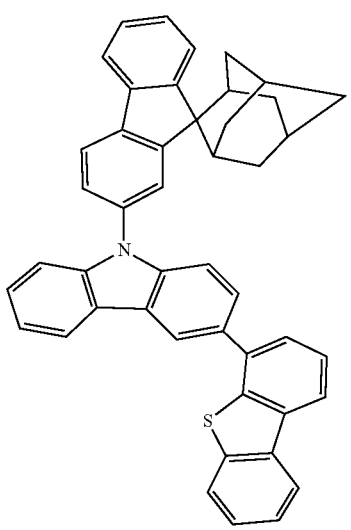
44
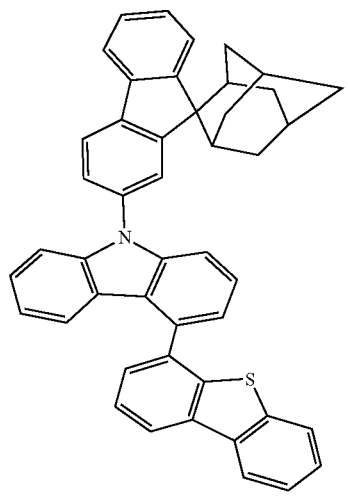
45
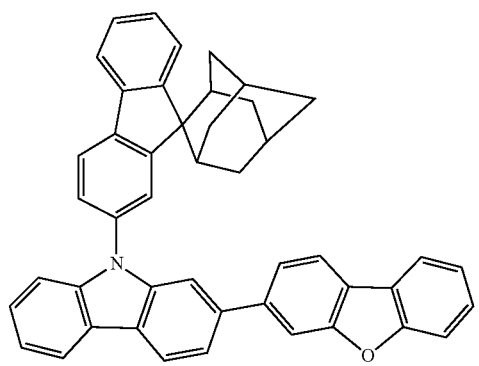

46
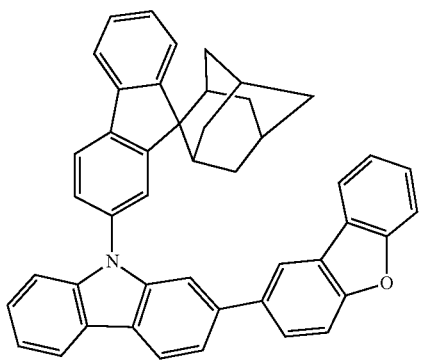
47
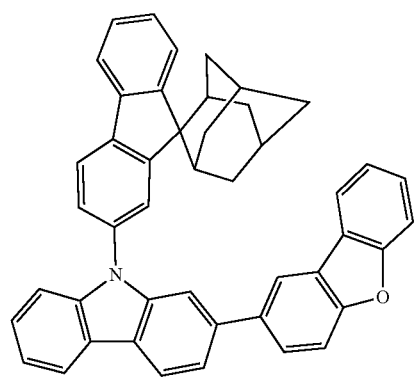
48
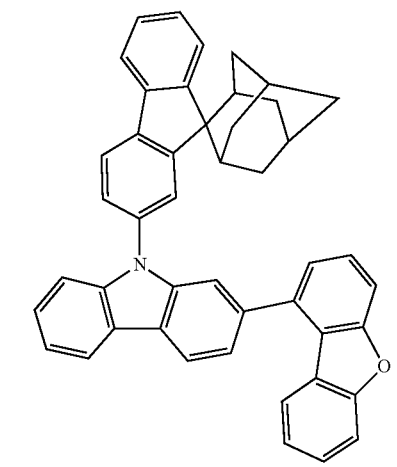
49
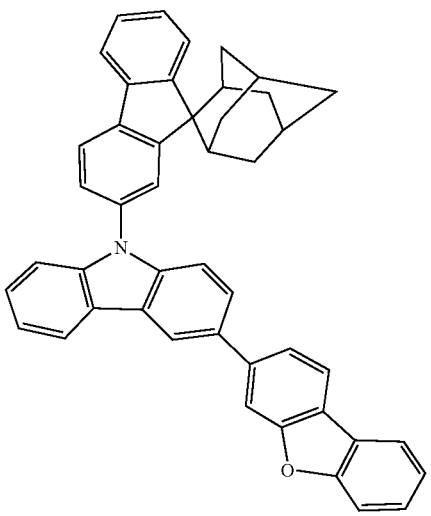
50
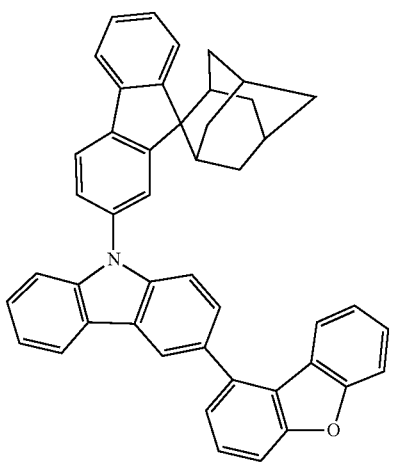
51
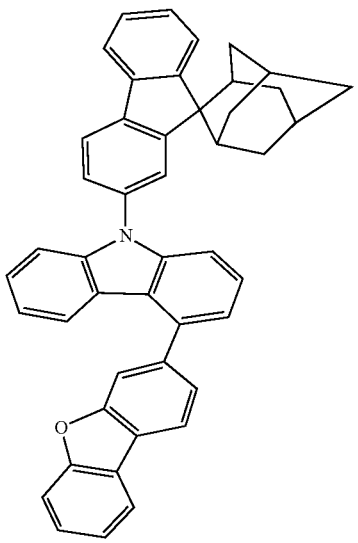

323
-continued
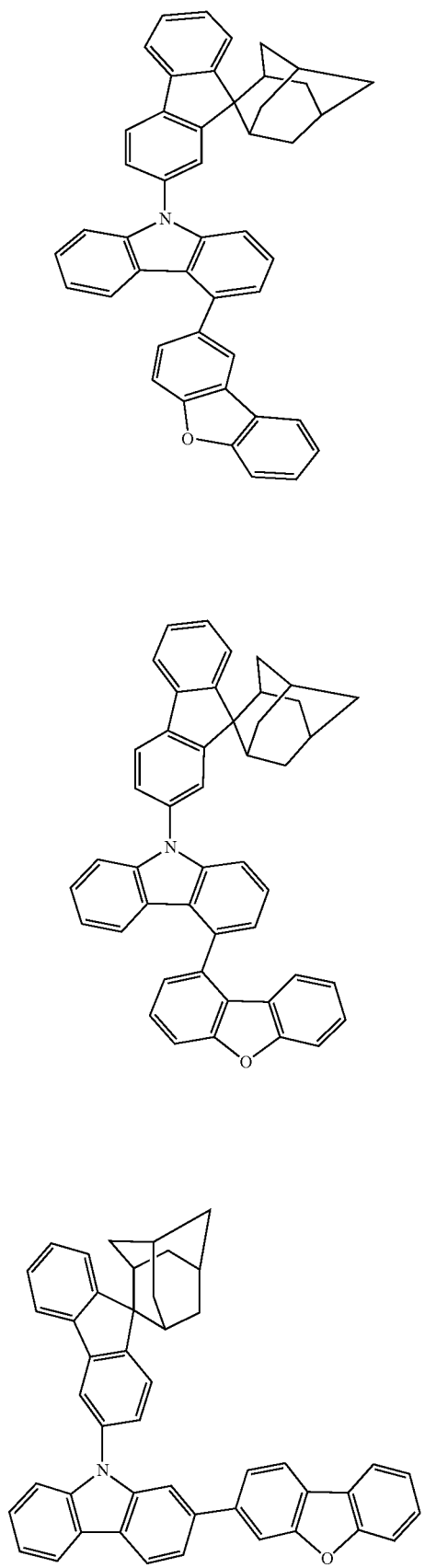
324
-continued
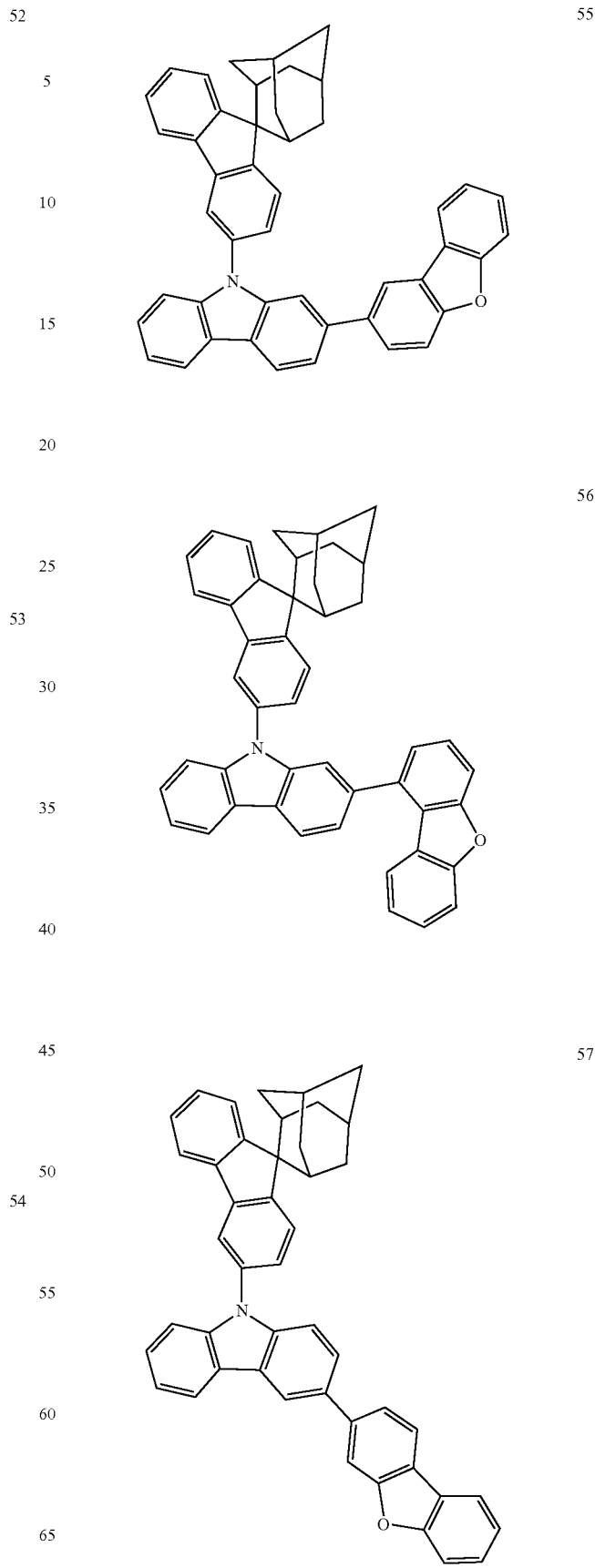

58
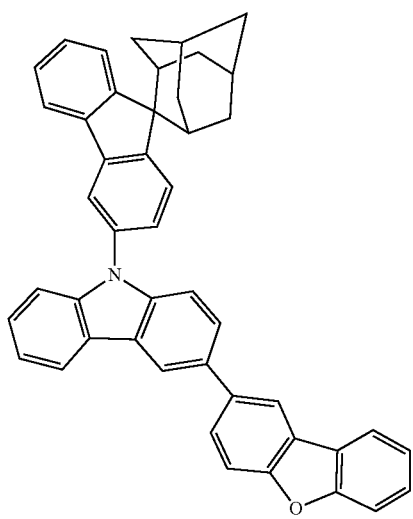
59
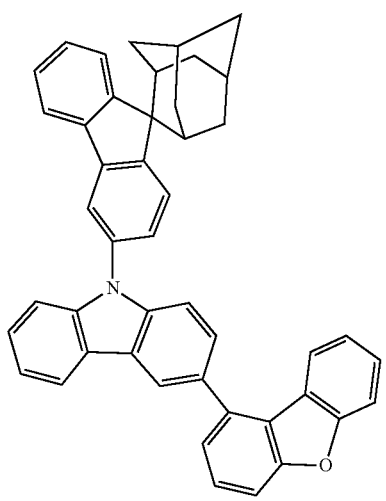
60
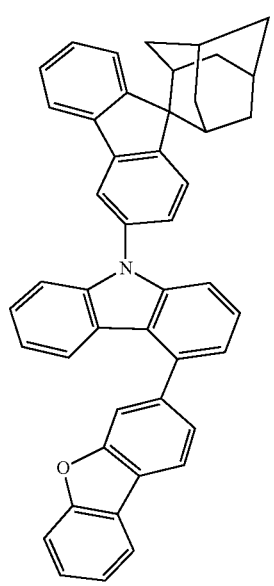
61
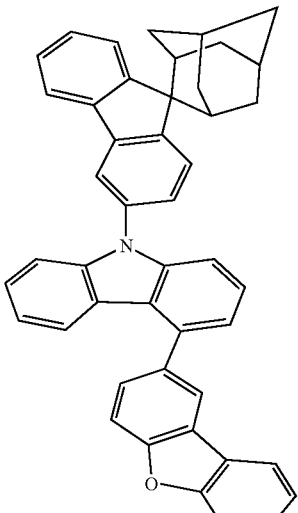
62
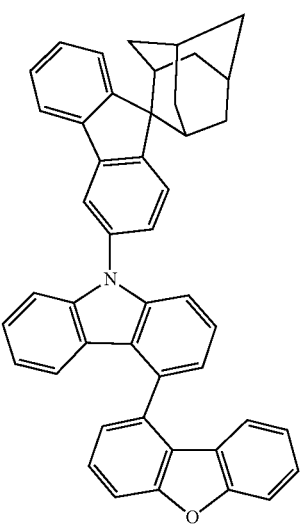
63
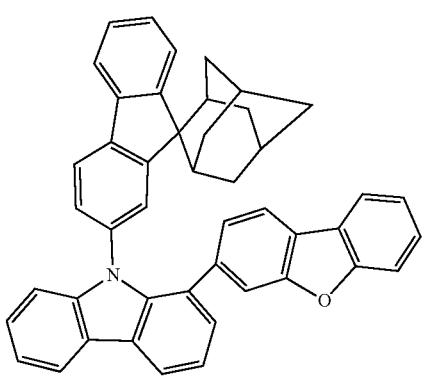

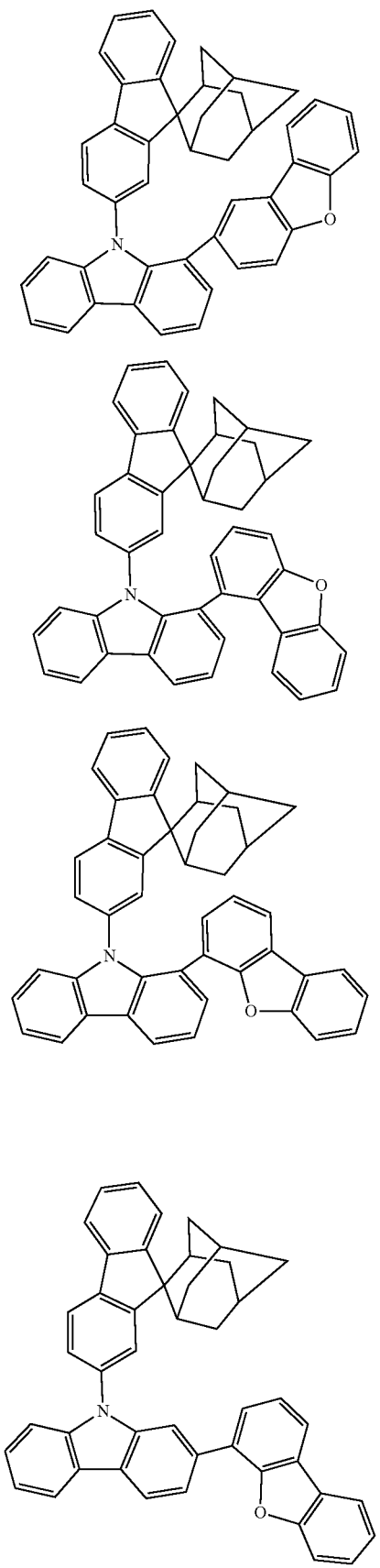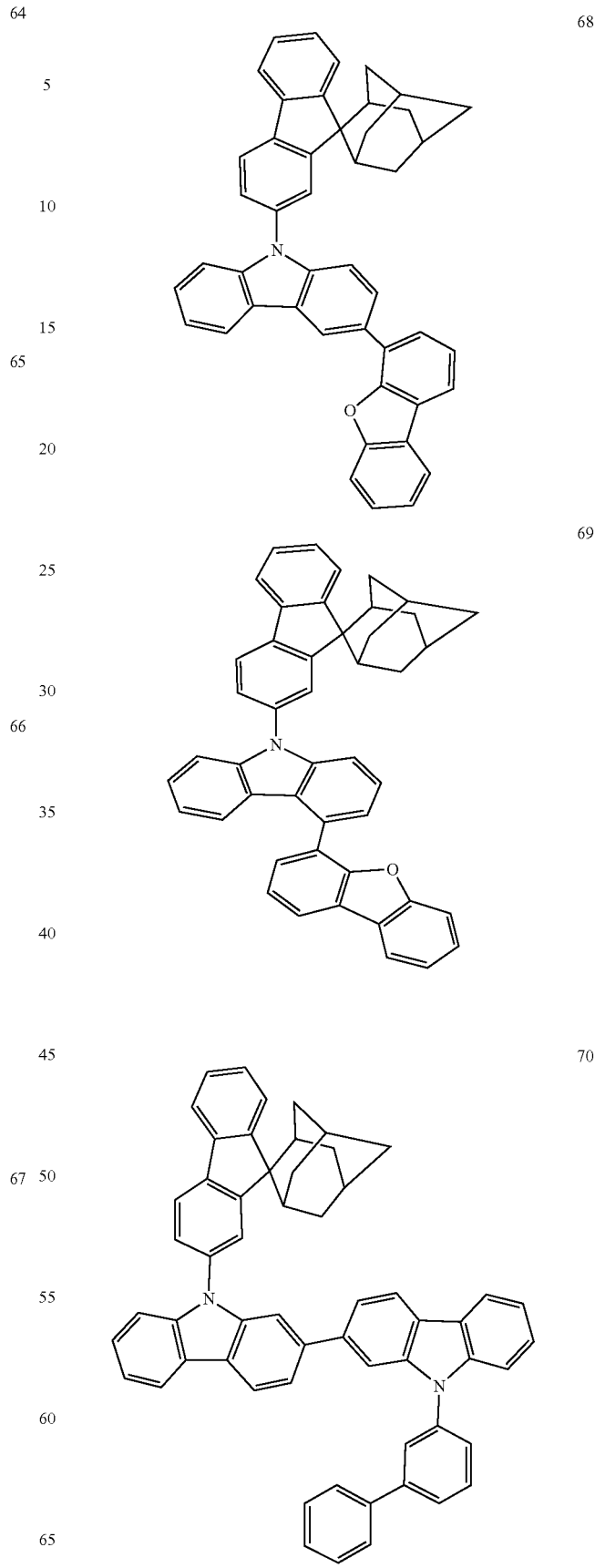

329
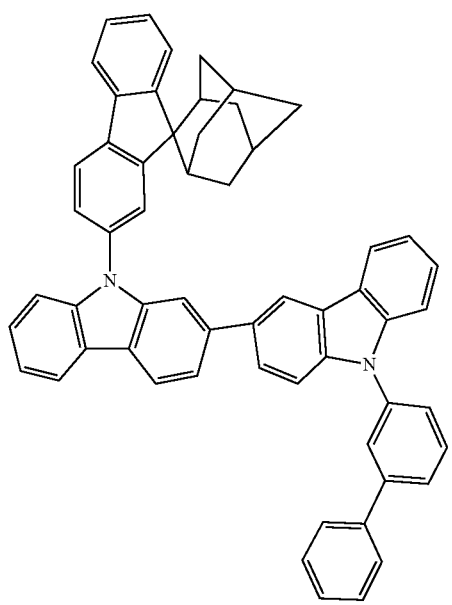
330
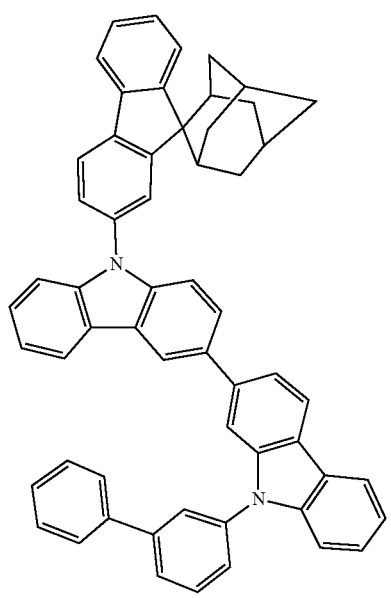
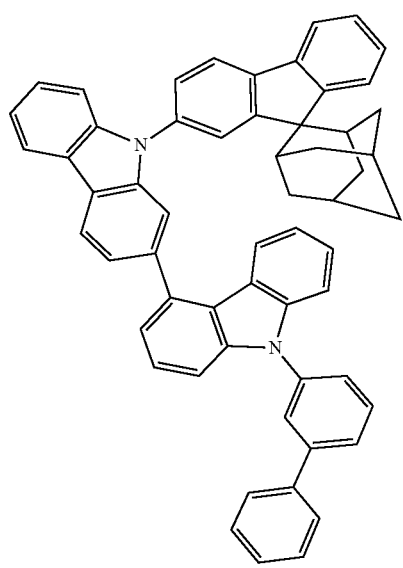
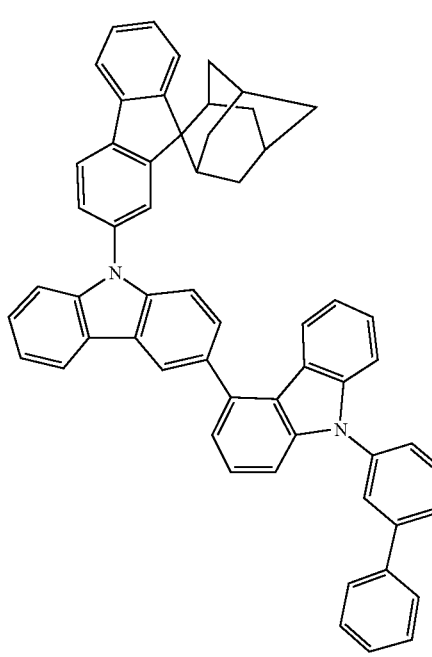

331
-continued
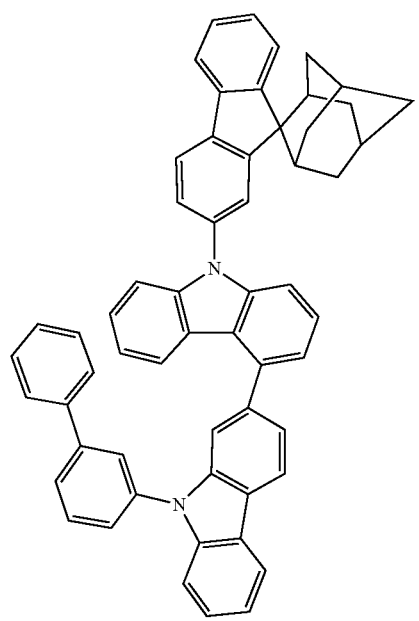
75
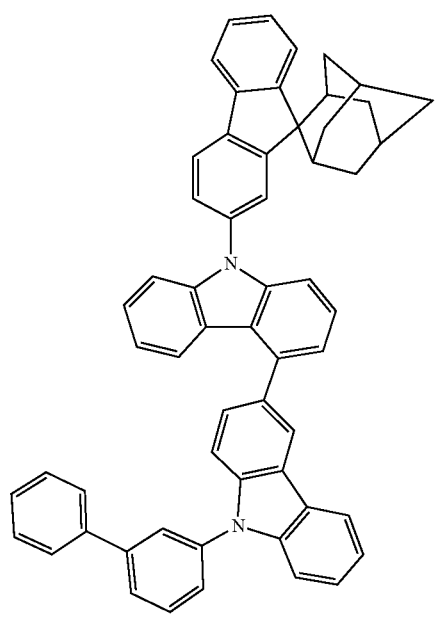
76
332
-continued
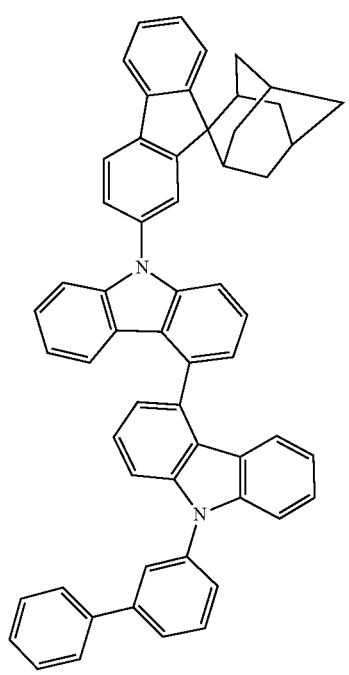
77
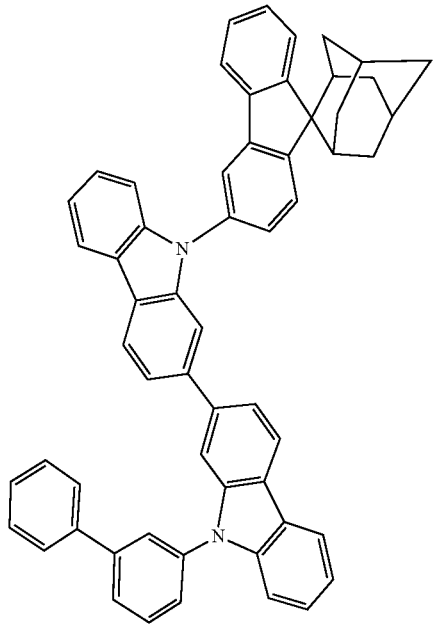
78

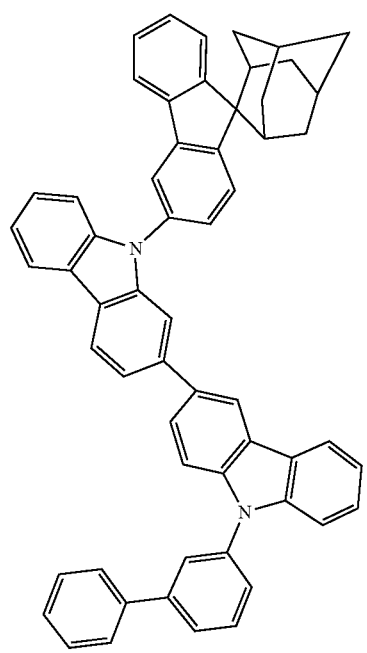
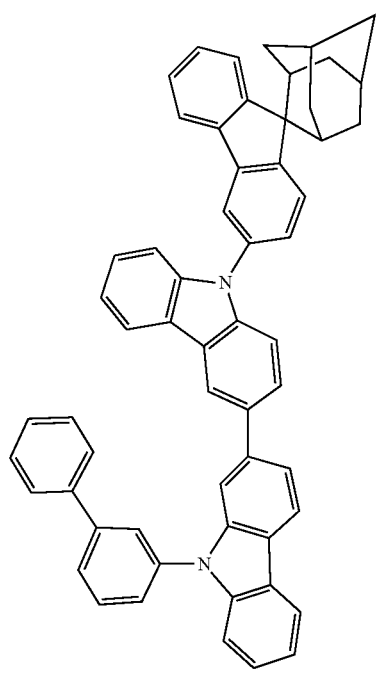
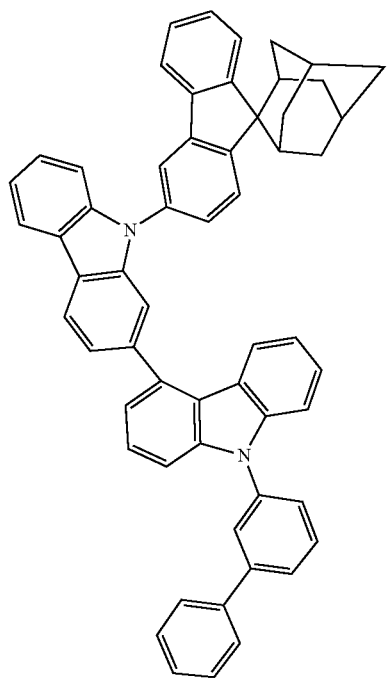
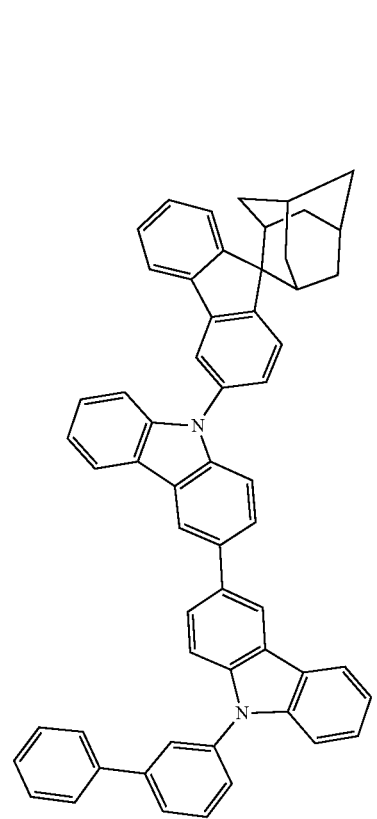

335
-continued
83
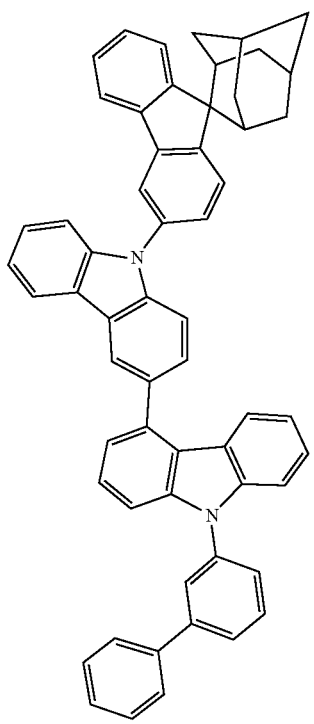
84
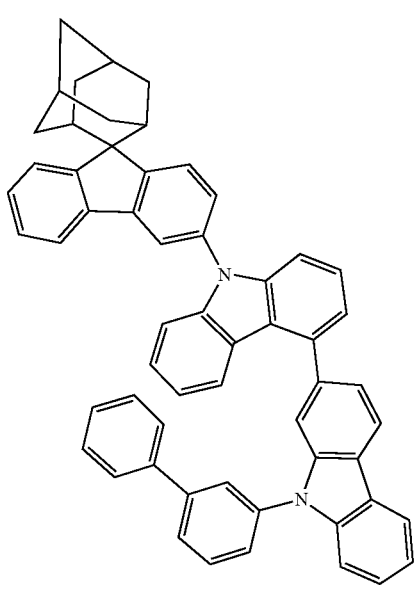
336
-continued
85
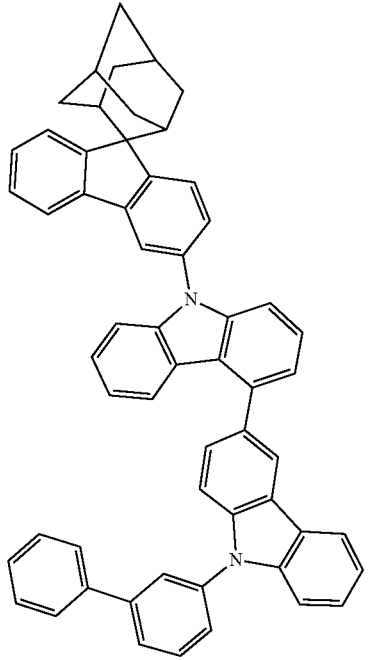
86

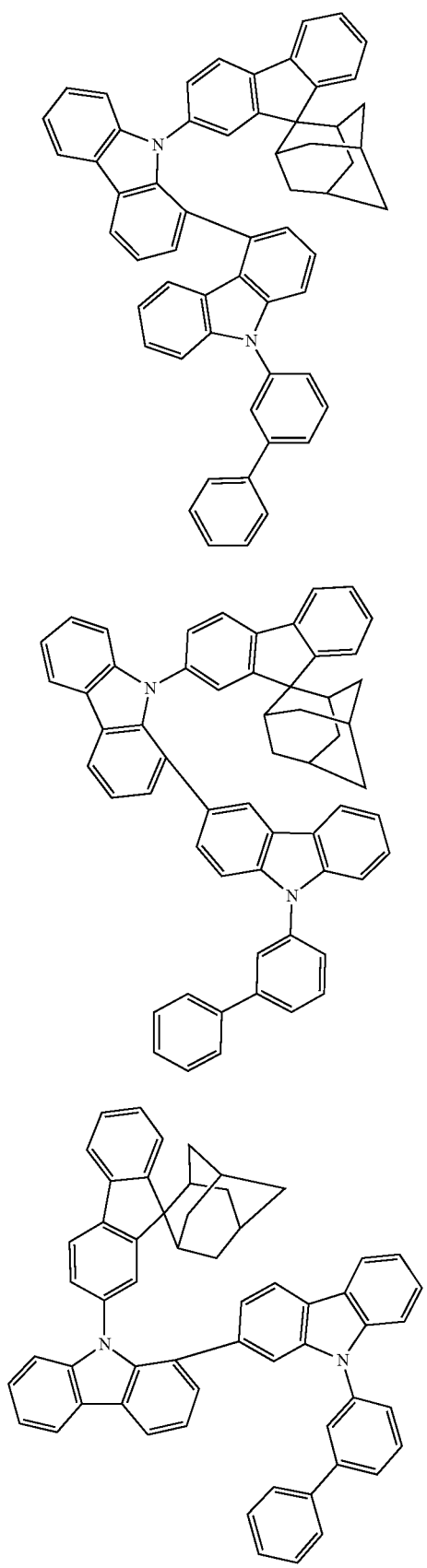
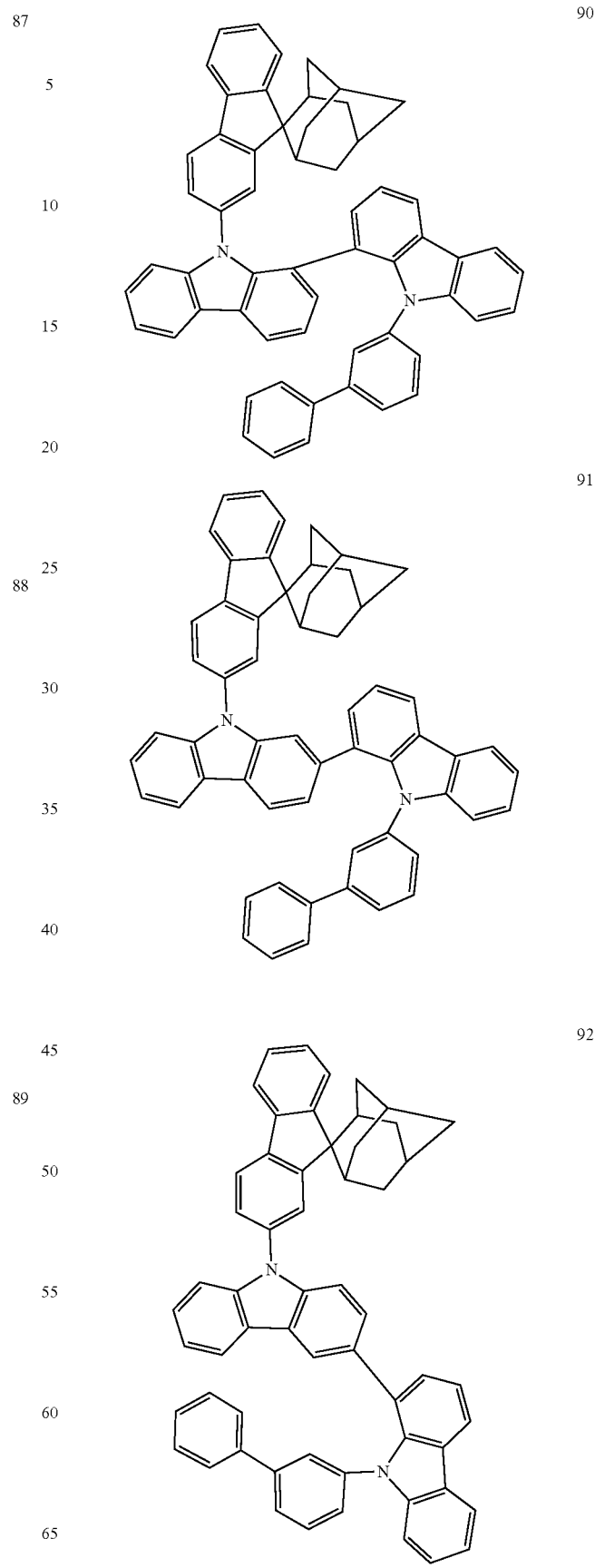

93
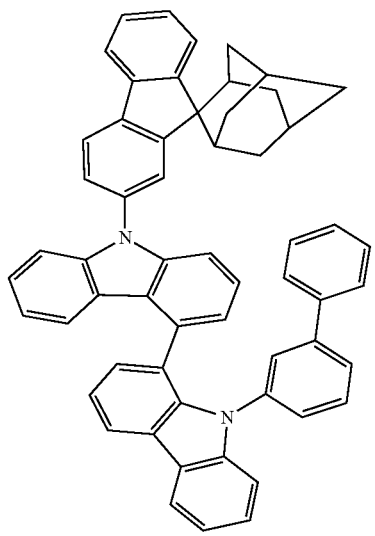
95
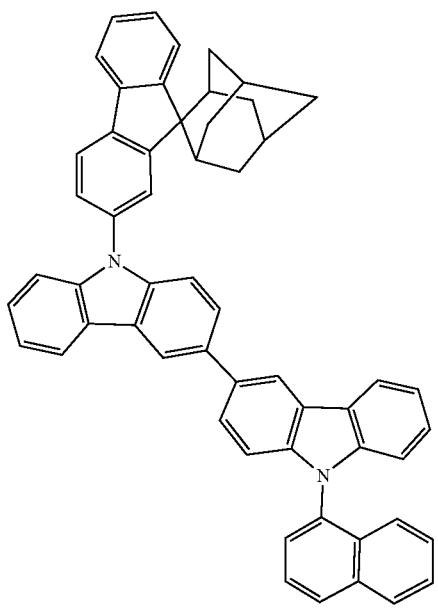
94
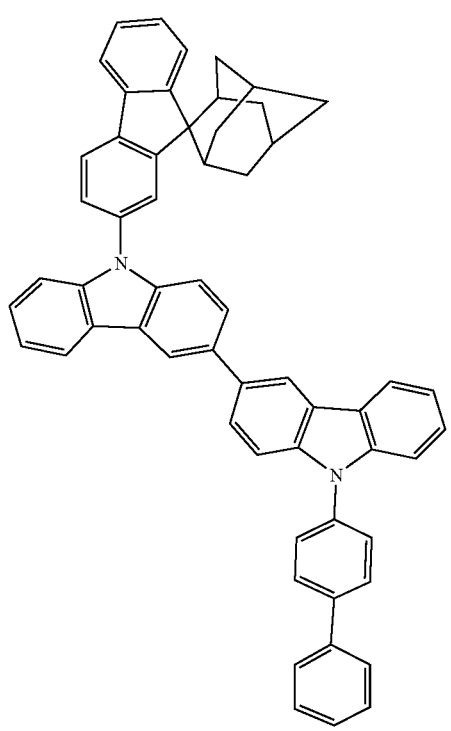
96
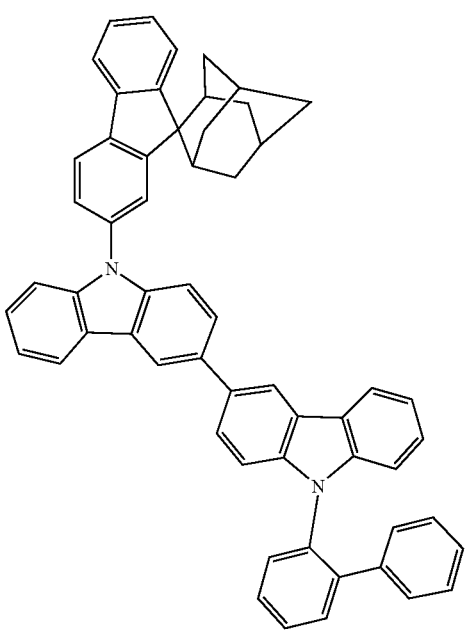

97
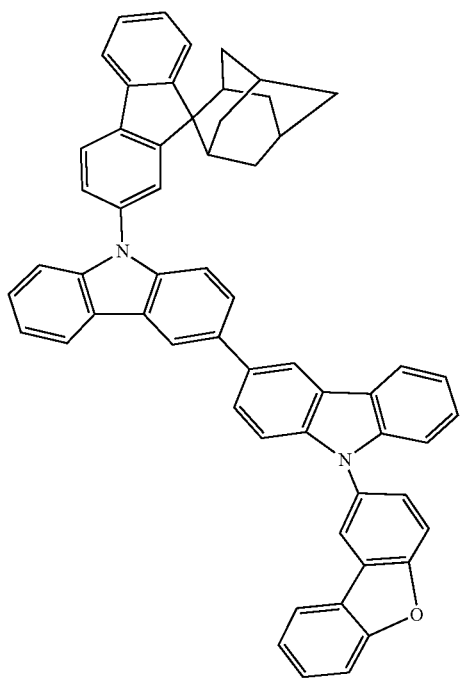
98
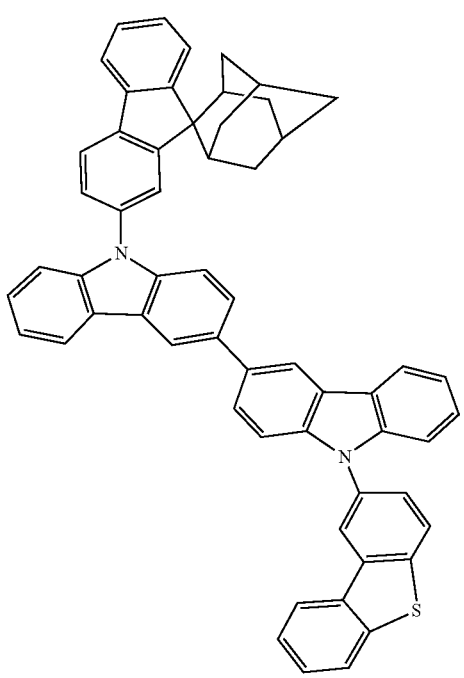
99
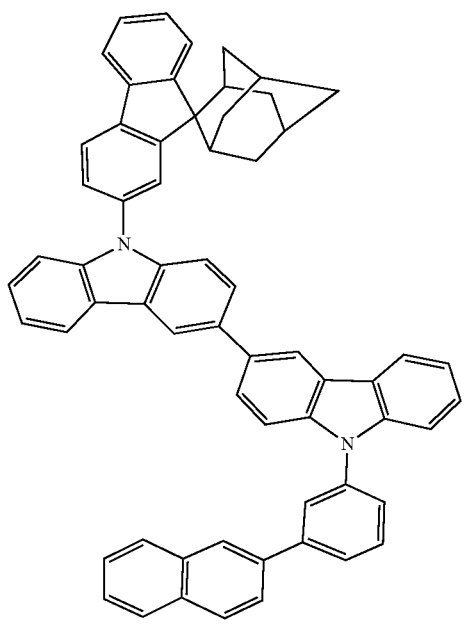
100
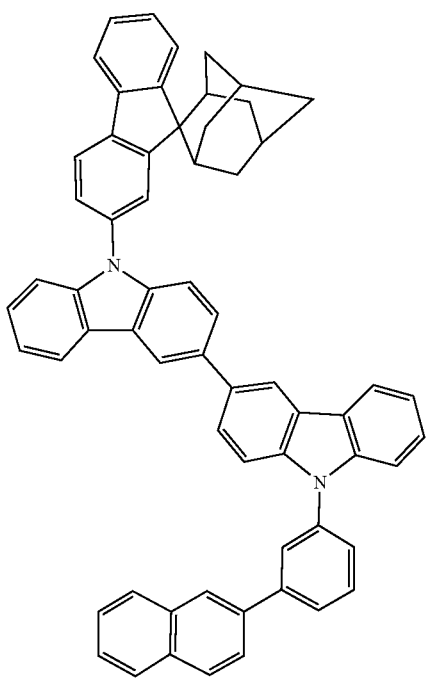

101
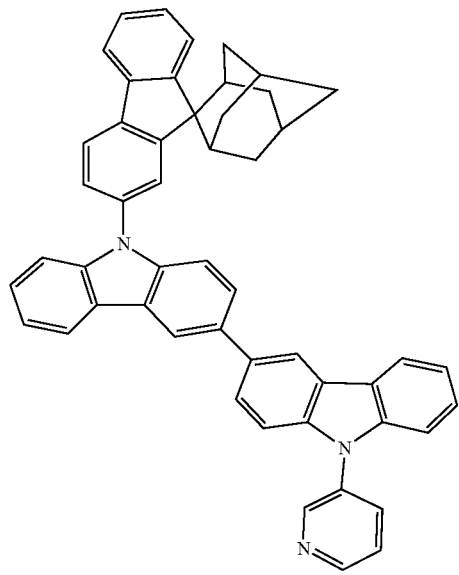
103
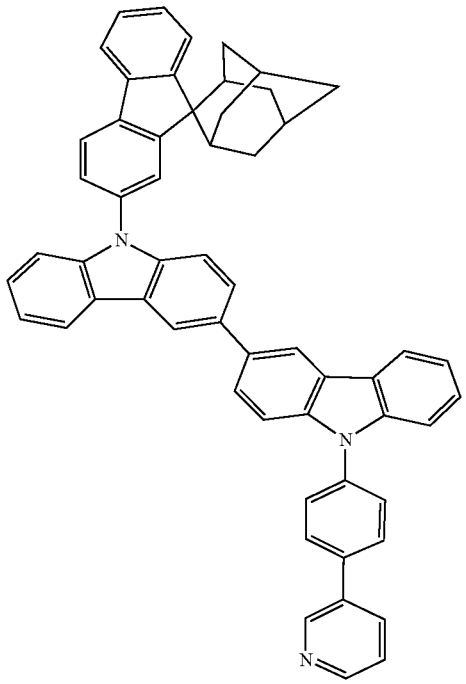
102
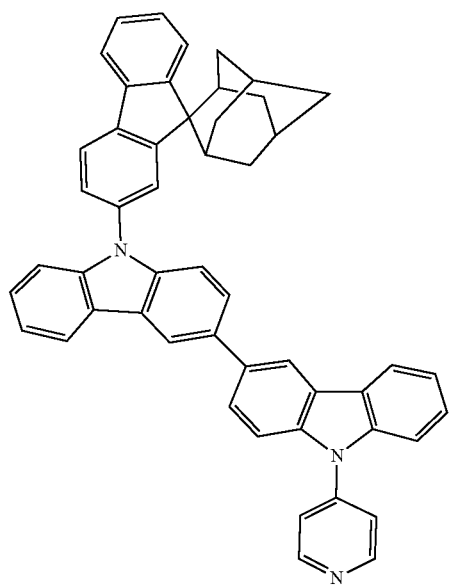
104
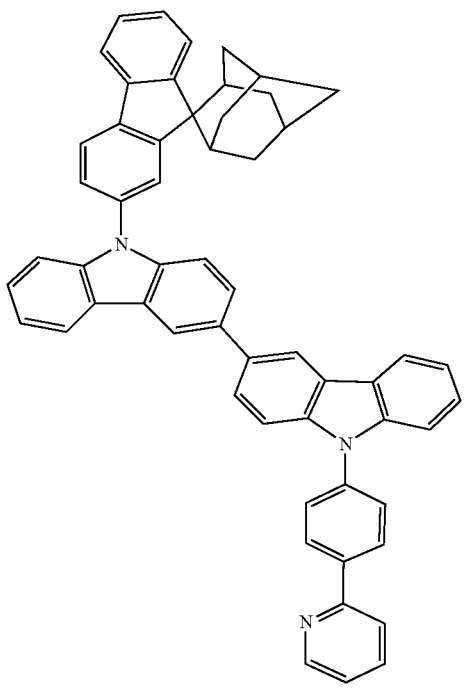

345
-continued
105
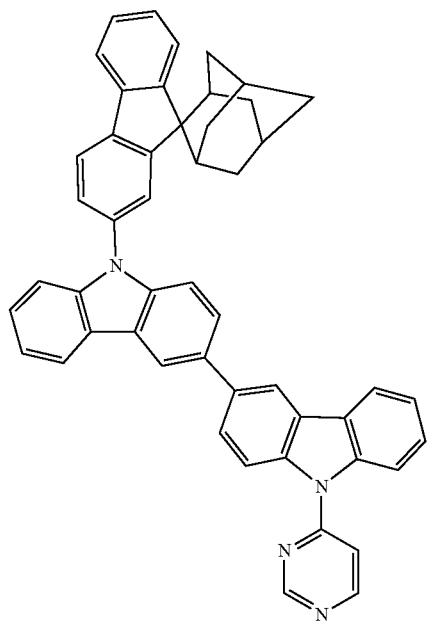
346
-continued
107
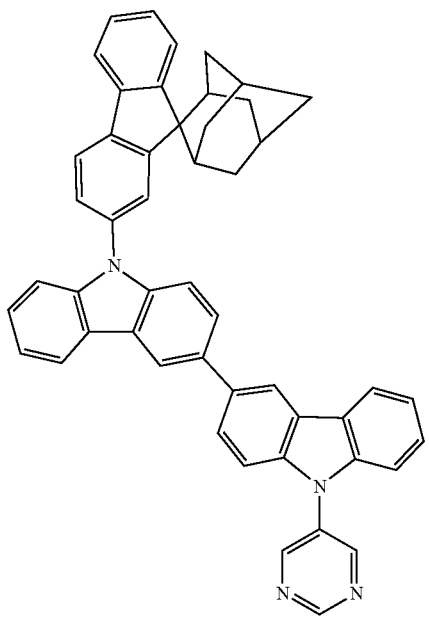
106
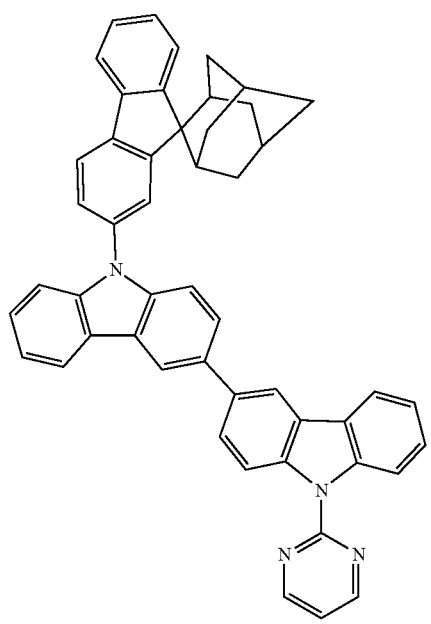
108
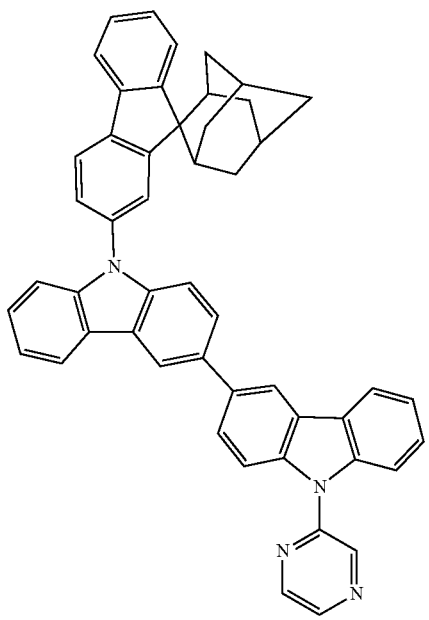

109
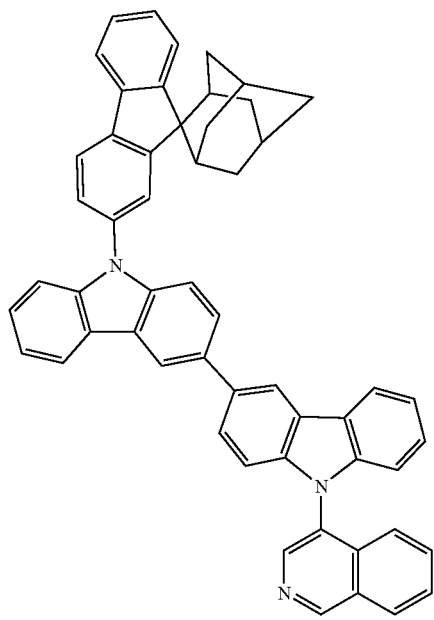
110
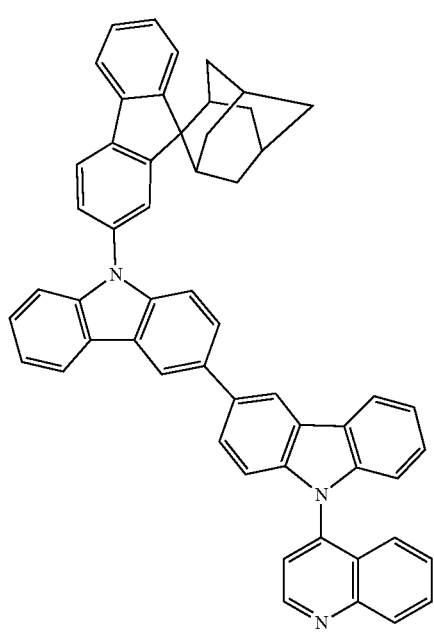
111
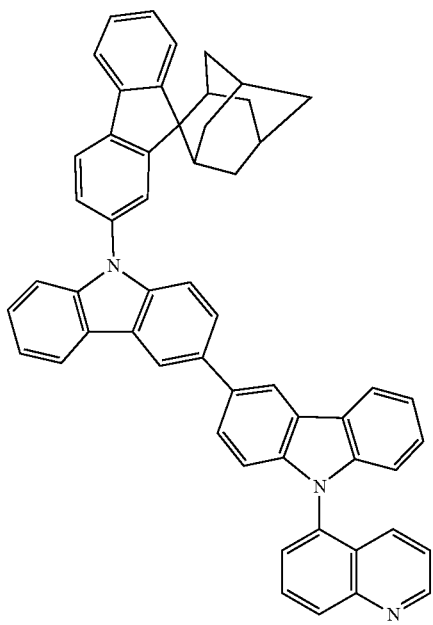
112
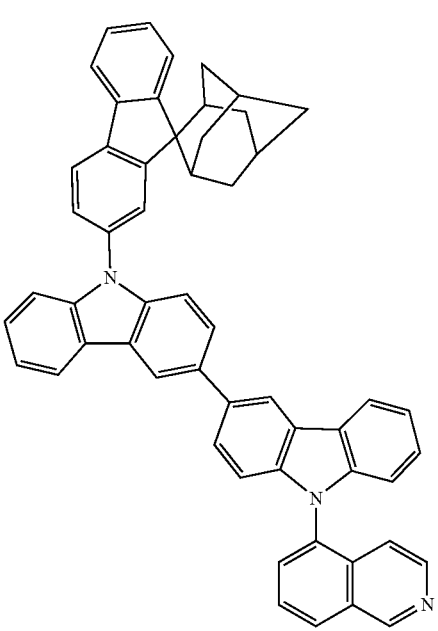

113
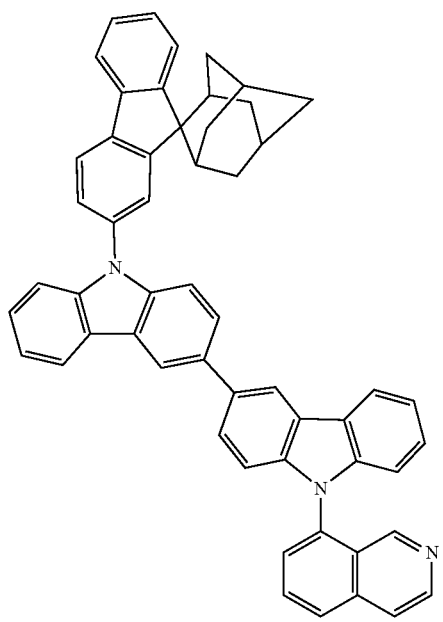
115
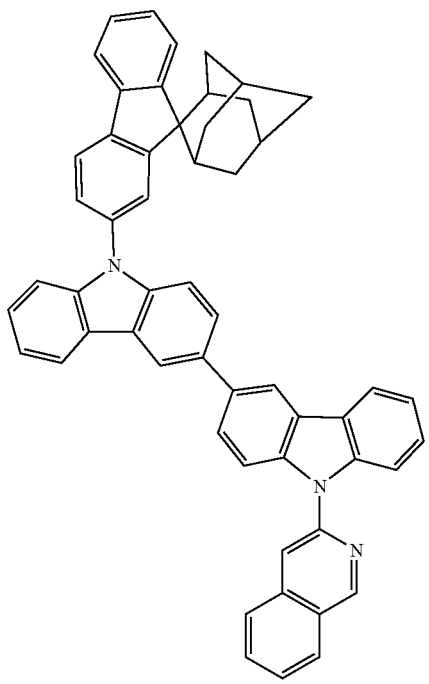
114
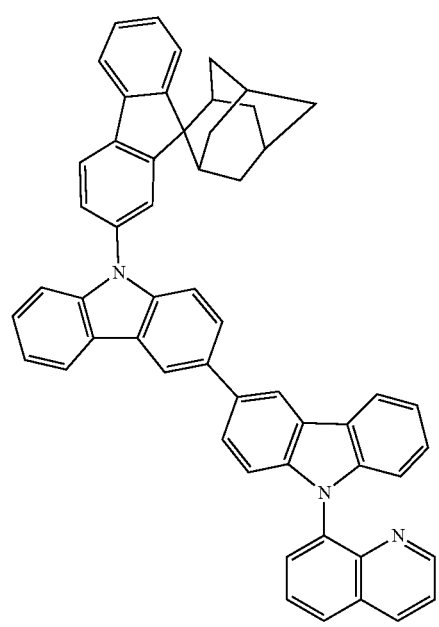
116
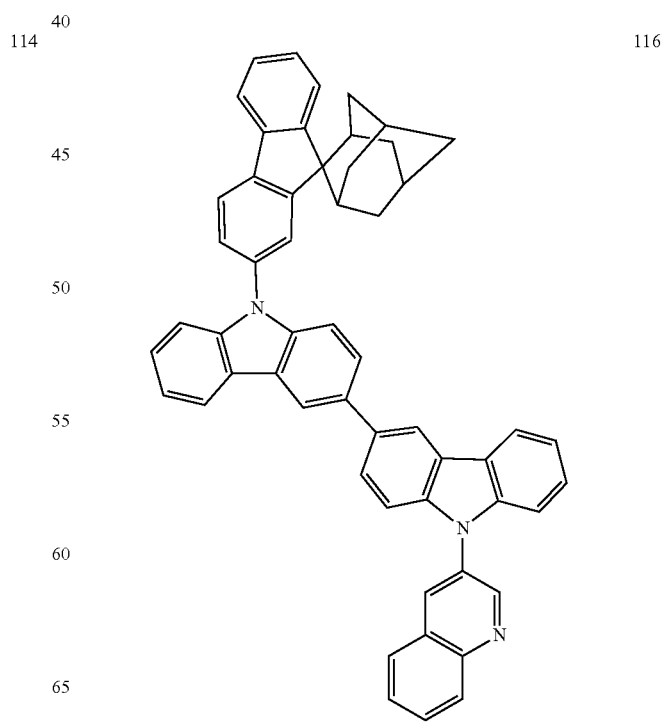

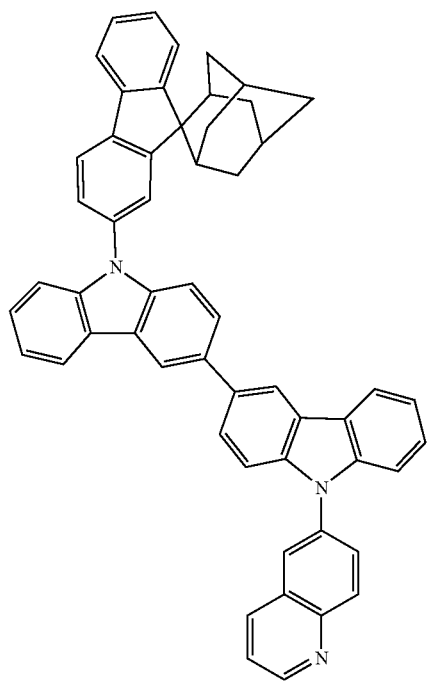
117
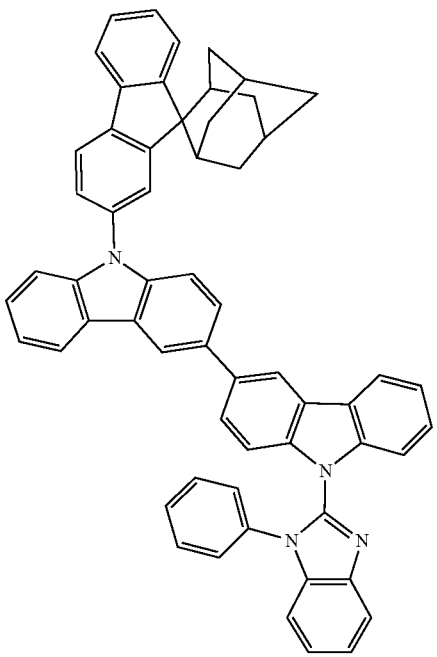
119
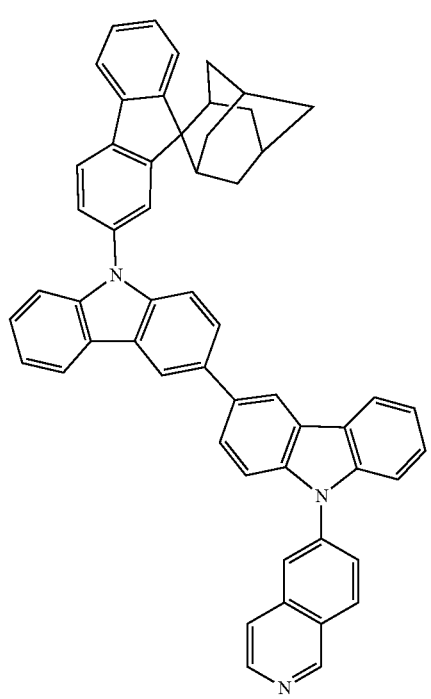
118
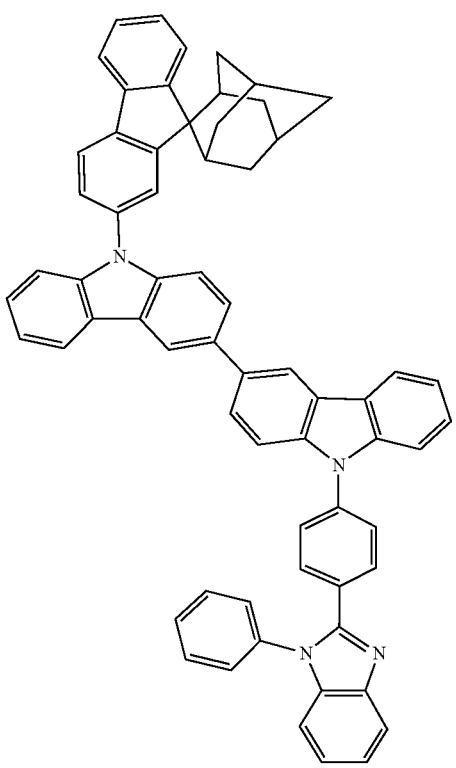
120

353
-continued
121
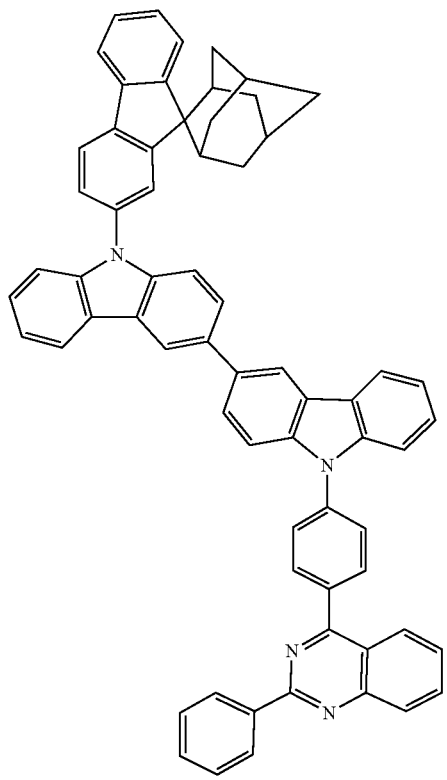
122
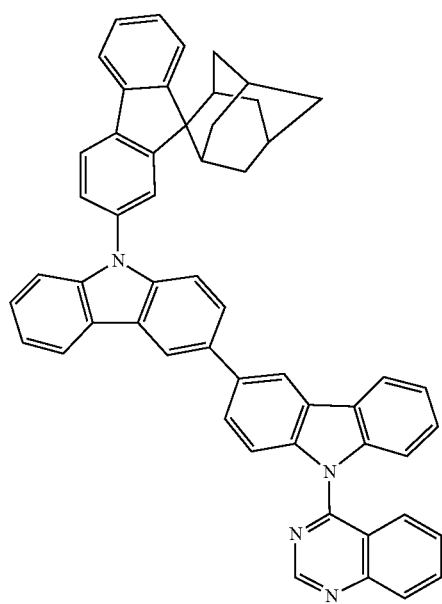
354
-continued
123
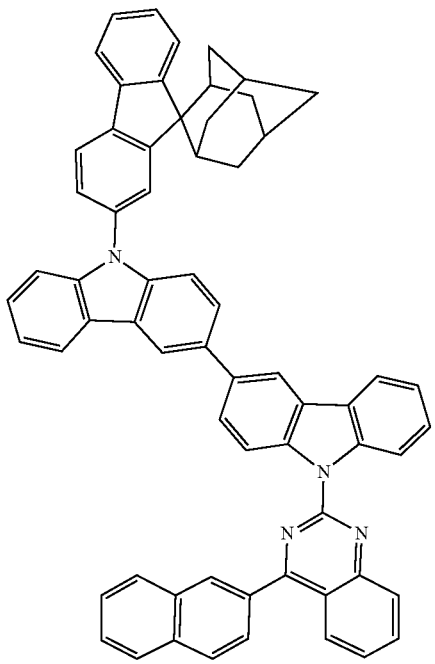
124
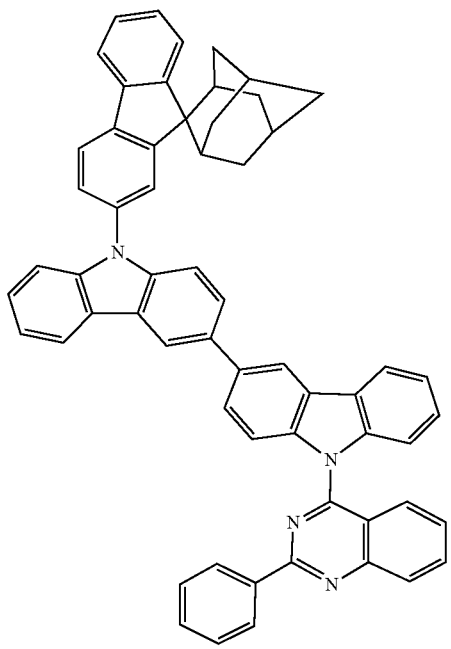

355
-continued
125
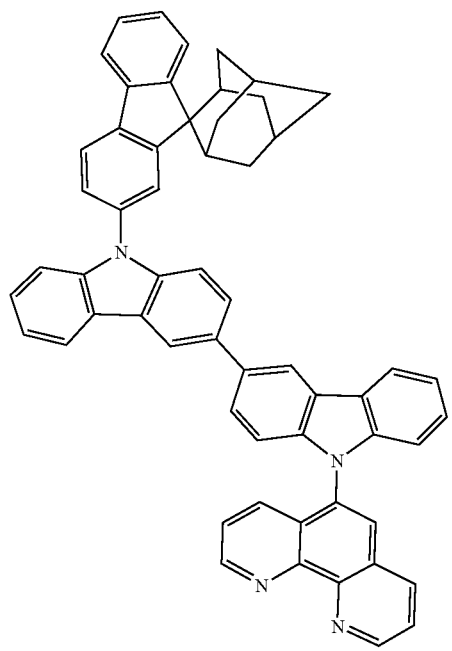
126
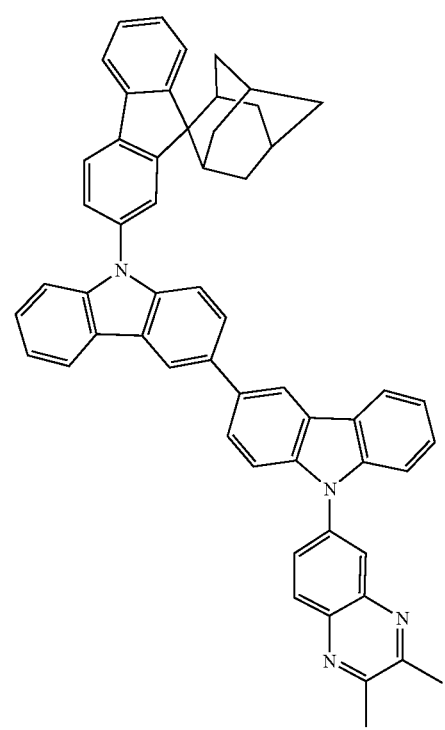
356
-continued
127
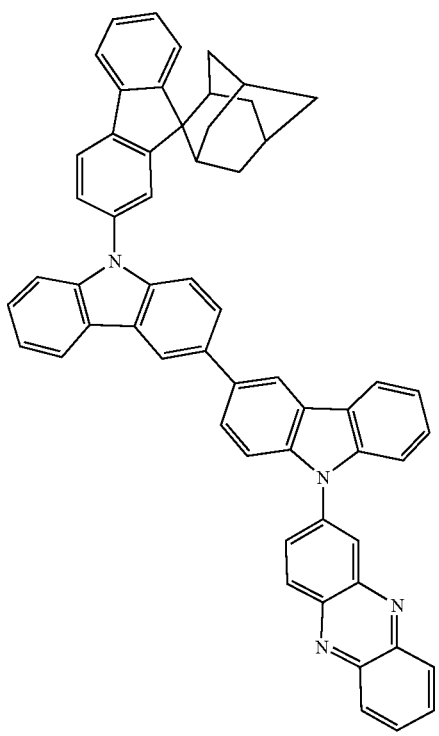
128
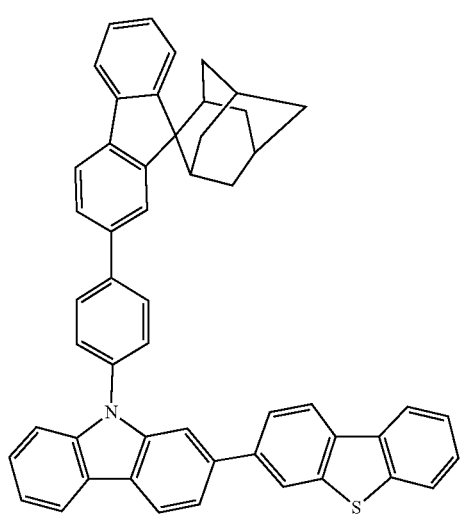

129
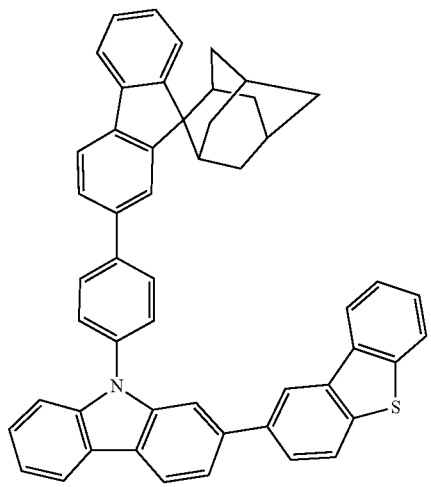
130
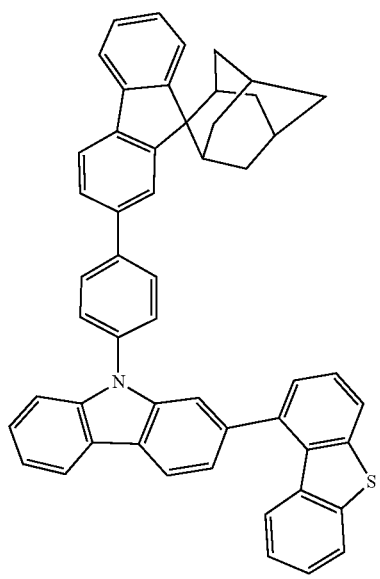
131
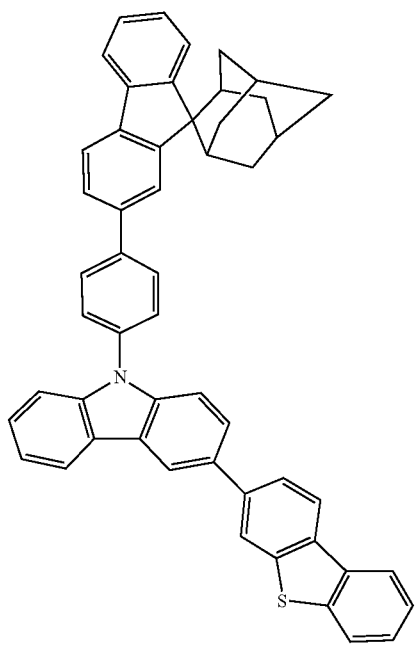
132
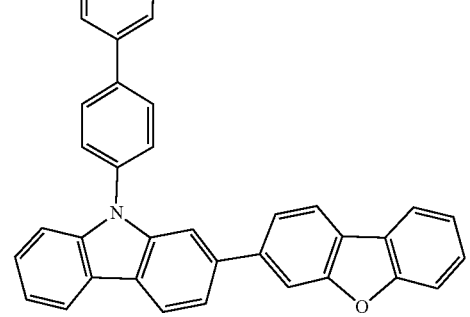
133
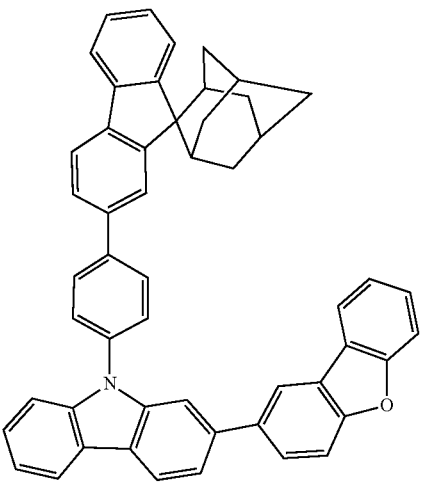

134
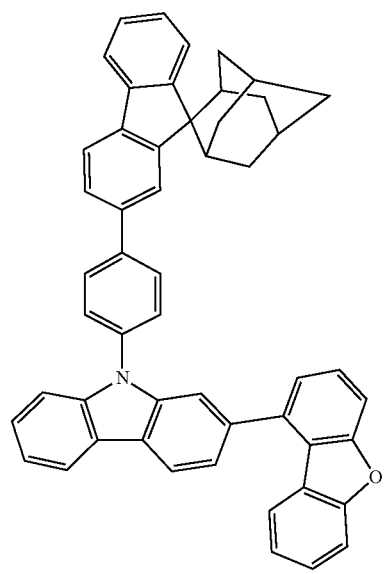
135
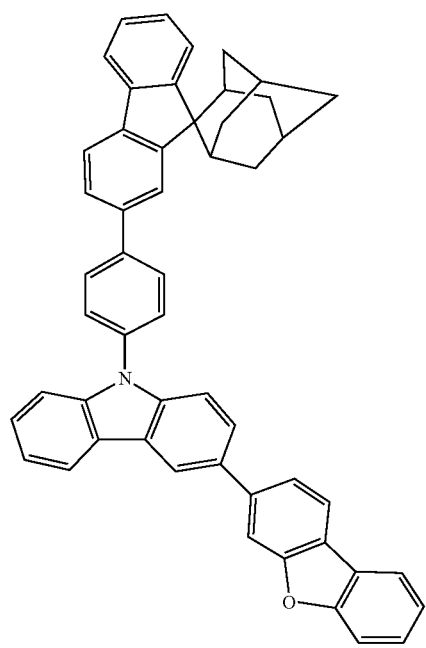
136
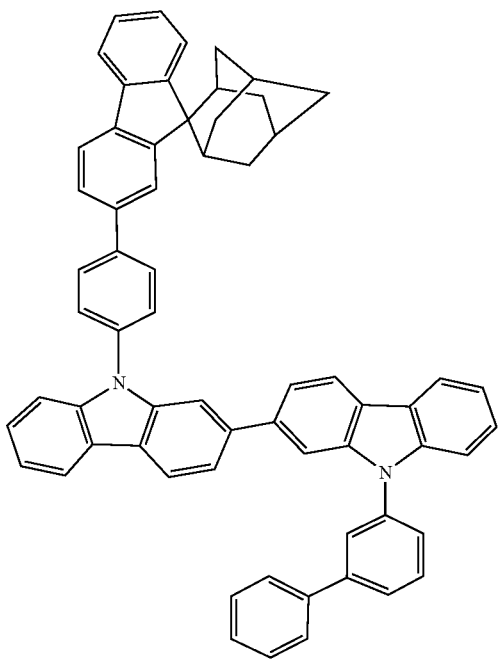
137
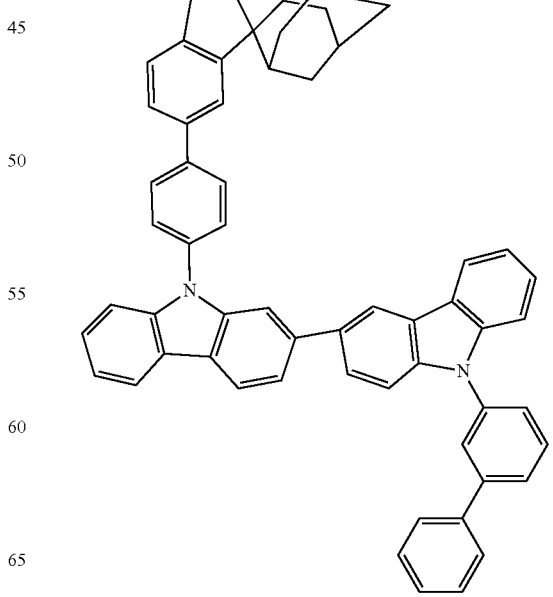

138
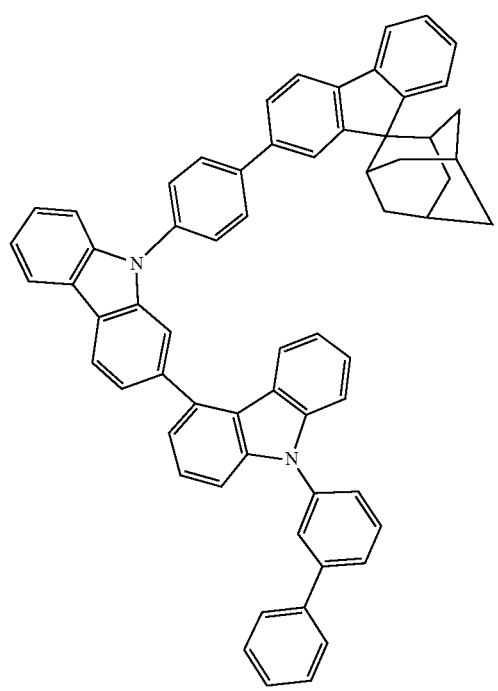
139
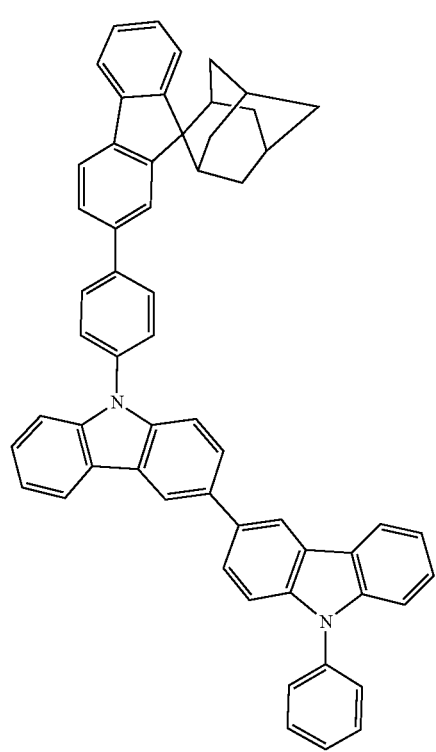
140
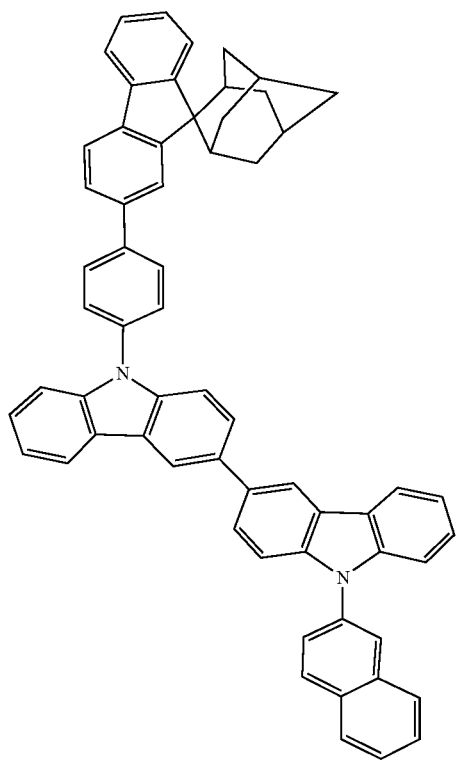
141
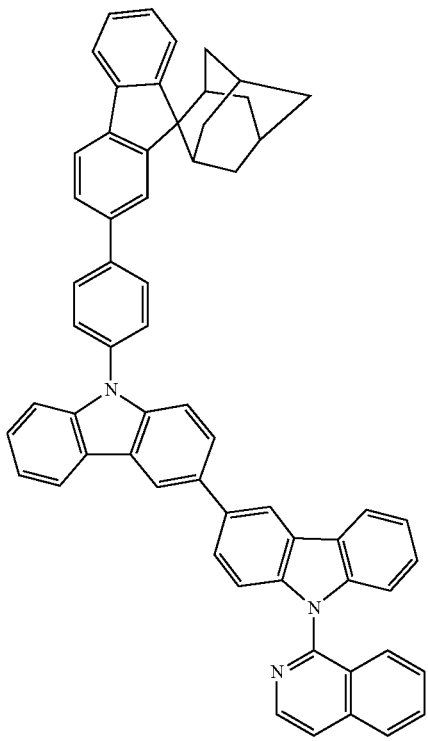

363
-continued
364
-continued
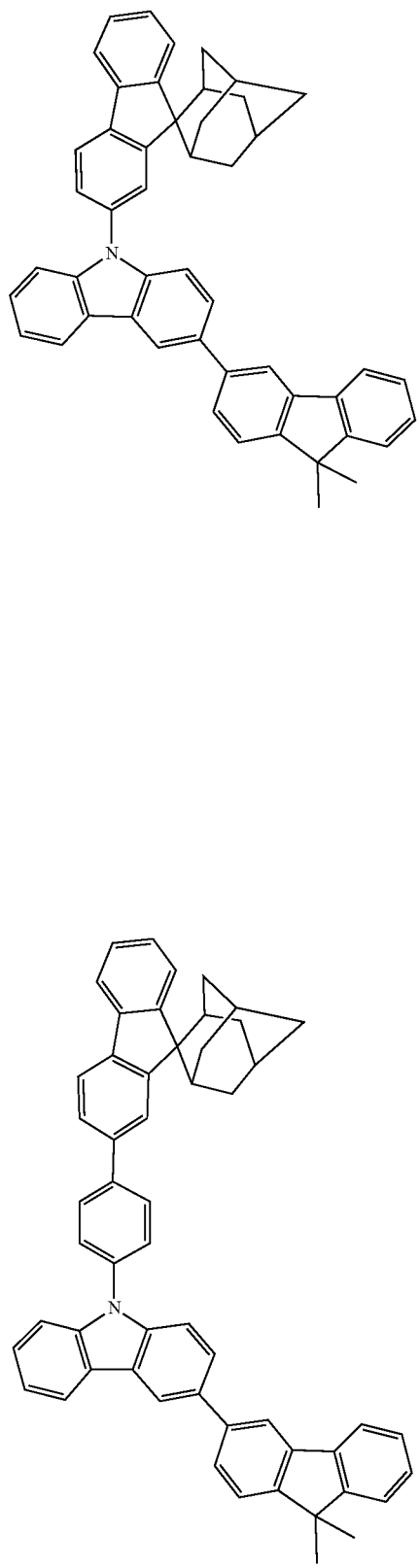
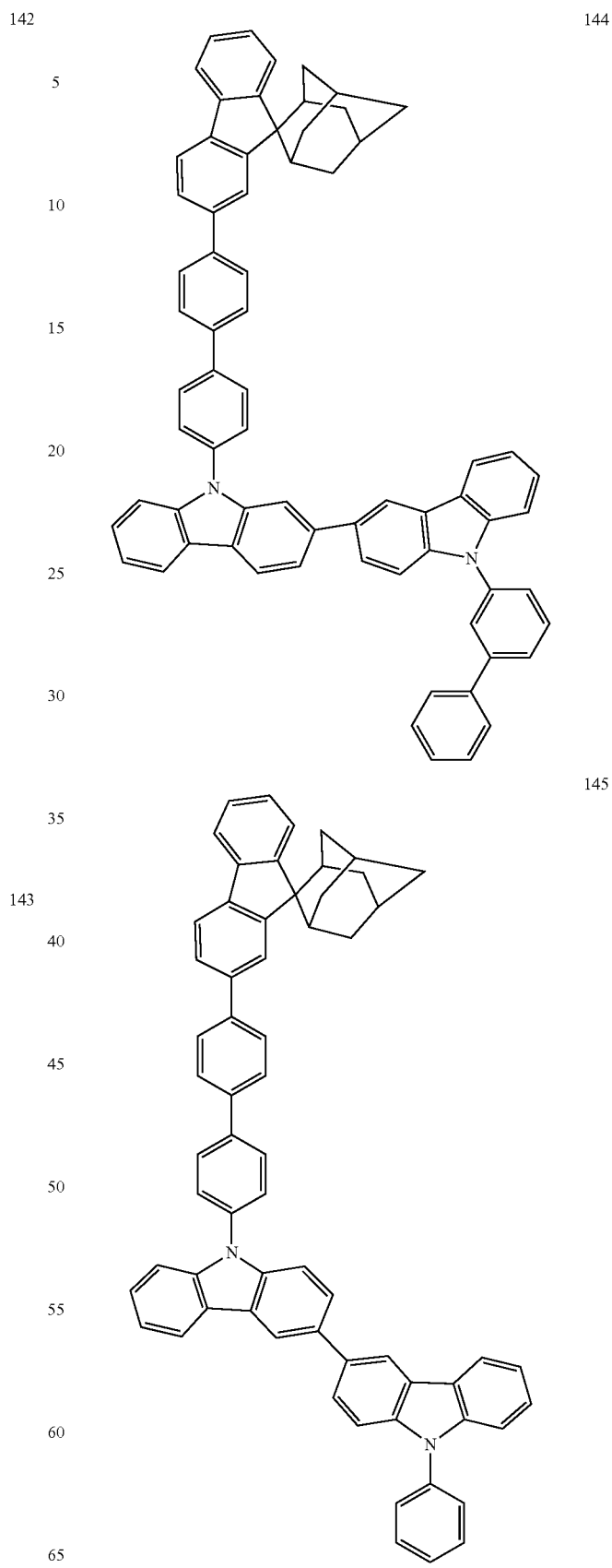

365
-continued
146
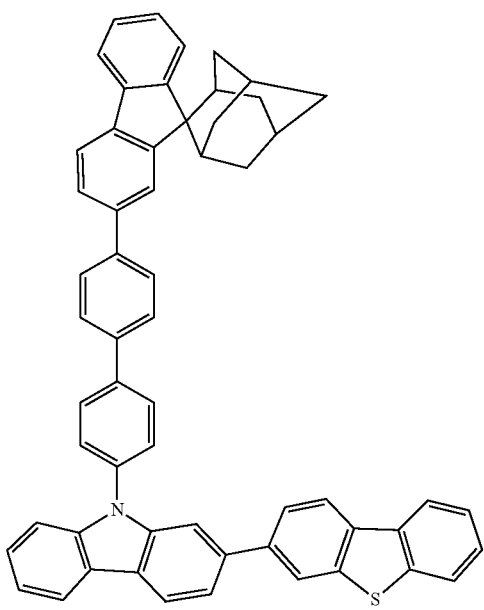
147
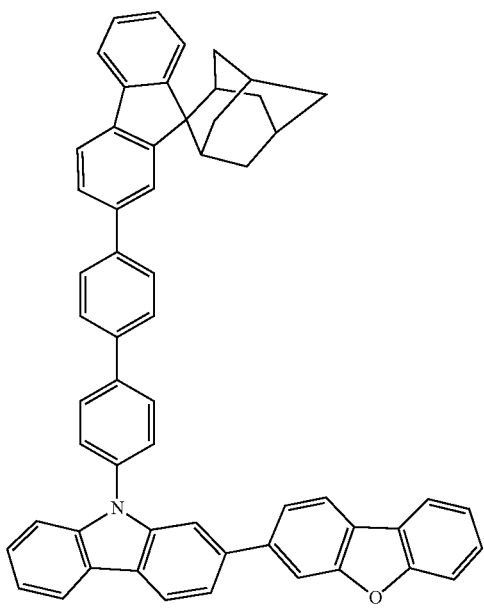
366
-continued
148
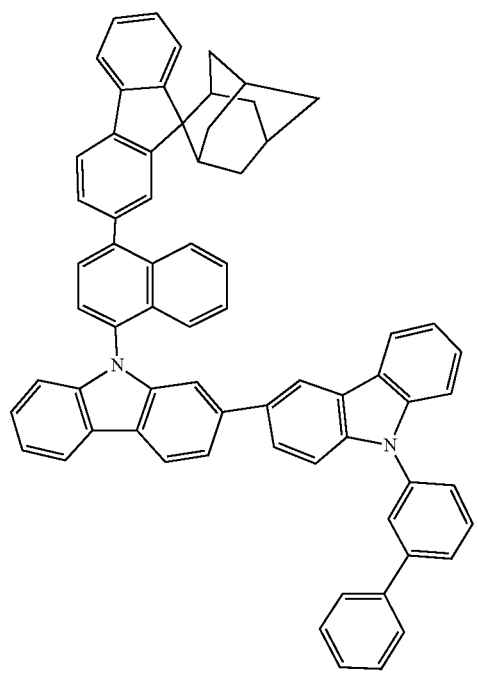
149
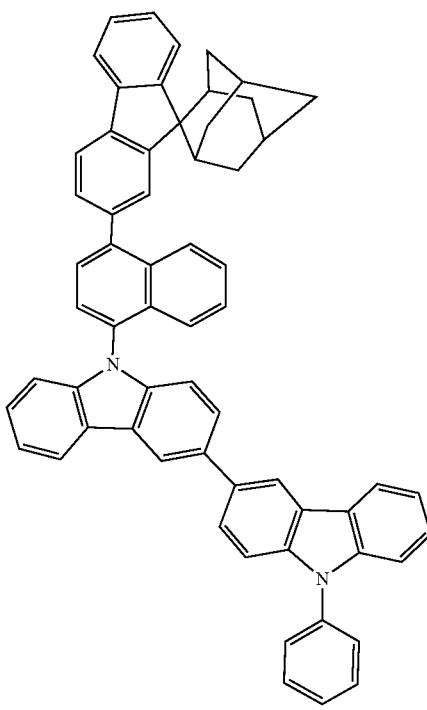

150
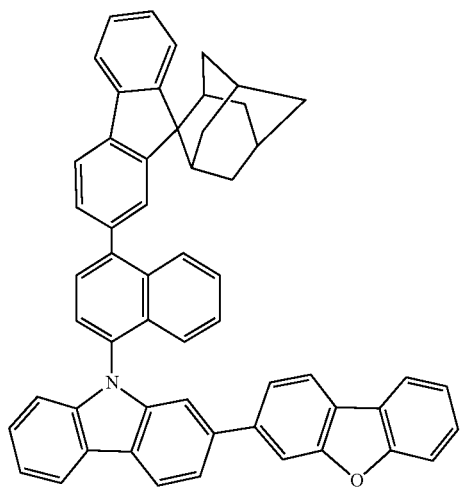
151
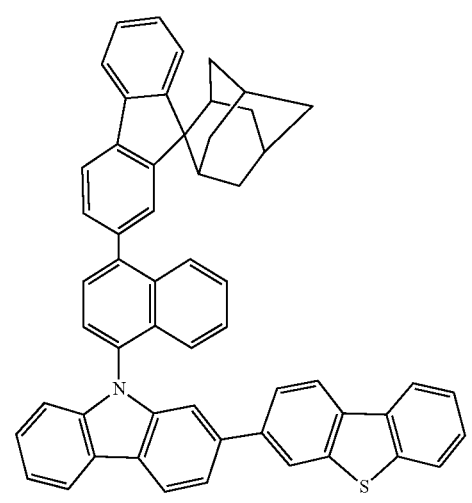
152
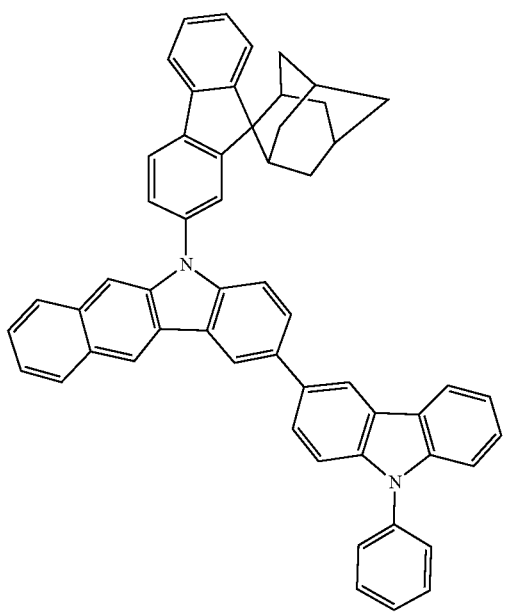
153
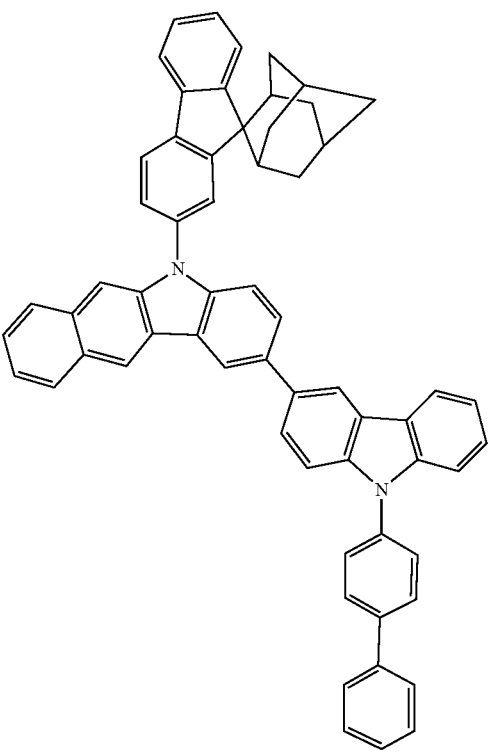
154
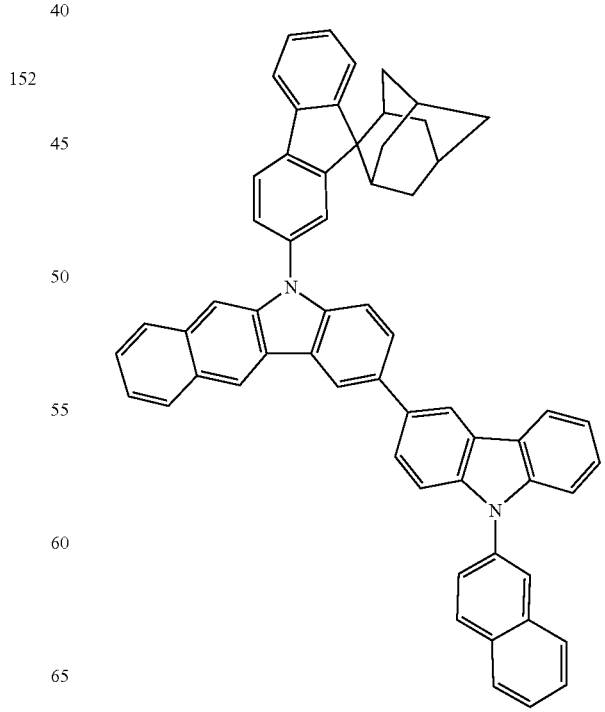

155
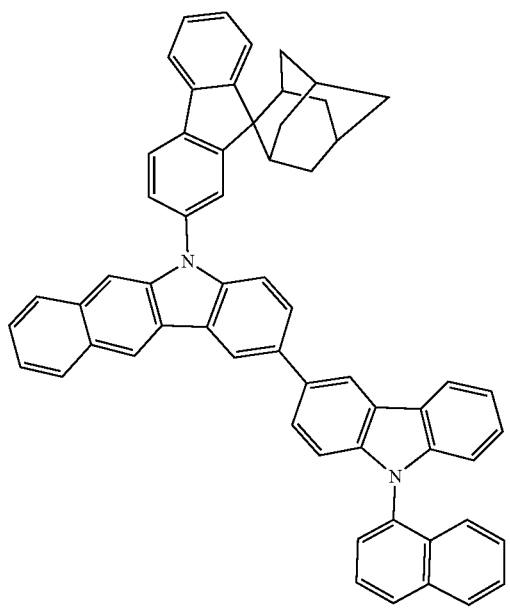
156
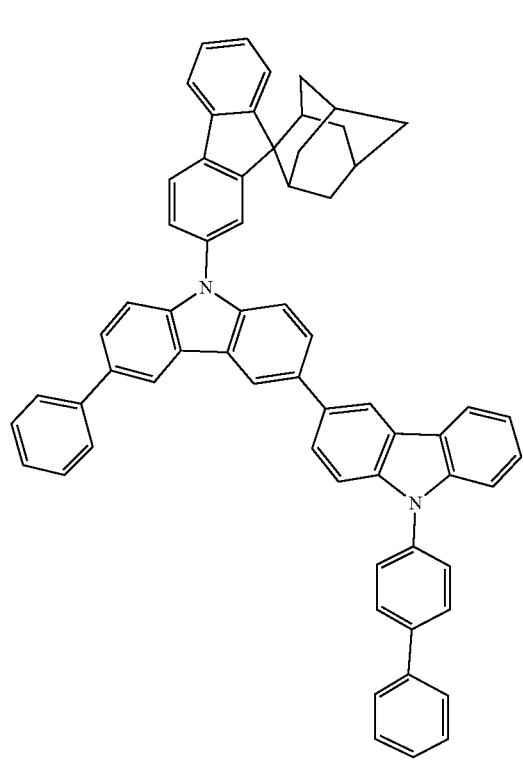
157
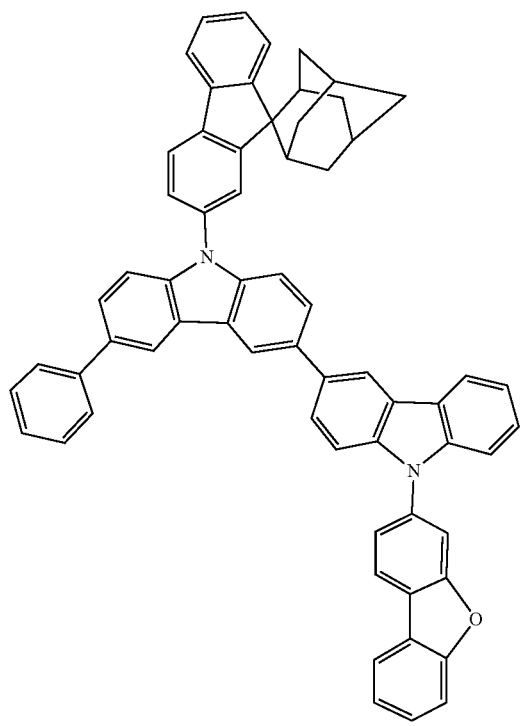
158
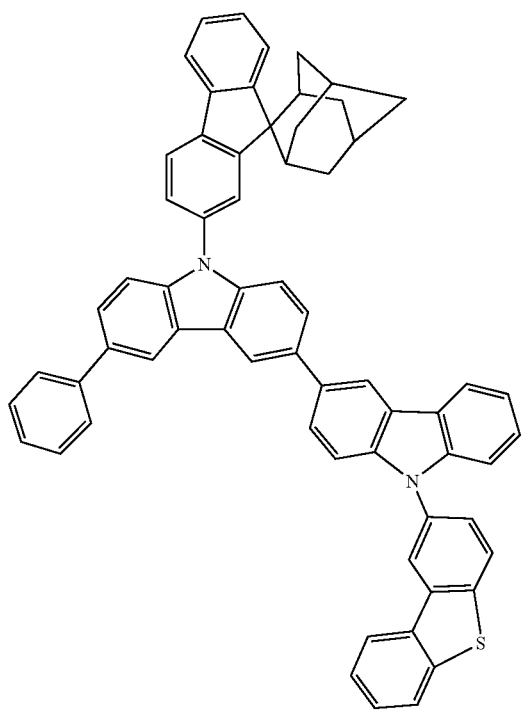

371
-continued
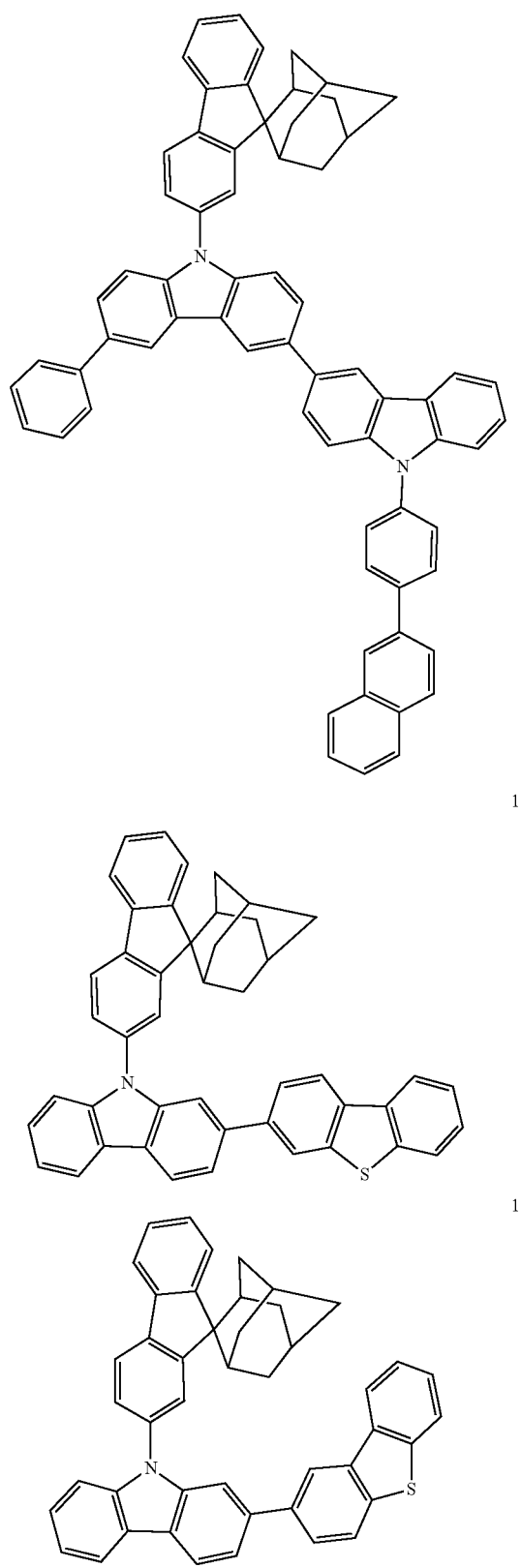
372
-continued
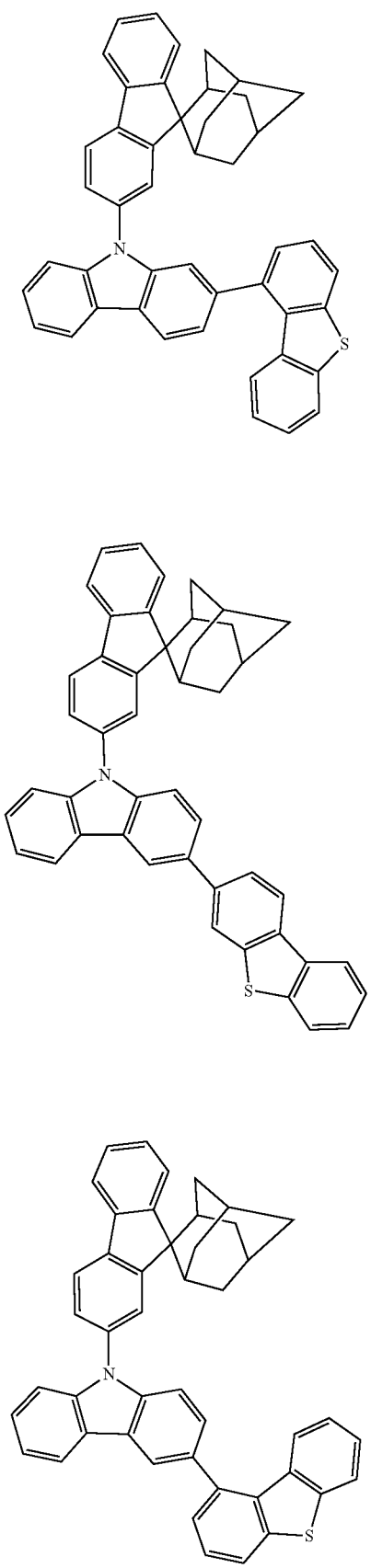

167
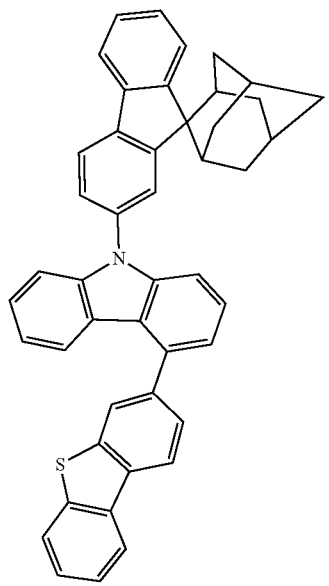
168
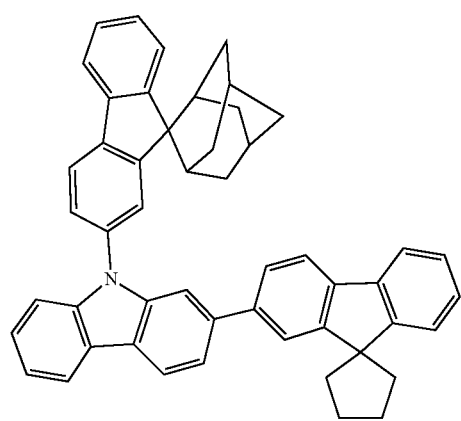
169
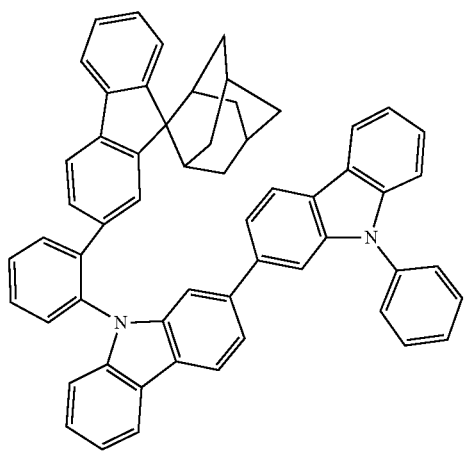
170
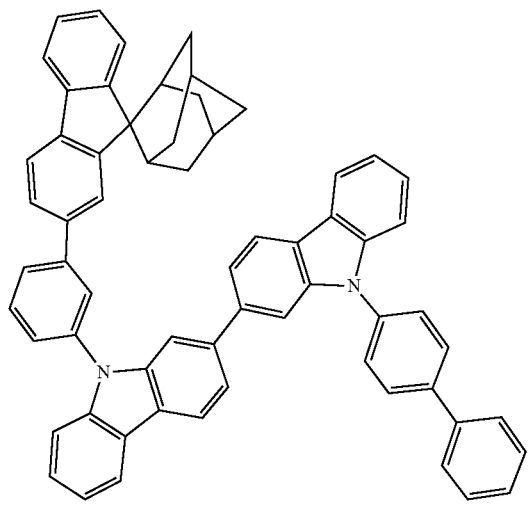
171
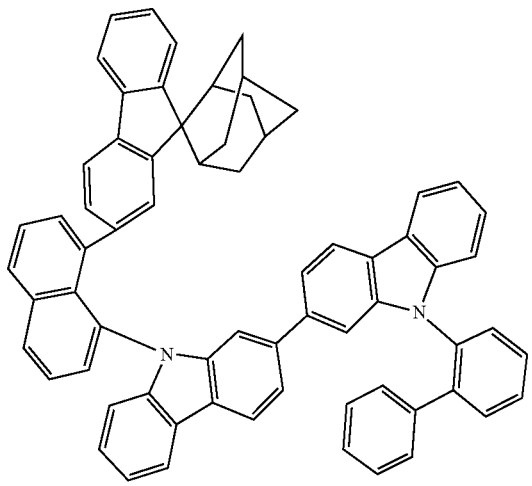

172
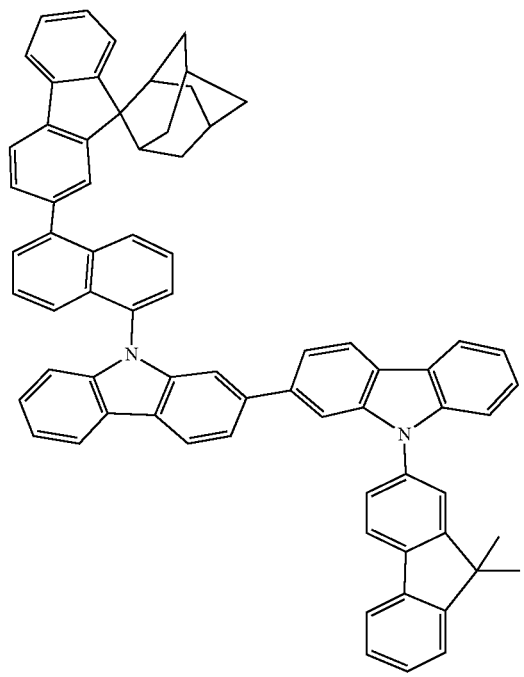
174
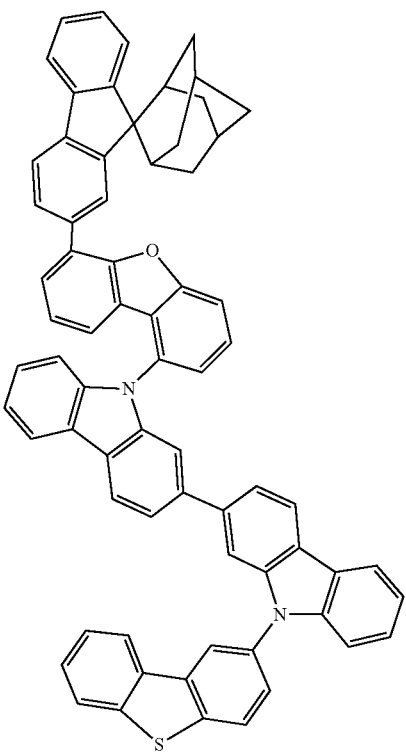
173
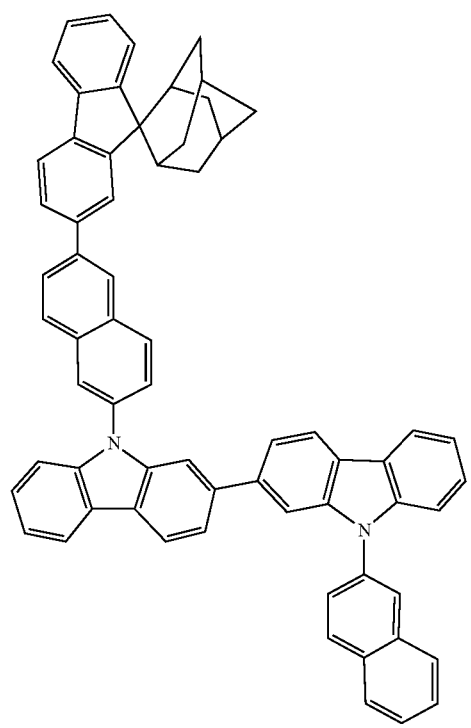
175
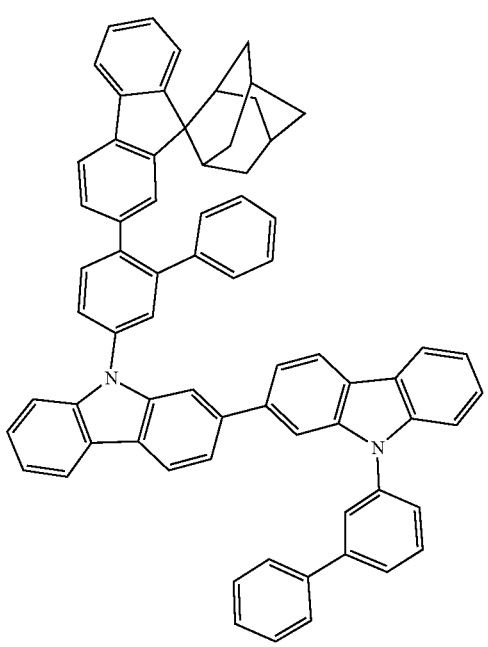

377
-continued
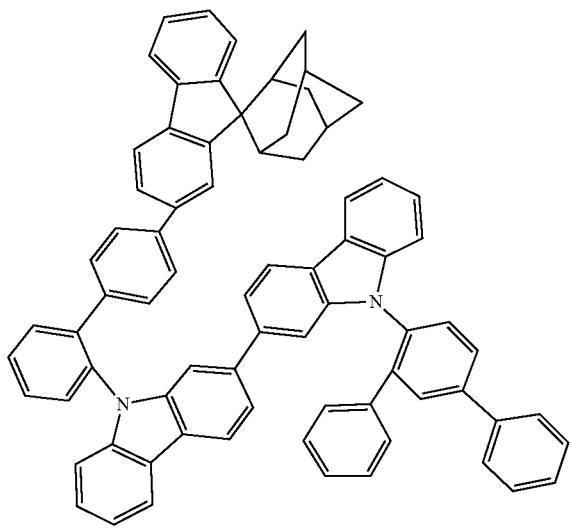
176
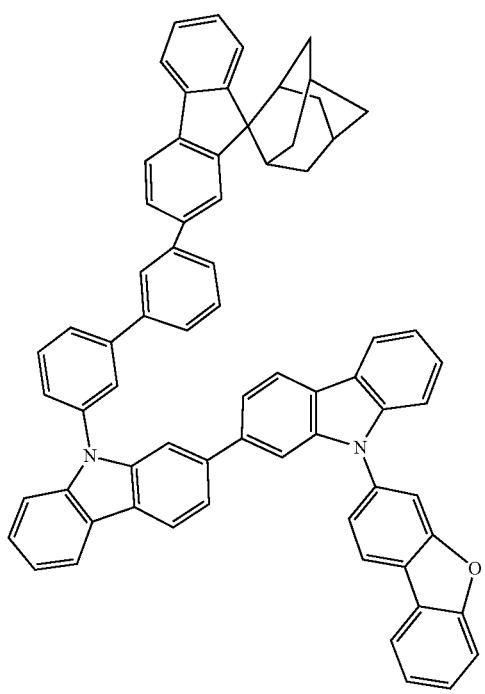
177
378
-continued
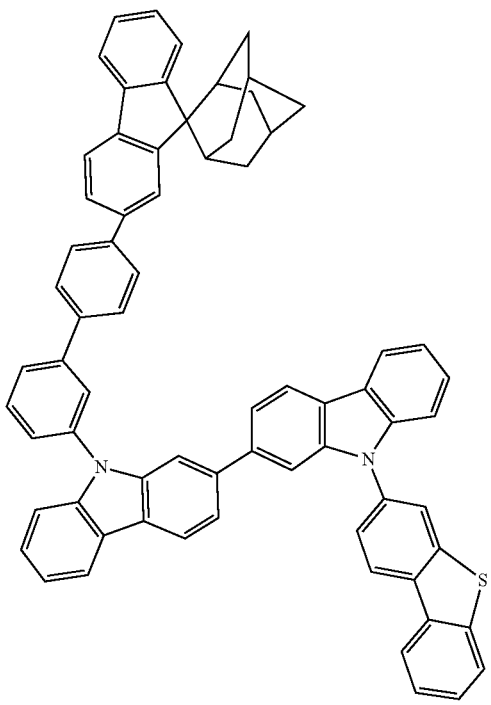
178
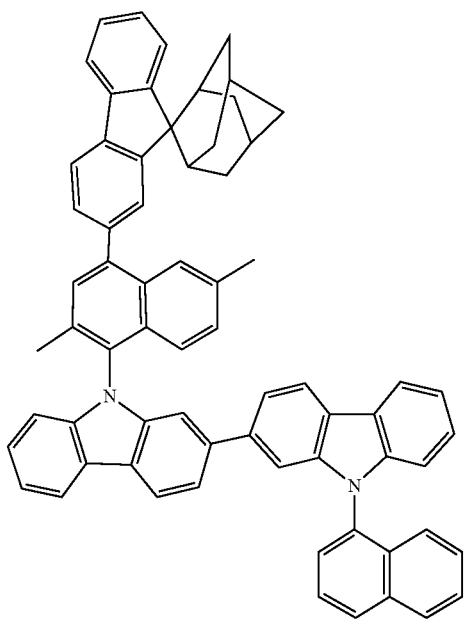
179

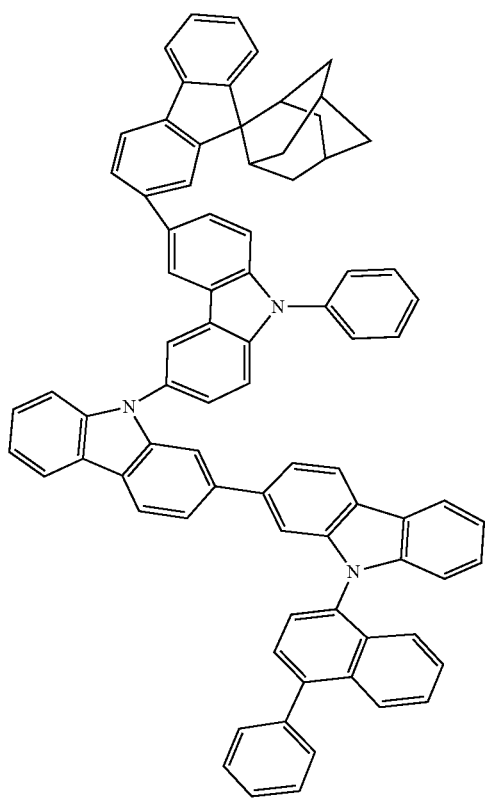
180
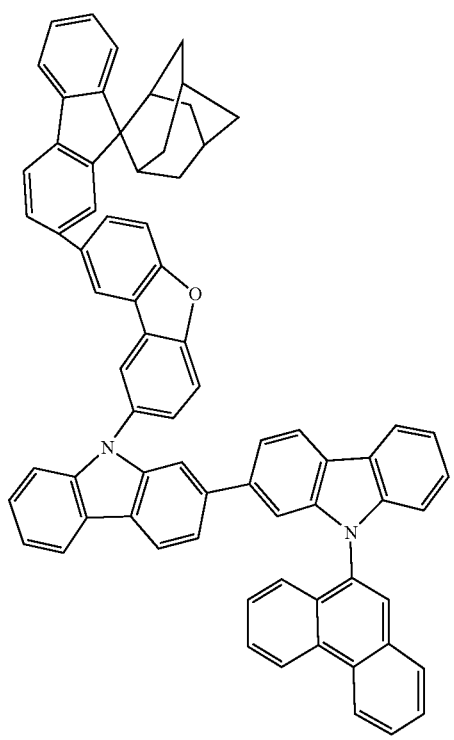
182
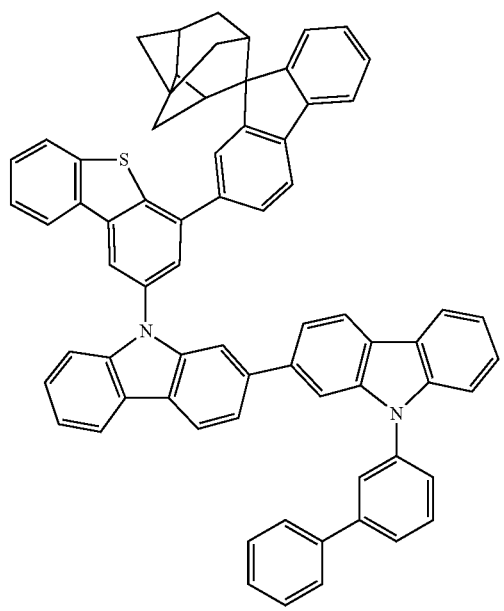
181
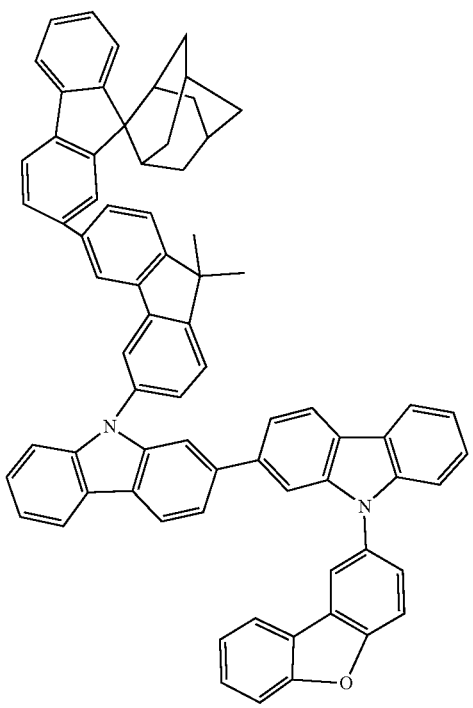
183

184
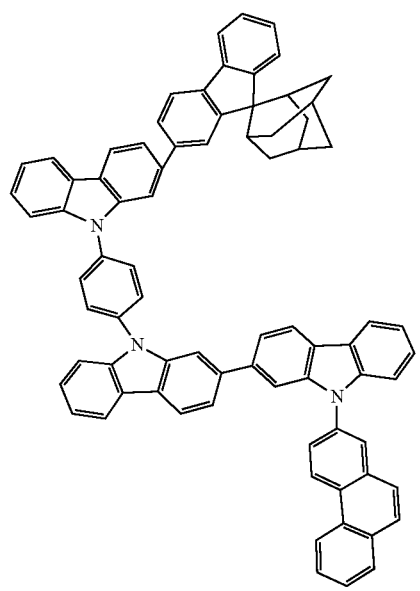
185
186
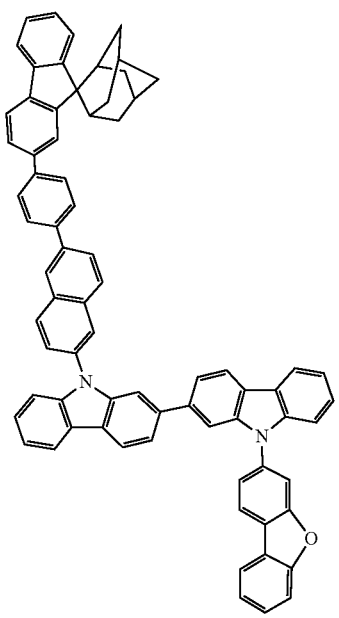
187
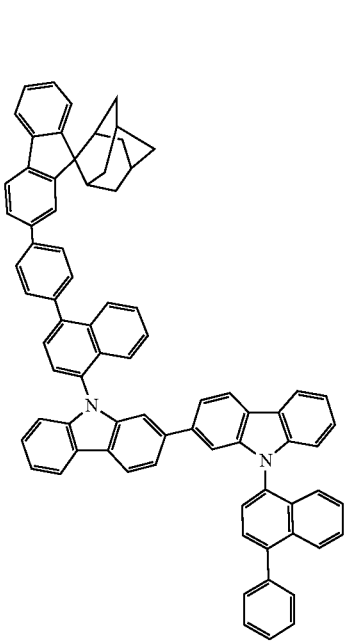

188
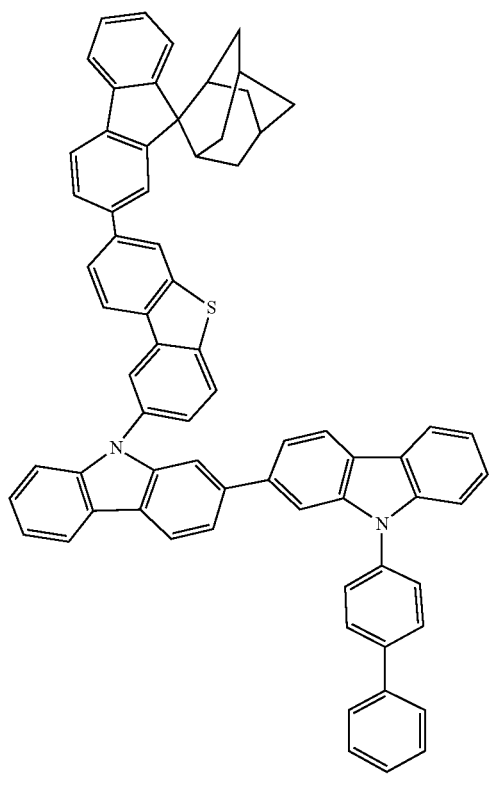
189
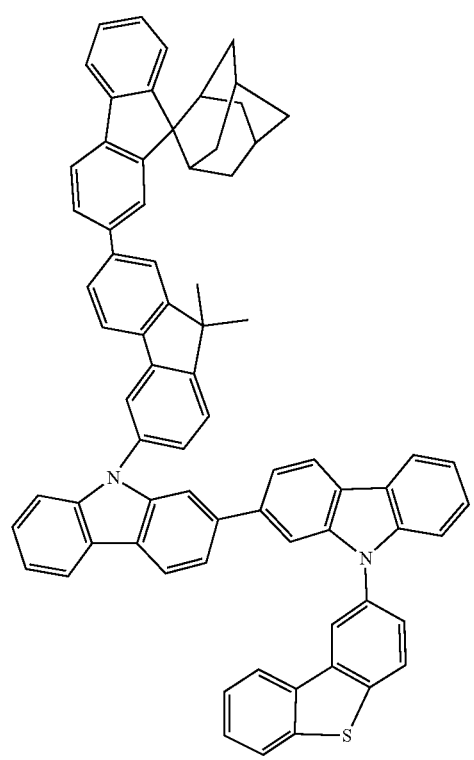
190
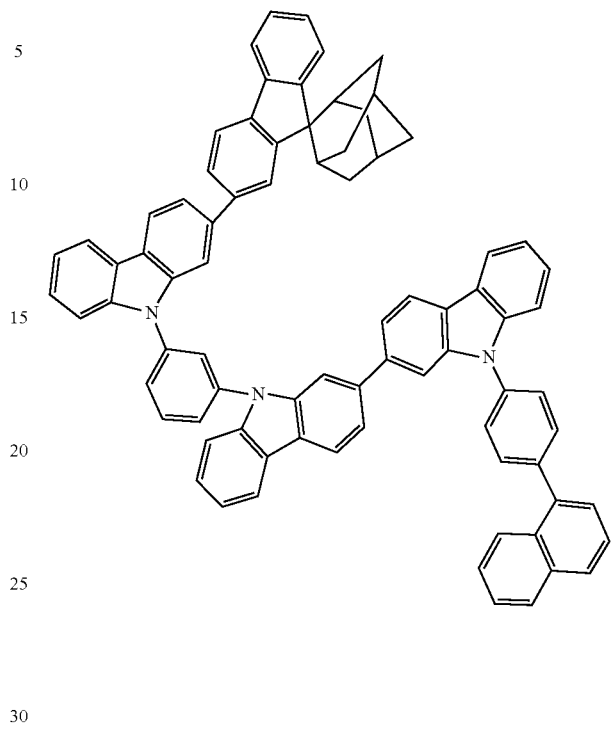
191
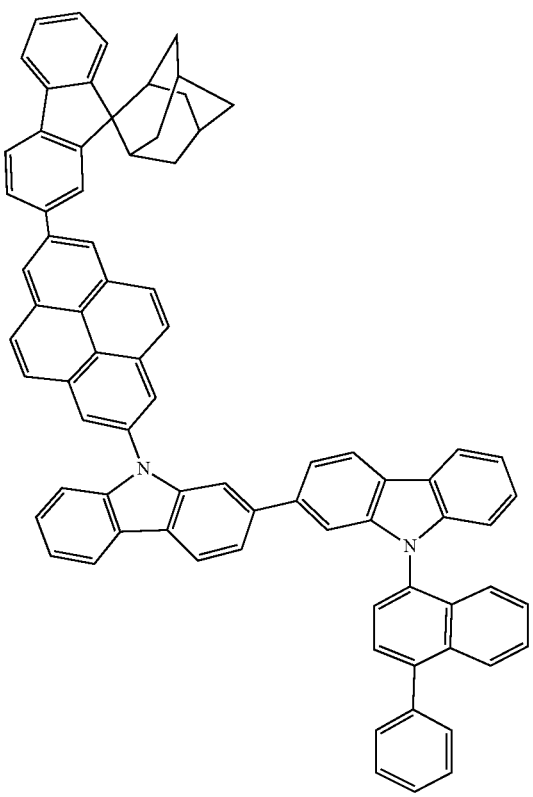

192
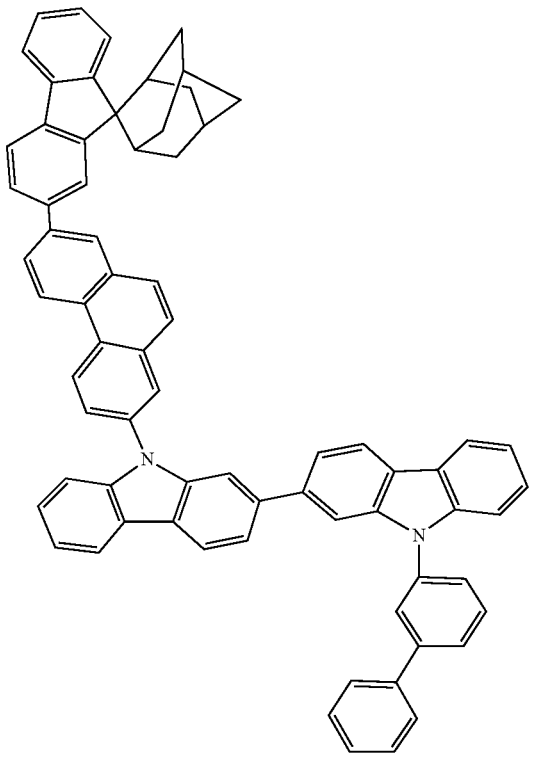
194
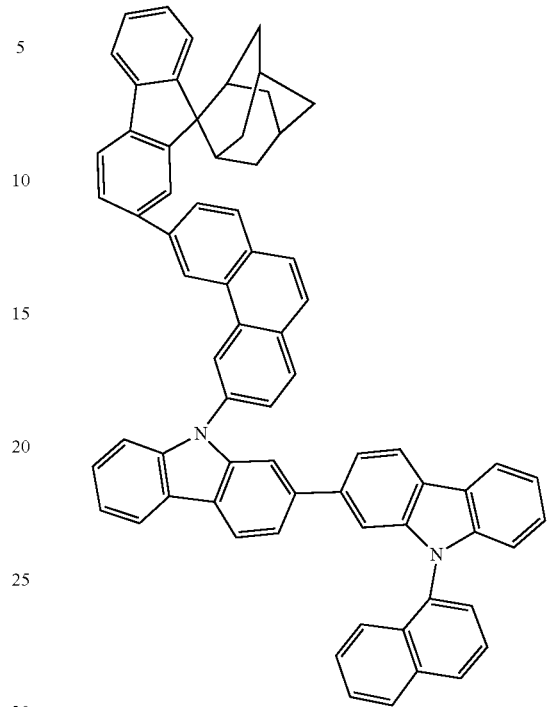
193
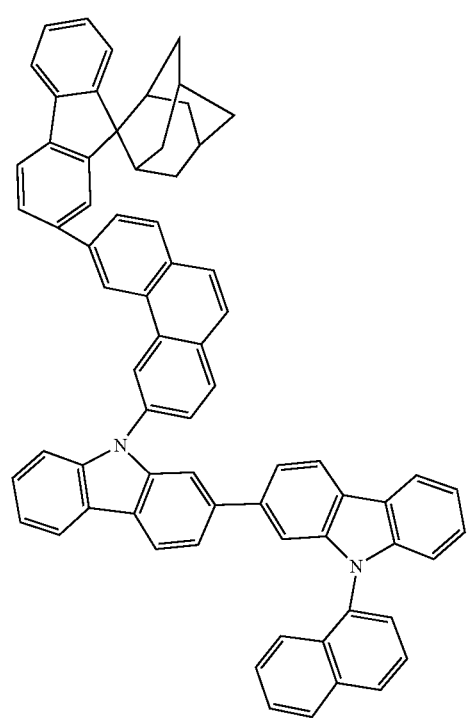
195
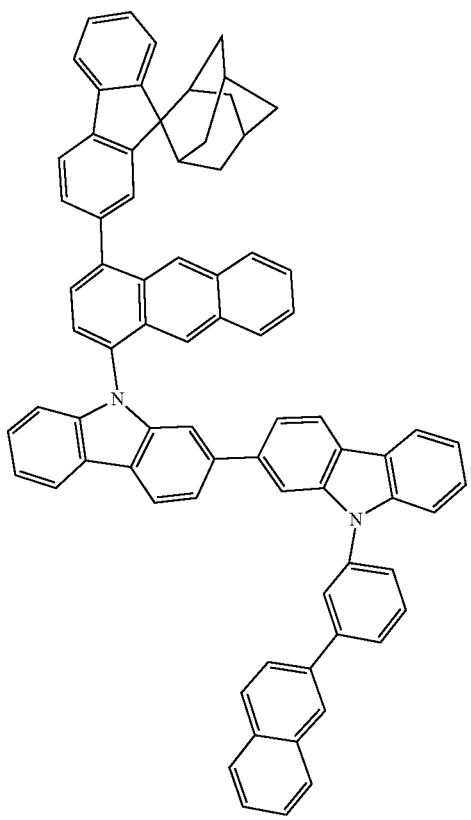

387
-continued
196
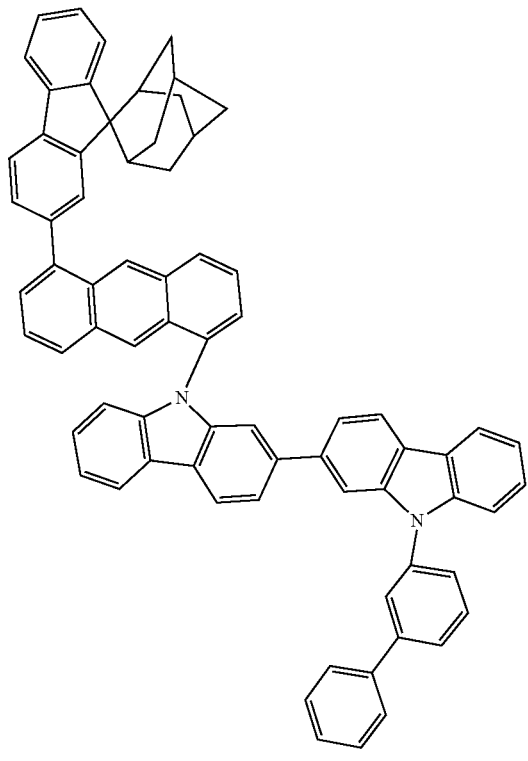
197
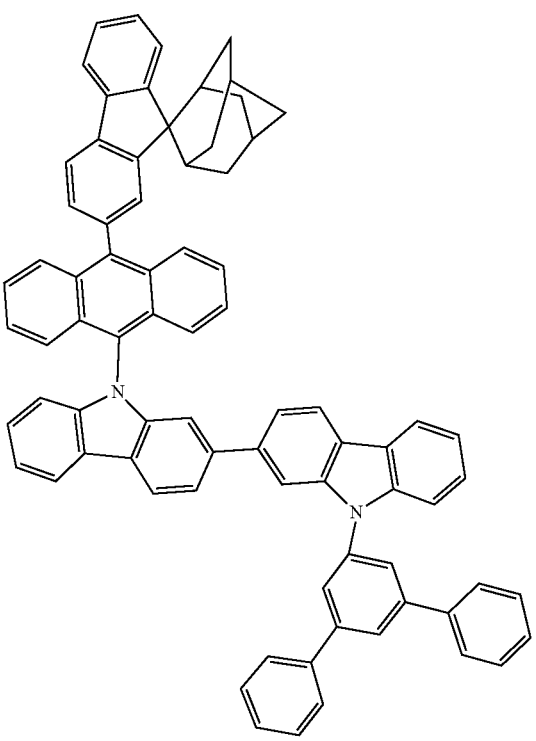
388
-continued
198
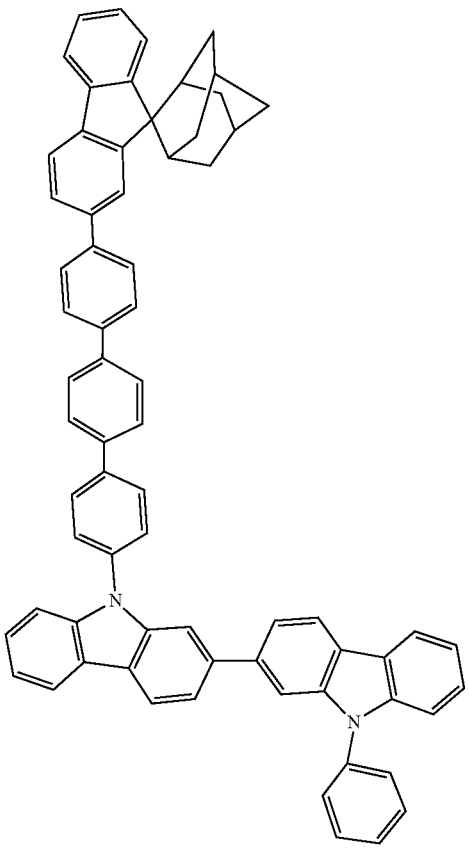
199
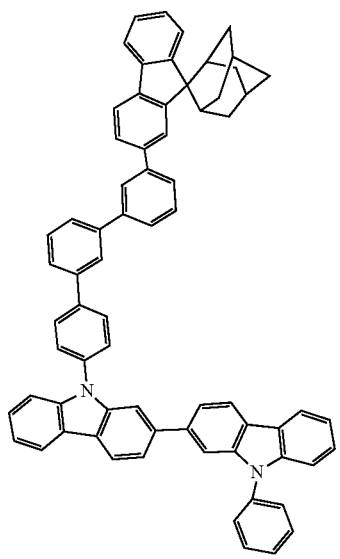

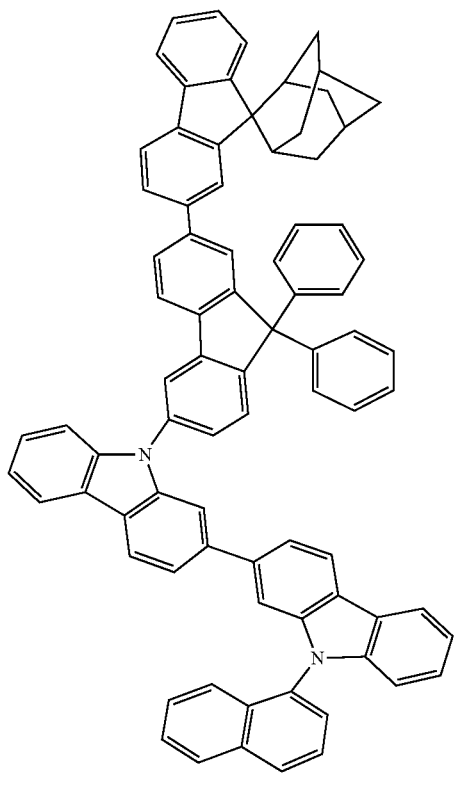
200
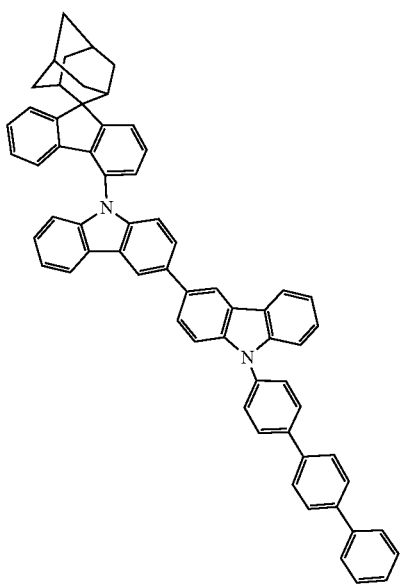
217
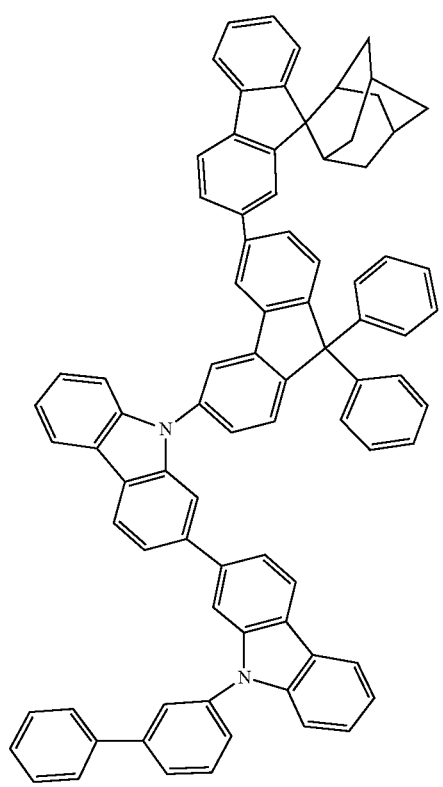
201
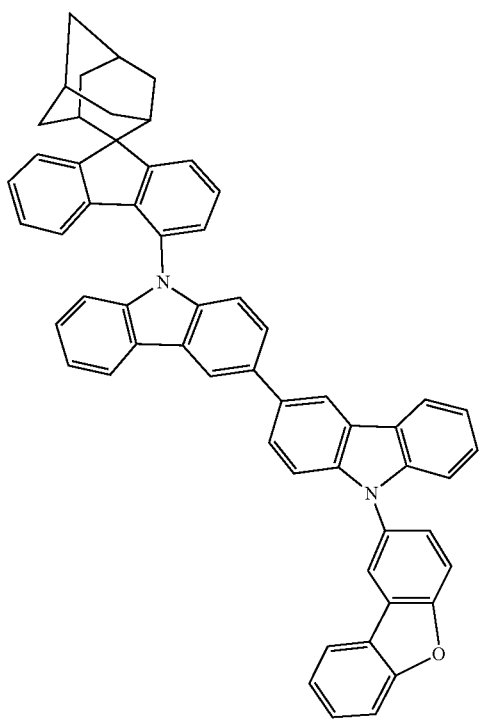
218

391
-continued
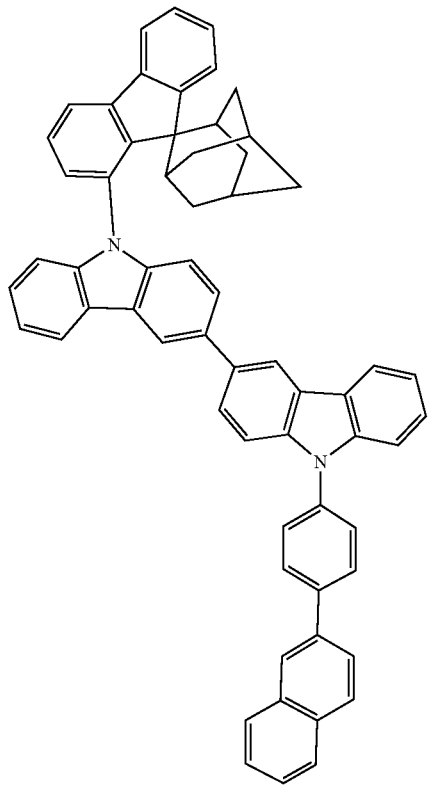
219
392
-continued
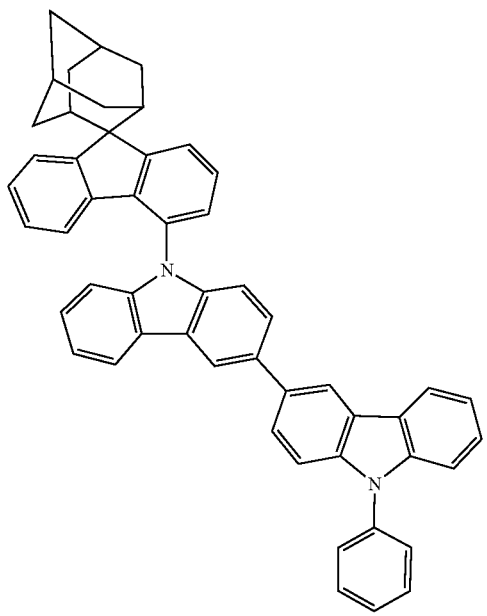
222
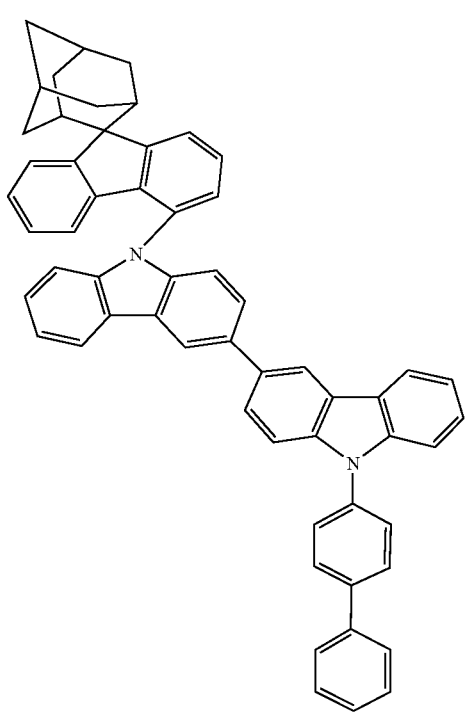
221
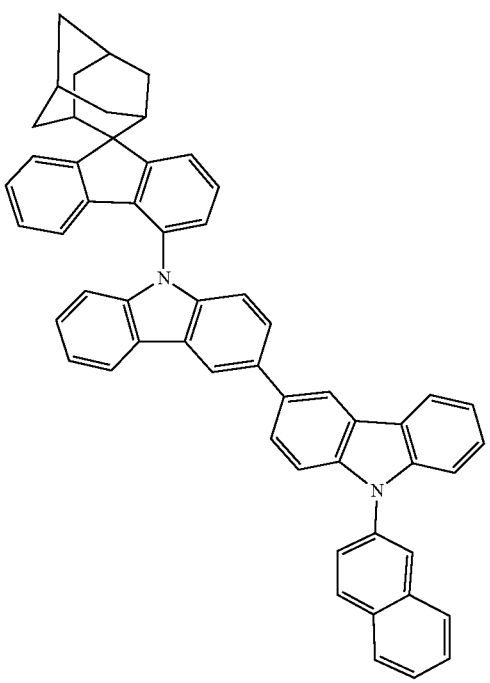
223

393
-continued
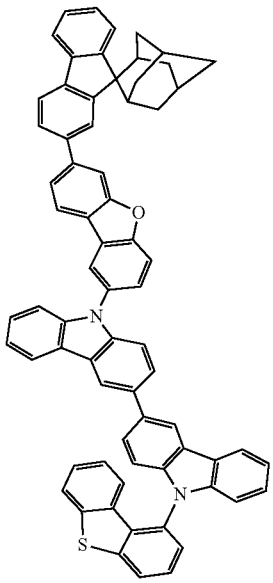
225
226
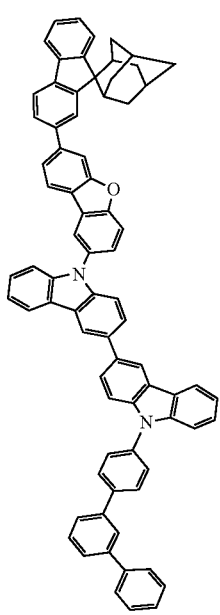
394
-continued
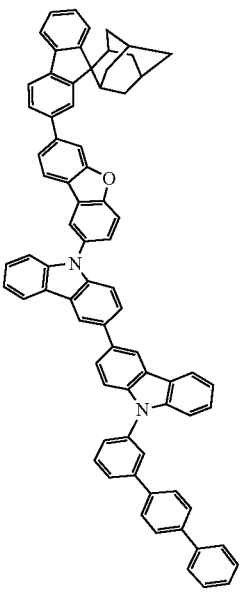
227
228
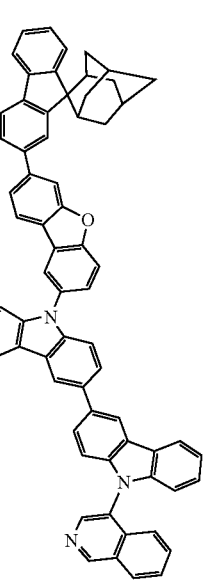

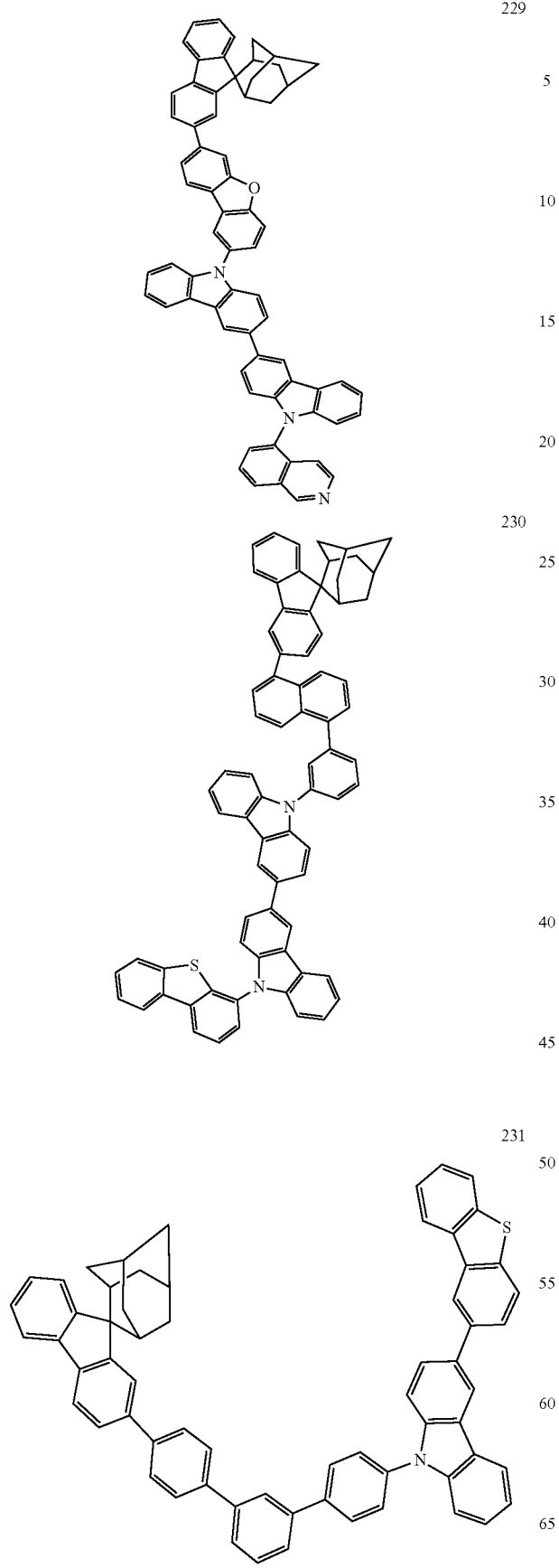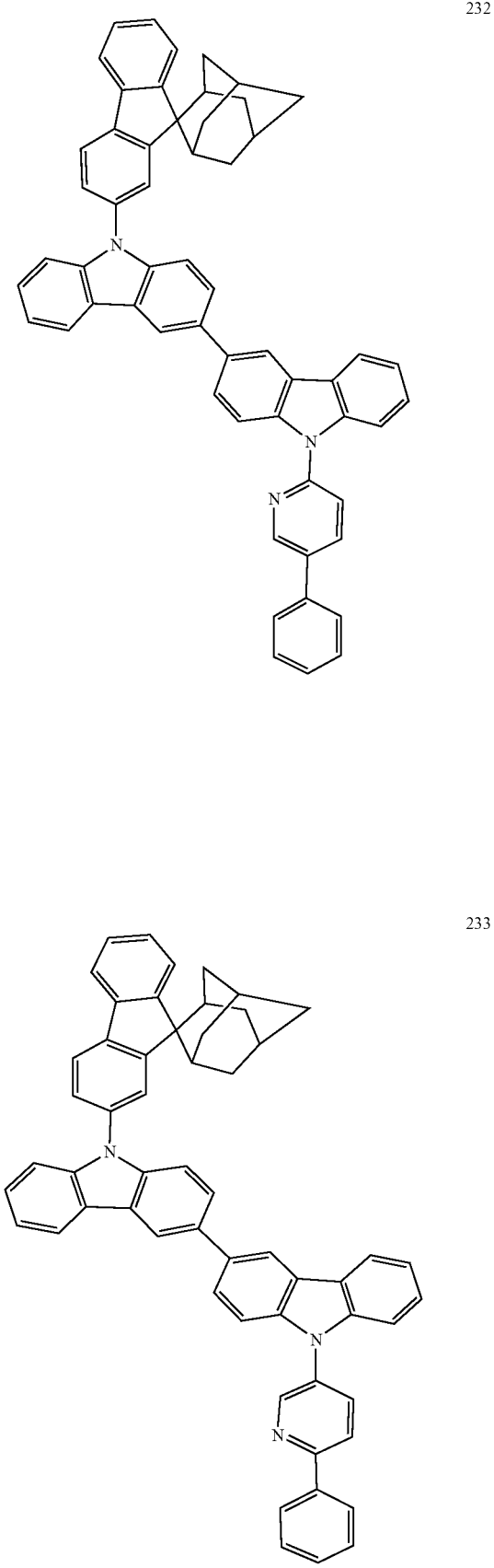

234
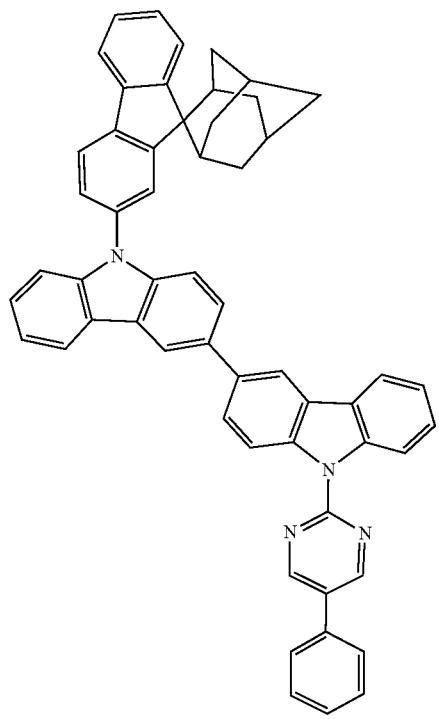
397-continued
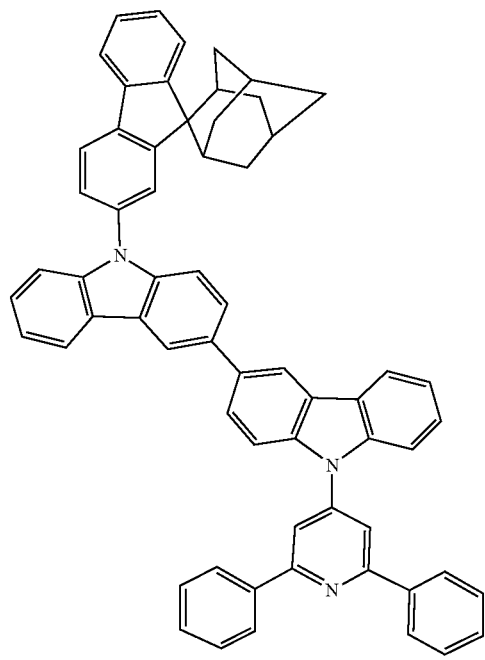
398-continued
236
235
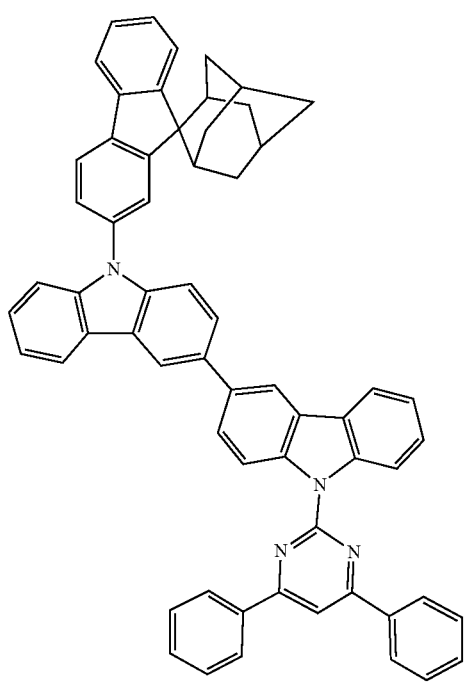
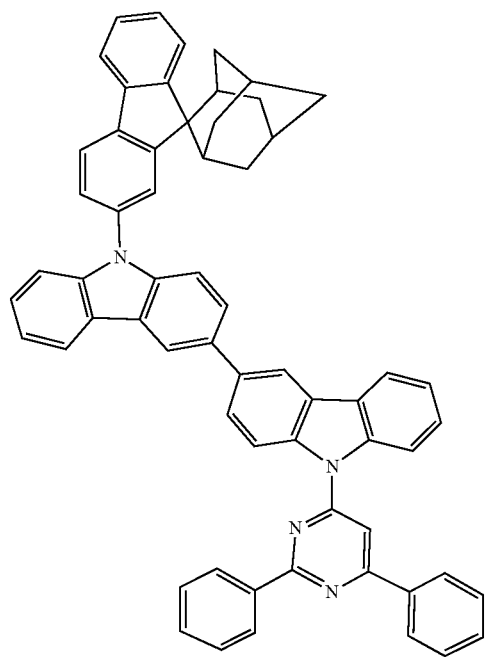
237

238
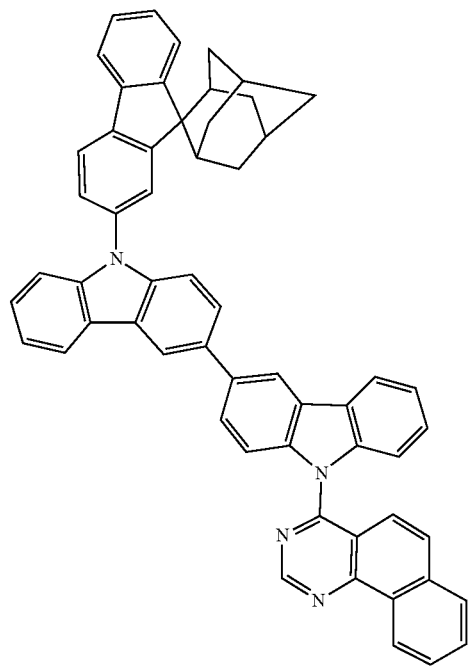
239
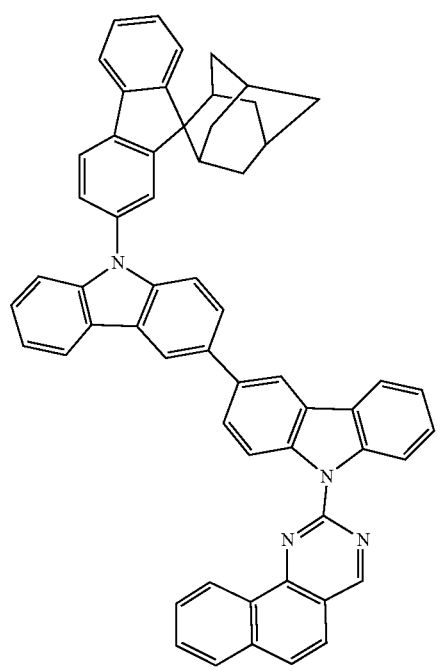
240
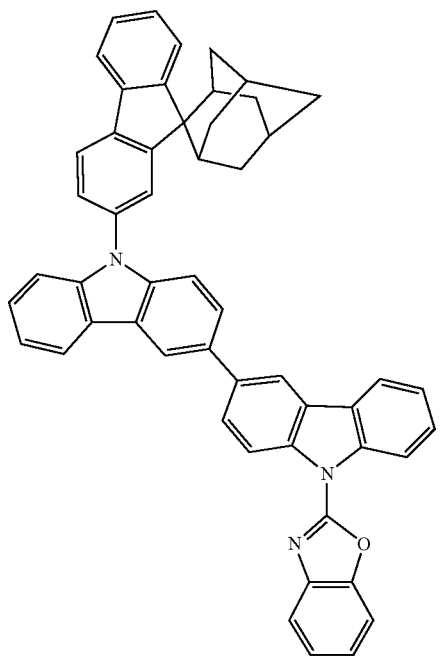
241
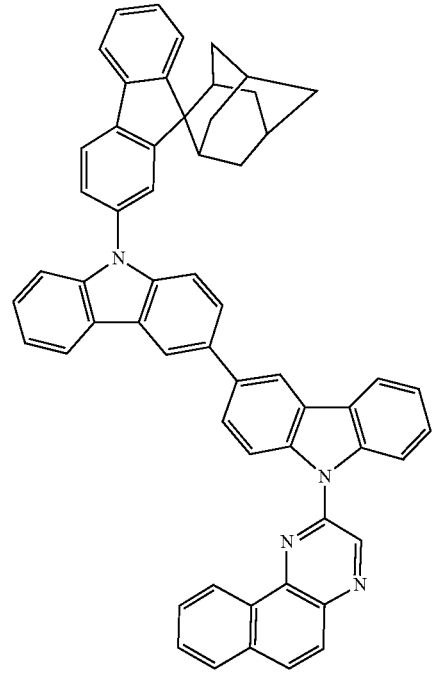

401
-continued
242
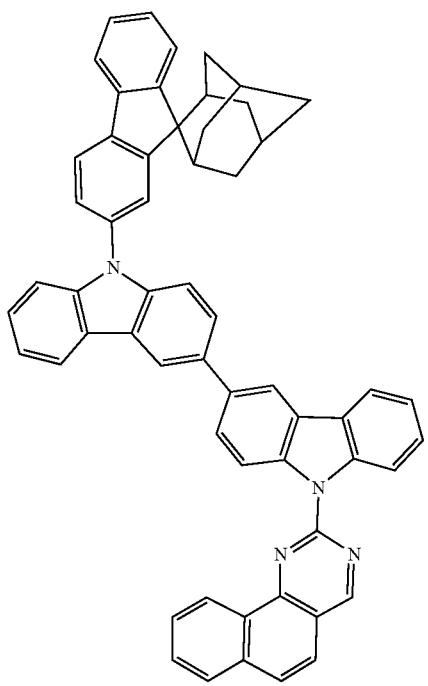
243
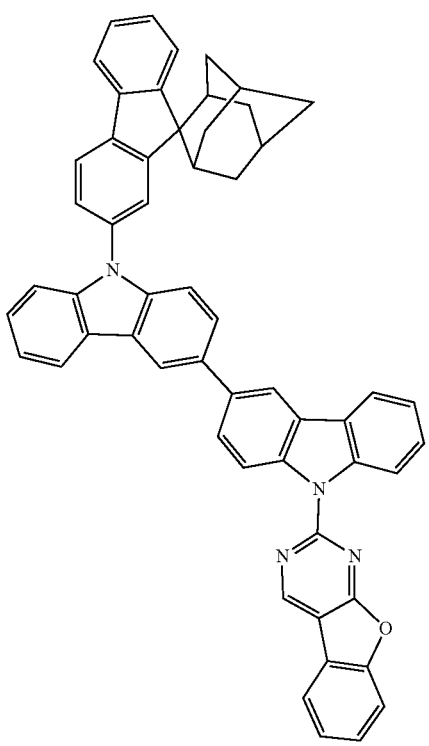
402
-continued
244
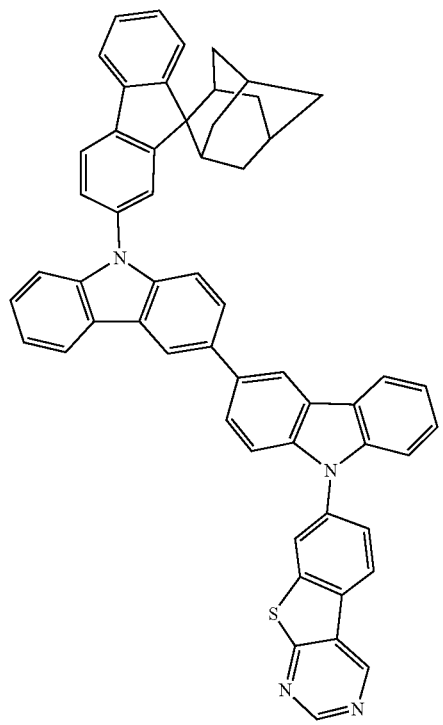
245
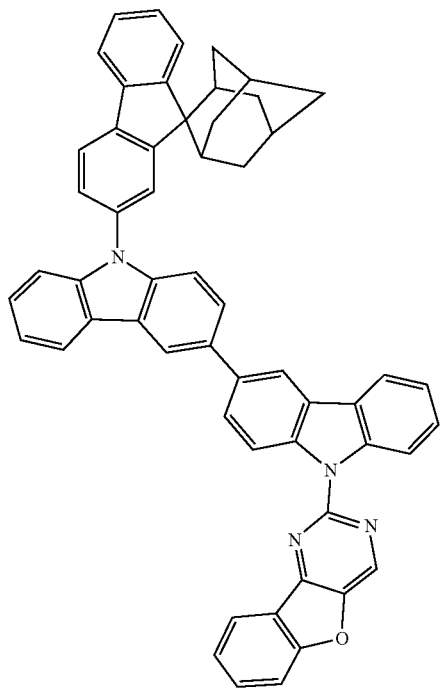

403
-continued
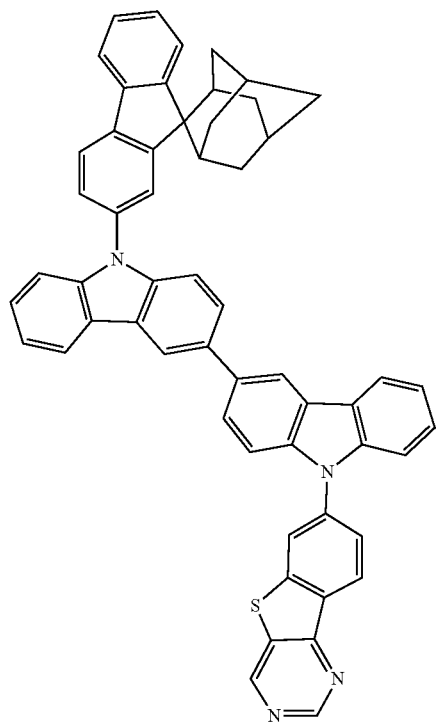
246
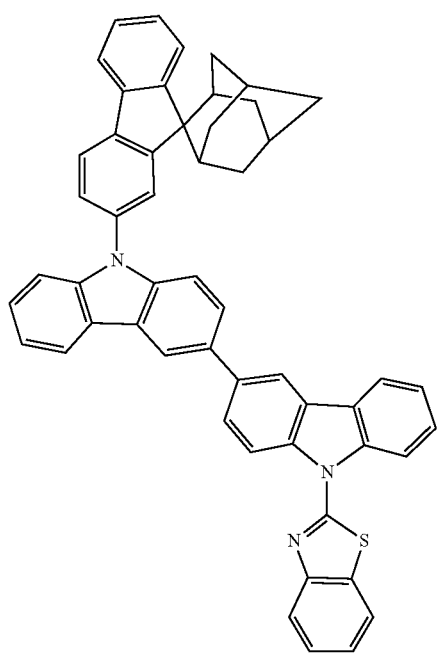
247
404
-continued
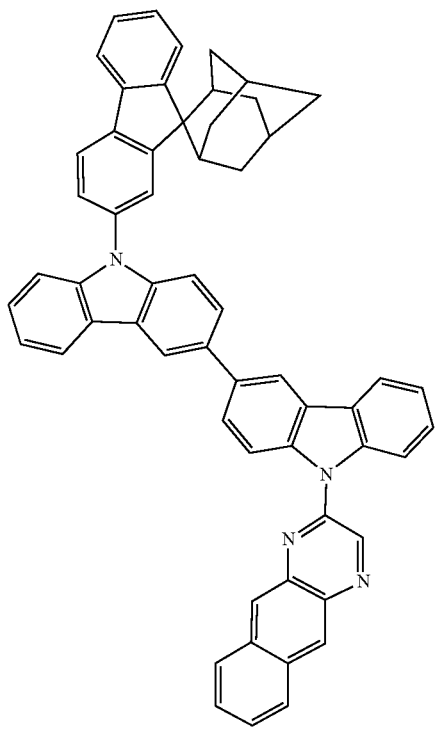
248
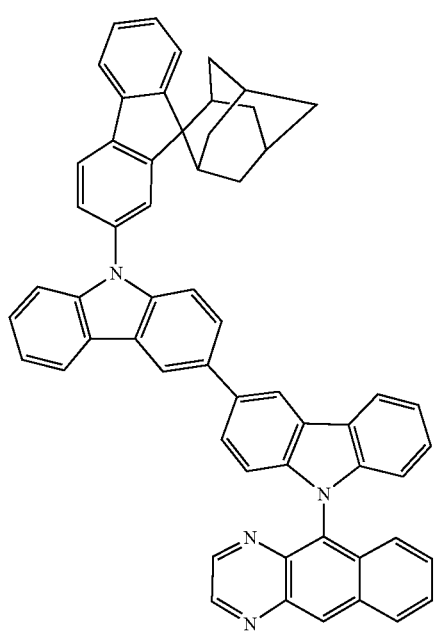
249

250
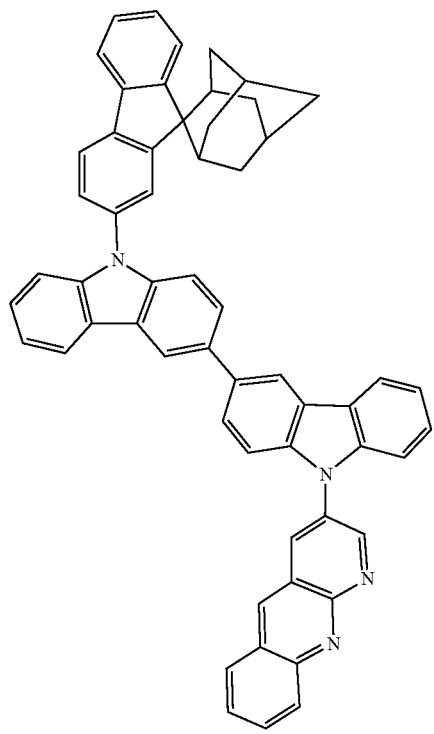
251
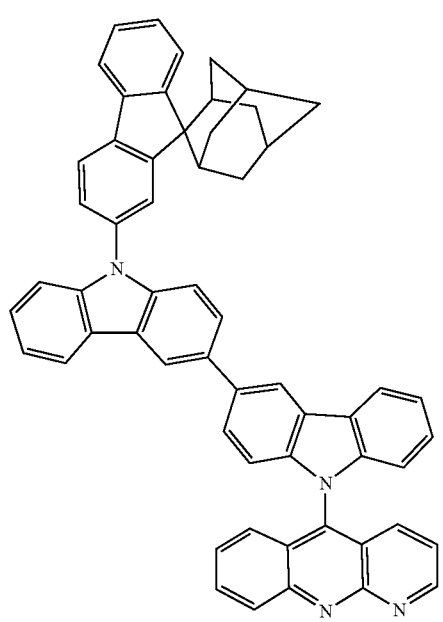
252
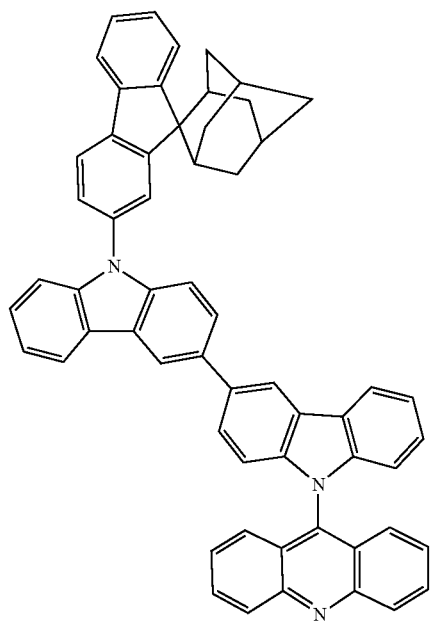
253
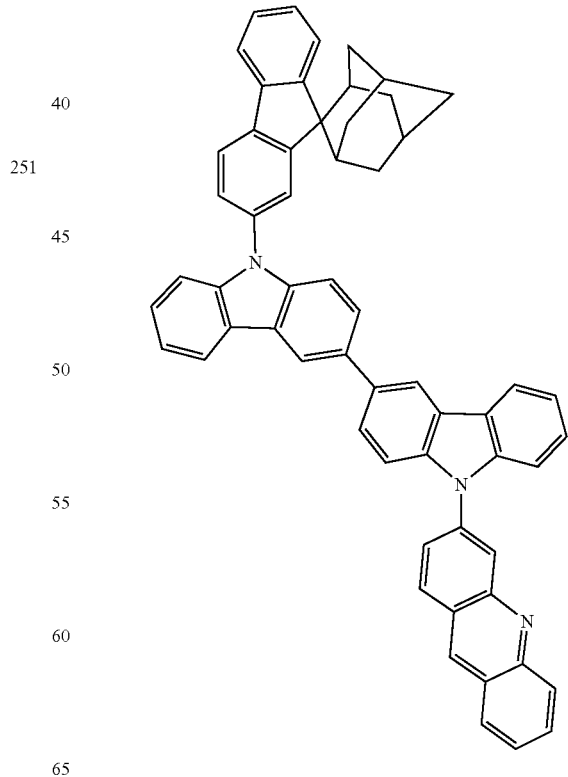

407
-continued
254
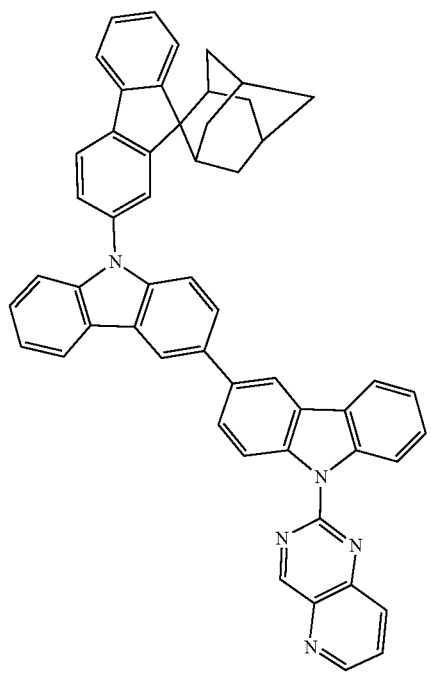
255
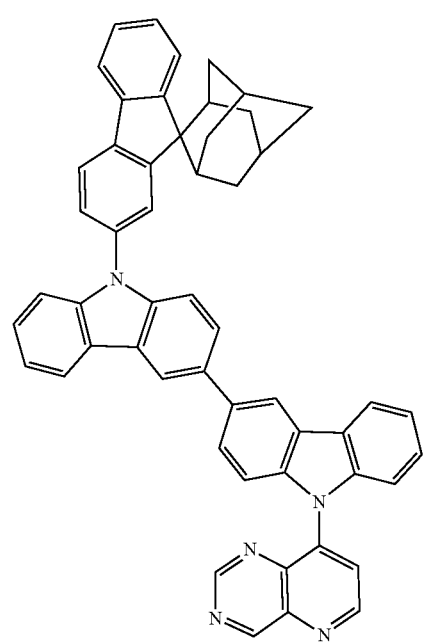
408
-continued
256
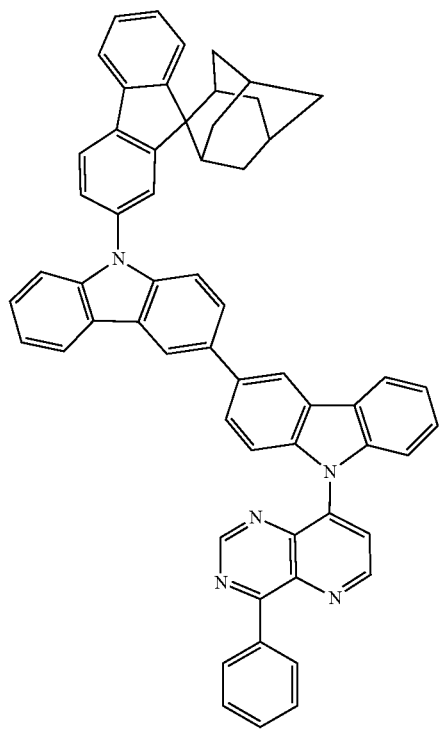
257
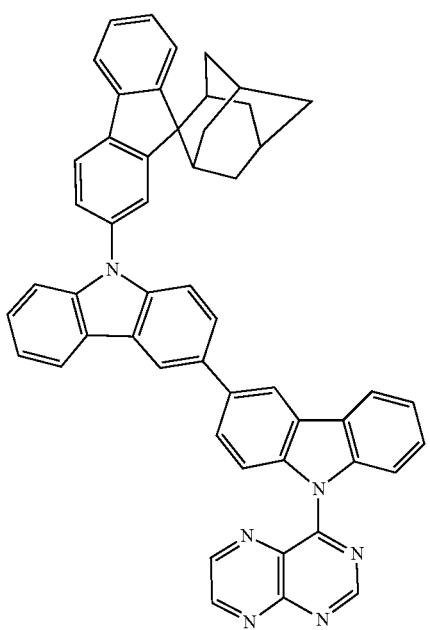

258
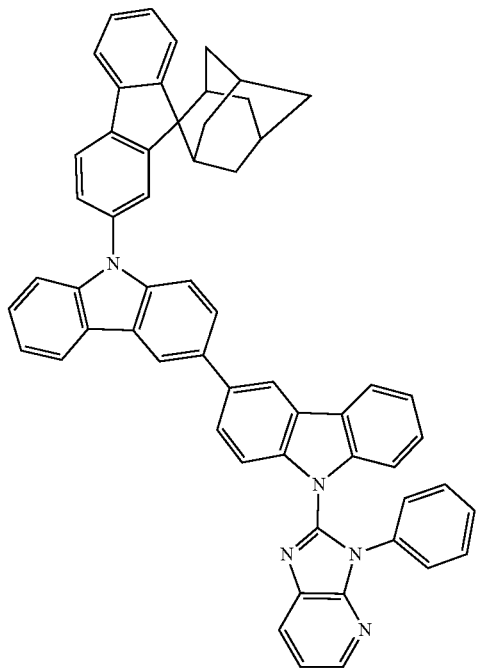
260
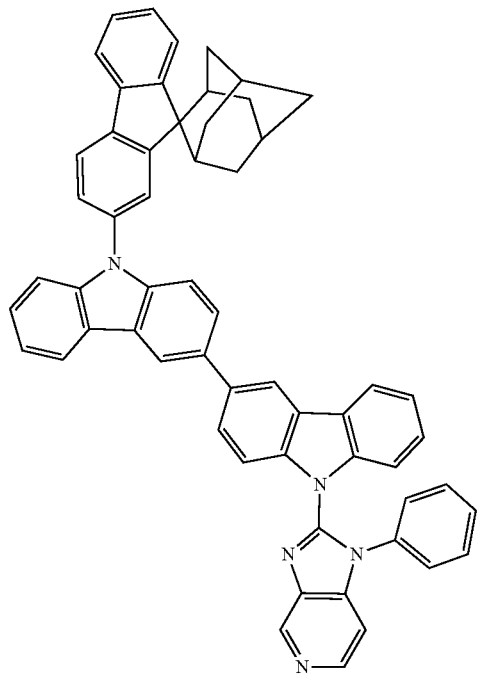
259
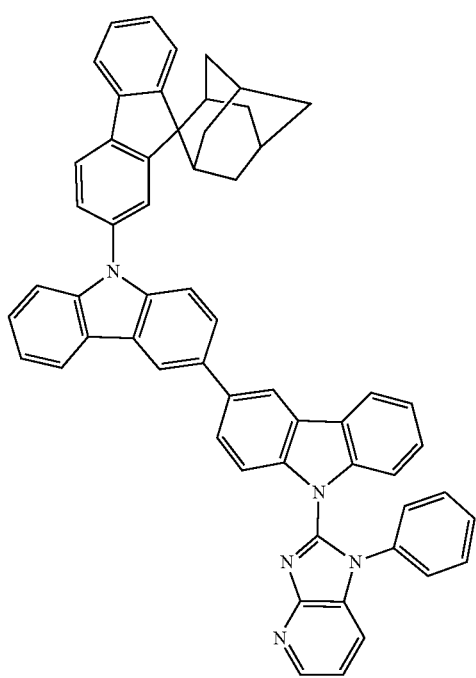
261
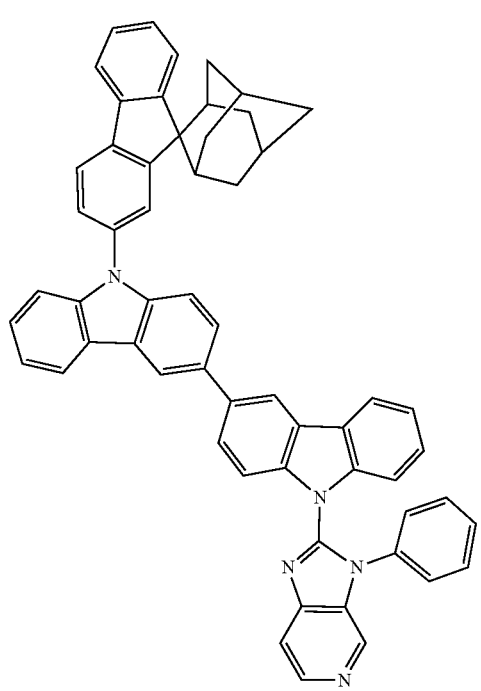

411
-continued
262
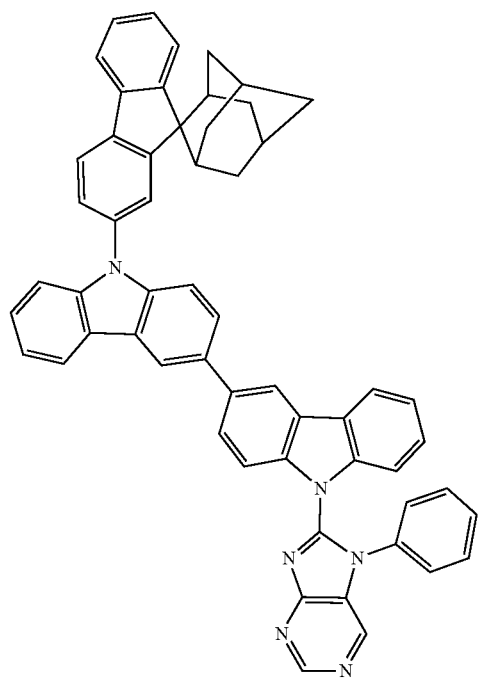
263
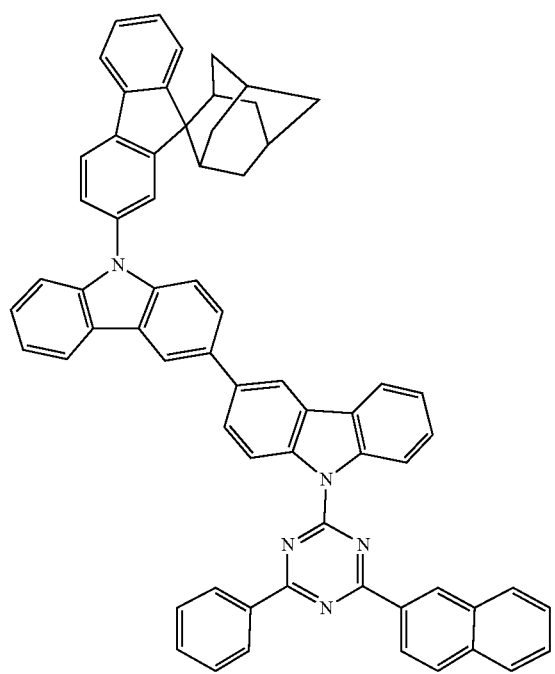
412
-continued
264
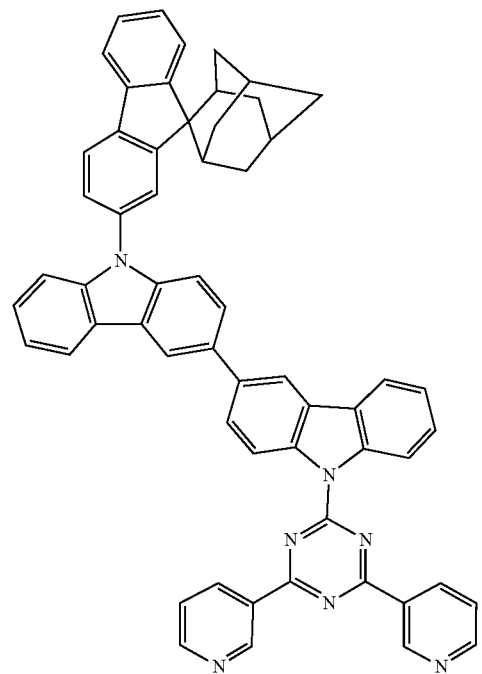
265
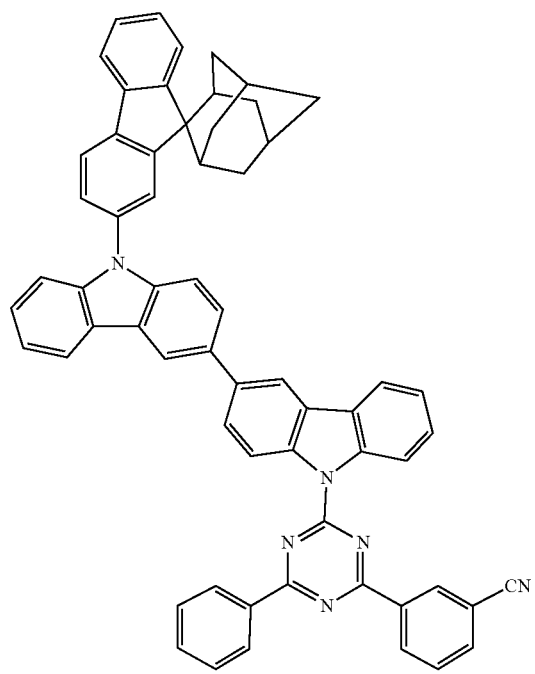

413
-continued
266
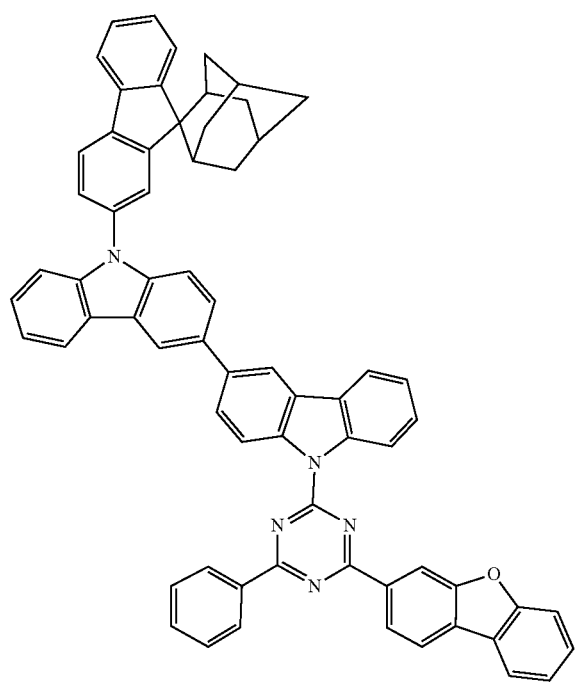
267
414
-continued
268
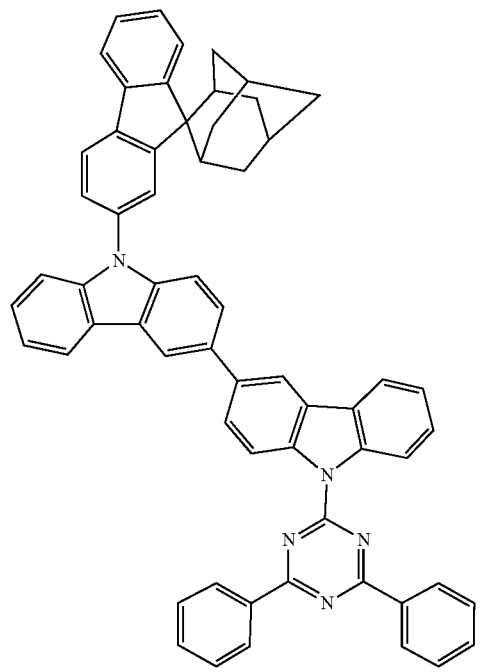
269

270

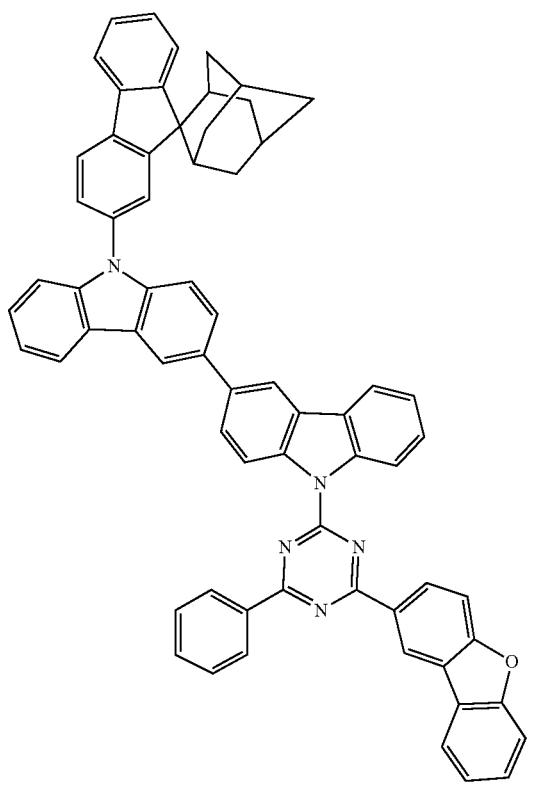

272

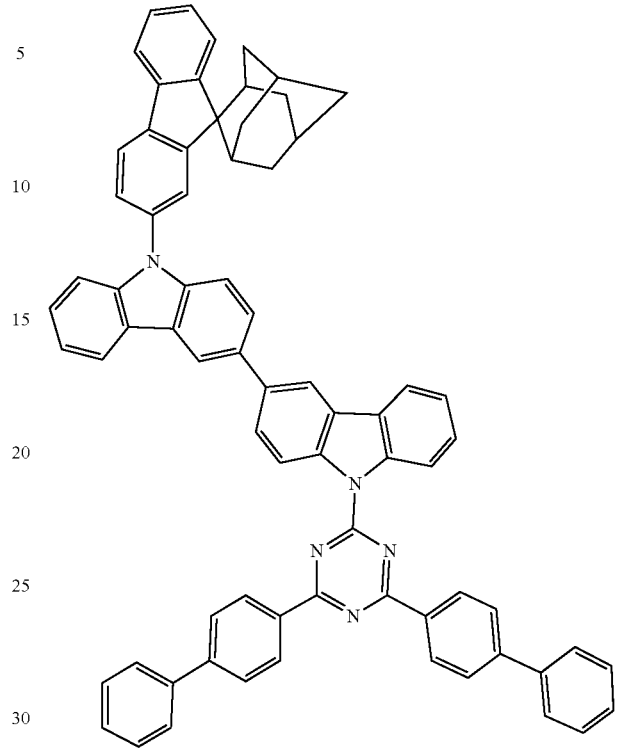

273

271

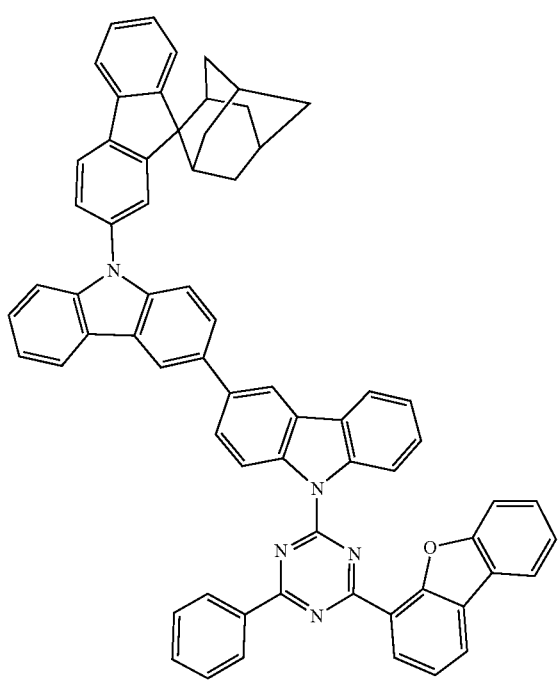

10. An organic electroluminescent device, comprising an anode, a cathode arranged opposite the anode, and a functional layer arranged between the anode and the cathode; wherein the functional layer contains the nitrogen-containing compound according to claim 1.

11. The organic electroluminescent device according to claim 10, wherein a host material of an organic light emitting layer in the functional layer comprises the nitrogen-containing compound.

12. An electronic apparatus, comprising the organic electroluminescent device according to claim 10.

13. An electronic apparatus, comprising the organic electroluminescent device according to claim 11.

* * * * *